US008362017B2

(12) United States Patent
Cheng et al.

(10) Patent No.: US 8,362,017 B2
(45) Date of Patent: Jan. 29, 2013

(54) C-KIT MODULATORS AND METHODS OF USE

(75) Inventors: Wei Cheng, South San Francisco, CA (US); Erick Wang Co, San Diego, CA (US); Moon Hwan Kim, Palo Alto, CA (US); Rhett Ronald Klein, Chicago, IL (US); Donna T. Le, San Jose, CA (US); Amy Lew, Milpitas, CA (US); John M. Nuss, Danville, CA (US); Wei Xu, Danville, CA (US); William Bajjalieh, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 514 days.

(21) Appl. No.: 10/569,873

(22) PCT Filed: Aug. 27, 2004

(86) PCT No.: PCT/US2004/028001
§ 371 (c)(1),
(2), (4) Date: Sep. 4, 2007

(87) PCT Pub. No.: WO2005/020921
PCT Pub. Date: Mar. 10, 2005

(65) Prior Publication Data
US 2008/0096892 A1  Apr. 24, 2008

Related U.S. Application Data

(60) Provisional application No. 60/499,224, filed on Aug. 29, 2003.

(51) Int. Cl.
| | |
|---|---|
| A61K 31/498 | (2006.01) |
| A61K 31/41 | (2006.01) |
| A61K 31/4192 | (2006.01) |
| A61K 31/505 | (2006.01) |
| A61K 31/4406 | (2006.01) |
| A61K 31/167 | (2006.01) |
| A61K 31/4196 | (2006.01) |
| C07D 257/04 | (2006.01) |
| C07D 249/06 | (2006.01) |
| C07D 213/30 | (2006.01) |
| C07D 239/26 | (2006.01) |
| C07D 249/08 | (2006.01) |
| C07D 241/42 | (2006.01) |
| C07C 233/15 | (2006.01) |

(52) U.S. Cl. ........ 514/249; 514/381; 514/359; 514/622; 514/383; 514/256; 514/357; 548/253; 548/255; 548/267.6; 564/161; 544/353; 544/335; 546/335

(58) Field of Classification Search ............ 514/249, 514/381, 359, 622, 383, 256, 357; 548/253, 548/255, 267.6; 564/161; 544/353, 335; 546/335; 436/501; 435/375, 15
See application file for complete search history.

(56) References Cited

U.S. PATENT DOCUMENTS

| 5,814,631 A | 9/1998 | Fukami et al. | |
|---|---|---|---|
| 2003/0092715 A1* | 5/2003 | Hobbs et al. | 514/247 |

FOREIGN PATENT DOCUMENTS

| EP | 0 503 162 A1 | 9/1992 |
|---|---|---|
| EP | 0 443 059 B1 | 6/1998 |
| EP | 1 295 867 A1 | 3/2003 |
| EP | 1 340 750 A1 | 9/2003 |
| JP | 60-233649 | 11/1985 |
| JP | 6-211814 A | 8/1994 |
| JP | 11-508570 | 7/1999 |
| JP | 2000-053570 A | 2/2000 |
| JP | 2001-501216 | 1/2001 |
| JP | 2003-501420 | 1/2003 |
| WO | WO 86/02642 | 5/1986 |
| WO | WO 97/02266 | 1/1997 |
| WO | WO 98/14450 | 4/1998 |
| WO | WO 99/52906 * | 10/1999 |
| WO | WO 00/26197 A1 * | 5/2000 |
| WO | WO 00/75120 | 12/2000 |
| WO | WO 01/25189 A1 * | 4/2001 |
| WO | 01/51456 A2 | 7/2001 |
| WO | WO 01/70678 A2 | 9/2001 |
| WO | WO 01/70741 | 9/2001 |
| WO | WO 02/06246 * | 1/2002 |
| WO | 02/055484 A1 | 7/2002 |
| WO | WO 02/057236 A1 | 7/2002 |
| WO | WO 02/079192 | 10/2002 |
| WO | WO 03/022852 | 3/2003 |
| WO | 03/028711 A2 | 4/2003 |
| WO | 03/093297 A2 | 11/2003 |
| WO | 2004/058762 A1 | 7/2004 |
| WO | 2004/060371 A1 | 7/2004 |
| WO | WO 2004/062475 A2 | 7/2004 |
| WO | 2005/016870 A | 2/2005 |
| WO | 2005/107687 A1 | 11/2005 |

OTHER PUBLICATIONS

Wolff et al., Burger's Medicinal Chemistry and Drug Discovery, 1994, Wiley-Interscience, Fifth Edition, vol. I: Principles and Practice, pp. 975-977.*
Metabolomics [online], Retrieved from the Internet Jun. 16, 2008, URL: http://www.en.wikipedia.org/wiki/Metabolomics.*

(Continued)

*Primary Examiner* — Kristin Bianchi
(74) *Attorney, Agent, or Firm* — McDonnell Boehnen Hulbert & Berghoff LLP

(57) ABSTRACT

The present invention provides compounds for modulating protein kinase enzymatic activity for modulating cellular activities such as proliferation, differentiation, programmed cell death, migration and chemoinvasion. Even more specifically, the invention provides compounds for modulating c-Kit kinase activity and methods of treating diseases mediated by c-Kit activity utilizing the compounds and pharmaceutical compositions thereof.

15 Claims, No Drawings

OTHER PUBLICATIONS

Kwon et al., Handbook of Essential Pharmacokinetics, Pharmacodynamics and Drug Metabolism for Industrial Scientists, 2001, URL: http://www.myilibrary.com/Browse/open.asp?ID=4284&loc=1, Retrieved from the Internet Jun. 16, 2008, p. 213.*

Vippagunta et al., Crystalline solids, 2001, Advanced Drug Delivery Reviews, 48, pp. 3 and 18.*

Meyer and Wolff (2000), "Water-binding solid scintillators: synthesis, emission properties, and tests in 3H and 14C counting." Chem. Eur. J. 6: 2809-2817.

Auzou et al. (1984), "Nouveaux dimethyl-2,5 pyrroles a activite analgesique." Eur. J. Med. Chem. 19: 283-4.

Database Registry ACS on STN, List of Compounds (List 1), 2010, 57 pages.

Database Registry ACS on STN, List of Compounds (List 2), 2010, 13 pages.

Ashton, W. et al., "Irreversible Enzyme Inhibitors. 198. Diaminodihydro-s-triazines and diaminopyrimidines bearing substituted (ureidomethyl)phenyl substituents as reversible inhibitors of dihydrofolate reductase", Journal of Medicinal Chemistry, 16(5), 453-6, 1971.

Auzou, G. et al., "2,5-Dimethylpyrroles as analgesics", STN Database Accession No. 1985:89665, Chemical Abstracts Service, Columbus, Ohio, 1 page, XP002486521.

Database Accession No. 8640850, Database Crossfire Beilstein, Beilstein Institut Zur Foerderung Der Chemischen Wissenschaften, Frankfurt AM Main, 1 page, XP002486522, 2000.

Database Accession No. 1495354, Database Crossfire Beilstein, Beilstein Institut Zur Foerderung Der Chemischen Wissenschaften, Frankfurt AM Main, 1 page, XP002486523, 1998.

Soliman, R. et al., "Preparation antidiabetic activity of new 3-methyl-5-phenylpyrazolesulfonylurea derivatives", Journal of Phamaceutical Sciences, 70(6), 602-605, 1981.

* cited by examiner

C-KIT MODULATORS AND METHODS OF USE

CROSS-REFERENCE TO RELATED APPLICATIONS

This application claims priority to U.S. provisional patent application 60/499,224 filed on Aug. 29, 2003, entitled "c-Kit Modulators and Method of Use," naming Cheng, Wei et. al as inventors; which is hereby incorporated by reference in its entirety for all purposes.

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion. Even more specifically, the invention relates to compounds which inhibit, regulate and/or modulate kinase receptor signal transduction pathways related to the changes in cellular activities as mentioned above, compositions which contain these compounds, and methods of using them to treat kinase-dependent diseases and conditions.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6): 334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers (GIST). Gleevec is a c-Kit and Abl kinase inhibitor.

Modulation (particularly inhibition) of cell proliferation and angiogenesis, two key cellular processes needed for tumor growth and survival (Matter A. Drug Disc Technol 2001 6, 1005-1024), is an alluring goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

One particularly attractive target for small-molecule modulation is c-Kit. The proto-oncogene c-kit was first identified as the oncogenic component of the acutely transforming Hardy-Zuckerman 4-feline sarcoma virus (Besmer et al Nature 1986 320:415-421). c-Kit (also called stem cell factor receptor or steel factor receptor) is a type 3 receptor tyrosine kinase (RTK) belonging to the platelet-derived growth factor receptor subfamily. c-Kit binds the ligand stem cell factor (SCF), and triggers its multiple signal transduction pathways including Src family kinases, phosphatidyl-inositol 3 kinase, the Ras-Raf-Map kinase cascade, and phospholipase C (Broudy et al Blood 1999 94: 1979-1986; Lennartsson et al Oncogene 1999 18: 5546-5553; Timokhina et al EMBO J 1998 17; 6250-6262; Chian et al Blood 2001 98(5)1365-1373; Blume-Jensen et al Curr Biol 1998 8:779-782; Kissel et al EMBO J 2000 19:1312-1326; Lennartsson et al. Oncogene 1999 18: 5546-5553; Sue et al Blood, 199892:1242-1149; Lev et al EMBO J 1991 10:647-654). c-Kit is required for normal hematopoiesis, melanonogenesis, and gametogenesis. c-Kit is expressed in mast cells, immature myeloid cells, melanocytes, epithelial breast cells and the interstitial cells of Cajal (ICC). In mast cells, it is required not only for the differentiation, maturation, chemotaxis, and haptotaxis but also for the promotion of survival and proliferation.

Mutations in c-Kit have been implicated in human disease. Mutations in the juxtamembrane domain are found in many human gastrointestinal stromal tumors, and mutations in the kinase domain are found in mastocytosis, germ cell tumors, acute myeloid leukemia (AML), NK lymphoma, and other hematologic disorders (Hirota et al Science 1998 279:577-580; Singer et al J Clin Oncol 2002 203898-3905; Longley et al Proc Natl Aca Sci USA 1999: 1609-1614; Tian et al Am J Pathol 1999 154: 1643-1647; Beghini et al Blood 2000 95:726-727; Hongyo et al Cancer Res 2000 60:2345-2347). These mutations result in ligand-independent tyrosine kinase activity, autophosphorylation of Kit, uncontrolled cell proliferation, and stimulation of downstream signaling pathways. Overexpression of Kit and Kit ligand have also been described in other tumors including small-cell lung cancer, neuroblastomas, gynecological tumors, and colon carcinoma, which might result in autocrine or paracrine Kit activation.

GISTs are the most common mesenchymal tumors of the gastrointestinal tract, and they are generally resistant to chemotherapy and radiation therapy. Malignant mast cell disease often suggests an extremely poor prognosis, and no reliable effective chemotherapeutic agents have been identified (Marone et al Leuk Res 2001 25:583-594). Systemic mast cell disorders have been treated with interferon-alpha, although the effectiveness of this therapy has been variable (Lehmann & Lammle Ann Hematol 1999 78:483-484; Butterfield Br J Dermatol 1998 138; 489-495). Therefore, activated Kit might serve as a therapeutic target in GISTs and mast cell disease, as well as other disorders associated with activated c-Kit.

Accordingly, the identification of small-molecule compounds that specifically inhibit, regulate, and/or modulate the signal transduction of kinases, particularly c-Kit, is desirable as a means to treat or prevent disease states associated with abnormal cell proliferation, and is an object of this invention.

SUMMARY OF THE INVENTION

In one aspect, the present invention provides compounds for modulating c-Kit kinase activity and methods of treating diseases mediated by c-Kit activity utilizing the compounds and pharmaceutical compositions thereof. Diseases mediated by c-Kit activity include, but are not limited to, diseases characterized in part by migration, invasion, proliferation and other biological activities associated with invasive cell growth.

In another aspect, the invention provides methods of screening for modulators of c-Kit activity. The methods comprise combining a composition of the invention, c-Kit, and at least one candidate agent and determining the effect of the candidate agent on the c-Kit activity.

In yet another aspect, the invention also provides pharmaceutical kits comprising one or more containers filled with one or more of the ingredients of pharmaceutical compounds and/or compositions of the present invention, including, one or more c-Kit enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflect approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below with reference to the associated drawings.

DETAILED DESCRIPTION OF THE INVENTION

The compositions of the invention are used to treat diseases associated with abnormal and or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as artheroscrosis, myocardioinfarction, ischemia, stroke and restenosis; other inflammatory and degenerative diseases such as interbowel diseases, osteoarthritis, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally", but proliferation and migration enhancement may be desired. Alternatively, reduction in "normal" cell proliferation and/or migration rate may be desired.

The present invention comprises a compound for modulating c-Kit activity according to Formula I (hereinafter referred to as embodiment [0022]),

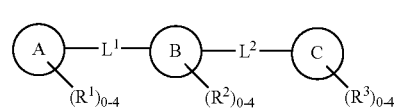

I or a pharmaceutically acceptable salt, hydrate, or prodrug thereof, wherein, ring A is a five- to fourteen-membered heteroaryl;

each $R^1$ is independently selected from —H, halogen, trihalomethyl, —CN, —NO$_2$, —OR$^4$, —N(R$^4$)R$^4$, —S(O)$_{0-2}$R$^4$, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, —C(=O)R$^4$, optionally substituted alkoxy, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

two adjacent of R$^1$, together with the annular atoms to which they are attached, can form a five- to six-membered ring containing up to two heteroatoms and optionally substituted with up to three of R$^{10}$;

L$^1$ is selected from a single bond, an optionally substituted C$_{1-2}$alkylene, —O—, —CH$_2$O—, —N(R$^7$)—, —C(=O)N(R$^7$)—, —SO$_2$N(R$^7$)—, —CH$_2$N(R$^7$)—, and —S(O)$_{0-2}$—;

ring B is a five- to ten-membered aryl or a five- to ten-membered heterocyclyl;

each $R^2$ is independently selected from —H, halogen, trihalomethyl, —CN, —NO$_2$, —OR$^4$, —N(R$^4$)R$^4$, —S(O)$_{0-2}$R$^4$, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, —C(=O)R$^4$, optionally substituted alkoxy, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

two adjacent of R$^2$, together with the annular atoms to which they are attached, can form a five- to six-membered ring containing up to two heteroatoms and optionally substituted with up to three of R$^{15}$;

L$^2$ is a selected from C$_4$alkylene, C$_4$alkylidene, C$_4$alkylidyne, —X(CH$_2$)$_2$O—, —X(CH$_2$)$_2$N(R$^7$)—, —XCH$_2$SO$_2$N(R$^7$)—, —XN(R$^7$)C(=O)N(R$^7$)—, —XCH$_2$C(=O)N(R$^7$)—, —(CH$_2$)$_3$X—, —XN(R$^7$)SO$_2$N(R$^7$)—, —XCH$_2$N(R$^7$)SO$_2$—, —CH$_2$X(CH$_2$)$_2$—, —CH=CHC(=O)N(R$^7$)—, —CH=CHSO$_2$N(R$^7$)—, —XCH$_2$N(R$^7$)C(=O)—, -M-M-, —CH$_2$N(R$^7$)C(=O)O—, and —CH$_2$C(=O)N(R$^7$)—; wherein X is selected from —CH$_2$—, —O—, —N(R$^7$)—, —C(=O)—, and —S(O)$_{0-2}$—; M is selected from —C(=O)N(R$^7$)— and —SO$_2$N(R$^7$)—; and any C—H of L$^2$ is optionally C—R$^{20}$;

ring C is either a five- to ten-membered aryl or a five- to ten-membered heteroaryl;

each R$^3$ is independently selected from —H, halogen, trihalomethyl, —CN, —NO$_2$, —OR$^4$, —N(R$^4$)R$^4$, —S(O)$_{0-2}$R$^4$, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, —C(=O)R$^4$, optionally substituted alkoxy, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl; provided R$^3$ is not a cyclic sulfonamide attached to ring C via the nitrogen of said cyclic sulfonamide;

two adjacent of R$^3$, together with the annular atoms to which they are attached, can form a five- to six-membered ring containing up to two heteroatoms and optionally substituted with up to three of R$^{25}$;

R$^4$ is selected from —H, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

two of R$^4$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;

R$^5$ is selected from —H, —CN, —NO$_2$, —OR$^4$, —S(O)$_{0-2}$R$^4$, —CO$_2$R$^4$, optionally substituted C$_{1-6}$alkyl, optionally substituted C$_{1-6}$alkenyl, and optionally substituted C$_{1-6}$alkynyl;

R$^7$ is selected from —H, optionally substituted C$_{1-6}$alkyl, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —C(=O)R$^4$, optionally substituted alkoxy, optionally substituted aryl, optionally substituted aryl C$_{1-6}$alkyl, optionally substituted heterocyclyl, and optionally substituted heterocyclyl C$_{1-4}$alkyl; and each of R$^{10}$, each of R$^{15}$, each of R$^{20}$, and each of R$^{25}$ is independently selected from —H, halogen, trihalomethyl, —CN, —NO$_2$, —OR$^4$, —N(R$^4$)R$^4$, —S(O)$_{0-2}$R$^4$, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, —C(=O)R$^4$, optionally substituted alkoxy, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

provided:
1) when both ring B and ring C are phenyl:
   a) and the compound comprises ring B—CH$_2$N(H)C(=O)N(H)-ring C, then L$^1$ must be a single bond; R$^3$ can not comprise a group of the formula —O(CH$_2$)$_{2-4}$—N-piperazine that is ortho- to L$^2$; and ring A cannot be a 5-methyl-[1,2,4]-oxadiazol-3-yl radical, a 4H-[1,2,4]-oxadiazol-5-one-3-yl radical, nor a 4'-[2,2';6',2'']terpyridinyl radical;
   b) and L$^1$ is single bond, then L$^2$ cannot comprise —N(H)C(=O)C(=O)N(H)— nor —N(H)C(=Q)C(H)CNC(=O)— (where Q is S or O);
   c) and L$^1$ is other than single bond, then A cannot be quinolin-2-yl-L$^1$, quinolin-3-yl-L$^1$, or quinolin-4-yl-L$^1$;
2) when ring A is a fused aryl system, then L$^1$ must be a single bond;
3) when ring B is phenyl, ring C is a C$_{6-16}$carbocyclic, L$^1$ is a single bond, and the compound comprises -ring B—OCH$_2$C(=O)N(H)— then ring A cannot be a 2,5-dimethyl-1H-pyrrole-1-yl radical;
4) ring A cannot be a pyrimidin-2-yl radical when L$^1$ is —N(H)— and ring B is phenyl;
5) when the compound comprises the formula,

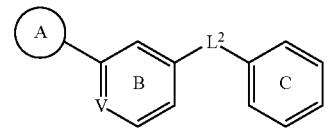

where V is =C(H)— or =N—, and there is a nitrogen of L$^2$ bound directly to zing B, then A can not comprise a [1,2,4]-oxadiazol-3-yl radical; and
6) the compound is not one of: N-naphthalen-1-yl-2-{[3-(1H-tetrazol-1-yl)phenyl]oxy}acetamide, N-[4-(phenyloxy)phenyl]-2-{[3-(1H-tetrazol-1-yl)phenyl]oxy}acetamide, N-(3,4-dimethylphenyl)-2-{[3-(1H-tetrazol-1-yl)phenyl]oxy}acetamide, N-(2,3-dimethylphenyl)-2-{[3-(1H-tetrazol-1-yl)phenyl]oxy}acetamide, N-(2,4-dimethylphenyl)-2-{[3-(1H-tetrazol-1-yl)phenyl]oxy}acetamide, N-(2,5-dimethylphenyl)-2-{[3-(1H-tetrazol-1-yl)phenyl]oxy}acetamide, N-(3,5-dimethylphenyl)-2-{[3-(1H-tetrazol-1-yl)phenyl]oxy}acetamide, N-(2,6-dimethylphenyl)-2-{[3-(1H-tetrazol-1-yl)phenyl]oxy}acetamide, 2-{[3-(1H-tetrazol-1-yl)phenyl]oxy}-N-(2,4,6-trimethylphenyl)acetamide, N-(2-ethylphenyl)-2-{[3-(1H-tetrazol-1-yl)phenyl]oxy}acetamide, N-(4-ethylphenyl)-2-{[3-(1H-tetrazol-1-yl)phenyl]oxy}acetamide, N-(2,6-diethylphenyl)-2-{[3-(1H-tetrazol-1-yl)phenyl]oxy}acetamide, N-[2-(methyloxy)phenyl]-2-{[3-(1H-tetrazol-1-yl)phenyl]oxy}acetamide, N-[2-(ethyloxy)phenyl]-2-{[3-(1H-tetrazol-1-yl)phenyl]oxy}acetamide, N-[3-(ethyloxy)phenyl]-2-{[3-(1H-tetrazol-1-yl)phenyl]oxy}acetamide, N-[2,4-bis(methyloxy)phenyl]-2-{[3-(1H-tetrazol-1-yl)phenyl]oxy}acetamide, N-[4-(dimethylamino)phenyl]-2-{[3-(1H-tetrazol-1-yl)phenyl]oxy}acetamide, N-(2,3-dichlorophenyl)-2-{[3-(1H-tetrazol-1-yl)phenyl]oxy}acetamide, N-(4-chloro-3-methylphenyl)-2-{[3-(1H-tetrazol-1-yl)phenyl]oxy}acetamide, N-(4-bromophenyl)-2-{[3-(1H-tetrazol-1-yl)phenyl]oxy}acetamide, N-(2-fluorophenyl)-2-{[3-(1H-tetrazol-1-yl)phenyl]oxy}acetamide, N-(4-fluorophenyl)-2-{[3-(1H- tetrazol-1-yl)phenyl]oxy}acetamide, 2-{[3-(1H-tetrazol-1-yl)phenyl]oxy}-N-[2-(trifluoromethyl)phenyl]acetamide, 2-{[3-(1H-tetrazol-1-yl)phenyl]oxy}-N-[3-(trifluoromethyl)phenyl]acetamide, methyl 4-[({[3-(1H-tetrazol-1-yl)phenyl]oxy}acetyl)amino]benzoate, ethyl 4-[({[3-(1H-tetrazol-1-yl)phenyl]oxy}acetyl)amino]benzoate, 3-[({[3-(1H-tetrazol-1-yl)phenyl]oxy}acetyl)amino]benzoic acid, N-[3-(methyloxy)phenyl]-2-{[3-(1H-tetrazol-1-yl)phenyl]oxy}acetamide, N-[4-(methyloxy)phenyl]-2-{[3-(1H-tetrazol-1-yl)phenyl]oxy}acetamide, N-[2-chloro-5-(trifluoromethyl)phenyl]-2-{[3-(1H-tetrazol-1-yl)phenyl]oxy}acetamide, N-[4-chloro-3-(trifluoromethyl)phenyl]-2-{[3-(4H-1,2,4-triazol-4-yl)phenyl]oxy}acetamide, N-(4-chlorophenyl)-2-{[3-(1H-tetrazol-1-yl)phenyl]oxy}acetamide, N-(4-aminophenyl)-2-{[3-(1H-tetrazol-1-yl)phenyl]oxy}acetamide, and N-(4-acetylphenyl)-2-{[3-(1H-tetrazol-1-yl)phenyl]oxy}acetamide.

In one example, the compound is according to embodiment [0022], wherein $L^1$ is a single bond, hereinafter referred to as embodiment [0023].

In another example, the compound is according to embodiment [0023], wherein ring A contains between one and four annular nitrogens, hereinafter referred to as embodiment [0024].

In another example, the compound is according to embodiment [0024], wherein ring A is selected from the following:

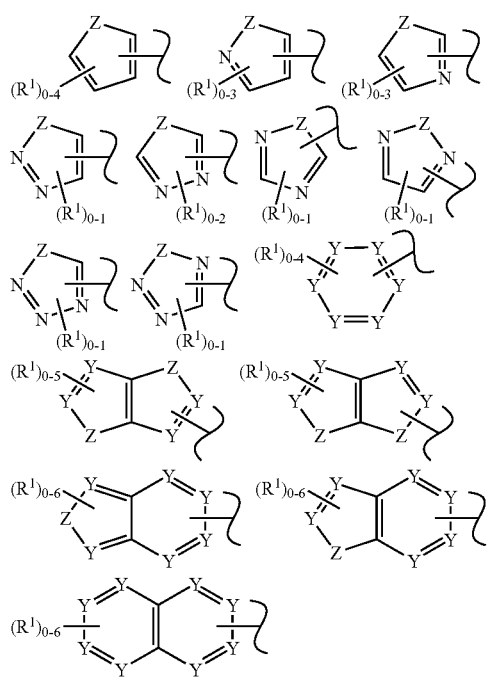

wherein each Y is independently either =C(H)— or =N—; and Z is selected from —O—, —S(O)$_{0-2}$—, and —N($R^7$)—, hereinafter referred to as embodiment [0025].

In another example, the compound is according to embodiment [0025], wherein ring B is phenylene or pyridylene, hereinafter referred to as embodiment [0026].

In another example, the compound is according to embodiment [0026], wherein the annular atoms of ring B to which $L^1$ and $L^2$ are attached are not contiguous, hereinafter referred to as embodiment [0027].

In another example, the compound is according to embodiment [0027], wherein $L^2$ is selected from —X(CH$_2$)$_2$O—, —X(CH$_2$)$_2$N($R^7$)—, —CH$_2$XC(=O)N($R^7$)—, —XCH$_2$SO$_2$N($R^7$)—, —XN($R^7$)C(=O)N($R^7$)— and —XCH$_2$C(=O)N($R^7$)—; wherein X is selected from —CH$_2$—, —O—, —S(O)$_{0-2}$— and —N($R^7$)—; and any C—H of $L^2$ is optionally C—$R^{20}$, hereinafter referred to as embodiment [0028]

In another example, the compound is according to embodiment [0028], wherein $L^2$ is selected from —N(H)N(H)C(=O)N(H)—, —CH$_2$N(H)C(=O)N(H)—, —CH$_2$C(=O)N(H)—, and —XCH$_2$C(=O)N(H)—; wherein X is selected from —O—, —S(O)$_{0-2}$—, and —N($R^7$)—; and any C—H of $L^2$ is optionally C—$R^{20}$, hereinafter referred to as embodiment [0029].

In another example, the compound is according to embodiment [0029], wherein ring A is selected from the following:

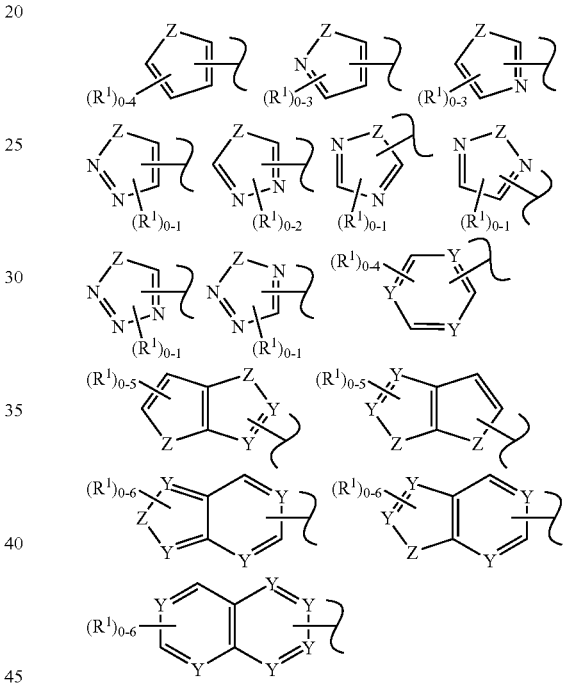

wherein each Y is independently either =C(H)— or =N—; and Z is selected from —O—, —S—, and —N($R^7$)—, hereinafter referred to as embodiment [0030]

In another example, the compound is according to embodiment [0030], wherein ring C is phenyl or pyridyl, hereinafter referred to as embodiment [0031].

In another example, the compound is according to embodiment[0031], wherein there exists at least one of $R^3$ that is halogen, hereinafter referred to as embodiment [0032].

In another example, the compound is according to embodiment [0031], wherein there exists at least one of $R^3$ that is trihalomethyl, hereinafter referred to as embodiment [0033].

In another example, the compound is according to embodiment [0031], wherein there exists at least one of $R^3$ that is trifluoromethyl, hereinafter referred to as embodiment [0034].

In another example, the compound is according to embodiment [0034], wherein ring C is a phenyl comprising a trifluoromethyl radical meta- to $L^2$, hereinafter referred to as embodiment [0035].

In another example, the compound is according to embodiment [0031], wherein each of $R^3$ is independently selected from —H, halogen, trihalomethyl, —$OR^4$, —$CO_2R^4$, —C(=O)$R^4$, and optionally substituted $C_{1-6}$alkyl, hereinafter referred to as embodiment [0036].

In another example, present invention comprises a compound for modulating c-Kit activity according to Formula II (hereinafter referred to as embodiment [0037])

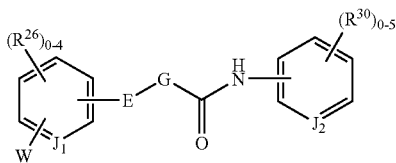

or a pharmaceutically acceptable salt, hydrate, or prodrug thereof, wherein,
W is selected from the following:

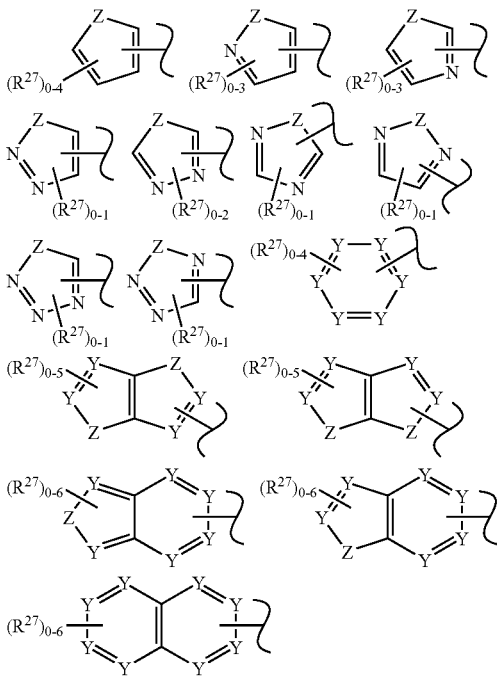

each of $R^{27}$ independently selected from halogen, trihalomethyl, —CN, —$NO_2$, —$OR^{55}$, —N($R^{55}$)$R^{55}$, —S(O)$_{0-2}R^{55}$, —$SO_2$N($R^{55}$)$R^{55}$, —$CO_2R^{55}$, —C(=O)N($R^{55}$)$R^{55}$, —C(=$NR^{50}$)N($R^{55}$)$R^{55}$, —C(=$NR^{50}$)$R^{55}$, —N($R^{55}$)$SO_2R^{55}$, —N($R^{55}$)C(O)$R^{55}$, —$NCO_2R^{55}$, —C(=O)$R^{55}$, optionally substituted alkoxy, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;
each Y is independently either =C(H)— or =N—;
Z is selected from —O—, —S(O)$_{0-2}$—, and —N($R^7$)—
E and G are each independently selected from —O—, —S(O)$_{0-2}$—, —C($R^{31}$)$R^{32}$—, and —N($R^{33}$)—;
$J_1$ and $J_2$ are each independently =C(H)— or =N—;
each of $R^{26}$ and $R^{30}$ is independently selected from —H, halogen, trihalomethyl, —CN, —$NO_2$, —$OR^{40}$, —N($R^{40}$)$R^{40}$, —S(O)$_{0-2}R^{40}$, —$SO_2$N($R^{40}$)$R^{40}$, —$CO_2R^{40}$, —C(=O)N($R^{40}$)$R^{40}$, —C(=$NR^{50}$)N($R^{40}$)$R^{40}$, —C(=$NR^{50}$)$R^{40}$, —N($R^{40}$)$SO_2R^{40}$, —N($R^{40}$)C(O)$R^{40}$, —$NCO_2R^{40}$, —C(=O)$R^{40}$, optionally substituted alkoxy, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;
two adjacent of $R^{26}$ or two adjacent of $R^{30}$, together with the annular atoms to which they are attached, can form a five- to six-membered ring containing up to two heteroatoms and optionally substituted with up to three of $R^{35}$;
$R^{31}$ and $R^{32}$ are each independently selected from —H, halogen, trihalomethyl, —CN, —$NO_2$, —$OR^{40}$, —N($R^{40}$)$R^{40}$, —S(O)$_{0-2}R^{40}$, —$SO_2$N($R^{40}$)$R^{40}$, —$CO_2R^{40}$, —C(=O)N($R^{40}$)$R^{40}$, —C(=$NR^{50}$)N($R^{40}$)$R^{40}$, —C(=$NR^{50}$)$R^{40}$, —N($R^{40}$)$SO_2R^{40}$, —N($R^{40}$)C(O)$R^{40}$, —$NCO_2R^{40}$, —C(=O)$R^{40}$, optionally substituted alkoxy, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;
$R^{33}$ is selected from —H, optionally substituted lower alkyl, —$SO_2$N($R^{40}$)$R^{40}$, —$CO_2R^{40}$, —C(=O)N($R^{40}$)$R^{40}$, —C(=$NR^{50}$)N($R^{40}$)$R^{40}$, —C(=$NR^{50}$)$R^{40}$, —C(O)$R^{40}$, optionally substituted alkoxy, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;
$R^{40}$ is selected from —H, optionally substituted alkoxy, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;
two of $R^{40}$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;
$R^{50}$ is selected from —H, —CN, —$NO_2$, —$OR^{40}$, —S(O)$_{0-2}R^{40}$, —$CO_2R^{40}$, optionally substituted $C_{1-6}$alkyl, optionally substituted $C_{1-6}$alkenyl, and optionally substituted $C_{1-6}$alkynyl;
$R^{55}$ is selected from —H, optionally substituted $C_{1-6}$alkyl, optionally substituted heterocyclyl, and optionally substituted heterocyclyl $C_{1-6}$alkyl; and
two of $R^{55}$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P.

In another example, the compound is according to embodiment [0037], wherein the annular carbons of ring B to which W and B are attached are not contiguous, hereinafter referred to as embodiment [0038].

In another example, the compound is according to embodiment [0038], wherein $R^{30}$ is selected from —H, halogen, trihalomethyl, —$OR^{40}$, —N($R^{40}$)$R^{40}$, —$CO_2R^{40}$, —C(=O)$R^{40}$, optionally substituted alkoxy, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl, hereinafter referred to as embodiment [0039].

In another example, the compound is according to embodiment [0039], wherein there exists at least one of $R^{30}$ that is trihalomethyl, hereinafter referred to as embodiment [0040].

In another example, the compound is according to embodiment [0039], wherein there exists at least one of $R^{30}$ that is trifluoromethyl, hereinafter referred to as embodiment [0041].

In another example, the compound is according to embodiment [0039], according to formula III (hereinafter referred to as embodiment [0042]).

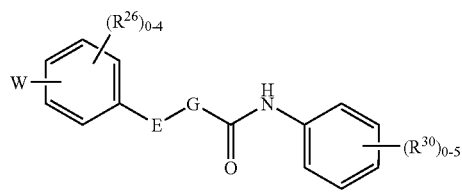

III

In another example, the compound is according to embodiment [0042], wherein W is selected from the following:

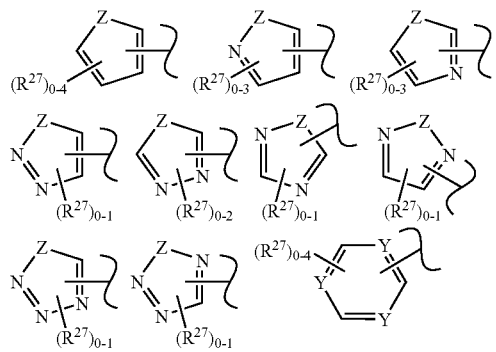

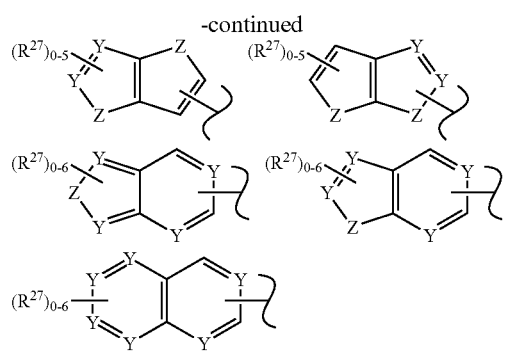

and $R^{27}$ is defined as above, hereinafter referred to as embodiment [0043].

In another example, the compound is according to embodiment [0043], wherein E is selected from —O—, —S(O)$_{0-2}$—, and —NH—; and G is —CH$_2$—, hereinafter referred to as embodiment [0044].

In another example, the compound is according to embodiment [0043], wherein E is either —CH$_2$— or —NH—; and G is selected from —O—, —S—, and —NH—, hereinafter referred to as embodiment [0045].

In another example, the compound is according to either of embodiments [0044] or [0045], wherein each of $R^3$ is independently selected from —H, halogen, trihalomethyl, —OR$^4$, —CO$_2$R$^4$, —C(=O)R$^4$, and optionally substituted C$_{1-6}$alkyl, hereinafter referred to as embodiment [0046].

In another example, the compound is according to embodiment [0046], wherein at least one of $R^{30}$ is a trifluoromethyl radical meta- to -E-G-C(=O)N(H)—, hereinafter referred to as embodiment [0047].

In another example, the compound is according to either embodiment [0022] or embodiment [0037], selected from Table 1 (hereinafter referred to as embodiment [0048]):

TABLE 1

| Entry | Name | Structure |
|---|---|---|
| 1 | N-[5-chloro-2-(methyloxy)phenyl]-2-{3-(1H-tetrazol-1-yl)phenyl]oxy}acetamide | 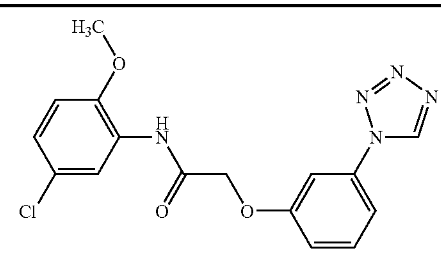 |
| 2 | N-phenyl-2-{[3-(1H-tetrazol-1-yl)phenyl]oxy}acetamide | 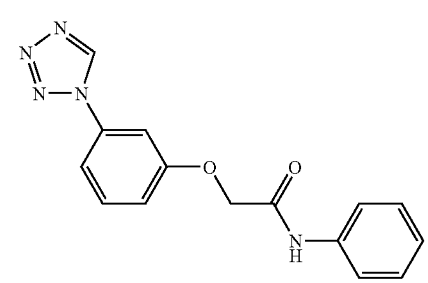 [SMILES: O=C(COc1cccc(-n2cnnn2)c1)Nc1ccccc1] |

TABLE 1-continued

| Entry | Name | Structure |
|---|---|---|
| 3 | N-(2-methylphenyl)-2-{[3-(1H-tetrazol-1-yl)phenyl]oxy}acetamide | 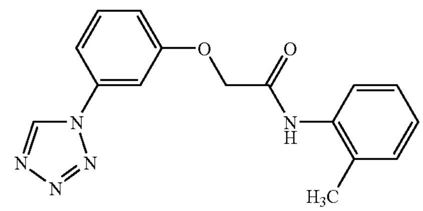 [SMILES: Cc1ccccc1NC(=O)COc1cccc(-n2cnnn2)c1] |
| 4 | N-(2-chlorophenyl)-2-{[3-(1H-tetrazol-1-yl)phenyl]oxy}acetamide | 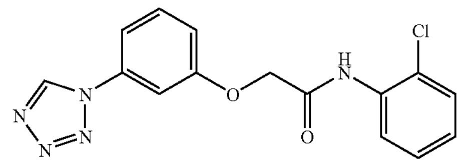 [SMILES: O=C(COc1cccc(-n2cnnn2)c1)Nc1ccccc1Cl] |
| 5 | N-[4-chloro-3-(trifluoromethyl)phenyl]-2-{[3-(1H-tetrazol-1-yl)phenyl]oxy}acetamide | 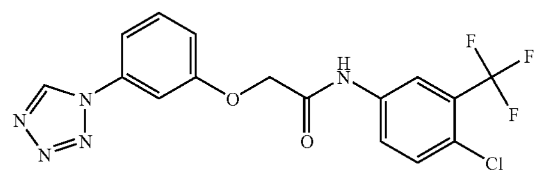 [SMILES: O=C(COc1cccc(-n2cnnn2)c1)Nc1ccc(Cl)c(C(F)(F)F)c1] |
| 6 | ethyl 2-[({[3-(1H-tetrazol-1-yl)phenyl]oxy}acetyl)amino]-4,5,6,7-tetrahydro-1-benzothiophene-3-carboxylate | 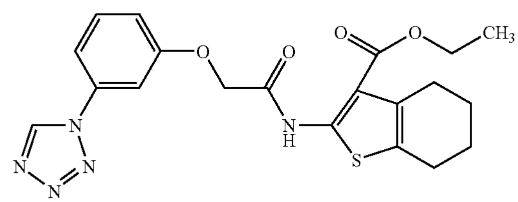 [SMILES: CCOC(=O)c1c(NC(=O)COc2cccc(-n3cnnn3)c2)sc2c1CCCC2] |
| 7 | N-(3-chloro-2-methylphenyl)-2-{[3-(1H-tetrazol-1-yl)phenyl]oxy}acetamide | 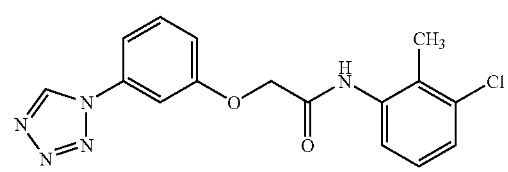 [SMILES: Cc1c(Cl)cccc1NC(=O)COc1cccc(-n2cnnn2)c1] |
| 8 | N-(3-fluorophenyl)-2-{[3-(1H-tetrazol-1-yl)phenyl]oxy}acetamide | 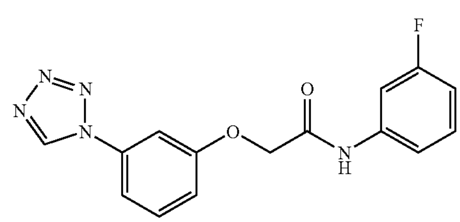 [SMILES: O=C(COc1cccc(-n2cnnn2)c1)Nc1cccc(F)c1] |
| 9 | N-[4-chloro-3-(trifluoromethyl)phenyl]-2-{[3-(2H-tetrazol-5-yl)phenyl]oxy}acetamide | 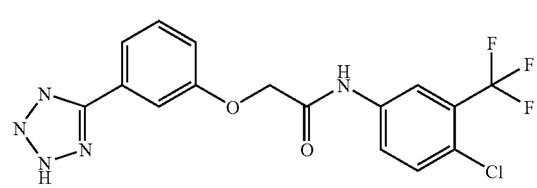 [SMILES: O=C(COc1cccc(C2=NNNN2)c1)Nc1ccc(Cl)c(C(F)(F)F)c1] |
| 10 | N-(4-chloro-2-fluorophenyl)-2-{[3-(1H-tetrazol-1-yl)phenyl]oxy}acetamide | 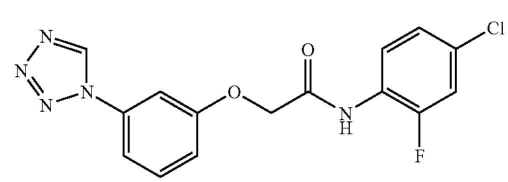 [SMILES: O=C(COc1cccc(-n2cnnn2)c1)Nc1ccc(Cl)cc1F] |

TABLE 1-continued

| Entry | Name | Structure |
|---|---|---|
| 11 | N-(4-bromo-3-methylphenyl)-2-{[3-(1H-tetrazol-1-yl)phenyl]oxy}acetamide | 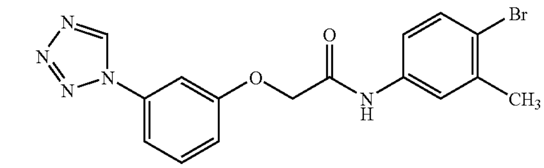 [SMILES: Cc1cc(NC(=O)COc2cccc(-n3cnnn3)c2)ccc1Br] |
| 12 | N-(4-morpholin-4-ylphenyl)-2-{[3-(1H-tetrazol-1-yl)phenyl]oxy}acetamide | 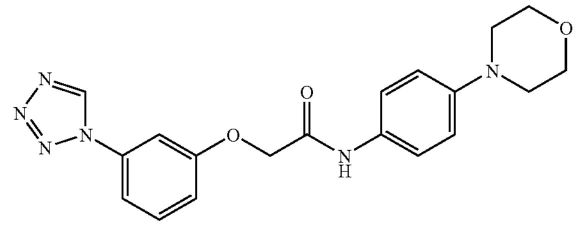 [SMILES: O=C(COc1cccc(-n2cnnn2)c1)Nc1ccc(N2CCOCC2)cc1] |
| 13 | N-[4-fluoro-3-(trifluoromethyl)phenyl]-2-{[3-(1H-tetrazol-1-yl)phenyl]oxy}acetamide | 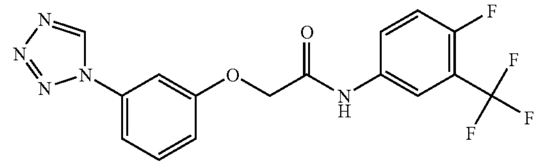 [SMILES: O=C(COc1cccc(-n2cnnn2)c1)Nc1ccc(F)c(C(F)(F)F)c1] |
| 14 | N-[4-bromo-3-(trifluoromethyl)phenyl]-2-{[3-(1H-tetrazol-1-yl)phenyl]oxy}acetamide | 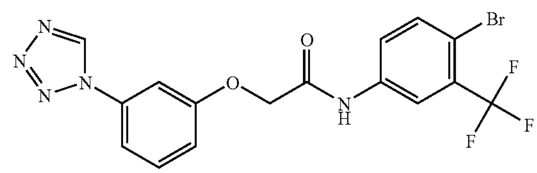 |
| 15 | N-[4-chloro-3-(trifluoromethyl)phenyl]-2-{[4-(1H-tetrazol-1-yl)phenyl]oxy}acetamide | 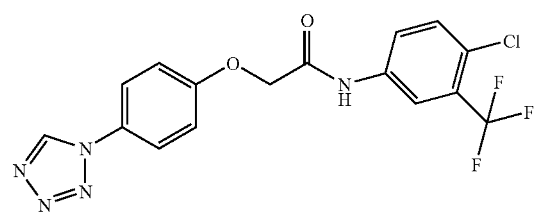 [SMILES: O=C(COc1ccc(-n2cnnn2)cc1)Nc1ccc(Cl)c(C(F)(F)F)c1] |
| 16 | N-[4-chloro-3-(trifluoromethyl)phenyl]-2-{[3-(1H-tetrazol-1-yl)phenyl]oxy}propanamide | 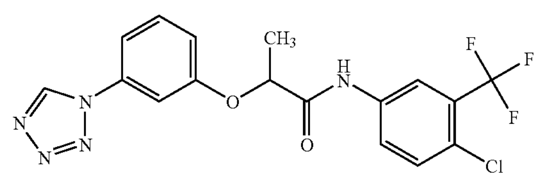 [SMILES: CC(Oc1cccc(-n2cnnn2)c1)C(=O)Nc1ccc(Cl)c(C(F)(F)F)c1] |
| 17 | N-[4-chloro-3-(trifluoromethyl)phenyl]-2-{[3-(5-methyl-1H-tetrazol-1-yl)phenyl]oxy}acetamide | 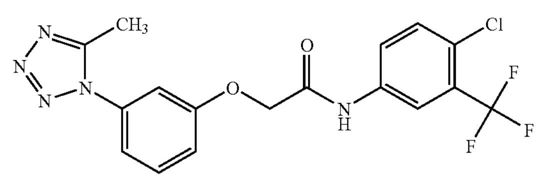 [SMILES: Cc1nnnn1-c1cccc(OCC(=O)Nc2ccc(Cl)c(C(F)(F)F)c2)c1] |
| 18 | N-[4-chloro-3-(trifluoromethyl)phenyl]-2-{[2-methyl-5-(1H-tetrazol-1-yl)phenyl]oxy}acetamide | 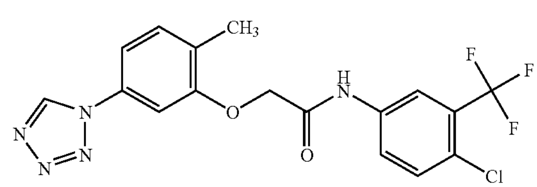 [SMILES: Cc1ccc(-n2cnnn2)cc1OCC(=O)Nc1ccc(Cl)c(C(F)(F)F)c1] |

TABLE 1-continued

| Entry | Name | Structure |
|---|---|---|
| 19 | N-(4-chlorophenyl)-N-methyl-2-{[3-(1H-tetrazol-1-yl)phenyl]oxy}acetamide | 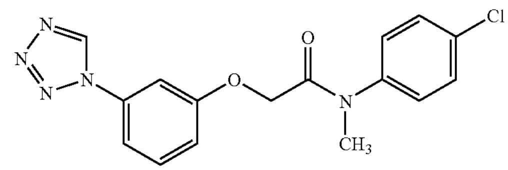 [SMILES: CN(C(=O)COc1cccc(-n2cnnn2)c1)c1ccc(Cl)cc1] |
| 20 | N-[4-chloro-2-(trifluoromethyl)phenyl]-2-{[3-(1H-tetrazol-1-yl)phenyl]oxy}acetamide | 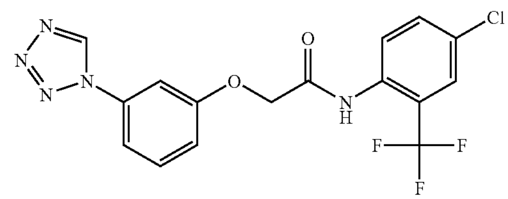 [SMILES: O=C(COc1cccc(-n2cnnn2)c1)Nc1ccc(Cl)cc1C(F)(F)F] |
| 21 | N-[4-chloro-3-(trifluoromethyl)phenyl]-2-{[3-(2,5-dioxopyrrolidin-1-yl)phenyl]oxy}acetamide | 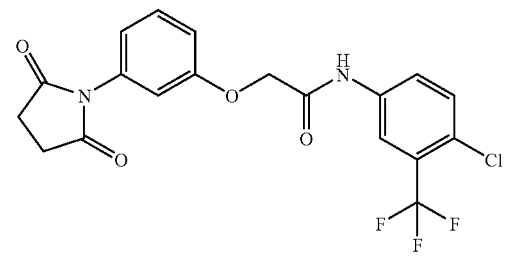 [SMILES: O=C(COc1cccc(N2C(=O)CCC2=O)c1)Nc1ccc(Cl)c(C(F)(F)F)c1] |
| 22 | (2E)-N-[4-chloro-3-(trifluoromethyl)phenyl]-3-[3-(1H-tetrazol-1-yl)phenyl]prop-2-enamide | 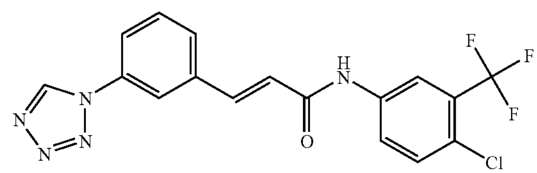 |
| 23 | N-[4-fluoro-3-(trifluoromethyl)phenyl]-2-{[4-(1H-tetrazol-1-yl)phenyl]oxy}acetamide | 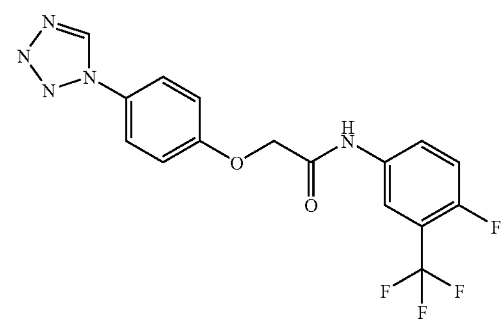 [SMILES: O=C(COc1ccc(N2C=NNN2)cc1)Nc1ccc(F)c(C(F)(F)F)c1] |
| 24 | N-[4-chloro-3-(trifluoromethyl)phenyl]-2-{[3-(2-methyl-2H-tetrazol-5-yl)phenyl]oxy}acetamide | 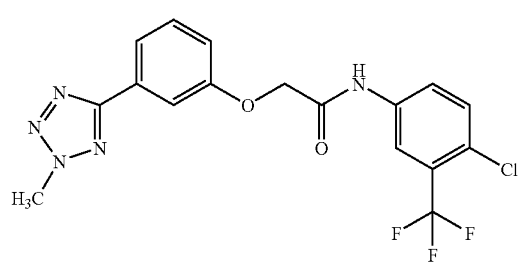 [SMILES: Cn1nnc(-c2cccc(OCC(=O)Nc3ccc(Cl)c(C(F)(F)F)c3)c2)n1] |

TABLE 1-continued

| Entry | Name | Structure |
|---|---|---|
| 25 | N-[4-chloro-3-(trifluoromethyl)phenyl]-2-{[2,4-dichloro-5-(1H-tetrazol-1-yl)phenyl]oxy}acetamide | 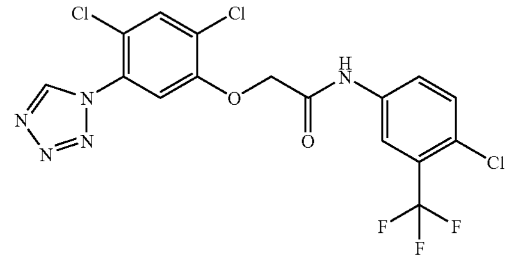 [SMILES: O=C(COc1cc(-n2cnnn2)c(Cl)cc1Cl)Nc1ccc(Cl)c(C(F)(F)F)c1] |
| 26 | N-[4-chloro-3-(trifluoromethyl)phenyl]-2-{[3-(1H-tetrazol-1-yl)phenyl]thio}acetamide | 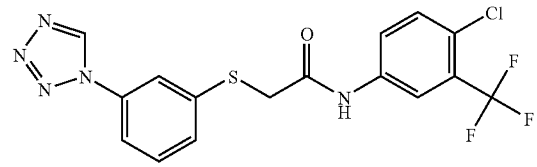 |
| 27 | N-[4-chloro-3-(trifluoromethyl)phenyl]-N~2~-[3-(1H-tetrazol-1-yl)phenyl]glycinamide | 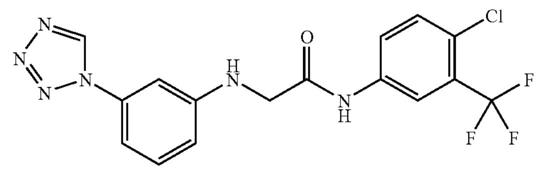 [SMILES: O=C(CNc1cccc(-n2cnnn2)c1)Nc1ccc(Cl)c(C(F)(F)F)c1] |
| 28 | N-[4-chloro-3-(trifluoromethyl)phenyl]-2-{[2-(1H-tetrazol-1-yl)phenyl]oxy}acetamide | 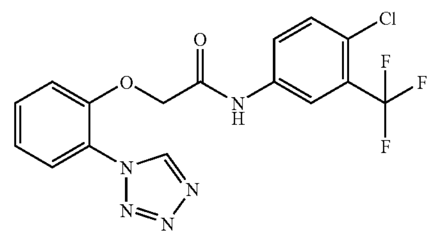 [SMILES: O=C(COc1ccccc1-n1cnnn1)Nc1ccc(Cl)c(C(F)(F)F)c1] |
| 29 | methyl 1-{3-[(2-{[4-chloro-3-(trifluoromethyl)phenyl]amino}-2-oxoethyl)oxy]phenyl}-1H-1,2,3-triazole-4-carboxylate | 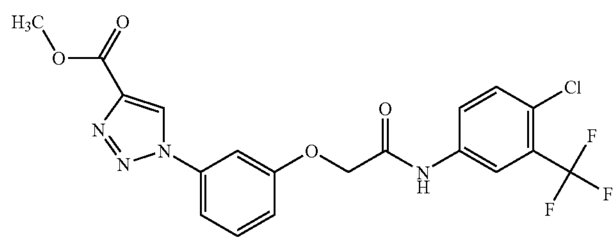 [SMILES: COC(=O)c1cn(-c2cccc(OCC(=O)Nc3ccc(Cl)c(C(F)(F)F)c3)c2)nn1] |
| 30 | 1,1-dimethylethyl {4-[({[3-(1H-tetrazol-1-yl)phenyl]oxy}acetyl)amino]phenyl}carbamate | 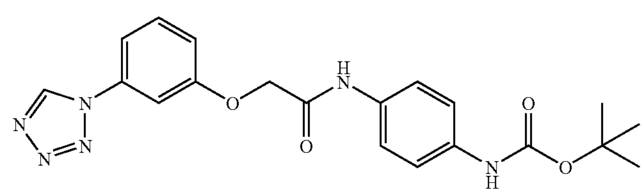 [SMILES: CC(C)(C)OC(=O)Nc1ccc(NC(=O)COc2cccc(-n3cnnn3)c2)cc1] |
| 31 | 1,1-dimethylethyl {4-[({[4-(1H-tetrazol-1-yl)phenyl]oxy}acetyl)amino]phenyl}carbamate | 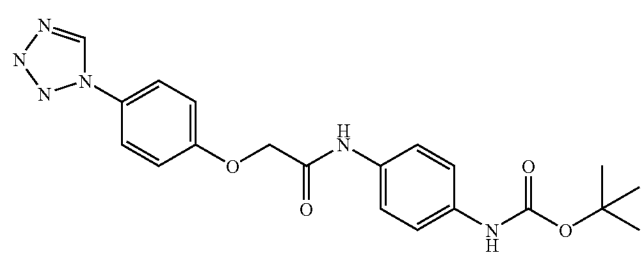 [SMILES: CC(C)(C)OC(=O)Nc1ccc(NC(=O)COc2ccc(N3C=NNN3)cc2)cc1] |

TABLE 1-continued

| Entry | Name | Structure |
|---|---|---|
| 32 | N-{4-[(1-ethylpiperidin-4-yl)amino]phenyl}-2-{3-(1H-tetrazol-1-yl)phenyl]oxy}acetamide | 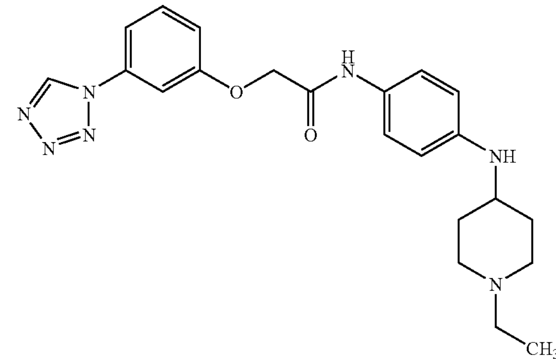 [SMILES: CCN1CCC(Nc2ccc(NC(=O)COc3cccc(-n4cnnn4)c3)cc2)CC1] |
| 33 | N-{4-[(1-ethylpiperidin-3-yl)amino]phenyl}-2-{[3-(1H-tetrazol-1-yl)phenyl]oxy}acetamide | 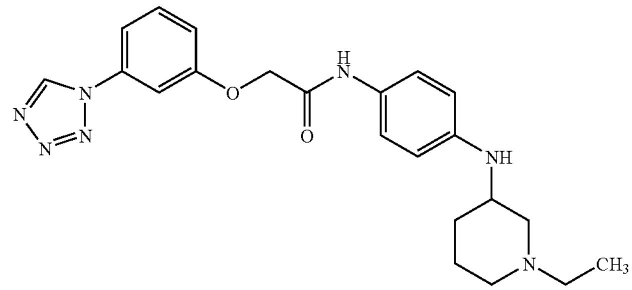 [SMILES: CCN1CCCC(Nc2ccc(NC(=O)COc3cccc(-n4cnnn4)c3)cc2)C1] |
| 34 | N-(4-aminophenyl)-2-{[4-(1H-tetrazol-1-yl)phenyl]oxy}acetamide | 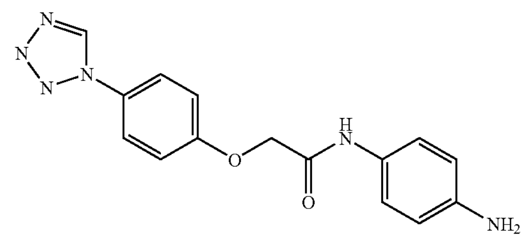 [SMILES: Nc1ccc(NC(=O)COc2ccc(N3C=NNN3)cc2)cc1] |
| 35 | N-{4-[(1-ethylpiperidin-4-yl)amino]phenyl}-2-{[4-(1H-tetrazol-1-yl)phenyl]oxy}acetamide | 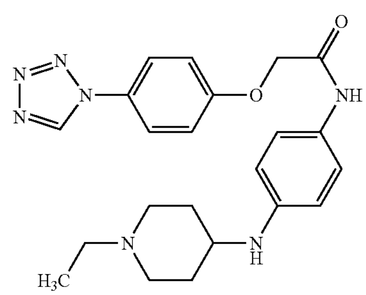 [SMILES: CCN1CCC(Nc2ccc(NC(=O)COc3ccc(-n4cnnn4)cc3)cc2)CC1] |
| 36 | N-{4-[(1-ethylpiperidin-3-yl)amino]phenyl}-2-{[4-(1H-tetrazol-1-yl)phenyl]oxy}acetamide | 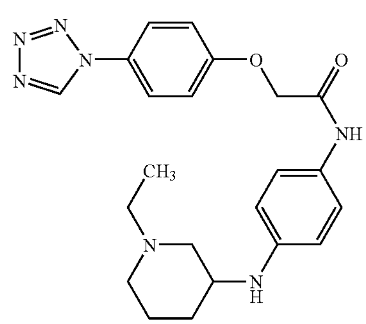 [SMILES: CCN1CCCC(Nc2ccc(NC(=O)COc3ccc(-n4cnnn4)cc3)cc2)C1] |

TABLE 1-continued

| Entry | Name | Structure |
|---|---|---|
| 37 | N-[4-chloro-3-(trifluoromethyl)phenyl]-2-[(3-pyridin-4-ylphenyl)oxy]acetamide | 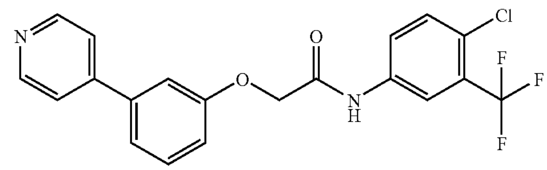 [SMILES: O=C(COc1cccc(-c2ccncc2)c1)Nc1ccc(Cl)c(C(F)(F)F)c1] |
| 38 | N-[4-chloro-3-(trifluoromethyl)phenyl]-N~2~-methyl-N~2~-[3-(1H-tetrazol-1-yl)phenyl]glycinamide | 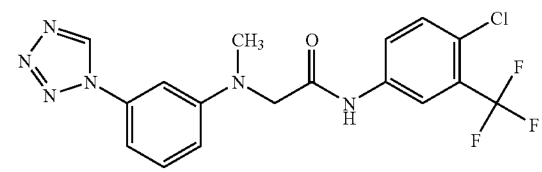 [SMILES: CN(CC(=O)Nc1ccc(Cl)c(C(F)(F)F)c1)c1cccc(-n2cnnn2)c1] |
| 39 | N-1,3-benzothiazol-2-yl-2-{[3-(1H-tetrazol-1-yl)phenyl]oxy}acetamide | 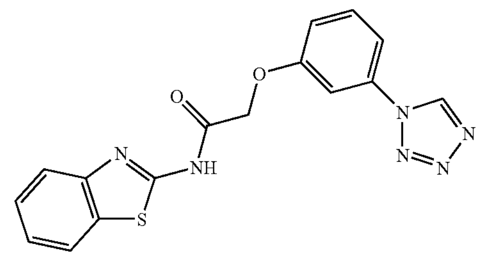 [SMILES: O=C(COc1cccc(-n2cnnn2)c1)Nc1nc2ccccc2s1] |
| 40 | N-quinolin-8-yl-2-{[3-(1H-tetrazol-1-yl)phenyl]oxy}acetamide | 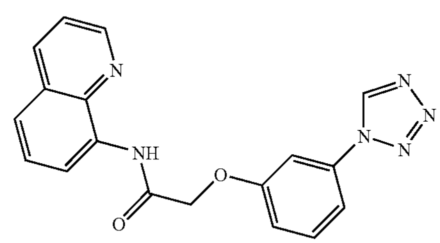 [SMILES: O=C(COc1cccc(-n2cnnn2)c1)Nc1cccc2cccnc12] |
| 41 | N-(2,3-dihydro-1,4-benzodioxin-6-yl)-2-{[3-(1H-tetrazol-1-yl)phenyl]oxy}acetamide | 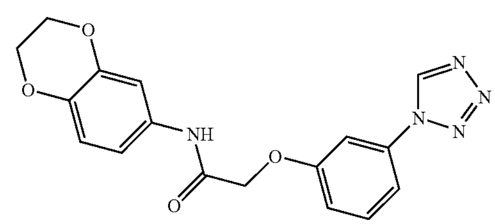 [SMILES: O=C(COc1cccc(-n2cnnn2)c1)Nc1ccc2c(c1)OCCO2] |
| 42 | N-isoquinolin-5-yl-2-{[3-(1H-tetrazol-1-yl)phenyl]oxy}acetamide | 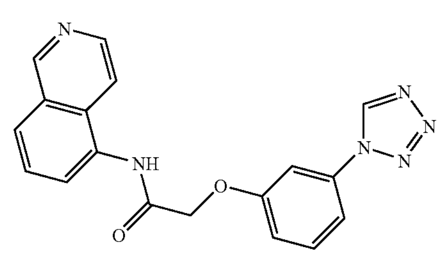 [SMILES: O=C(COc1cccc(-n2cnnn2)c1)Nc1cccc2cnccc12] |

TABLE 1-continued

| Entry | Name | Structure |
|---|---|---|
| 43 | N-{3-[(phenylmethyl)oxy]phenyl}-2-{[3-(1H-tetrazol-1-yl)phenyl]oxy}acetamide | 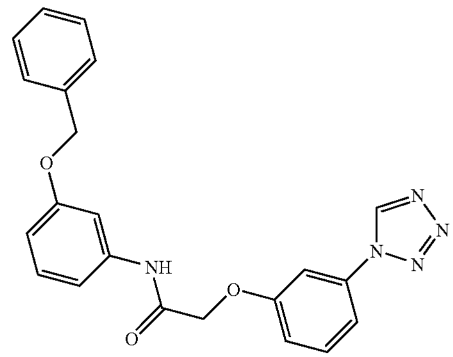 [SMILES: O=C(COc1cccc(-n2cnnn2)c1)Nc1cccc(OCc2ccccc2)c1] |
| 44 | N-[5-methyl-2-(methyloxy)phenyl]-2-{[3-(1H-tetrazol-1-yl)phenyl]oxy}acetamide | 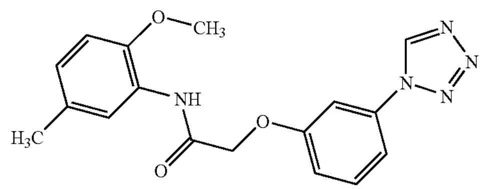 [SMILES: COc1ccc(C)cc1NC(=O)COc1cccc(-n2cnnn2)c1] |
| 45 | N-[2,5-bis(methyloxy)phenyl]-2-{[3-(1H-tetrazol-1-yl)phenyl]oxy}acetamide | 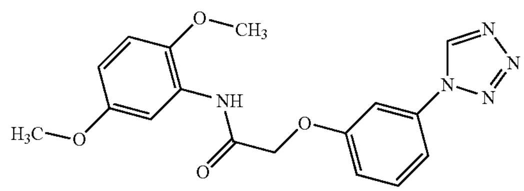 [SMILES: COc1ccc(OC)c(NC(=O)COc2cccc(-n3cnnn3)c2)c1] |
| 46 | N-(6-fluoro-1,3-benzothiazol-2-yl)-2-{[3-(1H-tetrazol-1-yl)phenyl]oxy}acetamide | 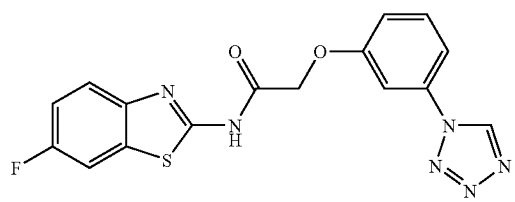 [SMILES: O=C(COc1cccc(-n2cnnn2)c1)Nc1nc2ccc(F)cc2s1] |
| 47 | methyl 3-[({[3-(1H-tetrazol-1-yl)phenyl]oxy}acetyl)amino]benzoate | 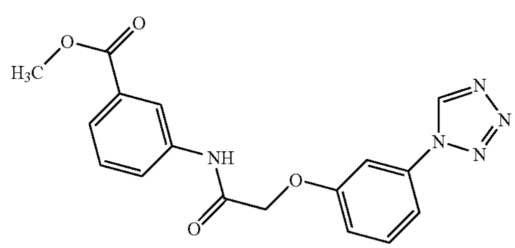 [SMILES: COC(=O)c1cccc(NC(=O)COc2cccc(-n3cnnn3)c2)c1] |
| 48 | 5-chloro-2-[({[3-(1H-tetrazol-1-yl)phenyl]oxy}acetyl)amino]benzamide | 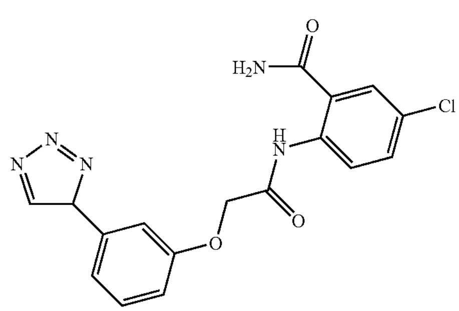 [SMILES: NC(=O)c1cc(Cl)ccc1NC(=O)COc1cccc(C2C=NN=N2)c1] |

TABLE 1-continued

| Entry | Name | Structure |
|---|---|---|
| 49 | N-[5-chloro-2,4-bis(methyloxy)phenyl]-2-{[3-(1H-tetrazol-1-yl)phenyl]oxy}acetamide | 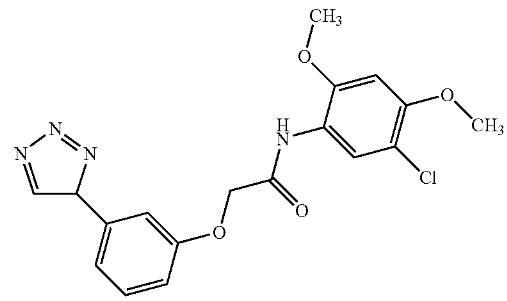 [SMILES: COc1cc(OC)c(NC(=O)COc2cccc(C3C=NN=N3)c2)cc1Cl] |
| 50 | N-[2-(phenyloxy)phenyl]-2-{[3-(1H-tetrazol-1-yl)phenyl]oxy}acetamide | 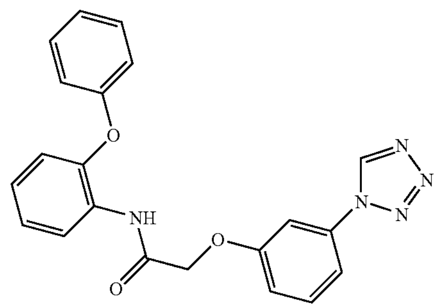 [SMILES: O=C(COc1cccc(-n2cnnn2)c1)Nc1ccccc1Oc1ccccc1] |
| 51 | N-[3-(aminosulfonyl)phenyl]-2-{[3-(1H-tetrazol-1-yl)phenyl]oxy}acetamide | 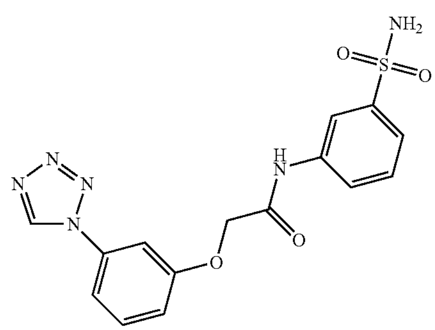 [SMILES: NS(=O)(=O)c1cccc(NC(=O)COc2cccc(-n3cnnn3)c2)c1] |
| 52 | N-[2-(methyloxy)-5-(trifluoromethyl)phenyl]-2-{[3-(1H-tetrazol-1-yl)phenyl]oxy}acetamide | 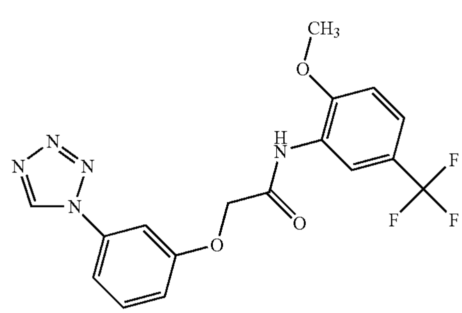 [SMILES: COc1ccc(C(F)(F)F)cc1NC(=O)COc1cccc(-n2cnnn2)c1] |

TABLE 1-continued

| Entry | Name |
|---|---|
| 53 | N-(4-{[(4-methylphenyl)sulfonyl]amino}phenyl)-2-{[3-(1H-tetrazol-1-yl)phenyl]oxy}acetamide |
| 54 | N-(5-phenyl-1H-pyrazol-3-yl)-2-{[3-(1H-tetrazol-1-yl)phenyl]oxy}acetamide |
| 55 | N-1,3-benzothiazol-2-yl-2-{[4-(1H-tetrazol-1-yl)phenyl]oxy}acetamide |
| 56 | N-quinolin-8-yl-2-{[4-(1H-tetrazol-1-yl)phenyl]oxy}acetamide |
| 57 | 1,1-dimethylethyl 2-{3-[(2-{[4-chloro-3-(trifluoromethyl)phenyl]amino}-2-oxoethyl)oxy]phenyl}-1H-pyrrole-1-carboxylate |
| 58 | N-[4-chloro-3-(trifluoromethyl)phenyl]-2-{[3-(1H-pyrrol-2-yl)phenyl]oxy}acetamide |

TABLE 1-continued

| Entry | Name | Structure |
|---|---|---|
| 59 | N-[4-chloro-3-(trifluoromethyl)phenyl]-2-[(3-pyrimidin-5-ylphenyl)oxy]acetamide | 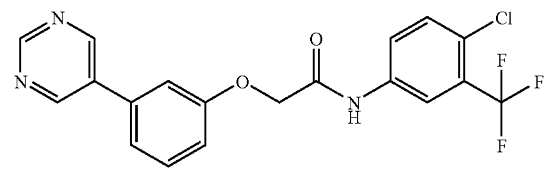 [SMILES: O=C(COc1cccc(-c2cncnc2)c1)Nc1ccc(Cl)c(C(F)(F)F)c1] |
| 60 | N-[4-chloro-3-(trifluoromethyl)phenyl]-2-{[3-(1H-1,2,3-triazol-1-yl)phenyl]oxy}acetamide | 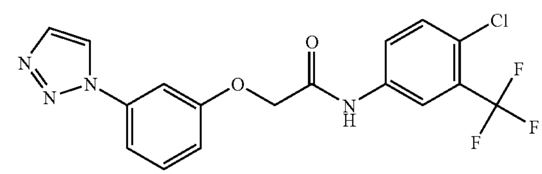 |
| 61 | 4-chloro-N-(2-{[3-(1H-tetrazol-1-yl)phenyl]oxy}ethyl)-3-(trifluoromethyl)aniline | 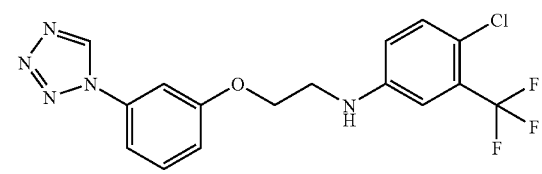 [SMILES: FC(F)(F)c1cc(NCCOc2cccc(-n3cnnn3)c2)ccc1Cl] |
| 62 | N-[4-chloro-3-(trifluoromethyl)phenyl]-N-(2-{[3-(1H-tetrazol-1-yl)phenyl]oxy}ethyl)formamide | 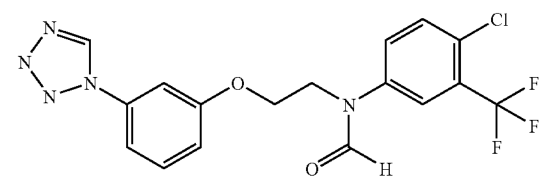 [SMILES: O=CN(CCOc1cccc(N2C=NNN2)c1)c1ccc(Cl)c(C(F)(F)F)c1] |
| 63 | N-[4-chloro-3-(trifluoromethyl)phenyl]-2-[(3-pyridin-3-ylphenyl)oxy]acetamide | 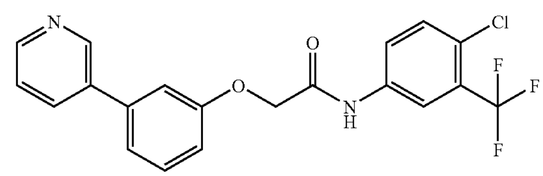 [SMILES: O=C(COc1cccc(-c2cccnc2)c1)Nc1ccc(Cl)c(C(F)(F)F)c1] |
| 64 | N-[4-chloro-3-(trifluoromethyl)phenyl]-2-[(3-furan-3-ylphenyl)oxy]acetamide | 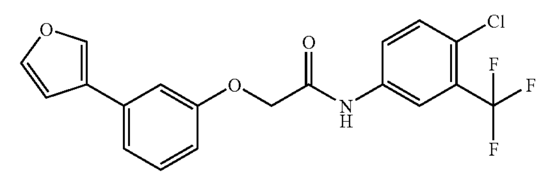 [SMILES: O=C(COc1cccc(-c2ccoc2)c1)Nc1ccc(Cl)c(C(F)(F)F)c1] |
| 65 | (2E)-N-[4-fluoro-3-(trifluoromethyl)phenyl]-3-[3-(1H-tetrazol-1-yl)phenyl]prop-2-enamide | 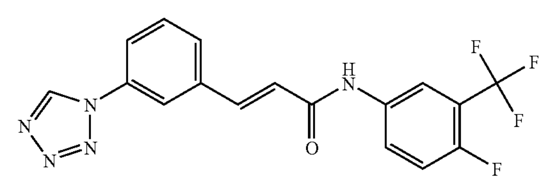 [SMILES: O=C(/C=C/c1cccc(-n2cnnn2)c1)Nc1ccc(F)c(C(F)(F)F)c1] |
| 66 | N-[4-fluoro-3-(trifluoromethyl)phenyl]-3-[3-(1H-tetrazol-1-yl)phenyl]propanamide | 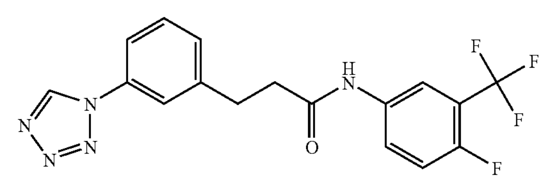 [SMILES: O=C(CCc1cccc(-n2cnnn2)c1)Nc1ccc(F)c(C(F)(F)F)c1] |
| 67 | N-[4-chloro-3-(trifluoromethyl)phenyl]-2-{[6-(1H-tetrazol-1-yl)pyrimidin-4-yl]oxy}acetamide | 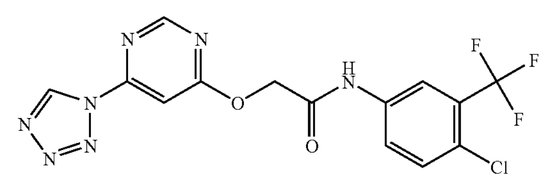 [SMILES: O=C(COc1cc(-n2cnnn2)ncn1)Nc1ccc(Cl)c(C(F)(F)F)c1] |

TABLE 1-continued

| Entry | Name | Structure |
|---|---|---|
| 68 | N-[4-chloro-3-(trifluoromethyl)phenyl]-2-{[3-(3,5-dimethylisoxazol-4-yl)phenyl]oxy}acetamide | 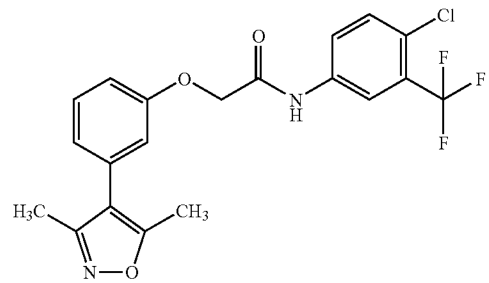 [SMILES: Cc1noc(C)c1-c1cccc(OCC(=O)Nc2ccc(Cl)c(C(F)(F)F)c2)c1] |
| 69 | N-[4-chloro-3-(trifluoromethyl)phenyl]-2-[(3-quinolin-7-ylphenyl)oxy]acetamide | 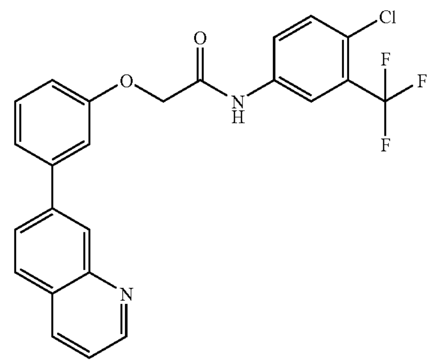 [SMILES: O=C(COc1cccc(-c2ccc3cccnc3c2)c1)Nc1ccc(Cl)c(C(F)(F)F)c1] |
| 70 | N-[4-chloro-3-(trifluoromethyl)phenyl]-2-[(3-furan-2-ylphenyl)oxy]acetamide | 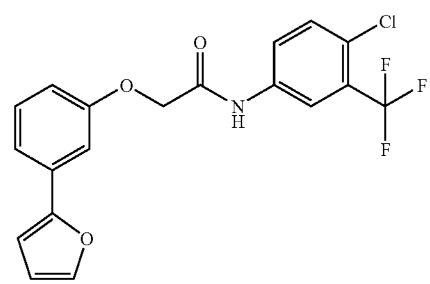 [SMILES: O=C(COc1cccc(-c2ccco2)c1)Nc1ccc(Cl)c(C(F)(F)F)c1] |
| 71 | N-[4-chloro-3-(trifluoromethyl)phenyl]-2-[3-(1H-tetrazol-1-yl)phenyl]hydrazinecarboxamide | 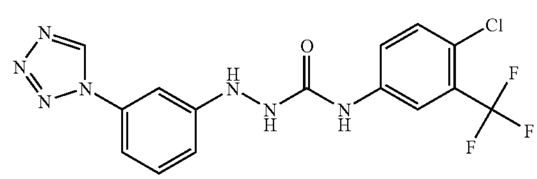 [SMILES: O=C(NNc1cccc(-n2cnnn2)c1)Nc1ccc(Cl)c(C(F)(F)F)c1] |
| 72 | N-[4-chloro-3-(trifluoromethyl)phenyl]-2-[(3-dibenzo[b,d]furan-4-ylphenyl)oxy]acetamide | 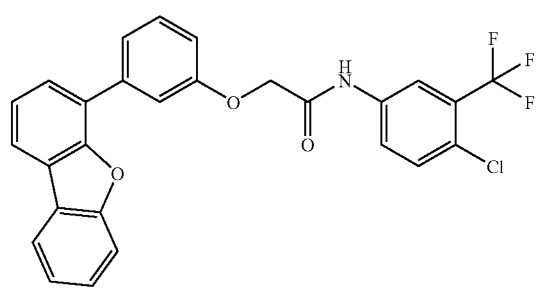 [SMILES: O=C(COc1cccc(-c2cccc3c2oc2ccccc23)c1)Nc1ccc(Cl)c(C(F)(F)F)c1] |

TABLE 1-continued

| Entry | Name |
|---|---|
| 73 | N-[4-chloro-3-(trifluoromethyl)phenyl]-2-[(4-pyrimidin-5-ylphenyl)oxy]acetamide |
| 74 | N-methyl-N-[4-(methyloxy)phenyl]-2-{[3-(1H-tetrazol-1-yl)phenyl]oxy}acetamide |
| 75 | N-[4-chloro-3-(trifluoromethyl)phenyl]-N'-{[3-(1H-tetrazol-1-yl)phenyl]methyl}urea |
| 76 | N-[4-chloro-3-(trifluoromethyl)phenyl]-N-methyl-2-{[3-(1H-tetrazol-1-yl)phenyl]oxy}acetamide |
| 77 | N-[4-fluoro-3-(trifluoromethyl)phenyl]-N~2~-[3-(1H-tetrazol-1-yl)phenyl]glycinamide |
| 78 | N-[4-fluoro-3-(trifluoromethyl)phenyl]-2-{[3-(pyridin-2-ylamino)phenyl]oxy}acetamide |

TABLE 1-continued

| Entry | Name | Structure |
|---|---|---|
| 79 | N-[2-fluoro-5-(trifluoromethyl)phenyl]-2-[3-(1H-tetrazol-1-yl)phenyl]hydrazinecarboxamide | 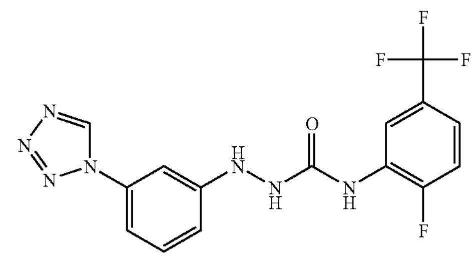 [SMILES: O=C(NNc1cccc(-n2cnnn2)c1)Nc1cc(C(F)(F)F)ccc1F] |
| 80 | N-[4-chloro-3-(trifluoromethyl)phenyl]-2-[(4-pyridin-3-ylphenyl)oxy]acetamide | 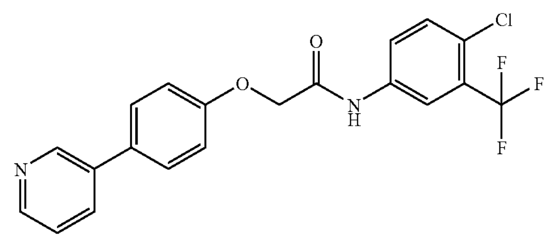 [SMILES: O=C(COc1ccc(-c2cccnc2)cc1)Nc1ccc(Cl)c(C(F)(F)F)c1] |
| 81 | N-[4-chloro-3-(trifluoromethyl)phenyl]-N'-[(3-pyrimidin-5-ylphenyl)methyl]urea | 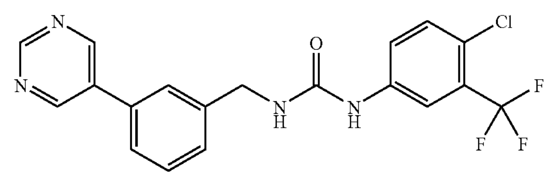 [SMILES: O=C(NCc1cccc(-c2cncnc2)c1)Nc1ccc(Cl)c(C(F)(F)F)c1] |
| 82 | N-[4-chloro-3-(trifluoromethyl)phenyl]-N'-[(4-pyrimidin-5-ylphenyl)methyl]urea | 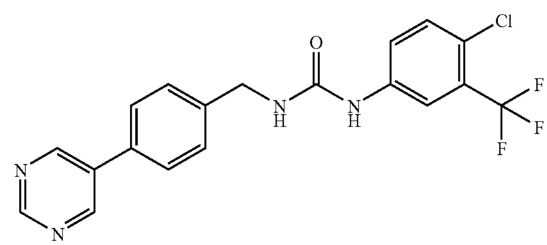 [SMILES: O=C(NCc1ccc(-c2cncnc2)cc1)Nc1ccc(Cl)c(C(F)(F)F)c1] |
| 83 | N-[4-chloro-3-(trifluoromethyl)phenyl]-N'-[(4-pyridin-3-ylphenyl)methyl]urea | 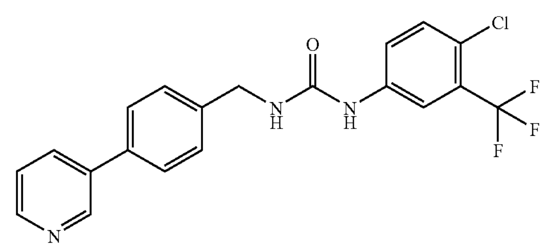 [SMILES: O=C(NCc1ccc(-c2cccnc2)cc1)Nc1ccc(Cl)c(C(F)(F)F)c1] |
| 84 | [3-(1H-tetrazol-1-yl)phenyl]methyl [4-chloro-3-(trifluoromethyl)phenyl]carbamate | 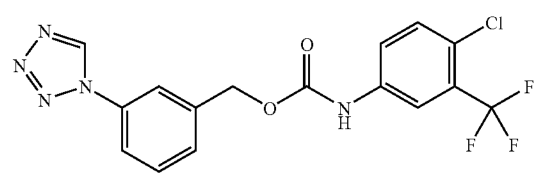 [SMILES: O=C(Nc1ccc(Cl)c(C(F)(F)F)c1)OCc1cccc(-n2cnnn2)c1] |
| 85 | N-[4-fluoro-3-(trifluoromethyl)phenyl]-2-[(4-pyrimidin-5-ylphenyl)oxy]acetamide | 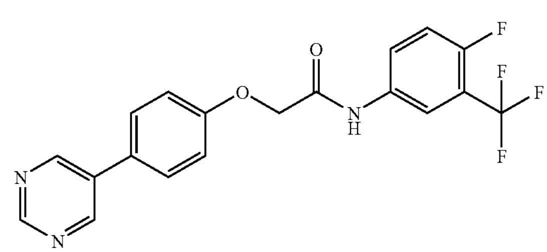 [SMILES: O=C(COc1ccc(-c2cncnc2)cc1)Nc1ccc(F)c(C(F)(F)F)c1] |

TABLE 1-continued

| Entry | Name |
|---|---|
| 86 | N~2~-[4-chloro-3-(trifluoromethyl)phenyl]-N-[3-(1H-tetrazol-1-yl)phenyl]glycinamide |
| 87 | 2-{[4-chloro-3-(trifluoromethyl)phenyl]oxy}-N-[3-(1H-tetrazol-1-yl)phenyl]acetamide |
| 88 | N-[4-chloro-3-(trifluoromethyl)phenyl]-2-{[3-methyl-4-(1H-tetrazol-1-yl)phenyl]oxy}acetamide |
| 89 | N-[4-chloro-3-(trifluoromethyl)phenyl]-2-{[4-(1H-1,2,3-triazol-1-yl)phenyl]oxy}acetamide |
| 90 | N-[4-chloro-3-(trifluoromethyl)phenyl]-2-{[3-fluoro-4-(1H-tetrazol-1-yl)phenyl]oxy}acetamide |
| 91 | N-[4-chloro-3-(trifluoromethyl)phenyl]-2-{[2-fluoro-4-(1H-tetrazol-1-yl)phenyl]oxy}acetamide |
| 92 | N-({[4-chloro-3-(trifluoromethyl)phenyl]amino}carbonyl)-3-(1H-tetrazol-1-yl)benzenesulfonamide |

TABLE 1-continued

| Entry | Name | Structure |
|---|---|---|
| 93 | N-({[4-chloro-3-(trifluoromethyl)phenyl]amino}carbonyl)-N-methyl-3-(1H-tetrazol-1-yl)benzenesulfonamide | 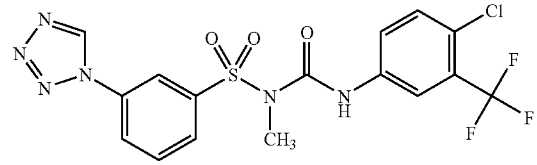 [SMILES: CN(C(=O)Nc1ccc(Cl)c(C(F)(F)F)c1)S(=O)(=O)c1cccc(-n2cnnn2)c1] |
| 94 | N-[4-fluoro-3-(trifluoromethyl)phenyl]-2-[(4-pyridin-3-ylphenyl)oxy]acetamide | 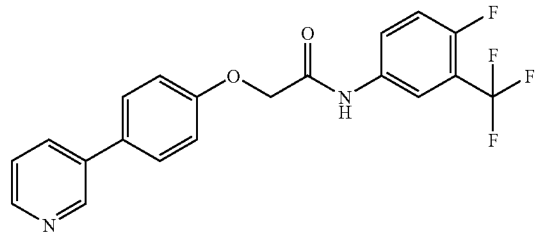 [SMILES: O=C(COc1ccc(-c2cccnc2)cc1)Nc1ccc(F)c(C(F)(F)F)c1] |
| 95 | 2-({4-[2,4-bis(methyloxy)pyrimidin-5-yl]phenyl}oxy)-N-[4-fluoro-3-(trifluoromethyl)phenyl]acetamide | 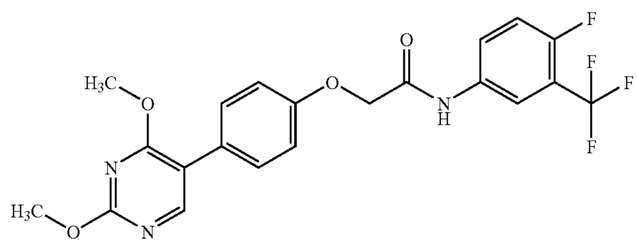 [SMILES: COc1ncc(-c2ccc(OCC(=O)Nc3ccc(Cl)c(C(F)(F)F)c3)cc2)c(OC)n1] |
| 96 | 2-({4-[2,4-bis(methyloxy)pyrimidin-5-yl]phenyl}oxy)-N-[4-chloro-3-(trifluoromethyl)phenyl]acetamide | 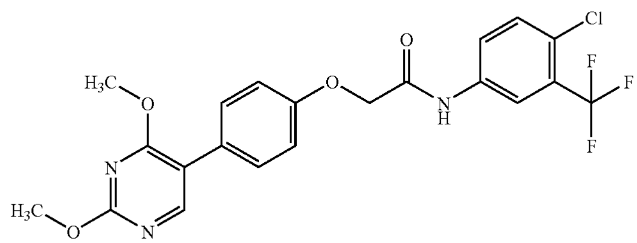 |
| 97 | N-[4-chloro-3-(trifluoromethyl)phenyl]-2-[(4-pyridin-4-ylphenyl)oxy]acetamide | 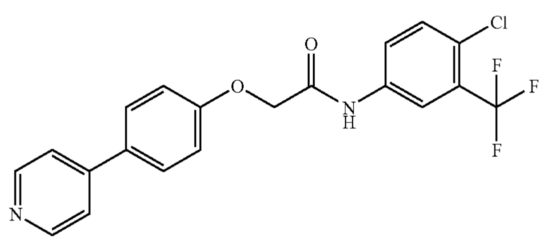 [SMILES: O=C(COc1ccc(-c2ccncc2)cc1)Nc1ccc(Cl)c(C(F)(F)F)c1] |
| 98 | N-[4-chloro-3-(trifluoromethyl)phenyl]-N~2~-[3-(methyloxy)-4-(1H-tetrazol-1-yl)phenyl]glycinamide | 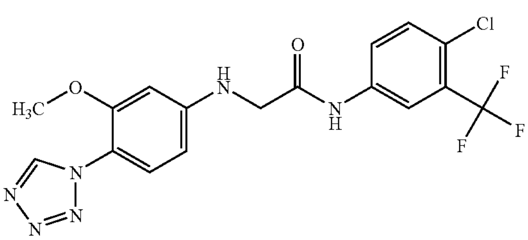 [SMILES: COc1cc(NCC(=O)Nc2ccc(Cl)c(C(F)(F)F)c2)ccc1-n1cnnn1] |

TABLE 1-continued

| Entry | Name | Structure |
|---|---|---|
| 99 | N-[4-chloro-3-(trifluoromethyl)phenyl]-N~2~-[4-(methyloxy)-3-(1H-tetrazol-1-yl)phenyl]glycinamide | 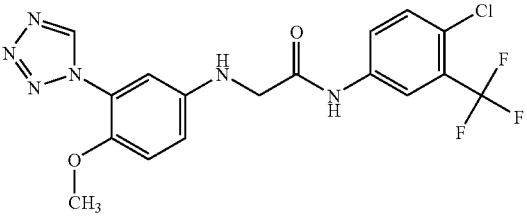 [SMILES: COc1ccc(NCC(=O)Nc2ccc(Cl)c(C(F)(F)F)c2)cc1-n1cnnn1] |
| 100 | N-[4-chloro-3-(trifluoromethyl)phenyl]-N~2~-[4-(1H-tetrazol-1-yl)phenyl]glycinamide | 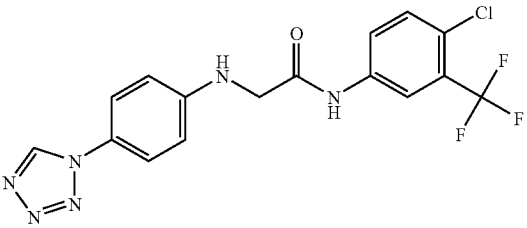 [SMILES: O=C(CNc1ccc(-n2cnnn2)cc1)Nc1ccc(Cl)c(C(F)(F)F)c1] |
| 101 | N-[4-chloro-3-(trifluoromethyl)phenyl]-2-(2,3,5,6-tetrafluoro-4-pyrimidin-5-ylphenyl)hydrazinecarboxamide | 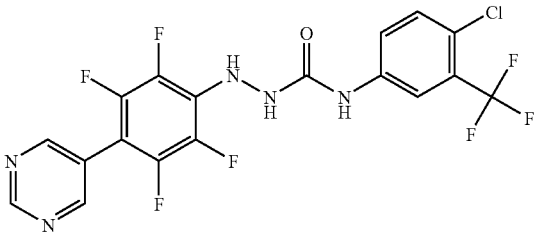 [SMILES: O=C(NNc1c(F)c(F)c(-c2cncnc2)c(F)c1F)Nc1ccc(Cl)c(C(F)(F)F)c1] |
| 102 | N-[4-chloro-3-(trifluoromethyl)phenyl]-N'-{[4-(1H-tetrazol-1-yl)phenyl]methyl}urea | 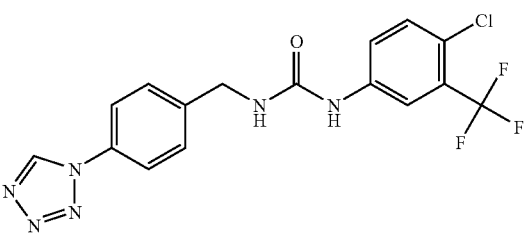 [SMILES: O=C(NCc1ccc(-n2cnnn2)cc1)Nc1ccc(Cl)c(C(F)(F)F)c1] |
| 103 | N-[4-chloro-3-(trifluoromethyl)phenyl]-2-(4-pyrimidin-5-ylphenyl)hydrazinecarboxamide | 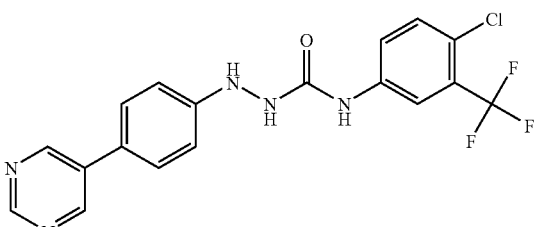 |
| 104 | N-[4-chloro-3-(trifluoromethyl)phenyl]-N'-[(3-pyridin-3-ylphenyl)methyl]urea | 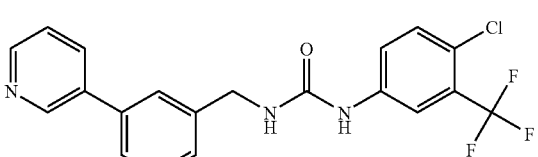 |
| 105 | N-[4-chloro-3-(trifluoromethyl)phenyl]-2-methyl-2-{[3-(1H-tetrazol-1-yl)phenyl]oxy}propanamide | 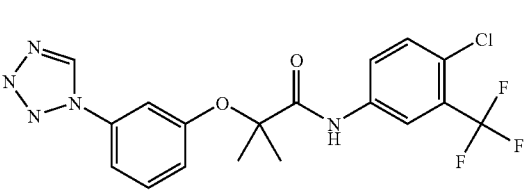 [SMILES: CC(C)(Oc1cccc(N2C=NNN2)c1)C(=O)Nc1ccc(Cl)c(C(F)(F)F)c1] |

TABLE 1-continued

| Entry | Name | Structure |
|---|---|---|
| 106 | N-[4-chloro-3-(trifluoromethyl)phenyl]-2-{[4-(1H-tetrazol-1-yl)phenyl]oxy}propanamide | 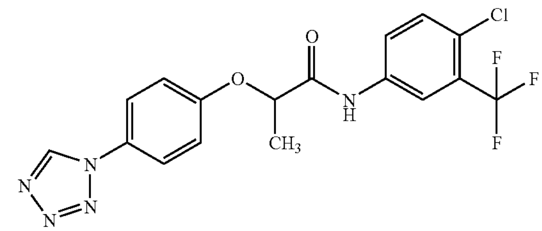 [SMILES: CC(Oc1ccc(-n2cnnn2)cc1)C(=O)Nc1ccc(Cl)c(C(F)(F)F)c1] |
| 107 | N-({4-[2,4-bis(methyloxy)pyrimidin-5-yl]phenyl}methyl)-N'-[4-chloro-3-(trifluoromethyl)phenyl]urea | 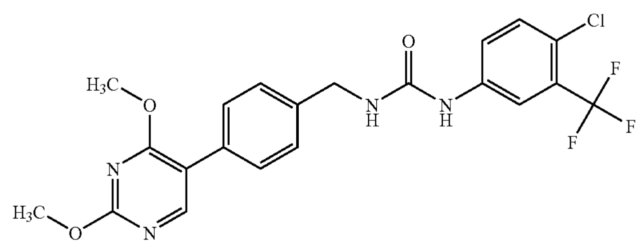 [SMILES: COc1ncc(-c2ccc(CNC(=O)Nc3ccc(Cl)c(C(F)(F)F)c3)cc2)c(OC)n1] |
| 108 | N-[4-chloro-3-(trifluoromethyl)phenyl]-N'-({3-[2-(methyloxy)pyrimidin-5-yl]phenyl}methyl)urea | 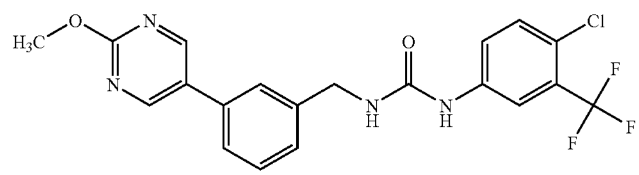 [SMILES: COc1ncc(-c2cccc(CNC(=O)Nc3ccc(Cl)c(C(F)(F)F)c3)c2)cn1] |
| 109 | N-[4-chloro-3-(trifluoromethyl)phenyl]-N'-({3-[6-(methyloxy)pyridin-3-yl]phenyl}methyl)urea | 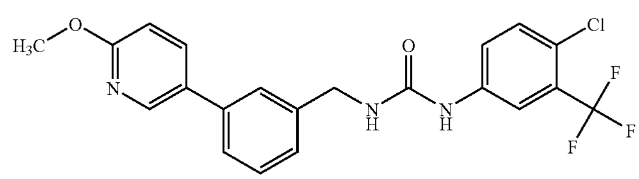 [SMILES: COc1ccc(-c2cccc(CNC(=O)Nc3ccc(Cl)c(C(F)(F)F)c3)c2)cn1] |
| 110 | N-[4-chloro-3-(trifluoromethyl)phenyl]-N'-({4-[2-(methyloxy)pyrimidin-5-yl]phenyl}methyl)urea | 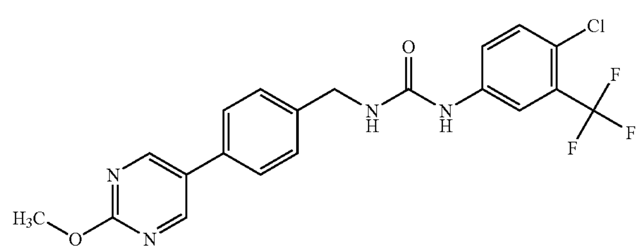 [SMILES: COc1ncc(-c2ccc(CNC(=O)Nc3ccc(Cl)c(C(F)(F)F)c3)cc2)cn1] |
| 111 | N-[4-chloro-3-(trifluoromethyl)phenyl]-N'-({4-[6-(methyloxy)pyridin-3-yl]phenyl}methyl)urea | 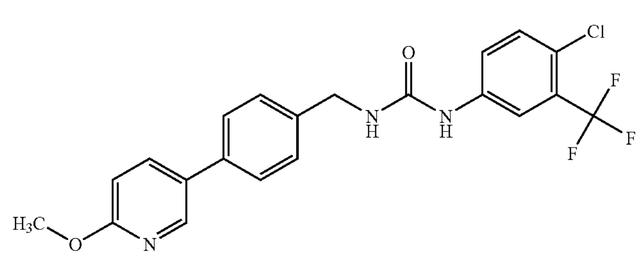 [SMILES: COc1ccc(-c2ccc(CNC(=O)Nc3ccc(Cl)c(C(F)(F)F)c3)cc2)cn1] |

TABLE 1-continued

| Entry | Name | Structure |
|---|---|---|
| 112 | 1,1-dimethylethyl 2-{4-[(2-{[4-chloro-3-(trifluoromethyl)phenyl]amino}-2-oxoethyl)oxy]phenyl}-1H-indole-1-carboxylate | 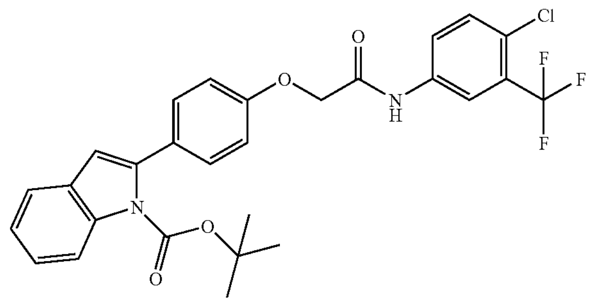 [SMILES: CC(C)(C)OC(=O)n1c(-c2ccc(OCC(=O)Nc3ccc(Cl)c(C(F)(F)F)c3)cc2)cc2ccccc21] |
| 113 | N-({[4-chloro-3-(trifluoromethyl)phenyl]amino}carbonyl)-4-(1H-tetrazol-1-yl)benzenesulfonamide | 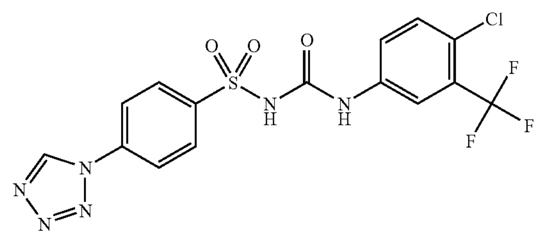 [SMILES: O=C(Nc1ccc(Cl)c(C(F)(F)F)c1)NS(=O)(=O)c1ccc(-n2cnnn2)cc1] |
| 114 | N-[4-chloro-3-(trifluoromethyl)phenyl]-N~2~-[3-(2H-tetrazol-5-yl)phenyl]glycinamide | 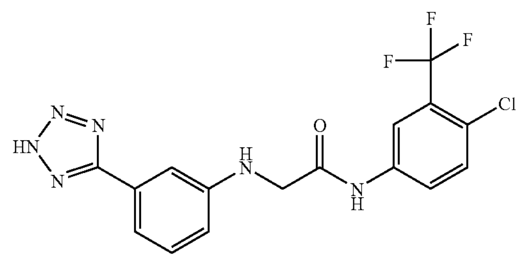 [SMILES: O=C(CNc1cccc(-c2nn[nH]n2)c1)Nc1ccc(Cl)c(C(F)(F)F)c1] |
| 115 | N-[4-chloro-3-(trifluoromethyl)phenyl]-2-{[2,6-difluoro-4-(1H-tetrazol-1-yl)phenyl]oxy}acetamide | 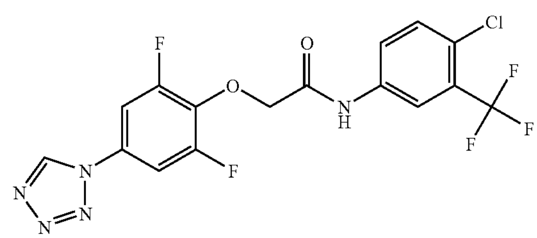 [SMILES: O=C(COc1c(F)cc(-n2cnnn2)cc1F)Nc1ccc(Cl)c(C(F)(F)F)c1] |
| 116 | (3-pyridin-3-ylphenyl)methyl [4-chloro-3-(trifluoromethyl)phenyl]carbamate | 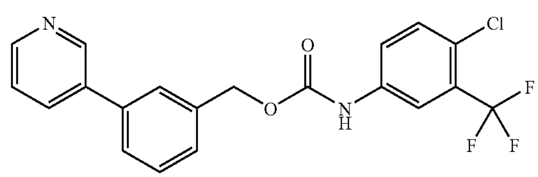 [SMILES: O=C(Nc1ccc(Cl)c(C(F)(F)F)c1)OCc1cccc(-c2cccnc2)c1] |
| 117 | (3-pyrimidin-5-ylphenyl)methyl [4-chloro-3-(trifluoromethyl)phenyl]carbamate | 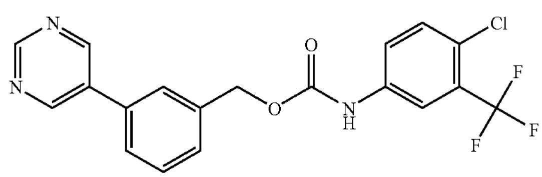 [SMILES: O=C(Nc1ccc(Cl)c(C(F)(F)F)c1)OCc1cccc(-c2cncnc2)c1] |
| 118 | (3-pyridin-4-ylphenyl)methyl [4-chloro-3-(trifluoromethyl)phenyl]carbamate | 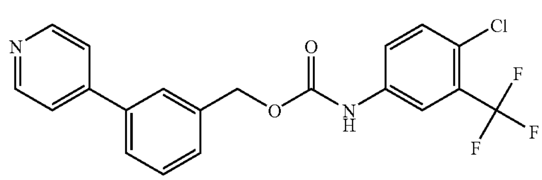 [SMILES: O=C(Nc1ccc(Cl)c(C(F)(F)F)c1)OCc1cccc(-c2ccncc2)c1] |

TABLE 1-continued

| Entry | Name | Structure |
|---|---|---|
| 119 | N-[4-chloro-3-(trifluoromethyl)phenyl]-2-[4-(1H-tetrazol-1-yl)phenyl]hydrazinecarboxamide | 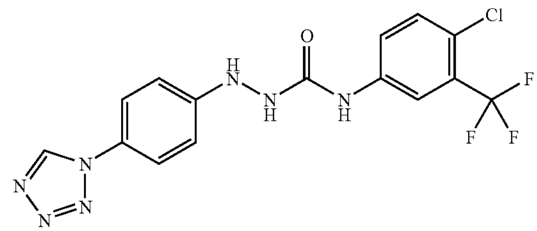 [SMILES: O=C(NNc1ccc(-n2cnnn2)cc1)Nc1ccc(Cl)c(C(F)(F)F)c1] |
| 120 | N-[4-chloro-3-(trifluoromethyl)phenyl]-2-(4-pyridin-3-ylphenyl)hydrazinecarboxamide | 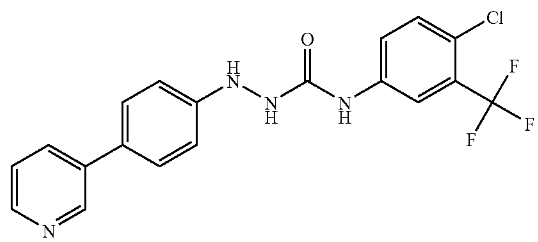 [SMILES: O=C(NNc1ccc(-c2cccnc2)cc1)Nc1ccc(Cl)c(C(F)(F)F)c1] |
| 121 | (4-pyridin-3-ylphenyl)methyl [4-chloro-3-(trifluoromethyl)phenyl]carbamate | 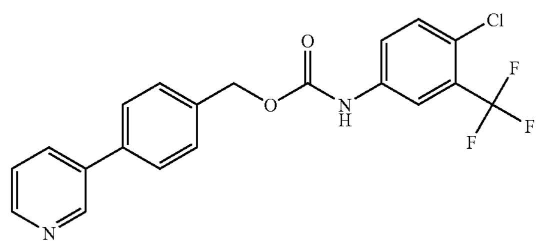 [SMILES: O=C(Nc1ccc(Cl)c(C(F)(F)F)c1)OCc1ccc(-c2cccnc2)cc1] |
| 122 | (4-pyridin-4-ylphenyl)methyl [4-chloro-3-(trifluoromethyl)phenyl]carbamate | 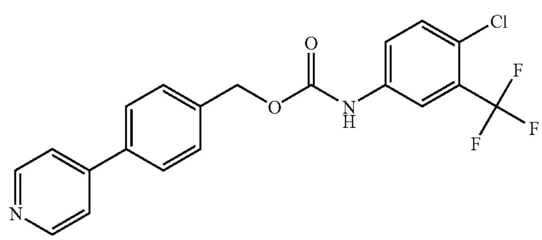 [SMILES: O=C(Nc1ccc(Cl)c(C(F)(F)F)c1)OCc1ccc(-c2ccncc2)cc1] |
| 123 | (4-pyrimidin-5-ylphenyl)methyl [4-chloro-3-(trifluoromethyl)phenyl]carbamate | 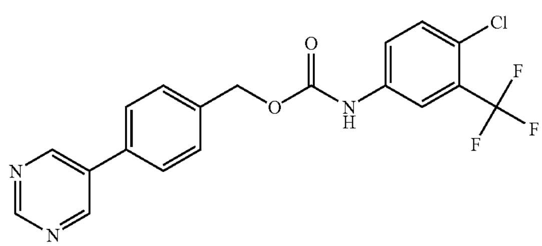 [SMILES: O=C(Nc1ccc(Cl)c(C(F)(F)F)c1)OCc1ccc(-c2cncnc2)cc1] |
| 124 | N-[4-chloro-3-(trifluoromethyl)phenyl]-N'-[(4-pyridin-4-ylphenyl)methyl]urea | 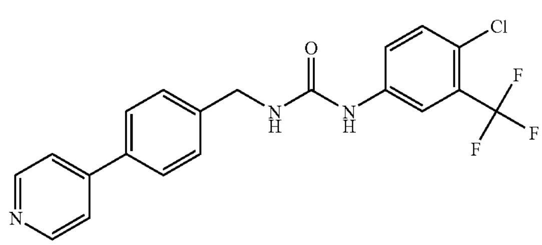 [SMILES: O=C(NCc1ccc(-c2ccncc2)cc1)Nc1ccc(Cl)c(C(F)(F)F)c1] |

TABLE 1-continued

| Entry | Name | Structure |
|---|---|---|
| 125 | N-[4-chloro-3-(trifluoromethyl)phenyl]-2-(3-pyridin-3-ylphenyl)hydrazinecarboxamide | 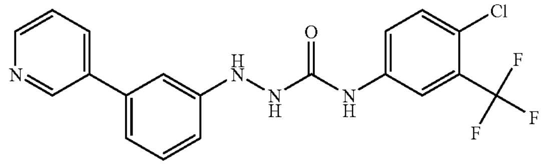 [SMILES: O=C(NNc1cccc(-c2cccnc2)c1)Nc1ccc(Cl)c(C(F)(F)F)c1] |
| 126 | N-[4-chloro-3-(trifluoromethyl)phenyl]-2-(3-pyrimidin-5-ylphenyl)hydrazinecarboxamide | 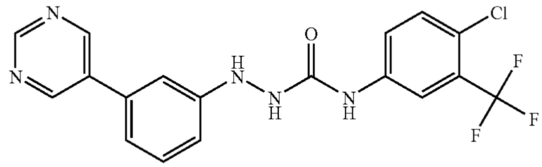 [SMILES: O=C(NNc1cccc(-c2cncnc2)c1)Nc1ccc(Cl)c(C(F)(F)F)c1] |
| 127 | N-[5-chloro-2,4-bis(methyloxy)phenyl]-N'-[(4-pyrimidin-5-ylphenyl)methyl]urea | 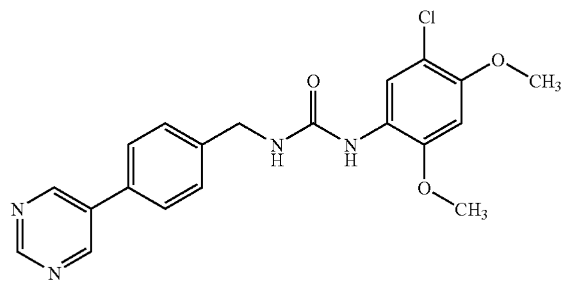 [SMILES: COc1cc(OC)c(NC(=O)NCc2ccc(-c3cncnc3)cc2)cc1Cl] |
| 128 | N-[5-chloro-2,4-bis(methyloxy)phenyl]-N'-[(4-pyridin-3-ylphenyl)methyl]urea | 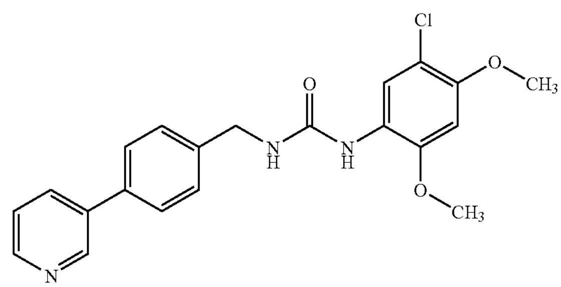 [SMILES: COc1cc(OC)c(NC(=O)NCc2ccc(-c3cccnc3)cc2)cc1Cl] |
| 129 | (4-pyrimidin-5-ylphenyl)methyl [5-chloro-2,4-bis(methyloxy)phenyl]carbamate | 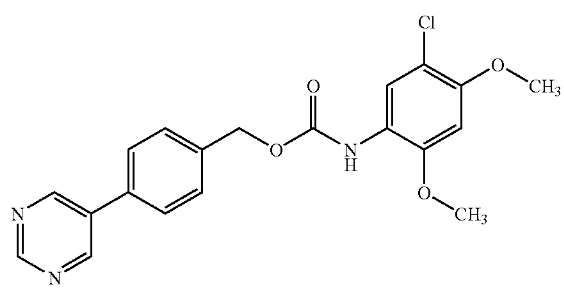 [SMILES: COc1cc(OC)c(NC(=O)OCc2ccc(-c3cncnc3)cc2)cc1Cl] |
| 130 | (4-pyridin-3-ylphenyl)methyl [5-chloro-2,4-bis(methyloxy)phenyl]carbamate | 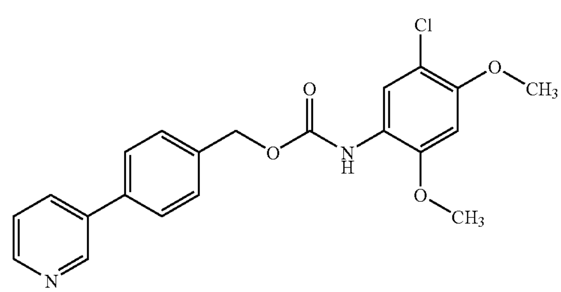 [SMILES: COc1cc(OC)c(NC(=O)OCc2ccc(-c3cccnc3)cc2)cc1Cl] |

TABLE 1-continued

| Entry | Name | Structure |
|---|---|---|
| 131 | 1-(4-pyridin-3-ylphenyl)ethyl [4-chloro-3-(trifluoromethyl)phenyl]carbamate | 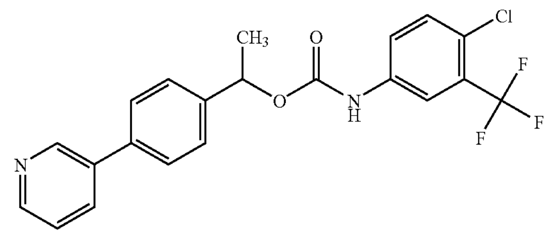 [SMILES: CC(OC(=O)Nc1ccc(Cl)c(C(F)(F)F)c1)c1ccc(-c2cccnc2)cc1] |
| 132 | 1-(4-pyrimidin-5-ylphenyl)ethyl [4-chloro-3-(trifluoromethyl)phenyl]carbamate | 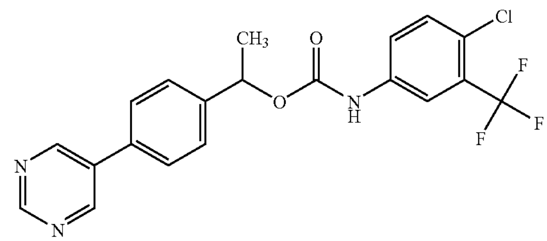 [SMILES: CC(OC(=O)Nc1ccc(Cl)c(C(F)(F)F)c1)c1ccc(-c2cncnc2)cc1] |
| 133 | N-[5-chloro-2,4-bis(methyloxy)phenyl]-N'-[(3-pyridin-3-ylphenyl)methyl]urea | 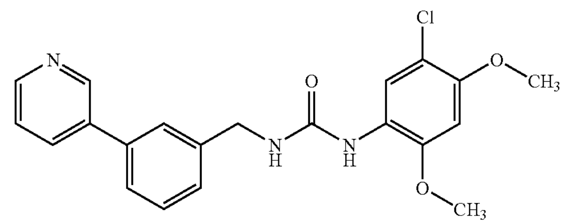 |
| 134 | N-[5-chloro-2,4-bis(methyloxy)phenyl]-N'-[(3-pyrimidin-5-ylphenyl)methyl]urea | 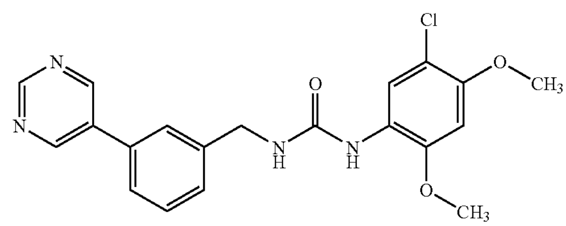 [SMILES: COc1cc(OC)c(NC(=O)NCc2cccc(-c3cncnc3)c2)cc1Cl] |
| 135 | (3-pyridin-3-ylphenyl)methyl [5-chloro-2,4-bis(methyloxy)phenyl]carbamate | 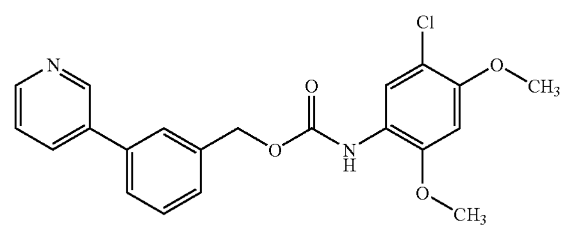 [SMILES: COc1cc(OC)c(NC(=O)OCc2cccc(-c3cccnc3)c2)cc1Cl] |
| 136 | (3-pyrimidin-5-ylphenyl)methyl [5-chloro-2,4-bis(methyloxy)phenyl]carbamate | 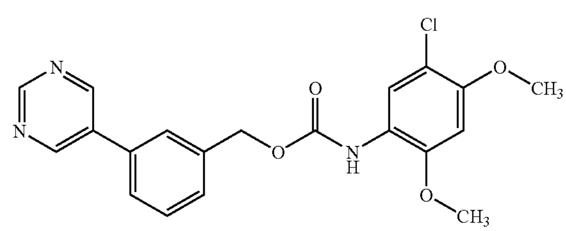 [SMILES: COc1cc(OC)c(NC(=O)OCc2cccc(-c3cncnc3)c2)cc1Cl] |
| 137 | N-[4-chloro-3-(trifluoromethyl)phenyl]-2-methyl-2-(3-pyrimidin-5-ylphenyl)hydrazinecarboxamide | 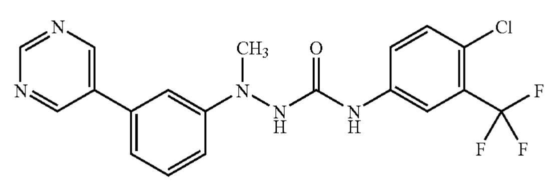 [SMILES: CN(NC(=O)Nc1ccc(Cl)c(C(F)(F)F)c1)c1cccc(-c2cncnc2)c1] |

TABLE 1-continued

| Entry | Name | Structure |
|---|---|---|
| 138 | N-[4-fluoro-3-(trifluoromethyl)phenyl]-N'-[(4-pyridin-3-ylphenyl)methyl]urea | 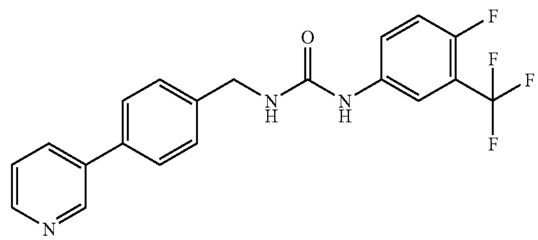 |
| 139 | N-{[3-(6-aminopyridin-3-yl)phenyl]methyl}-N'-[4-chloro-3-(trifluoromethyl)phenyl]urea | 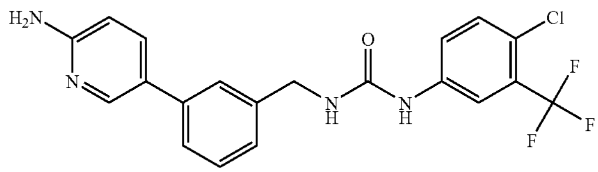 [SMILES: Nc1ccc(-c2cccc(CNC(=O)Nc3ccc(Cl)c(C(F)(F)F)c3)c2)cn1] |
| 140 | N-{[4-(6-aminopyridin-3-yl)phenyl]methyl}-N'-[4-chloro-3-(trifluoromethyl)phenyl]urea | 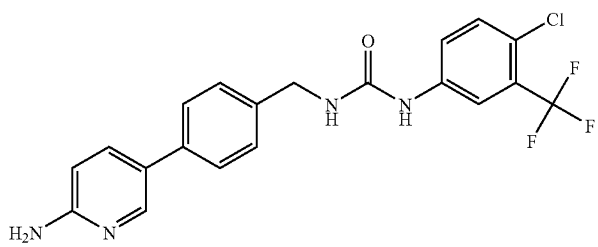 |
| 141 | N-{[3-(2-aminopyrimidin-5-yl)phenyl]methyl}-N'-[4-chloro-3-(trifluoromethyl)phenyl]urea | 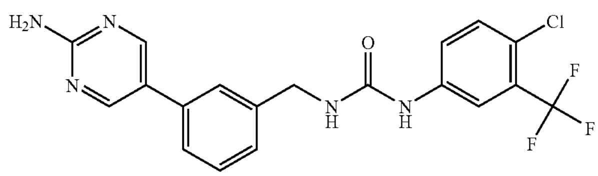 [SMILES: Nc1ncc(-c2cccc(CNC(=O)Nc3ccc(Cl)c(C(F)(F)F)c3)c2)cn1] |
| 142 | N-{[4-(2-aminopyrimidin-5-yl)phenyl]methyl}-N'-[4-chloro-3-(trifluoromethyl)phenyl]urea | 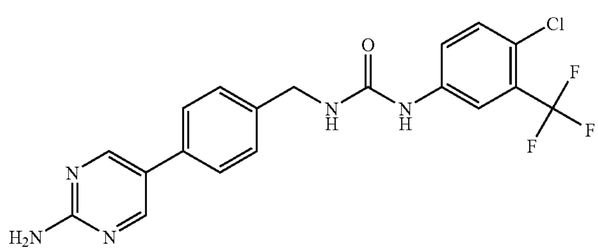 [SMILES: Nc1ncc(-c2ccc(CNC(=O)Nc3ccc(Cl)c(C(F)(F)F)c3)cc2)cn1] |
| 143 | N-[4-chloro-3-(trifluoromethyl)phenyl]-N'-[1-(4-pyridin-3-ylphenyl)ethyl]urea | 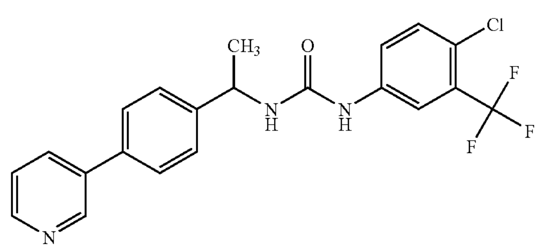 |
| 144 | N-[4-chloro-3-(trifluoromethyl)phenyl]-N'-[1-(4-pyrimidin-5-ylphenyl)ethyl]urea | 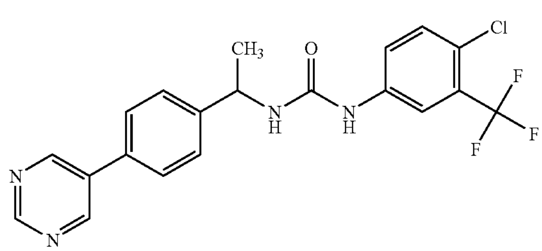 |

TABLE 1-continued

| Entry | Name | Structure |
|---|---|---|
| 145 | N-[4-chloro-3-(trifluoromethyl)phenyl]-2-{[4-(1H-indol-2-yl)phenyl]oxy}acetamide | 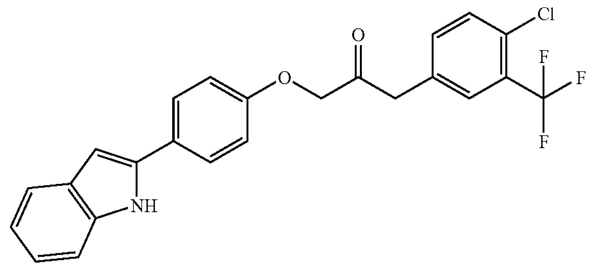 [SMILES: O=C(COc1ccc(-c2cc3ccccc3[nH]2)cc1)Cc1ccc(Cl)c(C(F)(F)F)c1] |
| 146 | N-[4-chloro-3-(trifluoromethyl)phenyl]-2-(isoquinolin-7-yloxy)acetamide | 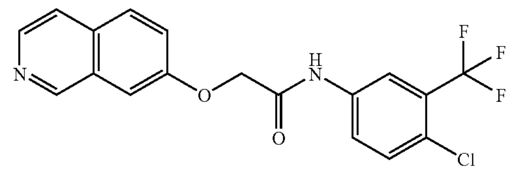 [SMILES: O=C(COc1ccc2ccncc2c1)Nc1ccc(Cl)c(C(F)(F)F)c1] |
| 147 | N-[4-chloro-3-(trifluoromethyl)phenyl]-2-(4-pyridin-4-ylphenyl)hydrazinecarboxamide | 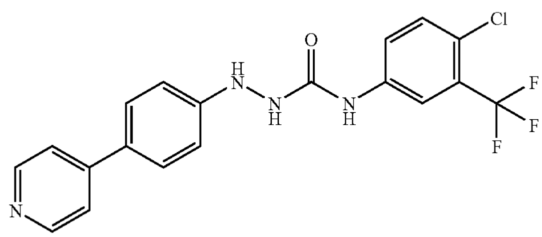 [SMILES: O=C(NNc1ccc(-c2ccncc2)cc1)Nc1ccc(Cl)c(C(F)(F)F)c1] |
| 148 | N-[4-chloro-3-(trifluoromethyl)phenyl]-2-(3-pyridin-4-ylphenyl)hydrazinecarboxamide | 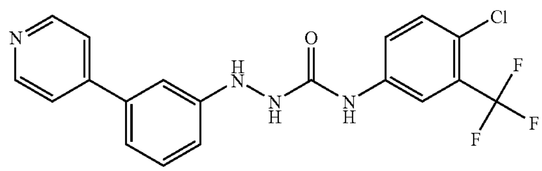 [SMILES: O=C(NNc1cccc(-c2ccncc2)c1)Nc1ccc(Cl)c(C(F)(F)F)c1] |
| 149 | N-[4-chloro-3-(trifluoromethyl)phenyl]-N'-[(3-pyridin-4-ylphenyl)methyl]urea | 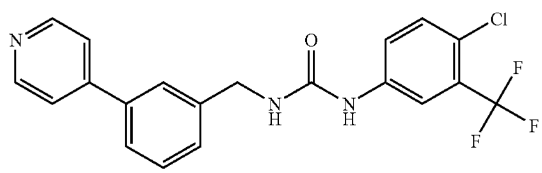 [SMILES: O=C(NCc1cccc(-c2ccncc2)c1)Nc1ccc(Cl)c(C(F)(F)F)c1] |
| 150 | N-[4-chloro-3-(trifluoromethyl)phenyl]-N'-[(3-quinoxalin-6-ylphenyl)methyl]urea | 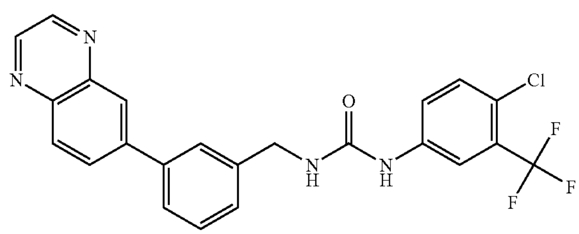 [SMILES: O=C(NCc1cccc(-c2ccc3nccnc3c2)c1)Nc1ccc(Cl)c(C(F)(F)F)c1] |
| 151 | methyl 3-amino-6-(3-{[({[4-chloro-3-(trifluoromethyl)phenyl]amino}carbonyl)amino]methyl}phenyl)pyrazine-2-carboxylate | 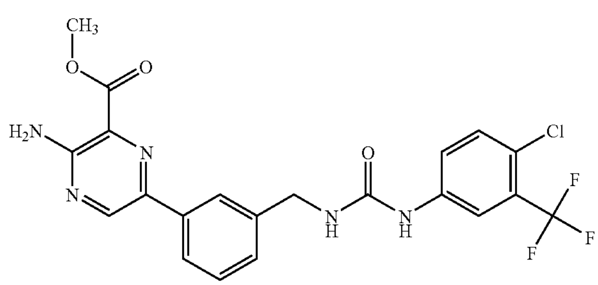 [SMILES: COC(=O)c1nc(-c2cccc(CNC(=O)Nc3ccc(Cl)c(C(F)(F)F)c3)c2)cnc1N] |

TABLE 1-continued

| Entry | Name | Structure |
|---|---|---|
| 152 | N-[4-chloro-3-(trifluoromethyl)phenyl]-N'-[(4-quinoxalin-6-ylphenyl)methyl]urea | 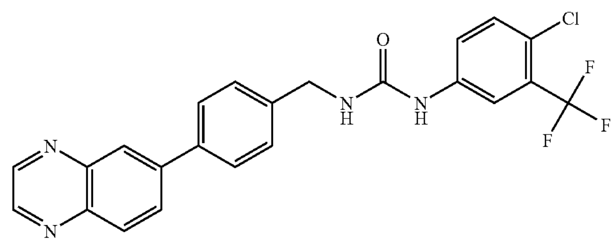 [SMILES: O=C(NCc1ccc(-c2ccc3nccnc3c2)cc1)Nc1ccc(Cl)c(C(F)(F)F)c1] |
| 153 | N-{[3-(2-amino-5-methylpyridin-3-yl)phenyl]methyl}-N'-[4-chloro-3-(trifluoromethyl)phenyl]urea | 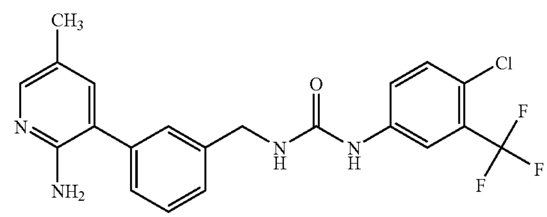 [SMILES: Cc1cnc(N)c(-c2cccc(CNC(=O)Nc3ccc(Cl)c(C(F)(F)F)c3)c2)c1] |
| 154 | methyl 3-amino-6-(4-{[({[4-chloro-3-(trifluoromethyl)phenyl]amino}carbonyl)amino]methyl}phenyl)pyrazine-2-carboxylate | 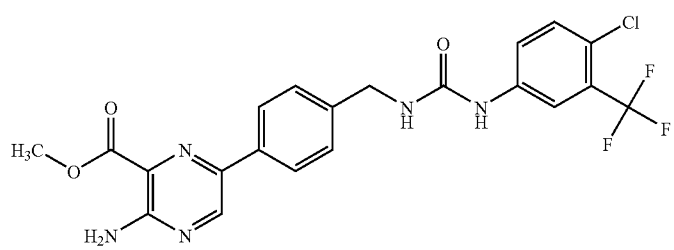 [SMILES: COC(=O)c1nc(-c2ccc(CNC(=O)Nc3ccc(Cl)c(C(F)(F)F)c3)cc2)cnc1N] |
| 155 | [3-(1H-tetrazol-1-yl)phenyl]methyl [3-chloro-4-(methyloxy)phenyl]carbamate | 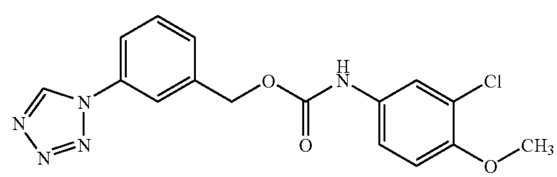 [SMILES: COc1ccc(NC(=O)OCc2cccc(-n3cnnn3)c2)cc1Cl] |
| 156 | N-[3-chloro-4-(methyloxy)phenyl]-N'-{[3-(1H-tetrazol-1-yl)phenyl]methyl}urea | 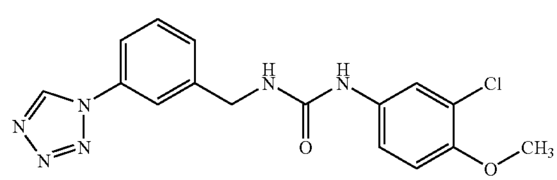 [SMILES: COc1ccc(NC(=O)NCc2cccc(-n3cnnn3)c2)cc1Cl] |
| 157 | N-[4-chloro-3-(trifluoromethyl)phenyl]-2-{[4-(5-hydroxy-1H-tetrazol-1-yl)phenyl]oxy}acetamide | 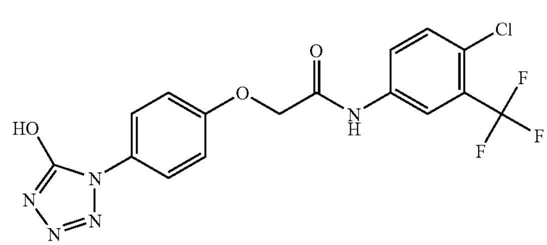 [SMILES: O=C(COc1ccc(-n2nnnc2O)cc1)Nc1ccc(Cl)c(C(F)(F)F)c1] |
| 158 | N-{[3-(2-amino-5-chloropyridin-3-yl)phenyl]methyl}-N'-[4-chloro-3-(trifluoromethyl)phenyl]urea | 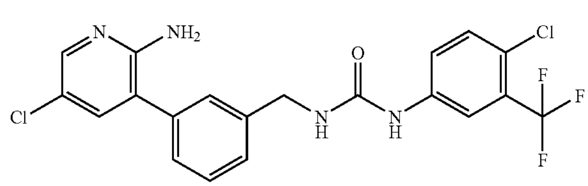 [SMILES: Nc1ncc(Cl)cc1-c1cccc(CNC(=O)Nc2ccc(Cl)c(C(F)(F)F)c2)c1] |

TABLE 1-continued

| Entry | Name | Structure |
|---|---|---|
| 159 | N-{[4-(2-amino-5-chloropyridin-3-yl)phenyl]methyl}-N'-[4-chloro-3-(trifluoromethyl)phenyl]urea | 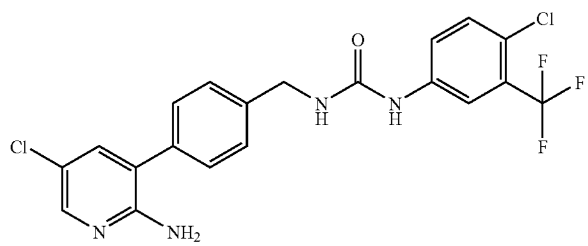 [SMILES: Nc1ncc(Cl)cc1-c1ccc(CNC(=O)Nc2ccc(Cl)c(C(F)(F)F)c2)cc1] |
| 160 | N-{[3-(6-chloropyridin-3-yl)phenyl]methyl}-N'-[4-chloro-3-(trifluoromethyl)phenyl]urea | 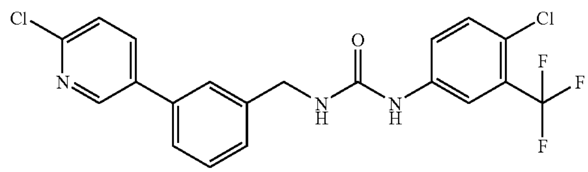 [SMILES: O=C(NCc1cccc(-c2ccc(Cl)nc2)c1)Nc1ccc(Cl)c(C(F)(F)F)c1] |
| 161 | N-{[4-(6-chloropyridin-3-yl)phenyl]methyl}-N'-[4-chloro-3-(trifluoromethyl)phenyl]urea | 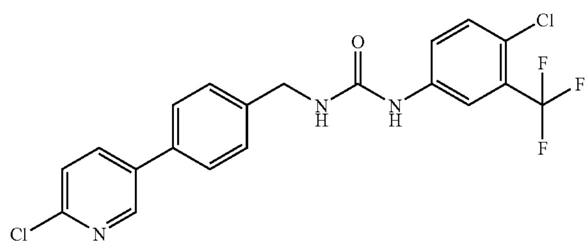 [SMILES: O=C(NCc1ccc(-c2ccc(Cl)nc2)cc1)Nc1ccc(Cl)c(C(F)(F)F)c1] |
| 162 | N-[4-chloro-3-(trifluoromethyl)phenyl]-N'-{[4-(pyrimidin-2-yloxy)phenyl]methyl}urea | 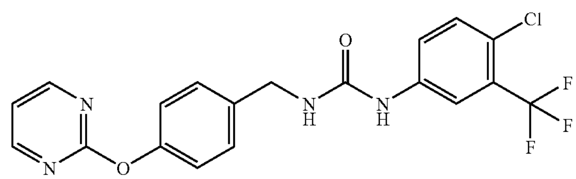 [SMILES: O=C(NCc1ccc(Oc2ncccn2)cc1)Nc1ccc(Cl)c(C(F)(F)F)c1] |
| 163 | N-({[4-chloro-3-(trifluoromethyl)phenyl]amino}carbonyl)-3-(1H-tetrazol-1-yl)benzamide | 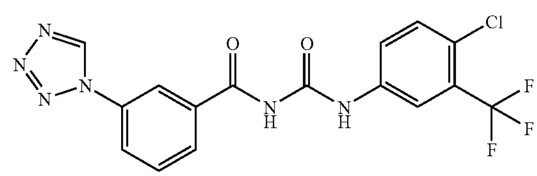 [SMILES: O=C(NC(=O)c1cccc(-n2cnnn2)c1)Nc1ccc(Cl)c(C(F)(F)F)c1] |
| 164 | 3-amino-6-(3-{[({[4-chloro-3-(trifluoromethyl)phenyl[amino}carbonyl)amino]methyl}phenyl)-N-[2-(dimethylamino)ethyl]pyrazine-2-carboxamide | 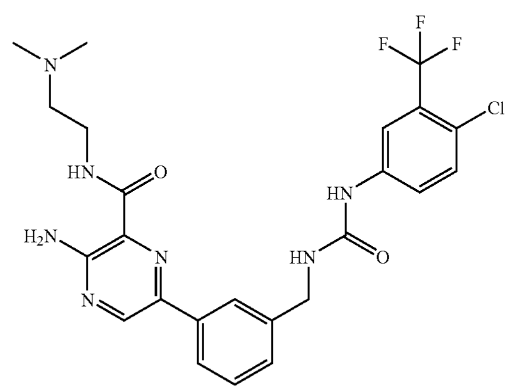 [SMILES: CN(C)CCNC(=O)c1nc(-c2cccc(CNC(=O)Nc3ccc(Cl)c(C(F)(F)F)c3)c2)cnc1N] |
| 165 | N-[4-chloro-3-(trifluoromethyl)phenyl]-N'-{[3-(6-fluoropyridin-3-yl)phenyl]methyl}urea | 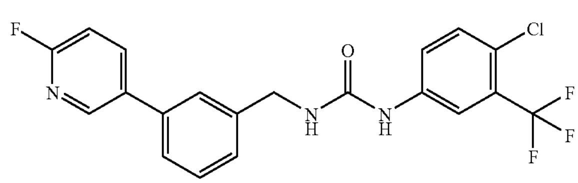 [SMILES: O=C(NCc1cccc(-c2ccc(F)nc2)c1)Nc1ccc(Cl)c(C(F)(F)F)c1] |

TABLE 1-continued

| Entry | Name | Structure |
|---|---|---|
| 166 | N-[4-chloro-3-(trifluoromethyl)phenyl]-N'-({3-[2-(methyloxy)pyridin-3-yl]phenyl}methyl)urea | 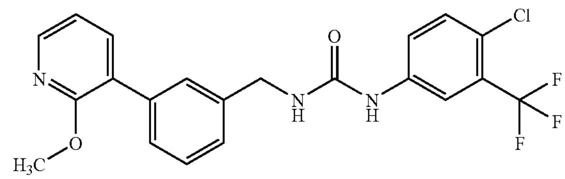 [SMILES: COc1ncccc1-c1cccc(CNC(=O)Nc2ccc(Cl)c(C(F)(F)F)c2)c1] |
| 167 | N-[4-chloro-3-(trifluoromethyl)phenyl]-N'-{[4-(6-fluoropyridin-3-yl)phenyl]methyl}urea | 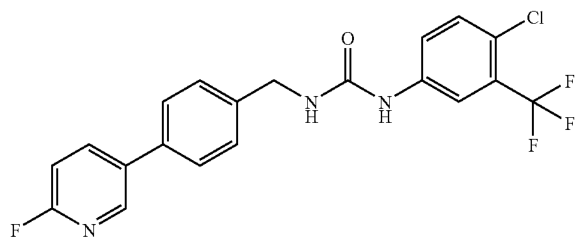 [SMILES: O=C(NCc1ccc(-c2ccc(F)nc2)cc1)Nc1ccc(Cl)c(C(F)(F)F)c1] |
| 168 | N-[4-chloro-3-(trifluoromethyl)phenyl]-N'-({4-[2-(methyloxy)pyridin-3-yl]phenyl}methyl)urea | 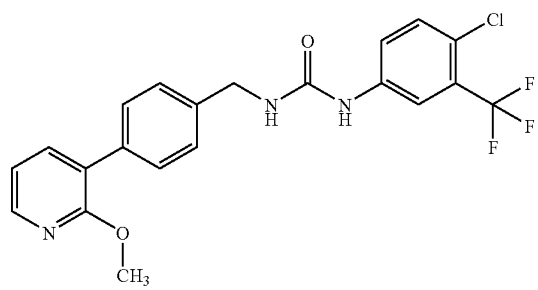 [SMILES: COc1ncccc1-c1ccc(CNC(=O)Nc2ccc(Cl)c(C(F)(F)F)c2)cc1] |
| 169 | N-[4-chloro-3-(trifluoromethyl)phenyl]-N'-{[4-(6-methylpyridin-3-yl)phenyl]methyl}urea | 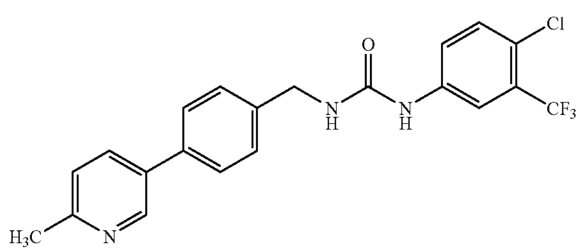 [SMILES: Cc1ccc(-c2ccc(CNC(=O)Nc3ccc(Cl)c(C(F)(F)F)c3)cc2)cn1] |
| 170 | N-{[4-(2-amino-5-fluoropyridin-3-yl)phenyl]methyl}-N'-[4-chloro-3-(trifluoromethyl)phenyl]urea | 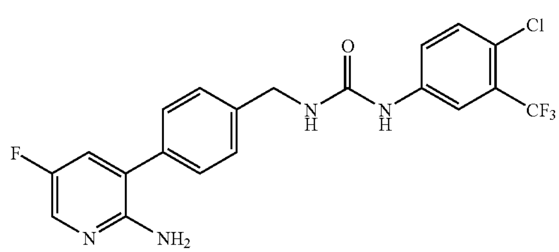 [SMILES: Nc1ncc(F)cc1-c1ccc(CNC(=O)Nc2ccc(Cl)c(C(F)(F)F)c2)cc1] |
| 171 | N-[4-chloro-3-(trifluoromethyl)phenyl]-N'-{[3-(6-methylpyridin-3-yl)phenyl]methyl}urea | 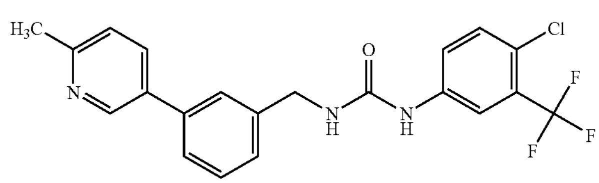 [SMILES: Cc1ccc(-c2cccc(CNC(=O)Nc3ccc(Cl)c(C(F)(F)F)c3)c2)cn1] |

TABLE 1-continued

| Entry | Name | Structure |
|---|---|---|
| 172 | N-{[4-(2-aminopyridin-3-yl)phenyl]methyl}-N'-[4-chloro-3-(trifluoromethyl)phenyl]urea | 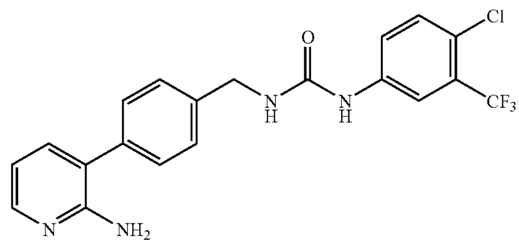 [SMILES: Nc1ncccc1-c1ccc(CNC(=O)Nc2ccc(Cl)c(C(F)(F)F)c2)cc1] |
| 173 | N-{[3-(2-aminopyridin-3-yl)phenyl]methyl}-N'-[4-chloro-3-(trifluoromethyl)phenyl]urea | 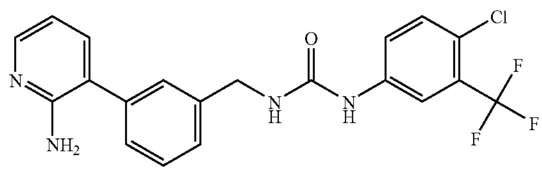 [SMILES: Nc1ncccc1-c1cccc(CNC(=O)Nc2ccc(Cl)c(C(F)(F)F)c2)c1] |
| 174 | [3-(6-methylpyridin-3-yl)phenyl]methyl [4-chloro-3-(trifluoromethyl)phenyl]carbamate | 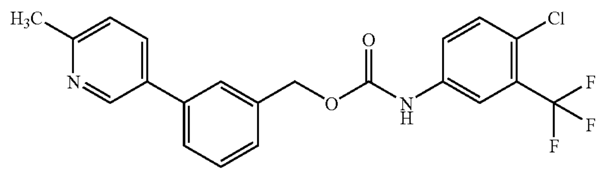 [SMILES: Cc1ccc(-c2cccc(COC(=O)Nc3ccc(Cl)c(C(F)(F)F)c3)c2)cn1] |
| 175 | [3-(2-amino-5-fluoropyridin-3-yl)phenyl]methyl [4-chloro-3-(trifluoromethyl)phenyl]carbamate | 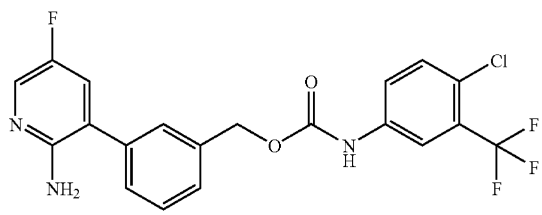 [SMILES: Nc1ncc(F)cc1-c1cccc(COC(=O)Nc2ccc(Cl)c(C(F)(F)F)c2)c1] |
| 176 | [3-(2-aminopyridin-3-yl)phenyl]methyl [4-chloro-3-(trifluoromethyl)phenyl]carbamate | 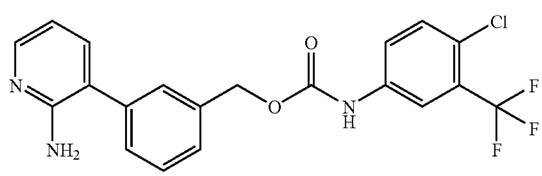 [SMILES: Nc1ncccc1-c1cccc(COC(=O)Nc2ccc(Cl)c(C(F)(F)F)c2)c1] |
| 177 | (3-pyrazin-2-ylphenyl)methyl [4-chloro-3-(trifluoromethyl)phenyl]carbamate | 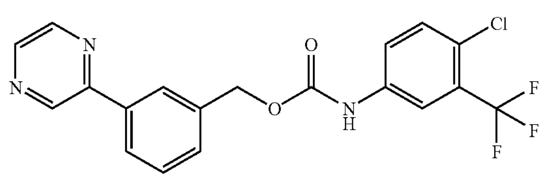 [SMILES: O=C(Nc1ccc(Cl)c(C(F)(F)F)c1)OCc1cccc(-c2cnccn2)c1] |
| 178 | N-[4-chloro-3-(trifluoromethyl)phenyl]-N'-({3-[6-(hydroxymethyl)pyridin-3-yl]phenyl}methyl)urea | 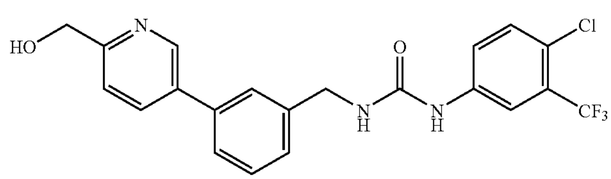 [SMILES: O=C(NCc1cccc(-c2ccc(CO)nc2)c1)Nc1ccc(Cl)c(C(F)(F)F)c1] |
| 179 | N-{[3-(6-acetylpyridin-3-yl)phenyl]methyl}-N'-[4-chloro-3-(trifluoromethyl)phenyl]urea | 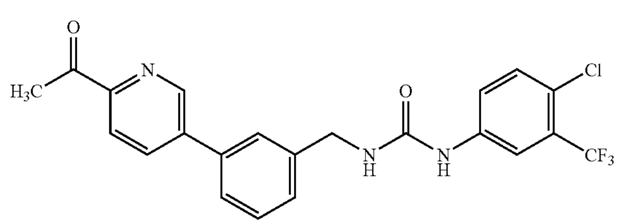 [SMILES: CC(=O)c1ccc(-c2cccc(CNC(=O)Nc3ccc(Cl)c(C(F)(F)F)c3)c2)cn1] |

TABLE 1-continued

| Entry | Name | Structure |
|---|---|---|
| 180 | N-[4-chloro-3-(trifluoromethyl)phenyl]-N'-{[3-(6-cyanopyridin-3-yl)phenyl]methyl}urea | 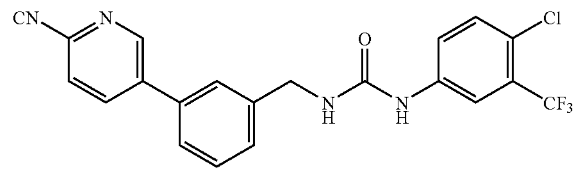 [SMILES: N#Cc1ccc(-c2cccc(CNC(=O)Nc3ccc(Cl)c(C(F)(F)F)c3)c2)cn1] |
| 181 | 1,1-dimethylethyl (3S)-3-({[3-amino-6-(3-{[({[4-chloro-3-(trifluoromethyl)phenyl]amino}carbonyl)amino]methyl}phenyl)pyrazin-2-yl]carbonyl}amino)piperidine-1-carboxylate | 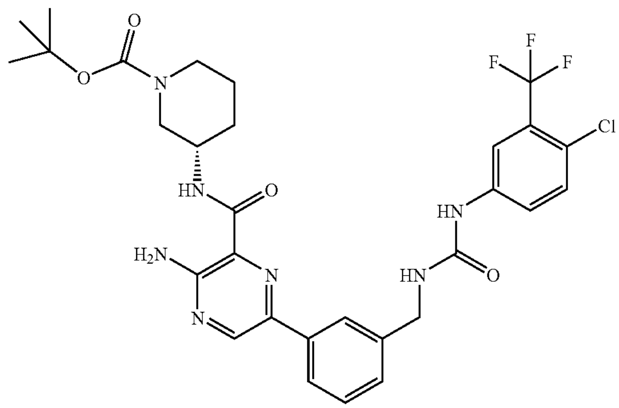 [SMILES: CC(C)(C)OC(=O)N1CCC[C@H](NC(=O)c2nc(-c3cccc(CNC(=O)Nc4ccc(Cl)c(C(F)(F)F)c4)c3)cnc2N)C1] |
| 182 | 3-amino-6-(3-{[({[4-chloro-3-(trifluoromethyl)phenyl]amino}carbonyl)amino]methyl}phenyl)-N-[(3S)-piperidin-3-yl]pyrazine-2-carboxamide | 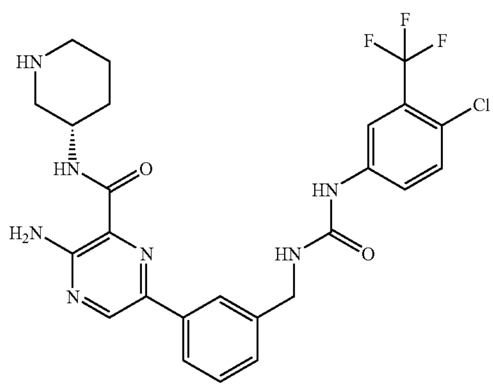 |
| 183 | 1,1-dimethylethyl (3S)-3-({[3-amino-6-(4-{[({[4-chloro-3-(trifluoromethyl)phenyl]amino}carbonyl)amino]methyl}phenyl)pyrazin-2-yl]carbonyl}amino)piperidine-1-carboxylate | 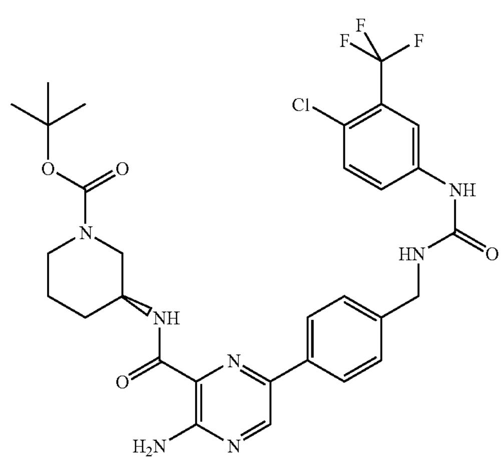 [SMILES: CC(C)(C)OC(=O)N1CCC[C@H](NC(=O)c2nc(-c3ccc(CNC(=O)Nc4ccc(Cl)c(C(F)(F)F)c4)cc3)cnc2N)C1] |

TABLE 1-continued

| Entry | Name | Structure |
|---|---|---|
| 184 | 3-amino-6-(4-{[({[4-chloro-3-(trifluoromethyl)phenyl]amino}carbonyl)amino]methyl}phenyl)-N-[(3S)-piperidin-3-yl]pyrazine-2-carboxamide | 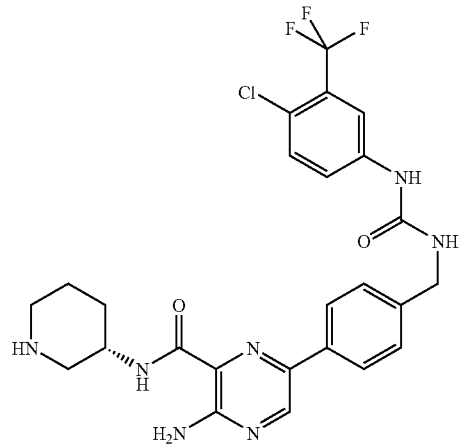 [SMILES: Nc1ncc(-c2ccc(CNC(=O)Nc3ccc(Cl)c(C(F)(F)F)c3)cc2)nc1C(=O)N[C@H]1CCCNC1] |
| 185 | [3-(7H-pyrrolo[2,3-d]pyrimidin-4-yl)phenyl]methyl [4-chloro-3-(trifluoromethyl)phenyl]carbamate | 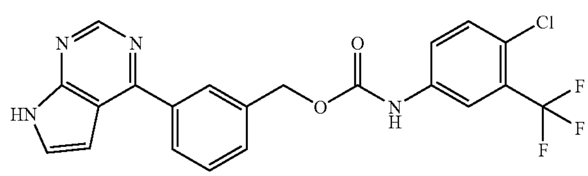 [SMILES: O=C(Nc1ccc(Cl)c(C(F)(F)F)c1)OCc1cccc(-c2ncnc3[nH]ccc23)c1] |
| 186 | N-{[3-(2-amino-5-fluoropyridin-3-yl)phenyl]methyl}-N'-[4-chloro-3-(trifluoromethyl)phenyl]urea | 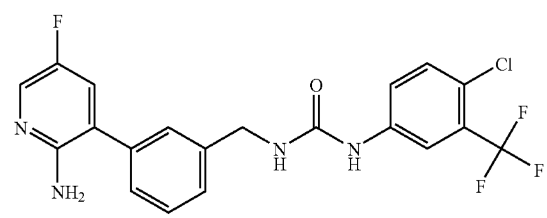 [SMILES: Nc1ncc(F)cc1-c1cccc(CNC(=O)Nc2ccc(Cl)c(C(F)(F)F)c2)c1] |
| 187 | [6-(1H-tetrazol-1-yl)pyridin-2-yl]methyl [4-chloro-3-(trifluoromethyl)phenyl]carbamate | 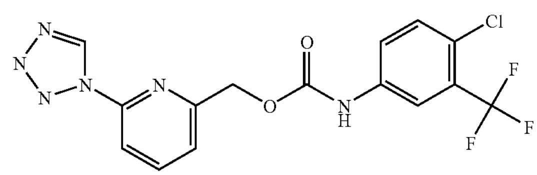 [SMILES: O=C(Nc1ccc(Cl)c(C(F)(F)F)c1)OCc1cccc(N2C=NNN2)n1] |
| 188 | [3-(1H-benzimidazol-2-yl)phenyl]methyl [4-chloro-3-(trifluoromethyl)phenyl]carbamate | 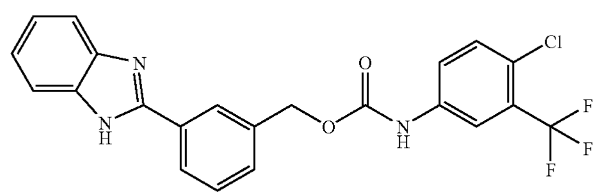 [SMILES: O=C(Nc1ccc(Cl)c(C(F)(F)F)c1)OCc1cccc(-c2nc3ccccc3[nH]2)c1] |
| 189 | [3-(6-amino-2-methylpyridin-3-yl)phenyl]methyl [4-chloro-3-(trifluoromethyl)phenyl]carbamate | 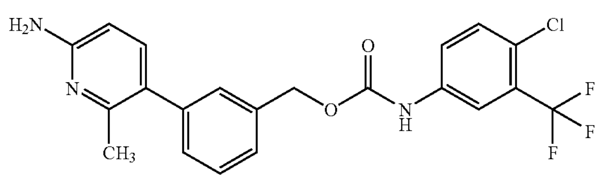 [SMILES: Cc1nc(N)ccc1-c1cccc(COC(=O)Nc2ccc(Cl)c(C(F)(F)F)c2)c1] |
| 190 | N-[4-chloro-3-(trifluoromethyl)phenyl]-N'-({3-[5-(methylthio)pyridin-3-yl]phenyl}methyl)urea | 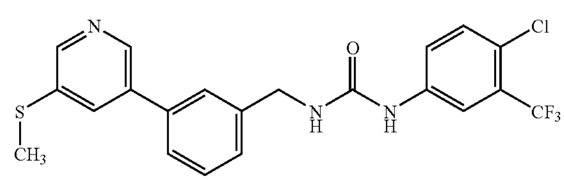 [SMILES: CSc1cncc(-c2cccc(CNC(=O)Nc3ccc(Cl)c(C(F)(F)F)c3)c2)c1] |

TABLE 1-continued

| Entry | Name | Structure |
|---|---|---|
| 191 | [4-(6-methylpyridin-3-yl)phenyl]methyl [4-chloro-3-(trifluoromethyl)phenyl]carbamate | 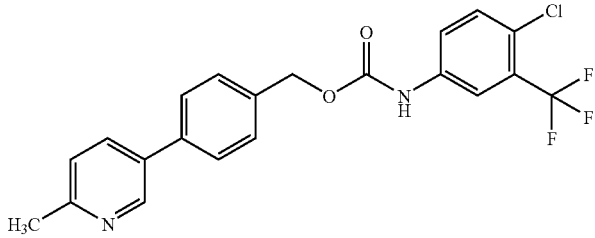 [SMILES: Cc1ccc(-c2ccc(COC(=O)Nc3ccc(Cl)c(C(F)(F)F)c3)cc2)cn1] |
| 192 | [4-(2-amino-5-fluoropyridin-3-yl)phenyl]methyl [4-chloro-3-(trifluoromethyl)phenyl]carbamate | 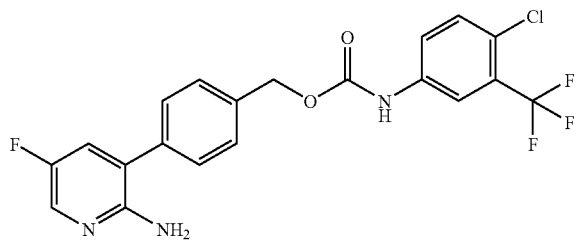 [SMILES: Nc1ncc(F)cc1-c1ccc(COC(=O)Nc2ccc(Cl)c(C(F)(F)F)c2)cc1] |
| 193 | [4-(2-aminopyridin-3-yl)phenyl]methyl [4-chloro-3-(trifluoromethyl)phenyl]carbamate | 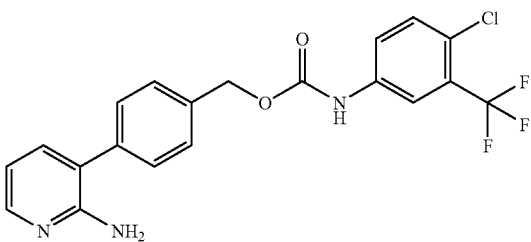 [SMILES: Nc1ncccc1-c1ccc(COC(=O)Nc2ccc(Cl)c(C(F)(F)F)c2)cc1] |
| 194 | (4-pyrazin-2-ylphenyl)methyl [4-chloro-3-(trifluoromethyl)phenyl]carbamate | 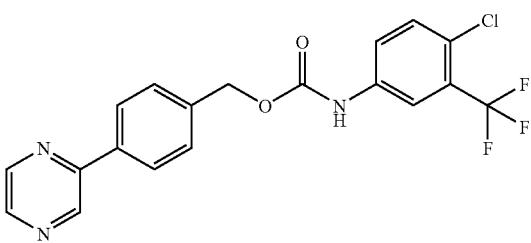 [SMILES: O=C(Nc1ccc(Cl)c(C(F)(F)F)c1)OCc1ccc(-c2cnccn2)cc1] |
| 195 | [4-(7H-pyrrolo[2,3-d]pyrimidin-4-yl)phenyl]methyl [4-chloro-3-(trifluoromethyl)phenyl]carbamate | 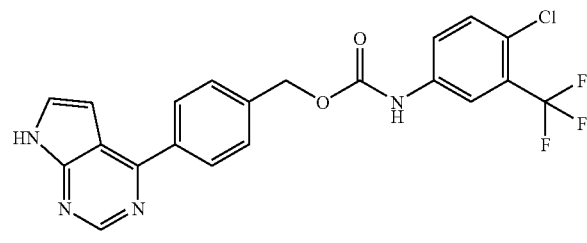 [SMILES: O=C(Nc1ccc(Cl)c(C(F)(F)F)c1)OCc1ccc(-c2ncnc3[nH]ccc23)cc1] |
| 196 | [4-(6-amino-2-methylpyridin-3-yl)phenyl]methyl [4-chloro-3-(trifluoromethyl)phenyl]carbamate | 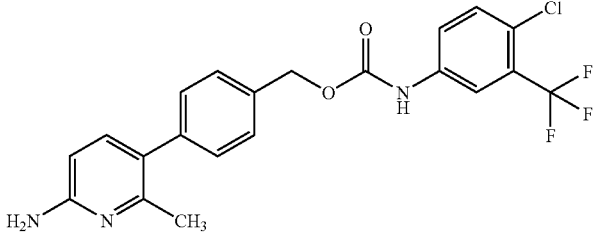 [SMILES: Cc1nc(N)ccc1-c1ccc(COC(=O)Nc2ccc(Cl)c(C(F)(F)F)c2)cc1] |

TABLE 1-continued

| Entry | Name | Structure |
|---|---|---|
| 197 | [3-(1H-tetrazol-1-yl)phenyl]methyl 1,3-benzothiazol-2-ylcarbamate | 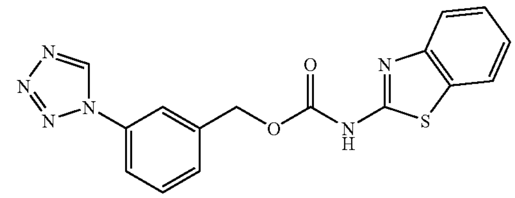 [SMILES: O=C(Nc1nc2ccccc2s1)OCc1cccc(-n2cnnn2)c1] |
| 198 | [3-(1H-tetrazol-1-yl)phenyl]methyl (5-bromopyridin-2-yl)carbamate | 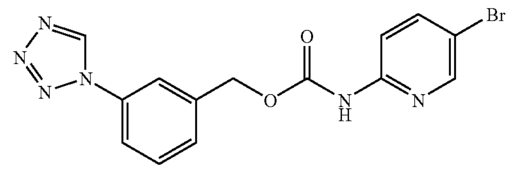 [SMILES: O=C(Nc1ccc(Br)cn1)OCc1cccc(-n2cnnn2)c1] |
| 199 | (3-pyridin-3-ylphenyl)methyl (3,5-dimethylphenyl)carbamate | 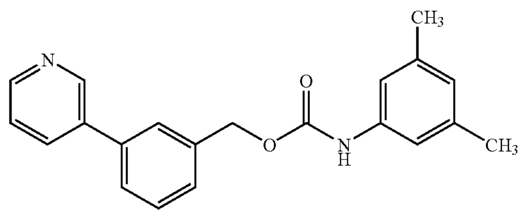 [SMILES: Cc1cc(C)cc(NC(=O)OCc2cccc(-c3cccnc3)c2)c1] |
| 200 | (3-pyridin-3-ylphenyl)methyl [5-chloro-2-(methyloxy)phenyl]carbamate | 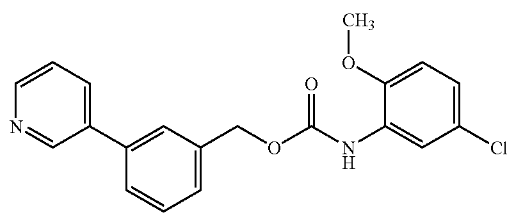 [SMILES: COc1ccc(Cl)cc1NC(=O)OCc1cccc(-c2cccnc2)c1] |
| 201 | [4-(1H-tetrazol-1-yl)phenyl]methyl [4-chloro-3-(trifluoromethyl)phenyl]carbamate | 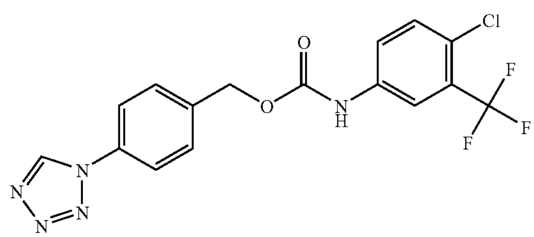 [SMILES: O=C(Nc1ccc(Cl)c(C(F)(F)F)c1)OCc1ccc(-n2cnnn2)cc1] |
| 202 | (3-pyrimidin-5-ylphenyl)methyl [5-chloro-2-(methyloxy)phenyl]carbamate | 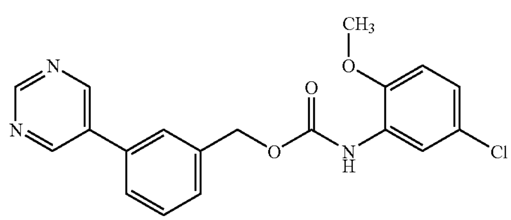 [SMILES: COc1ccc(Cl)cc1NC(=O)OCc1cccc(-c2cncnc2)c1] |
| 203 | (4-pyrimidin-5-ylphenyl)methyl (3,4-dimethylphenyl)carbamate | 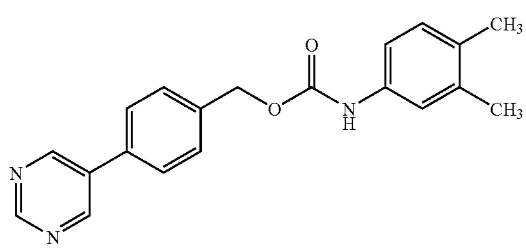 [SMILES: Cc1ccc(NC(=O)OCc2ccc(-c3cncnc3)cc2)cc1C] |

TABLE 1-continued

| Entry | Name | Structure |
|---|---|---|
| 204 | (3-pyridin-3-ylphenyl)methyl (3,4-dimethylphenyl)carbamate | 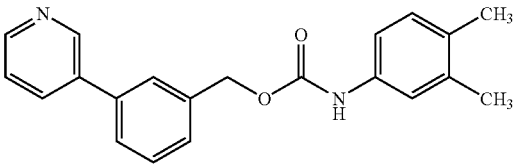 [SMILES: Cc1ccc(NC(=O)OCc2cccc(-c3cccnc3)c2)cc1C] |
| 205 | 1,1-dimethylethyl 3-({[3-amino-6-(3-{[({[4-chloro-3-(trifluoromethyl)phenyl]amino}carbonyl)amino]methyl}phenyl)pyrazin-2-yl]carbonyl}amino)piperidine-1-carboxylate | 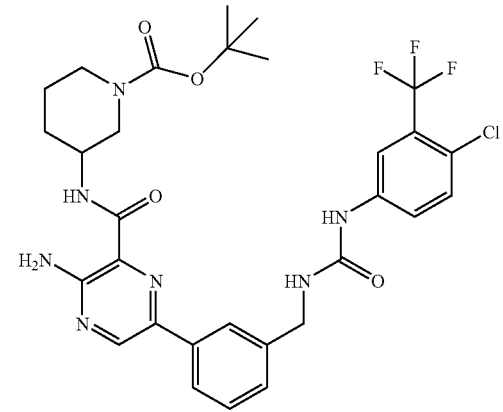 [SMILES: CC(C)(C)OC(=O)N1CCCC(NC(=O)c2nc(-c3cccc(CNC(=O)Nc4ccc(Cl)c(C(F)(F)F)c4)c3)cnc2N)C1] |
| 206 | 1,1-dimethylethyl 3-({[3-amino-6-(4-{[({[4-chloro-3-(trifluoromethyl)phenyl]amino}carbonyl)amino]methyl}phenyl)pyrazin-2-yl]carbonyl}amino)piperidine-1-carboxylate | 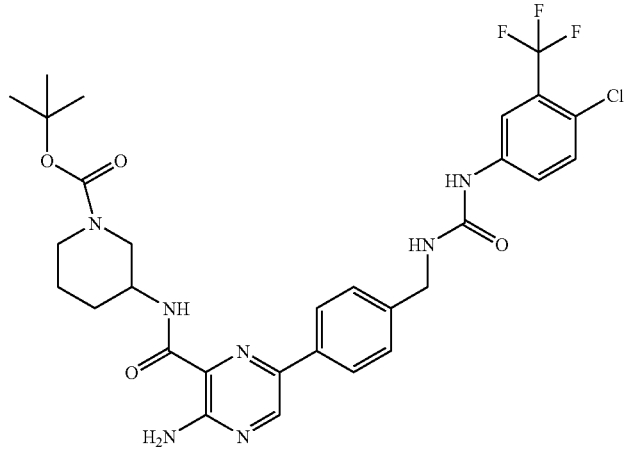 [SMILES: CC(C)(C)OC(=O)N1CCCC(NC(=O)c2nc(-c3ccc(CNC(=O)Nc4ccc(Cl)c(C(F)(F)F)c4)cc3)cnc2N)C1] |
| 207 | 3-amino-6-(3-{[({[4-chloro-3-(trifluoromethyl)phenyl]amino}carbonyl)amino]methyl}phenyl)-N-piperidin-3-ylpyrazine-2-carboxamide | 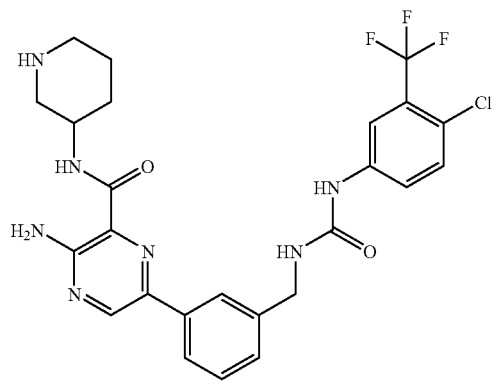 |

TABLE 1-continued

| Entry | Name | Structure |
|---|---|---|
| 208 | 3-amino-6-(4-{[({[4-chloro-3-(trifluoromethyl)phenyl]amino}carbonyl)amino]methyl}phenyl)-N-piperidin-3-ylpyrazine-2-carboxamide | 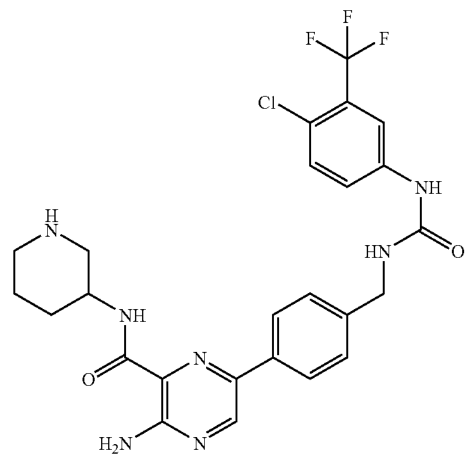 [SMILES: Nc1ncc(-c2ccc(CNC(=O)Nc3ccc(Cl)c(C(F)(F)F)c3)cc2)nc1C(=O)NC1CCCNC1] |
| 209 | 1,1-dimethylethyl 4-{[3-amino-6-(3-{[({[4-chloro-3-(trifluoromethyl)phenyl]amino}carbonyl)amino]methyl}phenyl)pyrazin-2-yl]carbonyl}piperazine-1-carboxylate | 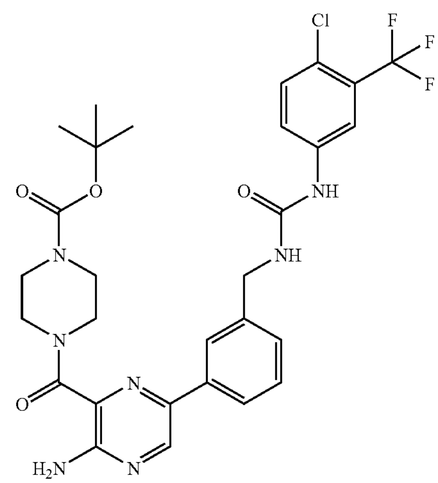 [SMILES: CC(C)(C)OC(=O)N1CCN(C(=O)c2nc(-c3cccc(CNC(=O)Nc4ccc(Cl)c(C(F)(F)F)c4)c3)cnc2N)CC1] |
| 210 | 1,1-dimethylethyl 4-{[3-amino-6-(4-{[({[4-chloro-3-(trifluoromethyl)phenyl]amino}carbonyl)amino]methyl}phenyl)pyrazin-2-yl]carbonyl}piperazine-1-carboxylate | 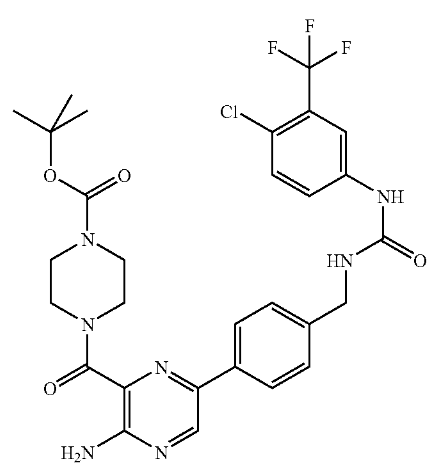 [SMILES: CC(C)(C)OC(=O)N1CCN(C(=O)c2nc(-c3ccc(CNC(=O)Nc4ccc(Cl)c(C(F)(F)F)c4)cc3)cnc2N)CC1] |

TABLE 1-continued

| Entry | Name | Structure |
|---|---|---|
| 211 | N-({3-[5-amino-6-(piperazin-1-ylcarbonyl)pyrazin-2-yl]phenyl}methyl)-N'-[4-chloro-3-(trifluoromethyl)phenyl]urea | 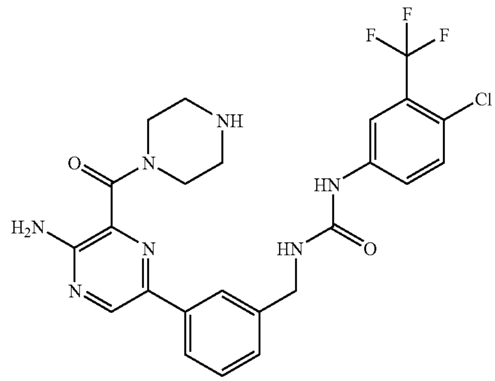 [SMILES: Nc1ncc(-c2cccc(CNC(=O)Nc3ccc(Cl)c(C(F)(F)F)c3)c2)nc1C(=O)N1CCNCC1] |
| 212 | N-({4-[5-amino-6-(piperazin-1-ylcarbonyl)pyrazin-2-yl]phenyl}methyl)-N'-[4-chloro-3-(trifluoromethyl)phenyl]urea | 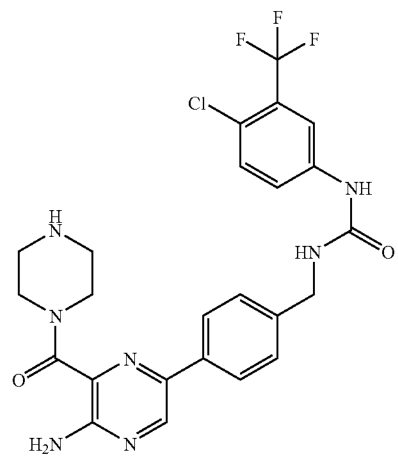 [SMILES: Nc1ncc(-c2ccc(CNC(=O)Nc3ccc(Cl)c(C(F)(F)F)c3)cc2)nc1C(=O)N1CCNCC1] |
| 213 | N-[4-chloro-3-(trifluoromethyl)phenyl]-N'-{[3-(1H-pyrazol-4-yl)phenyl]methyl}urea | 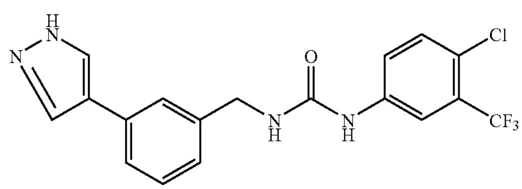 [SMILES: O=C(NCc1cccc(-c2cn[nH]c2)c1)Nc1ccc(Cl)c(C(F)(F)F)c1] |
| 214 | N-[4-chloro-3-(trifluoromethyl)phenyl]-N'-{[4-(1H-pyrazol-4-yl)phenyl]methyl}urea | 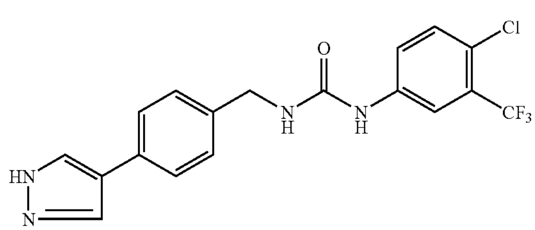 [SMILES: O=C(NCc1ccc(-c2cn[nH]c2)cc1)Nc1ccc(Cl)c(C(F)(F)F)c1] |
| 215 | [3-(2-piperazin-1-ylpyrimidin-5-yl)phenyl]methyl [4-chloro-3-(trifluoromethyl)phenyl]carbamate | 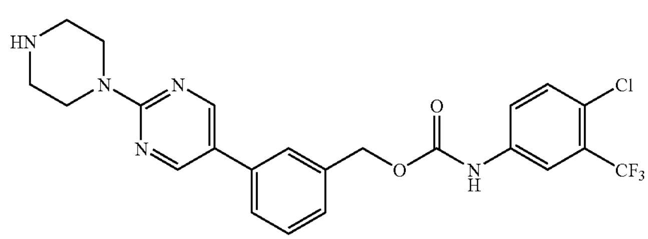 [SMILES: O=C(Nc1ccc(Cl)c(C(F)(F)F)c1)OCc1cccc(-c2cnc(N3CCNCC3)nc2)c1] |

TABLE 1-continued

| Entry | Name | Structure |
|---|---|---|
| 216 | [4-(2-piperazin-1-ylpyrimidin-5-yl)phenyl]methyl [4-chloro-3-(trifluoromethyl)phenyl]carbamate | 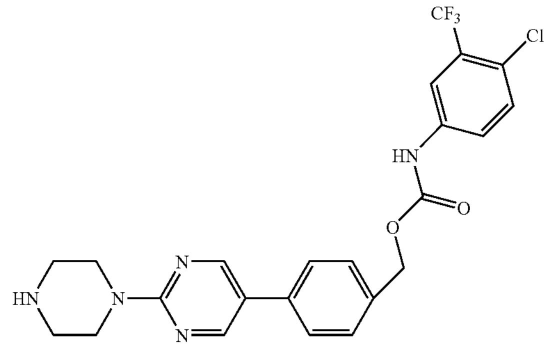 [SMILES: O=C(Nc1ccc(Cl)c(C(F)(F)F)c1)OCc1ccc(-c2cnc(N3CCNCC3)nc2)cc1] |
| 217 | N-{[3-(2-chloropyridin-3-yl)phenyl]methyl}-N'-[4-chloro-3-(trifluoromethyl)phenyl]urea | 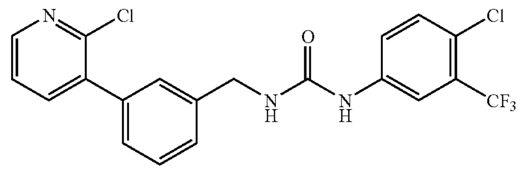 |
| 218 | N-{[4-(2-chloropyridin-3-yl)phenyl]methyl}-N'-[4-chloro-3-(trifluoromethyl)phenyl]urea | 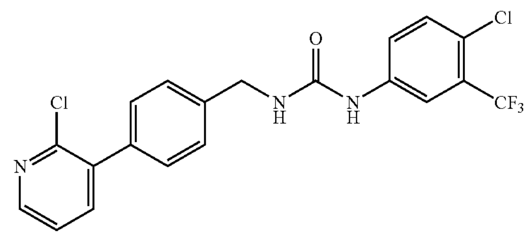 [SMILES: O=C(NCc1ccc(-c2cccnc2Cl)cc1)Nc1ccc(Cl)c(C(F)(F)F)c1] |
| 219 | N-[4-chloro-3-(trifluoromethyl)phenyl]-N'-{[3-(2-fluoropyridin-3-yl)phenyl]methyl}urea | 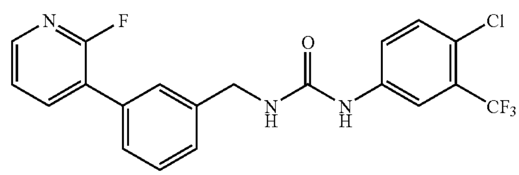 |
| 220 | N-[4-chloro-3-(trifluoromethyl)phenyl]-N'-{[4-(2-fluoropyridin-3-yl)phenyl]methyl}urea | 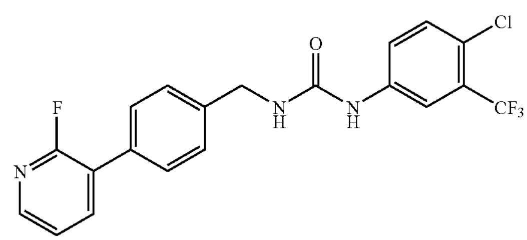 [SMILES: O=C(NCc1ccc(-c2cccnc2F)cc1)Nc1ccc(Cl)c(C(F)(F)F)c1] |
| 221 | [3-(1H-tetrazol-1-yl)phenyl]methyl [3-(trifluoromethyl)phenyl]carbamate | 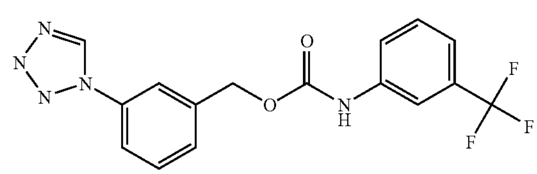 [SMILES: O=C(Nc1cccc(C(F)(F)F)c1)OCc1cccc(N2C=NNN2)c1] |
| 222 | [3-(1H-tetrazol-1-yl)phenyl]methyl [6-(trifluoromethyl)pyridin-2-yl]carbamate | 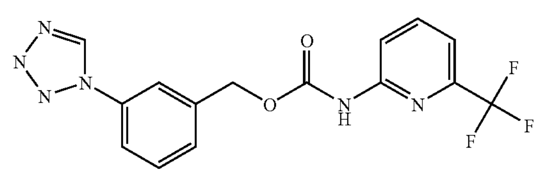 [SMILES: O=C(Nc1cccc(C(F)(F)F)n1)OCc1cccc(N2C=NNN2)c1] |

TABLE 1-continued

| Entry | Name |
|---|---|
| 223 | [3-(1H-tetrazol-1-yl)phenyl]methyl [4-(trifluoromethyl)pyridin-2-yl]carbamate |
| 224 | N-[4-chloro-3-(trifluoromethyl)phenyl]-N'-({3-[5-(methylthio)pyridin-2-yl]phenyl}methyl)urea |
| 225 | [3-(2,6-dimethylpyridin-3-yl)phenyl]methyl [4-chloro-3-(trifluoromethyl)phenyl]carbamate |
| 226 | {3-[5-(methyloxy)pyridin-3-yl]phenyl}methyl [4-chloro-3-(trifluoromethyl)phenyl]carbamate |
| 227 | 2,3'-bipyridin-6-ylmethyl [4-chloro-3-(trifluoromethyl)phenyl]carbamate |
| 228 | (6-pyrimidin-5-ylpyridin-2-yl)methyl [4-chloro-3-(trifluoromethyl)phenyl]carbamate |
| 229 | N-[4-chloro-3-(trifluoromethyl)phenyl]-N'-[(3-isoquinolin-4-ylphenyl)methyl]urea |
| 230 | N-[4-chloro-3-(trifluoromethyl)phenyl]-N'-[(4-isoquinolin-4-ylphenyl)methyl]urea |

TABLE 1-continued

| Entry | Name | Structure |
|---|---|---|
| 231 | [6-(1H-tetrazol-1-yl)pyridin-2-yl]methyl [4-(trifluoromethyl)pyridin-2-yl]carbamate | 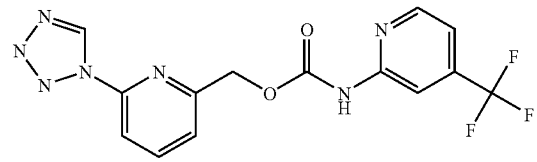 [SMILES: O=C(Nc1cc(C(F)(F)F)ccn1)OCc1cccc(N2C=NNN2)n1] |
| 232 | [3-(1H-pyrazol-4-yl)phenyl]methyl [4-chloro-3-(trifluoromethyl)phenyl]carbamate | 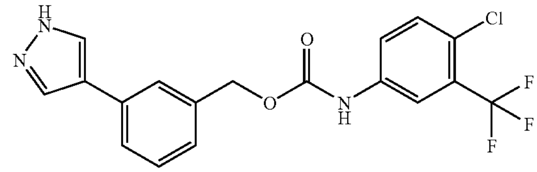 [SMILES: O=C(Nc1ccc(Cl)c(C(F)(F)F)c1)OCc1cccc(-c2cn[nH]c2)c1] |
| 233 | [4-(1H-pyrazol-4-yl)phenyl]methyl [4-chloro-3-(trifluoromethyl)phenyl]carbamate | 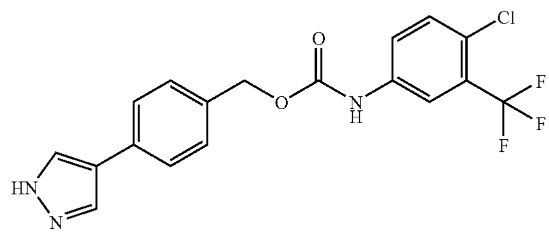 [SMILES: O=C(Nc1ccc(Cl)c(C(F)(F)F)c1)OCc1ccc(-c2cn[nH]c2)cc1] |

Another aspect of the invention is a pharmaceutical composition comprising the compound according to any one of embodiments [0022]-[0048] and a pharmaceutically acceptable carrier, hereinafter referred to as embodiment [0049].

Another aspect of the invention is a metabolite of the compound or the pharmaceutical composition according to any one of embodiments [0022]-[0049], hereinafter referred to as embodiment [0050].

Another aspect of the invention is a method for modulating the in-vivo activity of a kinase, the method comprising administering to a subject an effective amount of the compound according any of embodiments [0022]-[0048] or a compound selected from N-naphthalen-1-yl-2-{[3-(1H-tetrazol-1-yl)phenyl]oxy}acetamide, N-[4-(phenyloxy)phenyl]-2-{[3-(1H-tetrazol-1-yl)phenyl]oxy}acetamide, N-(3,4-dimethylphenyl)-2-{[3-(1H-tetrazol-1-yl)phenyl] oxy}acetamide, N-(2,3-dimethylphenyl)-2-{[3-(1H-tetrazol-1-yl)phenyl]oxy}acetamide, N-(2,4-dimethylphenyl)-2-{[3-(1H-tetrazol-1-yl)phenyl] oxy}acetamide, N-(2,5-dimethylphenyl)-2-{[3-(1H-tetrazol-1-yl)phenyl]oxy}acetamide, N-(3,5-dimethylphenyl)-2-{[3-(1H-tetrazol-1-yl)phenyl] oxy}acetamide, N-(2,6-dimethyl-phenyl)-2-{[3-(1H-tetrazol-1-yl)phenyl]oxy}acetamide, 2-{[3-(1H-tetrazol-1-yl)phenyl]oxy}-N-(2,4,6-trimethylphenyl)acetamide, N-(2-ethylphenyl)-2-{[3-(1H-tetrazol-1-yl)phenyl] oxy}acetamide, N-(4-ethylphenyl)-2-{[3-(1H-tetrazol-1-yl) phenyl]oxy}acetamide, N-(2,6-diethylphenyl)-2-{[3-(1H-tetrazol-1-yl)phenyl]oxy}acetamide, N-[2-(methyloxy) phenyl]-2-{[3-(1H-tetrazol-1-yl)phenyl]oxy}acetamide, N-[2-(ethyloxy)phenyl]-2-{[3-(1H-tetrazol-1-yl)phenyl] oxy}acetamide, N-[3-(ethyloxy)phenyl]-2-{[3-(1H-tetrazol-1-yl)phenyl]oxy}acetamide, N-[2,4-bis(methyloxy)phenyl]-2-{[3-(1H-tetrazol-1-yl)phenyl]oxy}acetamide, N-[4-(dimethylamino)phenyl]-2-{[3-(1H-tetrazol-1-yl)phenyl] oxy}acetamide, N-(2,3-dichlorophenyl)-2-{[3-(1H-tetrazol-1-yl)phenyl]oxy}acetamide, N-(4-chloro-3-methylphenyl)-2-{[3-(1H-tetrazol-1-yl)phenyl]oxy}acetamide, N-(4-bromophenyl)-2-{[3-(1H-tetrazol-1-yl)phenyl] oxy}acetamide, N-(2-fluorophenyl)-2-{[3-(1H-tetrazol-1-yl)phenyl]oxy}acetamide, N-(4-fluorophenyl)-2-{[3-(1H-tetrazol-1-yl)phenyl]oxy}acetamide, 2-{[3-(1H-tetrazol-1-yl)phenyl]oxy}-N-[2(trifluoro-methyl)phenyl]acetamide, 2-{[3-(1H-tetrazol-1-yl)phenyl]oxy}-N-[3-(trifluoromethyl) phenyl]acetamide, methyl 4-[({[3-(1H-tetrazol-1-yl)phenyl] oxy}acetyl)amino]benzoate, ethyl 4-[({[3-(1H-tetrazol-1-yl) phenyl]oxy}acetyl)amino]benzoate, 3-[({[3-(1H-tetrazol-1-yl)phenyl]oxy}acetyl)amino]benzoic acid, N-[3-(methyloxy)phenyl]-2-{[3-(1H-tetrazol-1-yl)phenyl] oxy}acetamide, N-[4-(methyloxy)phenyl]-2-{[3-(1H-tetrazol-1-yl)phenyl]oxy}acetamide, N-[2-chloro-5-(trifluoromethyl)phenyl]-2-{[3-(1H-tetrazol-1-yl)phenyl] oxy}acetamide, N-[4-chloro-3-(trifluoromethyl)phenyl]-2-{[3-(4H-1,2,4-triazol-4-yl)phenyl]oxy}acetamide, N-(4-chlorophenyl)-2-{[3-(1H-tetrazol-1-yl)phenyl] oxy}acetamide, N-(4-aminophenyl)-2-{[3-(1H-tetrazol-1-yl)phenyl]oxy}acetamide, and N-(4-acetylphenyl)-2-{[3-(1H-tetrazol-1-yl)phenyl]oxy}acetamide, hereinafter referred to as embodiment [0051].

Another aspect of the invention is the method according to embodiment [0051], wherein the kinase is c-Kit, hereinafter referred to as embodiment [0052].

Another aspect of the invention is the method according to embodiment [0052], wherein modulating the in vivo activity of c-Kit comprises inhibition of c-Kit, hereinafter referred to as embodiment [0053].

Another aspect of the invention is a method of treating diseases or disorders associated with uncontrolled, abnormal, and/or unwanted cellular activities, the method comprising administering, to a mammal in need thereof, a therapeutically effective amount of the compound or the pharmaceutical composition as described in any one of embodiments [0022]-[0049] or a compound, or a pharmaceutical composition comprising said compound, selected from N-naphthalen-1-yl-2-

{[3-(1H-tetrazol-1-yl)phenyl]oxy}acetamide, N-[4-(phenyloxy)phenyl]-2-{[3-(1H-tetrazol-1-yl)phenyl]oxy}acetamide, N-(3,4-dimethylphenyl)-2-{[3-(1H-tetrazol-1-yl)phenyl]oxy}acetamide, N-(2,3-dimethylphenyl)-2-{[3-(1H-tetrazol-1-yl)phenyl]oxy}acetamide, N-(2,4-dimethylphenyl)-2-{[3-(1H-tetrazol-1-yl)phenyl]oxy}acetamide, N-(2,5-dimethylphenyl)-2-{[3-(1H-tetrazol-1-yl)phenyl]oxy}acetamide, N-(3,5-dimethylphenyl)-2-{[3-(1H-tetrazol-1-yl)phenyl]oxy}acetamide, N-(2,6-dimethyl-phenyl)-2-{[3-(1H-tetrazol-1-yl)phenyl]oxy}acetamide, 2-{[3-(1H-tetrazol-1-yl)phenyl]oxy}-N-(2,4,6-trimethylphenyl)acetamide, N-(2-ethyl-phenyl)-2-{[3-(1H-tetrazol-1-yl)phenyl]oxy}acetamide, N-(4-ethylphenyl)-2-{[3-(1H-tetrazol-1-yl)phenyl]oxy}acetamide, N-(2,6-diethylphenyl)-2-{[3-(1H-tetrazol-1-yl)phenyl]oxy}acetamide, N-[2-(methyloxy)phenyl]-2-{[3-(1H-tetrazol-1-yl)phenyl]oxy}acetamide, N-[2-(ethyloxy)phenyl]-2-{[3-(1H-tetrazol-1-yl)phenyl]oxy}acetamide, N-[3-(ethyloxy)phenyl]-2-{[3-(1H-tetrazol-1-yl)phenyl]oxy}acetamide, N-[2,4-bis(methyl-oxy)phenyl]-2-{[3-(1H-tetrazol-1-yl)phenyl]oxy}acetamide, N-[4-(dimethylamino)-phenyl]-2-{[3-(1H-tetrazol-1-yl)phenyl]oxy}acetamide, N-(2,3-dichlorophenyl)-2-{[3-(1H-tetrazol-1-yl)phenyl]oxy}acetamide, N-(4-chloro-3-methylphenyl)-2-{[3-(1H-tetrazol-1-yl)phenyl]oxy}acetamide, N-(4-bromophenyl)-2-{[3-(1H-tetrazol-1-yl)phenyl]oxy}acetamide, N-(2-fluorophenyl)-2-{[3-(1H-tetrazol-1-yl)phenyl]oxy}acetamide, N-(4-fluorophenyl)-2-{[3-(1H-tetrazol-1-yl)phenyl]oxy}acetamide, 2-{[3-(1H-tetrazol-1-yl)phenyl]oxy}-N-[2-(trifluoro-methyl)phenyl]acetamide, 2-{[3-(1H-tetrazol-1-yl)phenyl]oxy}-N-[3-(trifluoromethyl)phenyl]acetamide, methyl 4-[({[3-(1H-tetrazol-1-yl)phenyl]oxy}acetyl)amino]benzoate, ethyl 4-[({[3-(1H-tetrazol-1-yl)phenyl]oxy}acetyl)amino]benzoate, 3-[({[3-(1H-tetrazol-1-yl)phenyl]oxy}acetyl)amino]benzoic acid, N-[3-(methyloxy)phenyl]-2-{[3-(1H-tetrazol-1-yl)phenyl]oxy}acetamide, N-[4-(methyloxy)phenyl]-2-{[3-(1H-tetrazol-1-yl)phenyl]oxy}acetamide, N-[2-chloro-5-(trifluoromethyl)phenyl]-2-{[3-(1H-tetrazol-1-yl)phenyl]oxy}acetamide, N-[4-chloro-3-(trifluoromethyl)phenyl]-2-{[3-(4H-1,2,4-triazol-4-yl)phenyl]oxy}acetamide, N-(4-chlorophenyl)-2-{[3-(1H-tetrazol-1-yl)phenyl]oxy}acetamide, N-(4-aminophenyl)-2-{[3-(1H-tetrazol-1-yl)phenyl]oxy}acetamide, and N-(4-acetylphenyl)-2-{[3-(1H-tetrazol-1-yl)phenyl]oxy}acetamide, hereinafter referred to as embodiment [0054].

Another aspect of the invention is a method of screening for modulators of c-Kit, the method comprising combining the compound according to any one of embodiments [0022]-[0048] or a compound selected from N-naphthalen-1-yl-2-{[3-(1H-tetrazol-1-yl)phenyl]oxy}acetamide, N-[4-(phenyloxy)phenyl]-2-{[3-(1H-tetrazol-1-yl)phenyl]oxy}acetamide, N-(3,4-dimethylphenyl)-2-{[3-(1H-tetrazol-1-yl)phenyl]oxy}acetamide, N-(2,3-dimethylphenyl)-2-{[3-(1H-tetrazol-1-yl)phenyl]oxy}acetamide, N-(2,4-dimethylphenyl)-2-{[3-(1H-tetrazol-1-yl)phenyl]oxy}acetamide, N-(2,5-dimethylphenyl)-2-{[3-(1H-tetrazol-1-yl)phenyl]oxy}acetamide, N-(3,5-dimethylphenyl)-2-{[3-(1H-tetrazol-1-yl)phenyl]oxy}acetamide, N-(2,6-dimethyl-phenyl)-2-{[3-(1H-tetrazol-1-yl)phenyl]oxy}acetamide, 2-{[3-(1H-tetrazol-1-yl)phenyl]oxy}-N-(2,4,6-trimethylphenyl)acetamide, N-(2-ethylphenyl)-2-{[3-(1H-tetrazol-1-yl)phenyl]oxy}acetamide, N-(4-ethylphenyl)-2-{[3-(1H-tetrazol-1-yl)phenyl]oxy}acetamide, N-(2,6-diethylphenyl)-2-{[3-(1H-tetrazol-1-yl)phenyl]oxy}acetamide, N-[2-(methyloxy)phenyl]-2-{[3-(1H-tetrazol-1-yl)phenyl]oxy}acetamide, N-[2-(ethyloxy)phenyl]-2-{[3-(1H-tetrazol-1-yl)phenyl]oxy}acetamide, N-[3-(ethyloxy)phenyl]-2-{[3-(1H-tetrazol-1-yl)phenyl]oxy}acetamide, N-[2,4-bis(methyloxy)phenyl]-2-{[3-(1H-tetrazol-1-yl)phenyl]oxy}acetamide, N-[4-(dimethylamino)phenyl]-2-{[3-(1H-tetrazol-1-yl)phenyl]oxy}acetamide, N-(2,3-dichlorophenyl)-2-{[3-(1H-tetrazol-1-yl)phenyl]oxy}acetamide, N-(4-chloro-3-methylphenyl)-2-{[3-(1H-tetrazol-1-yl)phenyl]oxy}acetamide, N-(4-bromophenyl)-2-{[3-(1H-tetrazol-1-yl)phenyl]oxy}acetamide, N-(2-fluorophenyl)-2-{[3-(1H-tetrazol-1-yl)phenyl]oxy}acetamide, N-(4-fluorophenyl)-2-{[3-(1H-tetrazol-1-yl)phenyl]oxy}acetamide, 2-{[3-(1H-tetrazol-1-yl)phenyl]oxy}-N-[2-(trifluoro-methyl)phenyl]acetamide, and at least one candidate agent and determining the effect of the candidate agent on c-Kit activity, hereinafter referred to as embodiment [0055].

Another aspect of the invention is a method of inhibiting proliferative activity in a cell, the method comprising administering an effective amount of a composition comprising the compound according any one of embodiments [0022]-[0048] or a compound selected from N-naphthalen-1-yl-2-{[3-(1H-tetrazol-1-yl)phenyl]oxy}acetamide, N-[4-(phenyloxy)phenyl]-2-{[3-(1H-tetrazol-1-yl)phenyl]oxy}acetamide, N-(3,4-dimethylphenyl)-2-{[3-(1H-tetrazol-1-yl)phenyl]oxy}acetamide, N-(2,3-dimethylphenyl)-2-{[3-(1H-tetrazol-1-yl)phenyl]oxy}acetamide, N-(2,4-dimethylphenyl)-2-{[3-(1H-tetrazol-1-yl)phenyl]oxy}acetamide, N-(2,5-dimethylphenyl)-2-{[3-(1H-tetrazol-1-yl)phenyl]oxy}acetamide, N-(3,5-dimethylphenyl)-2-{[3-(1H-tetrazol-1-yl)phenyl]oxy}acetamide, N-(2,6-dimethyl-phenyl)-2-{[3-(1H-tetrazol-1-yl)phenyl]oxy}acetamide, 2-{[3-(1H-tetrazol-1-yl)phenyl]oxy}-N-(2,4,6-trimethylphenyl)acetamide, N-(2-ethylphenyl)-2-{[3-(1H-tetrazol-1-yl)phenyl]oxy}acetamide, N-(4-ethylphenyl)-2-{[3-(1H-tetrazol-1-yl)phenyl]oxy}acetamide, N-(2,6-diethylphenyl)-2-{[3-(1H-tetrazol-1-yl)phenyl]oxy}acetamide, N-[2-(methyloxy)phenyl]-2-{[3-(1H-tetrazol-1-yl)phenyl]oxy}acetamide, N-[2-(ethyloxy)phenyl]-2-{[3-(1H-tetrazol-1-yl)phenyl]oxy}acetamide, N-[3-(ethyloxy)phenyl]-2-{[3-(1H-tetrazol-1-yl)phenyl]oxy}acetamide, N-[2,4-bis(methyloxy)phenyl]-2-{[3-(1H-tetrazol-1-yl)phenyl]oxy}acetamide, N-[4-(dimethylamino)phenyl]-2-{[3-(1H-tetrazol-1-yl)phenyl]oxy}acetamide, N-(2,3-dichlorophenyl)-2-{[3-(1H-tetrazol-1-yl)phenyl]oxy}acetamide, N-(4-chloro-3-methylphenyl)-2-{[3-(1H-tetrazol-1-yl)phenyl]oxy}acetamide, N-(4-bromophenyl)-2-{[3-(1H-tetrazol-1-yl)phenyl]oxy}acetamide, N-(2-fluorophenyl)-2-{[3-(1H-tetrazol-1-yl)phenyl]oxy}acetamide, N-(4-fluorophenyl)-2-{[3-(1H-tetrazol-1-yl)phenyl]oxy}acetamide, 2-{[3-(1H-tetrazol-1-yl)phenyl]oxy}-N-[2-(trifluoro-methyl)phenyl]acetamide, 2-{[3-(1H-tetrazol-1-yl)phenyl]oxy}-N-[3-(trifluoromethyl)phenyl]acetamide, methyl 4-[({[3-(1H-tetrazol-1-yl)phenyl]oxy}acetyl)amino]benzoate, ethyl 4-[({[3-(1H-tetrazol-1-yl)phenyl]oxy}acetyl)amino]benzoate, 3-[({[3-(1H-tetrazol-1-yl)phenyl]oxy}acetyl)amino]benzoic acid, N-[3-(methyloxy)phenyl]-2-{[3-(1H-tetrazol-1-yl)phenyl]oxy}acetamide, N-[4-(methyloxy)phenyl]-2-{[3-(1H-tetrazol-1-yl)phenyl]oxy}acetamide, N-[2-chloro-5-(trifluoromethyl)phenyl]-2-{[3-(1H-tetrazol-1-yl)phenyl]oxy}acetamide, N-[4-chloro-3-(trifluoromethyl)phenyl]-2-{[3-(4H-1,2,4-triazol-4-yl)phenyl]oxy}acetamide, N-(4-chlorophenyl)-2-{[3-(1H-tetrazol-1-yl)phenyl]oxy}acetamide, N-(4-aminophenyl)-2-{[3-(1H-tetrazol-1-yl)phenyl]oxy}acetamide, and N-(4-acetylphenyl)-2-{[3-(1H-tetrazol-1-yl)phenyl]oxy}acetamide, to a cell or a plurality of cells, hereinafter referred to as embodiment [0056].

DEFINITIONS

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond. The symbol " " refers to a group on a double-bond as occupying either position on the terminus of a double bond to which the symbol is attached; that is, the geometry, E- or Z-, of the double bond is ambiguous. When a group is depicted removed from its parent formula, the " " symbol will be used at the end of the bond which was theoretically cleaved in order to separate the group from its parent structural formula.

If a group "R" is depicted as "floating" on a ring system, as for example in the formula:

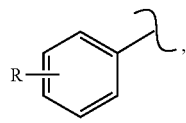

then, unless otherwise defined, a substituent "R" may reside on any atom of the ring system, assuming replacement of a depicted, implied, or expressly defined hydrogen from one of the ring atoms, so long as a stable structure is formed.

if a group "R" is depicted as floating on a fused ring system, as for example in the formulae:

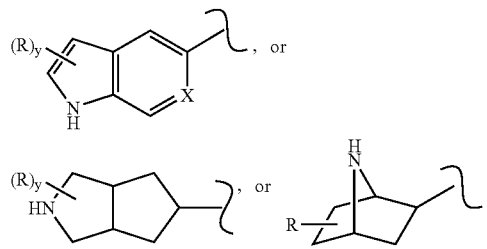

then, unless otherwise defined, a substituent "R" may reside on any atom of the fused ring system, assuming replacement of a depicted (for example the —NH— in the formula above), implied (for example as in the formula above, where the hydrogens are not shown but understood to be present), or expressly defined hydrogen (for example where in the formula above, "X" equals ═C(H)—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When there are more than one such depicted "floating" groups, as for example in the formulae:

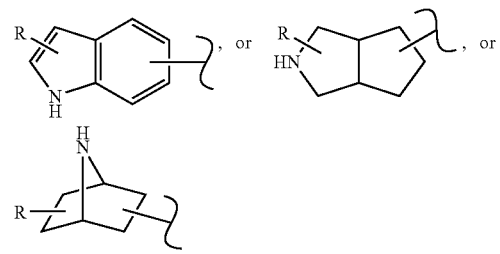

where there are two groups, namely, the "R" and the bond indicating attachment to a parent structure; then, unless otherwise defined, the "floating" groups may reside on any atoms of the ring system, again assuming each replaces a depicted, implied, or expressly defined hydrogen on the ring system.

When a group "R" is depicted as existing on a ring system containing saturated carbons, as for example in the formula:

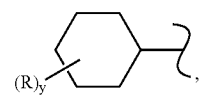

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

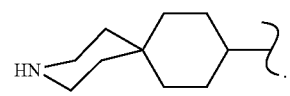

When a compound is described as "comprising" and then a graphical depiction is used, for example;

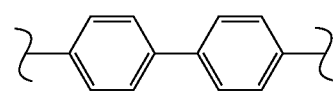

then it is meant to mean that the compound comprises at least that core structural formula as depicted, wherein substituents that are not depicted (hydrogen or other) are implied. The example shows a biphenylene divalent radical, thus if a compound is said to comprise the structural formula as depicted, then any compound containing a substituted or non-substituted biphenylene radical of the geometry specified in the graphic would be meant to be included in such a definition. In most cases such a definition will be much more narrowly defined than in the example above, for example including letter variables that designate particular substituents or atoms.

"Alkyl" is intended to include linear, branched, or cyclic hydrocarbon structures and combinations thereof, inclusively. For example, "$C_8$alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$alkyl" is meant to include n-butyl, sec-butyl, isobutyl, t-butyl, isobutenyl and but-2-yne radicals; and for example, "propyl" or "$C_3$alkyl" each include n-propyl, propenyl, and isopropyl.

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—CH$_2$CH$_2$—), propylene (—CH$_2$CH$_2$CH$_2$—), dimethylpropylene (—CH$_2$C(CH$_3$)$_2$CH$_2$—), and cyclohexylpropylene (—CH$_2$CH$_2$CH(C$_6$H$_{13}$)).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —OCH$_2$CH$_2$OCH$_3$, and glycol ethers such as polyethyleneglycol and —O(CH$_2$CH$_2$O)$_x$CH$_3$, where x is an integer of between about two and about twenty, in another example, between about two and about ten, and in a further example between about two and about five. Another exemplary substituted alkoxy group is hydroxyalkoxy or —OCH$_2$(CH$_2$)$_y$OH, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —NH$_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, furanyl-oxy-sulfonamino.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two groups attached thereto. For a more specific example, "phenylene" refers to a divalent phenyl ring radical. A phenylene, thus may have more than two groups attached, but is defined by the minimum of two groups attached thereto.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted.

"Lower arylalkyl" refers to an arylalkyl where the "alkyl" portion of the group has one to six carbons; this can also be referred to as $C_{1-6}$ arylalkyl.

"Exo-alkenyl" refers to a double bond that emanates from an annular carbon, and is not within the ring system, for example the double bond depicted in the formula below.

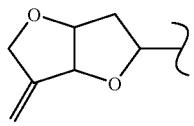

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroatom" refers to O, S, N, or P.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by the minimum of two groups attached thereto.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic.

Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted aryl$C_{1-8}$ alkyl," optional substitution may occur on both the "$C_{1-8}$ alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitution are listed below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

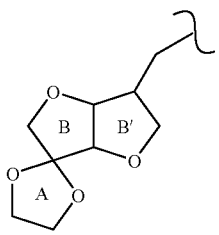

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from: optionally substituted alkyl (for example, fluoromethyl), optionally substituted aryl (for example, 4-hydroxyphenyl), optionally substituted arylalkyl (for example, 1-phenyl-ethyl), optionally substituted heterocyclylalkyl (for example, 1-pyridin-3-yl-ethyl), optionally substituted heterocyclyl (for example, 5-chloro-pyridin-3-yl or 1-methyl-piperidin-4-yl), optionally substituted alkoxy, alkylenedioxy (for example methylenedioxy), optionally substituted amino (for example, alkylamino and dialkylamino), optionally substituted amidino, optionally substituted aryloxy (for example, phenoxy), optionally substituted arylalkyloxy (for example, benzyloxy), carboxy (—$CO_2$H), carboalkoxy (that is, acyloxy or —OC(=O)R), carboxyalkyl (that is, esters or —$CO_2$R), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —$S(O_2)$—H, —$S(O_2)$-(optionally substituted alkyl), —$S(O_2)$-optionally substituted aryl), —$S(O_2)$-(optionally substituted heterocyclyl), —$S(O_2)$-(optionally substituted alkoxy), —$S(O_2)$-optionally substituted aryloxy), and —$S(O_2)$-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —$OCH_2$—, then it is understood that either of two potential partners may be bound to the divalent radical at one end, and the other partner is necessarily bound to the other end of the divalent radical, unless stated explicitly otherwise. Stated another way, divalent radicals are not to be construed as limited to the depicted orientation, for example "—$OCH_2$—" is meant to mean not only "—$OCH_2$—" as drawn, but also "—$CH_2O$—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "klinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealomal], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular c-Kit-ligand complexes, and their corresponding x-ray structure coordinates can be used to reveal new structural information useful for understanding biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket General Administration Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example c-Kit receptor kinase, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, c-Kit protein may be done in a number of ways. In one example, the candidate agent (the compound of the invention) is labeled, for example, with a fluorescent or radioactive moiety and binding determined directly. For example, thus may be done by attaching all or a portion of the c-Kit protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, for example, radioisotope, fluorescent tag, enzyme, antibodies, particles such as magnetic particles, chemiluminescent tags or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, c-Kit protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to c-Kit.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to c-Kit, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to c-Kit protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to c-Kit and thus is capable of binding to, and potentially modulating, the activity of the c-Kit. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to c-Kit with a higher affinity. Thus, if the candidate agent is labeled, the presence of the label on the support, coupled with a lack of competitor binding, may indicate the candidate agent is capable of binding to c-Kit.

It may be of value to identify the binding site of c-Kit. This can be done in a variety of ways. In one embodiment, once c-Kit has been identified as binding to the candidate agent, the c-Kit is fragmented or modified and the assays repeated to identify the necessary components for binding.

Modulation is tested by screening for candidate agents capable of modulating the activity of c-Kit comprising the steps of combining a candidate agent with c-Kit, as above, and determining an alteration in the biological activity of the c-Kit. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native c-Kit, but cannot bind to modified c-Kit.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

Abbreviations and their Definitions

The following abbreviations and terms have the indicated meanings throughout:

| Abbreviation | Meaning |
| --- | --- |
| Ac | acetyl |
| ACN | acetonitrile |
| ATP | adenosine triphosphate |
| BNB | 4-bromomethyl-3-nitrobenzoic acid |
| Boc | t-butyloxy carbonyl |
| br | broad |
| Bu | butyl |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DBU | Diazabicyclo[5.4.0]undec-7-ene |
| DCM | dichloromethane = methylene chloride = $CH_2Cl_2$ |
| DCE | dichloroethylene |
| DEAD | diethyl azodicarboxylate |
| DIC | diisopropylcarbodiimide |
| DIEA | N,N-diisopropylethyl amine |
| DMAP | 4-N,N-dimethylaminopyridine |
| DMF | N,N-dimethylfonnamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | ethyl |
| Fmoc | 9-fluorenylmethoxycarbonyl |
| g | gram(s) |
| GC | gas chromatography |
| h or hr | hour(s) |
| HATU | O-(7-Azabenzotriazol-1-yl)-1,1,3,3-tetramethyluronium hexafluorophosphate |
| HMDS | hexamethyldisilazane |
| HOAc | acetic acid |
| HOBt | hydroxybenzotriazole |
| HPLC | high pressure liquid chromatography |
| L | liter(s) |
| M | molar or molarity |
| m | multiplet |
| Me | methyl |
| mesyl | methanesulfonyl |
| mg | milligram(s) |
| MHz | megahertz (frequency) |
| Min | minute(s) |
| mL | milliliter(s) |
| mM | millimolar |
| mmol | millimole(s) |
| mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | nanomolar |
| NMM | N-methylmorpholine |
| NMO | N-methylmorpholine oxide |
| NMR | nuclear magnetic resonance spectroscopy |
| PEG | polyethylene glycol |
| pEY | poly-glutamine, tyrosine |
| Ph | phenyl |
| PhOH | phenol |
| PfP | pentafluorophenol |
| PfPy | pentafluoropyridine |
| PPTS | Pyridinium p-toluenesulfonate |
| Py | pyridine |
| PyBroP | bromo-tris-pyrrolidino-phosphonium hexafluorophosphate |
| q | quartet |
| RT | Room temperature |
| Sat'd | saturated |
| s | singlet |
| SEM-Cl | chloromethyl 2-trimethylsilylethyl ether |
| s- | secondary |
| t- | tertiary |
| t or tr | triplet |
| TBDMS | t-butyldimethylsilyl |
| TES | triethylsilane |
| TFA | trifluoroacetic acid |
| THF | tetrahydrofuran |
| TMOF | trimethyl orthoformate |
| TMS | trimethylsilyl |
| tosyl | p-toluenesulfonyl |
| Trt | triphenylmethyl |
| μL | microliter(s) |
| μM | Micromole(s) or micromolar |

Synthesis of Compounds

Schemes 1-3 depict general synthetic routes for compounds of the invention and are not intended to be limiting. Specific examples are described subsequently to this general synthetic description. With the descriptions of the general routes and the specific examples thereafter, one of ordinary skill in the art would be able to make compounds of the invention as described.

Scheme 1 shows that in general, compounds of formula I can be made, for example, via a linear route. For example, ring A and ring B can be linked via functionality a' and b', respectively. Functionality a' and b' are used to construct linking group $L^1$ of formula I. In the case that $L^1$ is absent, functionality a' and b' are used to couple ring A and ring B directly via a single bond. Analogously, functionality b' and c' are used to make linking group $L^2$ of formula I. The order of the steps described above can be varied, that is, ring A and B can be linked first, followed by ring C to ring B (as a part of A-$L^1$-B); or ring B and C can be linked first, followed by ring A to ring B (as a part of B-$L^2$-C). Substitution $R^1$, $R^2$, and $R^3$ can be introduced and or modified at any stage of the synthesis of compounds of formula I.

Scheme 1

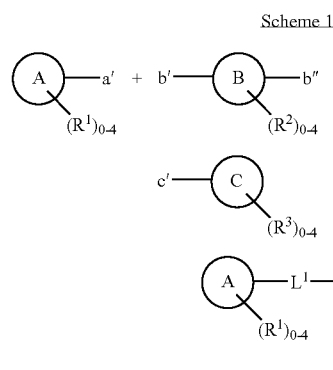

Scheme 2 shows another example, where in this case ring A is synthesized from functionality b', rather than coupled to it as a pre-existing ring. In these examples generally, but not necessarily, $L^1$ is a direct bond between ring A and ring B. Once ring A is made, then functionality b" is used to couple ring C and thereby form linking group $L^2$ (for example see "Example 1" below).

Scheme 2

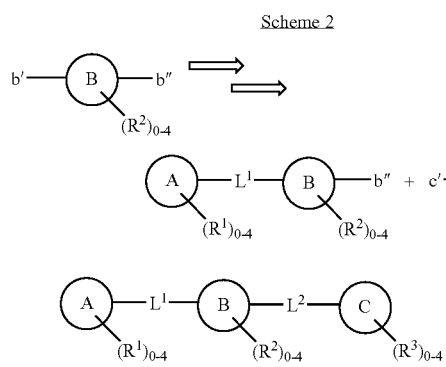

Scheme 3 shows yet another example, where in this case, linking group $L^2$, for example, is pre-existing with functionality $1^{2'}$ and $1^{2''}$ thereon. In this example, ring B is coupled to linking group $L^2$, by using functionality (not depicted) on ring B and functionality $1^{2'}$ on linking group $L^2$ to make intermediate b'-B-$L^2$-C. Alternatively, ring B is synthesized on linking group $L^2$, by using functionality $1^{2'}$ to make intermediate b'-B-$L^2$-C. Either way, functionality b' is then used, for example, to synthesize or link ring A to ring B as depicted.

Scheme 3

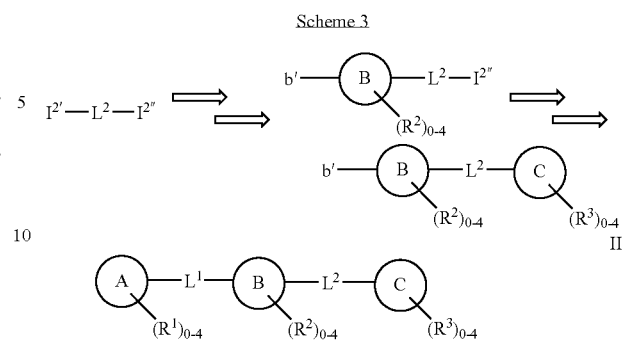

One of ordinary skill in the art would recognize that the descriptions associated with Schemes 1-3 are generalizations; provided below are exemplary chemistries used to make compounds in accordance with Schemes 1-3 and Formula I. One of ordinary skill in the art would also appreciate that there are other combinations of steps and chemistries that can be used to make compounds of the invention.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety. Generally, but not necessarily, each example set out below describes a multi-step synthesis as outlined above.

Example 1

Synthesis of N-[4-chloro-3-(trifluoromethyl)phenyl]-2-{(3-(1H-tetrazol-1-yl)-phenyl]oxy}acetamide 4

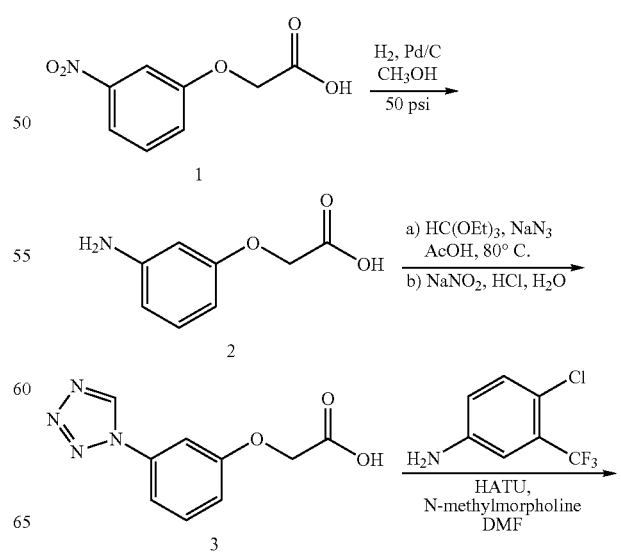

3-Aminophenoxyacetic acid 2: To a 2 L pressure vessel was added 3-nitrophenoxyacetic acid 1 (21.7 g, 110 mmol, 1.0 eq.) and methanol (600 mL). The resulting solution was purged with $N_2$ for 5 min. 10% Pd/C (900 mg) was added to the solution and the vessel was placed on a Parr hydrogenator at 50 psi for 3 h. After removal from the Parr apparatus, the reaction mixture was gray in color, indicating the precipitation of product. DMF (400 mL) was added and was stirred until it was evident that the precipitated product had dissolved in the solvent phase. The Pd/C was removed by filtration and the filtrate was concentrated under high vacuum to yield a dark brown solid (14 g, 76%). LC/MSD (HP Series 1100 MSD) MS (ES+) m/z 168.0 (M+H)$^{+1}$ $^1$H-NMR, Varian 400 MHz (DMSO-d$_6$) δ 7.93 (s, 1H), 6.86 (t, 1H), 6.14-5.99 (m, 3H), 4.50 (s, 2H) ppm.

3-Tetrazol-1-ylphenoxyacetic acid 3: To a 250 mL round-bottomed flask was added 3-aminophenoxyacetic acid 2 (10.3 g, 61.6 mmol, 1.0 eq.) and a stirbar. Triethylorthoformate (33 mL, 197 mmol, 3.2 eq.) was added followed by sodium azide (5.00 g, 77.0 mmol; 1.25 eq.) and acetic acid (56 mL, 986 mmol, 16 eq.). The viscous mixture was heated at 80° C. in an oil bath with stirring for 2 h. Upon heating, the mixture became homogeneous. The reaction mixture was removed from the oil bath and transferred to a 500 mL Erlenmeyer flask. The flask was cooled to 0° C. in an ice bath upon which $H_2O$ (150 mL) and 6N HCl (80 mL) was added. In a separate flask, a solution of NaNO$_2$ (5 g) in $H_2O$ (20 mL) was prepared. The NaNO$_2$ solution was added slowly to the reaction mixture. Vigorous bubbling was evident. Upon completion of addition, a gray precipitate formed in the flask. The suspension was filtered to yield a light gray solid (8.31 g, 61%). LC/MSD (HP Series 1100 MSD) MS (ES+) m/z 219.1 (M−H)$^{-1}$ $^1$H-NMR, Varian 400 MHz (DMSO-d$_6$) δ 13.12 (bs, 1H), 10.10 (s, 1H), 7.56-7.48 (m, 3H), 7.13-7.10 (m, 1H), 4.81 (s, 2H) ppm.

N-[4-chloro-3-(trifluoromethyl)phenyl]-2-{(3-(1H-tetrazol-1-yl)-phenyl]oxy}acetamide 4: To a 25 mL recovery flask was added 3-tetrazol-1-ylphenoxyacetic acid 3 (200 mg, 0.908 mmol, 1.0 eq.) and a stirbar. 1-Ethyl-3-(3'-dimethylaminopropyl)carbodiimide hydrochloride (261 mg, 1.36 mmol, 1.5 eq.) and 1-hydroxybenzotriazole (184 mg, 1.36 mmol, 1.5 eq.) were added to the flask. DMF (10 mL) and N-methylmorpholine (300 µL, 2.72 mmol, 3.0 eq.) were added to the reaction flask. The mixture was allowed to stir for 30 min at room temperature. 5-amino-2-chlorobenzotrifluoride (355 mg, 1.82 mmol, 2.0 eq.) was added to the flask and the resulting mixture was allowed to stir overnight at room temperature. The reaction mixture was diluted with ethyl acetate (100 mL) and washed with a succession of $H_2O$ (1×50 mL), 10% aq. LiCl (3×50 mL), and sat'd aq. NaCl (1×50 mL). The aqueous phases were combined and extracted with ethyl acetate (2×30 mL). The combined organic phases were dried over anhydrous Na$_2$SO$_4$, filtered, and concentrated to yield an off-white solid, which did not require further purification (165 mg, 46%). LC/MSD (HP Series 1100 MSD) MS (ES+) m/z 398.0 (M+H)$^{+1}$ $^1$H-NMR, Varian 400 MHz (DMSO-d$_6$) δ 10.55 (bs, 1H), 10.09 (s, 1H), 8.22 (d, 1H), 7.93-7.91 (m, 1H), 7.68 (d, 1H), 7.61-7.51 (m, 3H), 7.21-7.18 (m, 1H), 4.88 (s, 2H) ppm.

Example 2

Synthesis of N-[4-chloro-3-(trifluoromethyl)phenyl]-2-{[3-(1H-1,2,3-triazol-1-yl)phenyl]oxy}acetamide 8

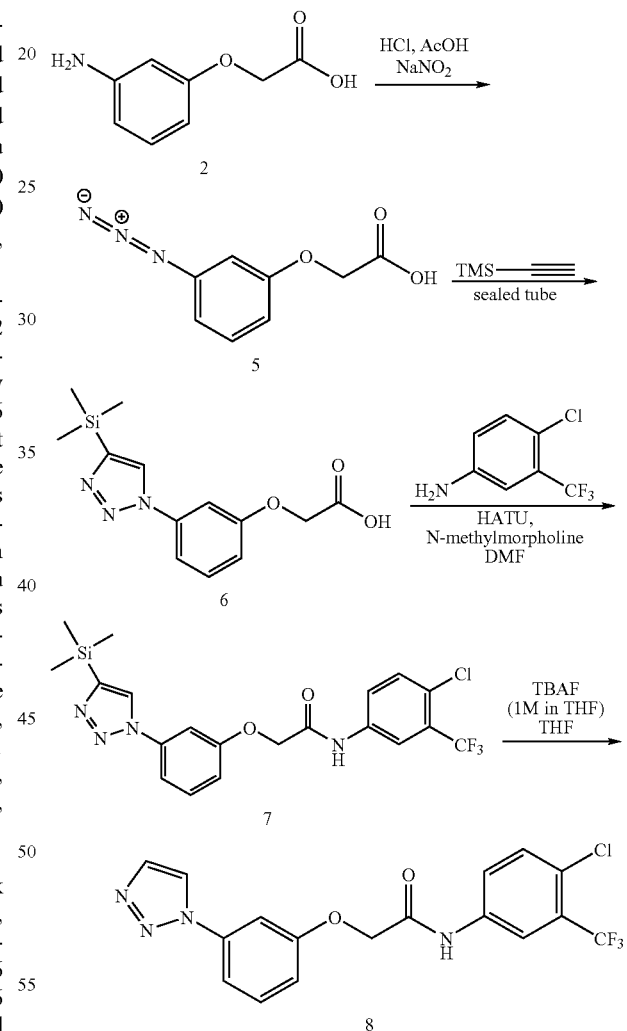

(3-azidophenoxy)-acetic acid 5: To a 100 mL recovery flask was added 3-aminophenoxyacetic acid 2 (2.00 g, 12.0 mmol, 1.0 eq.) and a stirbar. Acetic acid (5 mL), conc. HCl (2 mL) and $H_2O$ (3 mL) were added to the flask. The reaction mixture was cooled to 0° C. upon which a solution of NaNO$_2$ (0.908 g, 13.2 mmol, 1.1 eq.) in $H_2O$ (3 mL) was added over a period of 20 sec. The mixture was stirred for 5 minutes. A solution of NaN₃ (0.855 g, 13.2 mmol, 1.1 eq.) in H₂O (3 mL) was added slowly to the reaction mixture upon which the mixture foamed. The reaction mixture was stirred at 0° C. for 30 min and at room temperature for an additional 1 h. A light brown solid precipitates out of solution. The suspension was filtered and washed with cold H₂O to yield a light-brown solid (1.48 g). Upon drying, the more precipitate formed in the filtrate. The precipitate was refiltered to yield more product (0.17 g). Total yield: 1.65 g, 71%. LC/MSD (HP Series 1100 MSD) MS (ES+) m/z 192.1 (M−H)⁻¹ ¹H-NMR, Varian 400 MHz (DMSO-d₆) δ 7.31-7.27 (t, 1H), 6.73-7.69 (m, 2H), 6.59-6.58 (m, 1H), 4.62 (s, 2H) ppm.

[3-(4-trimethylsilanyl-[1,2,3]triazol-1-yl)-phenoxy]-acetic acid 6: To a 15 mL sealed tube was added (3-azidophenoxy)-acetic acid 5 (527 mg, 2.73 mmol, 1.0 eq.) and trimethylsilylacetylene (10 mL) and a stirbar. The tube was sealed and reaction mixture was stirred overnight at room temperature. The reaction mixture was filtered and solid was washed with ethyl ether to yield a dark gray solid (483 mg, 61%). ¹H-NMR, Varian 400 MHz (DMSO-d₆) δ 13.11 (bs, 1H), 8.86 (s, 1H), 7.52-7.46 (m, 3H), 7.03-7.00 (m, 1H), 4.80 (d, 2H), 0.31 (s, 9H) ppm.

N-(4-chloro-3-trifluoromethylphenyl)-2-[3-(4-trimethylsilanyl-[1,2,3]-triazol-1-yl)-phenoxy]-acetamide 7: To a 25 mL recovery flask was added [3-(4-Trimethylsilanyl-[1,2,3]triazol-1-yl)-phenoxy]-acetic acid 6 (483 mg, 1.66 mmol, 1.0 eq.) and a stirbar. O-(7-azabenzotriazol-1-yl)-N,N,N',N'-tetramethyluronium hexafluorophosphate (1.26 g, 3.3 mmol, 2.0 eq.), DMF (8 mL), and N-methylmorpholine (503 µL, 4.98 mmol, 3.0 eq.) were added. The mixture was stirred at room temperature for 30 min. 5-amino-2-chlorobenzotrifluoride (649 mg, 3.3 mmol, 2.0 eq.) was added and the reaction mixture was stirred overnight at room temperature. The reaction mixture was diluted with ethyl acetate (100 mL) and washed with a succession of 10% aq. LiCl (3×50 mL), H₂O (50 mL), and sat'd aq. NaCl (50 mL). The organic phase was dried over anhydrous Na₂SO₄, filtered, and concentrated to give a grayish solid. The solid was recrystallized in hot MeOH to give a light gray solid, which by LC/MS was a mixture of product and the corresponding de-silylated material (200 mg). The mixture was taken on to the next step without further purification. LC/MSD (HP Series 1100 MSD) MS (ES+) m/z 469.1 (M+H)⁺¹

N-[4-chloro-3-(trifluoromethyl)phenyl]-2-{[3-(1H-1,2,3-triazol-1-yl)phenyl]oxy}acetamide 8: To a 25 mL recovery flask was added a mixture of N-(4-Chloro-3-trifluoromethyl-phenyl)-2-[3-(4-trimethylsilanyl-[1,2,3]triazol-1-yl)-phenoxy]-acetamide 7 and N-(4-chloro-3-trifluoromethylphenyl)-2-(3-[1,2,3]triazol-1-yl-phenoxy)-acetamide 8 (200 mg, 0.426 mmol, 1.0 eq.) and a stirbar. THF (10 mL) and tetrabutylammonium fluoride (1.0 M in THF, 2 mL, 2.00 mmol) was added. The reaction was stirred for two days at room temperature. The reaction mixture was concentrated and taken up in ethyl acetate (50 mL). The organic phase was washed with sat'd aq. NH₄Cl and then dried over anhydrous Na₂SO₄, filtered, and concentrated to give an off-white solid (182 mg, 28% over two steps from 6). LC/MSD (HP Series 1100 MSD) MS (ES+) m/z 397.0 (M+H)⁺¹ ¹H-NMR, Varian 400 MHz (DMSO-d₆) δ 10.58 (s, 1H), 8.88 (d, 1H), 8.25 (d, 1H), 7.99-7.95 (m, 2H), 7.70 (d, 1H), 7.62 (m, 1H), 7.56-7.54 (m, 2H), 7.15 (m, 1H), 4.89 (s, 2H) ppm.

Example 3

Synthesis of N-[4-chloro-3-(trifluoromethyl)phenyl]-2-[3-(1H-tetrazol-1-yl)phenyl]hydrazine carboxamide 13

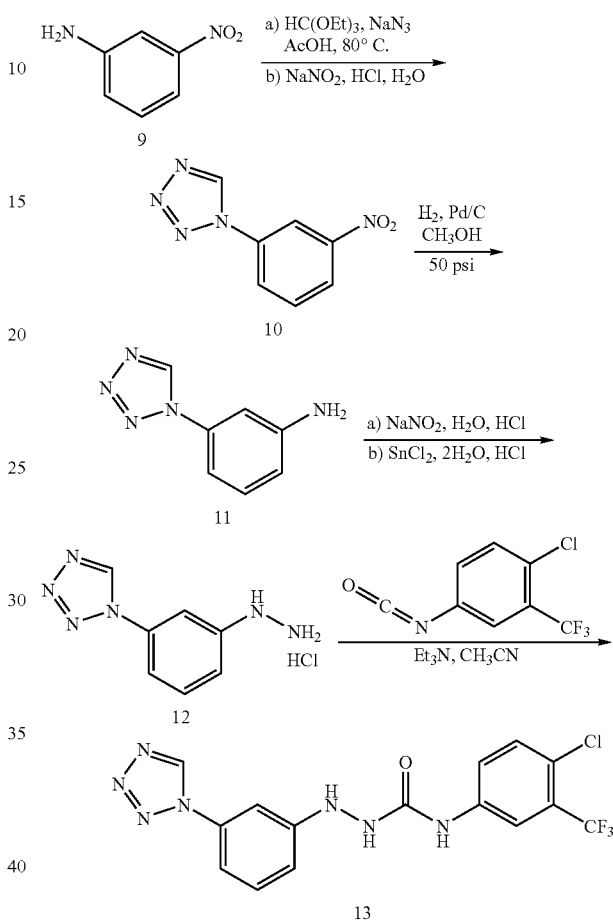

1-(3-nitrophenyl)-1H-tetrazole 10: To a 250 mL recovery flask was added 3-nitroaniline 8 (10.00 g, 72.4 mmol, 1.0 eq.) and a stirbar. Triethylorthoformate (38.5 mL, 232 mmol, 3.2 eq.) was added followed by sodium azide (5.88 g, 90.5 mmol, 1.25 eq.) and acetic acid (66.0 mL, 1.16 mmol, 16 eq). The viscous mixture was heated at 80° C. in an oil bath. Upon heating, the mixture solidified. Additional acetic acid (70 mL) was added and the resulting suspension was agitated with a spatula. While heating for 2 h the reaction mixture became homogeneous. The reaction mixture was removed from the oil bath and transferred to a 500 mL Erlenmeyer flask. The flask was cooled to 0° C. in an ice bath upon which H₂O (70 mL) and 6N HCl (30 mL) was added. In a separate flask, a solution of NaNO₂ (3.5 g) in H₂O (15 mL) was prepared. The NaNO₂ solution was added slowly to the reaction mixture. Vigorous bubbling was evident. Upon completion of addition, a bright yellow precipitate formed in the flask. The suspension was filtered to yield a bright yellow solid (10.4 g, 75%). LC/MSD (HP Series 1100 MSD) MS (ES+) m/z 192.0 (M+H)⁺¹ ¹H-NMR, Varian 400 MHz (MSO-d₆) δ 10.27 (s, 1H), 8.77 (s, 1H), 8.40-8.38 (d, 2H), 7.94 (t, 1H) ppm.

1-(3-aminophenyl)-1H-tetrazole 11: To a 2 L pressure vessel was added 1-(3-nitrophenyl)-1H-tetrazole 10 (10.0 g, 52.3 mmol, 1.0 eq.) and methanol (500 mL). The resulting solution was purged with N₂ for 5 min. 10% Pd/C (500 mg) was added to the solution and the vessel was placed on a Parr hydrogenator at 50 psi for 3 h. The Pd/C was removed by filtration and the filtrate was concentrated to yield a light gray solid (7.66 g, 91%). LC/MSD (HP Series 1100 MSD) MS (ES+) m/z 162.1 (M+H)⁺¹ ¹H-NMR, Varian 400 MHz (DMSO-d) δ 9.96 (s, 1H), 7.23-7.19 (m, 1H), 7.01-7.00 (m, 1H), 6.93-6.91 (m, 1H), 6.70-6.67 (m, 1H), 5.64 (m, 2H) ppm.

(3-tetrazol-1-yl-phenyl)-hydrazine hydrochloride 12: To a 100 mL recovery flask was added 1-(3-aminophenyl)-1H-tetrazole 11 (1.60 g, 9.93 mmol, 1.0 eq.) and a stirbar. A mixture of conc. HCl (23 mL) and H₂O (3 mL) was added to the flask. The resulting suspension was cooled to −20° C. A solution of NaNO₂ (685 mg, 9.93 mmol, 1.0 eq) in H₂O (8 mL) was prepared and added slowly to the reaction mixture while maintaining a temperature of −20° C. The reaction mixture was stirred for 30 min. A solution of SnCl₂ dihydrate (8.96 g, 39.7 mmol, 4.0 eq.) in conc. HCl (17 mL) was prepared and cooled to −20° C. This solution was added rapidly to the reaction mixture and the reaction mixture was stirred at −20° C. for 20 min and at room temperature for 1 h. A light gray precipitate formed in the reaction mixture. The mixture was filtered to yield a light gray solid (1.48 g, 70%). LC/MSD (HP Series 1100 MSD) MS (ES+) m/z 177.1 (M+H)⁺¹ ¹H-NMR, Varian 400 MHz (DMSO-d₆) δ 10.53 (bs, 2H), 10.12 (s, 1H), 7.60-7.54 (m, 2H), 7.48-7.45 (m, 2H), 7.17-7.14 (m, 1H) ppm.

N-[4-chloro-3-(trifluoromethyl)phenyl]-2-[3-(1H-tetrazol-1-yl)phenyl]hydrazine carboxamide 13: To a 50 mL recovery flask was added 1-chloro-4-isocyanato-2-trifluoromethylbenzene (627 mg, 2.83 mmol, 1.0 eq.) and acetonitrile (12 mL). The solution was cooled to 0° C. in an ice bath. In a separate flask a solution of (3-tetrazol-1-yl-phenyl)-hydrazine hydrochloride 12 (600 mg, 2.83 mmol, 1.0 eq.) in acetonitrile (6 mL) was prepared. DMP (15 mL) was added to aid in the solubility of the hydrazine. This solution was added to the reaction flask over a period of 1 min. The reaction mixture was homogeneous upon addition. After 1 h stirring while warming to room temperature, a precipitate formed. The reaction mixture was filtered and the solid was washed with acetonitrile to yield a white solid (552 mg, 49%). No further purification was necessary. LC/MSD (HP Series 1100 MSD). MS (ES+) m/z 398.1 (M+H)⁺ ¹H-NMR, Varian 400 MHz (DMSO-d₆) δ 10.07 (s, 1H), 9.37 (s, 1H), 8.64 (s, 1H), 8.29 (s, 1H), 8.16 (s, 1H), 7.90 (s, 1H), 7.57-7.55 (d, 1H), 7.43 (t, 1H), 7.26-7.24 (m, 2H), 6.93-6.91 (d, 1H) ppm.

Example 4

Synthesis of N-[4-chloro-3-(trifluoromethyl)phenyl]-2-{[3-(1H-tetrazol-1-yl)ₚ-phenyl]oxy}acetamide 15

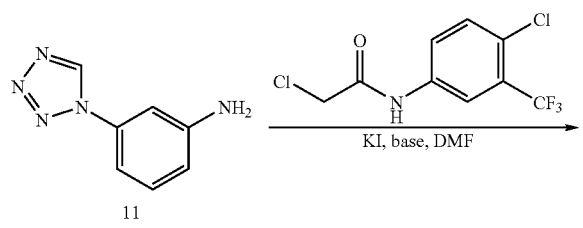

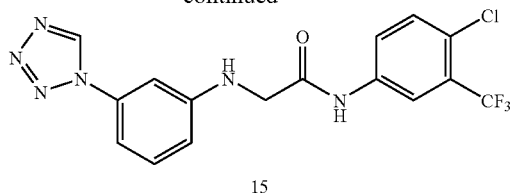

15

N-[4-chloro-3-(trifluoromethyl)phenyl]-2-{[3-(1H-tetrazol-1-yl)-phenyl]oxy}acetamide 15: To a 50 mL recovery flask was added 2-chloro-N-(4-chloro-3-trifluoromethylphenyl)-acetamide (400 mg, 1.47 mmol, 1.0 eq.) and 1-(3-aminophenyl)-1H-tetrazole 11 (710 mg, 4.40 mmol, 3 eq.) and DMF (10 mL). A catalytic amount of potassium iodide was added. The reaction mixture was heated at 70° C. overnight. The reaction mixture was diluted with ethyl acetate (100 mL) and washed with a succession of 10% aq. LiCl (3×50 mL) and sat'd aq. NaCl (50 mL). The combined aqueous phases were extracted with ethyl acetate (2×50 mL). The combined organic phases were dried over anhydrous Na₂SO₄, filtered, and concentrated to give a tan solid. The solid was recrystallized in methanol and acetonitrile (10:1) to give a white solid (63 mg). Subsequent crops were isolated from the mother liquor (91 mg). Total yield: 154 mg, 26%. LC/MSD (HP Series 1100 MSD) MS (ES+) m/z 397.1 (M+H)⁺¹ ¹H-NM, Varian 400 MHz (DMSO-d₆) δ 10.51 (s, 1H), 10.00 (s, 1H), 8.19 (d, 1H), 7.88-7.85 (dd, 1H), 7.65 (d, 1H), 7.34-7.30 (t, 1H), 7.09 (t, 1H), 7.05-7.03 (dd, 1H), 6.75 (dd, 1H), 6.74 (t, 1H), 4.00 (d, 2H) ppm.

Example 5

Synthesis of N-[4-chloro-3-(trifluoromethyl)phenyl]-2-{[3-(5-methyl-1H-tetrazol-1-yl)phenyl]oxy}acetamide 17

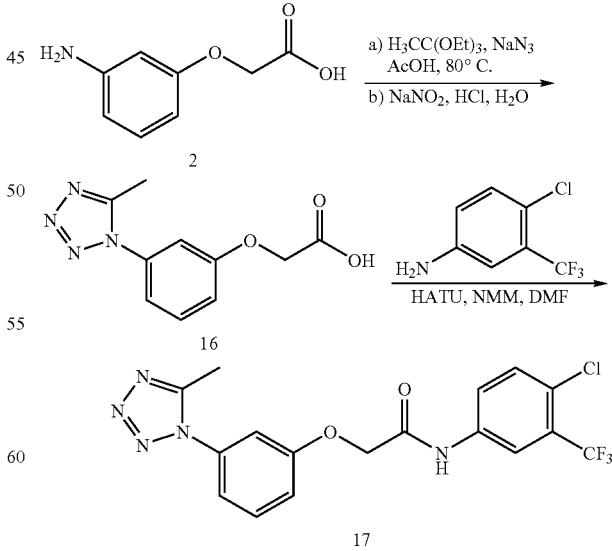

[3-(5-methyl-tetrazol-1-yl)-phenoxy]-acetic acid 16: To a 25 mL recovery flask was added 3-aminophenoxyacetic acid 2 (308 mg, 1.84 mmol, 1.0 eq.) and a stirbar. Triethylorthoacetate (0.75 mL, 5.89 mmol, 3.2 eq.) was added followed by sodium azide (150 mg, 2.30 mmol, 1.25 eq.) and acetic acid (1.7 mL, 29.4 mmol, 16 eq). The viscous mixture was heated at 80° C. in an oil bath with stirring for 2 h. Upon heating, the mixture became homogeneous. The reaction mixture was removed from the oil bath and was cooled to 0° C. in an ice bath upon which H$_2$O (10 mL) and 6N HCl (5 mL) was added. In a separate flask, a solution of NaNO$_2$ (1 g) in H$_2$O (4 mL) was prepared. The NaNO$_2$ solution was added slowly to the reaction mixture. Vigorous bubbling was evident. Upon completion of addition, a gray precipitate formed in the flask. The suspension was filtered to yield a light gray solid (424 mg, 98%). LC/MSD (HP Series 1100 MSD) MS (ES+) m/z 233.1 (M+H)$^{+1}$ N-[4-chloro-3-(trifluoromethyl)phenyl]-2-{[3-(5-methyl-1H-tetrazol-1-yl)phenyl]oxy}acetamide 17: To a 25 mL recovery flask was added [3-(5-methyl-tetrazol-1-yl)-phenoxy]-acetic acid 16 (424 mg, 1.81 mmol, 1.0 eq.) and a stirbar. 1-ethyl-3-(3'-dimethylaminopropyl)carbodiimide hydrochloride (521 mg, 2.72 mmol, 1.5 eq.) and 1-hydroxybenzotriazole (367 mg, 2.72 mmol, 1.5 eq.) were added to the flask. DMF (12 mL) and N-methylmorpholine (611 μL, 5.44 mmol, 3.0 eq.) were added to the reaction flask. The mixture was allowed to stir for 30 min at room temperature. 5-Amino-2-chlorobenzotrifluoride (709 mg, 3.62 mmol, 2.0 eq.) was added to the flask and the resulting mixture was allowed to stir overnight at room temperature. The reaction mixture was diluted with ethyl acetate (100 mL) and washed with a succession of H$_2$O (1×50 mL), 10% aq. LiCl (3×50 mL), and sat'd aq. NaCl (1×50 mL). The aqueous phases were combined and extracted with ethyl acetate (2×30 mL). The combined organic phases were dried over anhydrous Na$_2$SO$_4$, filtered, concentrated and purified by flash chromatography to yield an off-white solid (40 mg, 5%). LC/MSD (HP Series 1100 MSD) MS (ES+) m/z 412.0 (M+H)$^{+1}$ $^1$H-NMR, Varian 400 MHz (DMSO-d$_6$) δ 10.55 (s, 1H), 8.21 (d, 1H), 7.92-7.89 (m, 1H), 7.70-7.68 (m, 1H), 7.57 (t, 1H), 7.36-7.35 (m, 1H), 7.29-7.27 (m, 2H), 4.85 (s, 2H), 2.53 (s, 3H) ppm.

Example 6

Synthesis of N-[4-chloro-3-(trifluoromethyl)phenyl]-2-{[3-1H-tetrazol-1-yl)phenyl]thio}acetamide 20

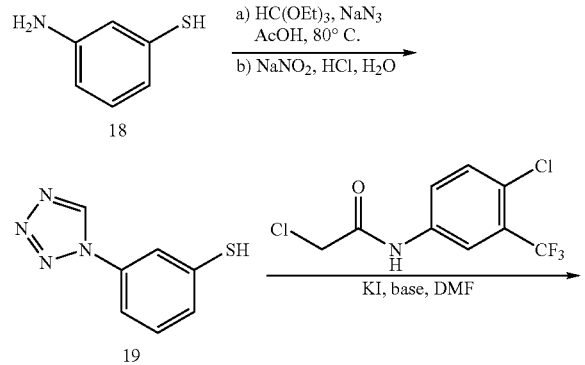

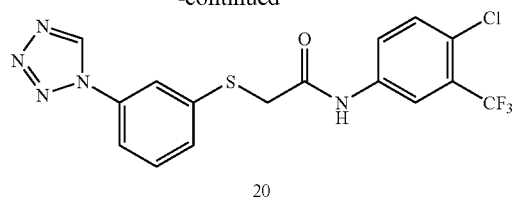

3-tetrazol-1-yl-benzenethiol 19: To a 100 mL recovery flask was added 3-aminobenzenethiol 18 (3.537 g, 28.3 mmol, 1.0 eq.) and a stirbar. Triethylorthoformate (15 mL, 90.4 mmol, 3.2 eq.) was added followed by sodium azide (2.30 g, 35.3 mmol, 1.25 eq.) and acetic acid (25.9 mL, 452 mmol, 16 eq). The viscous mixture was heated at 80° C. in an oil bath. While heating for 2 h the reaction mixture became homogeneous. The reaction mixture was removed from the oil bath and transferred to a 500 mL Erlenmeyer flask. The flask was cooled to 0° C. in an ice bath upon which H$_2$O (70 mL) and 6N HCl (30 mL) was added. In a separate flask, a solution of NaNO$_2$ (1 g) in H$_2$O (5 mL) was prepared. The NaNO$_2$ solution was added slowly to the reaction mixture. Vigorous bubbling was evident. Upon completion of addition, a brown precipitate formed in the flask. The suspension was filtered and washed with H$_2$O to yield a light tan solid (5.00 g, 99%).

N-[4-chloro-3-(trifluoromethyl)phenyl]-2-{[3-1H-tetrazol-1-yl)phenyl]thio}acetamide 20: To a 25 mL recovery flask was added 3-tetrazol-1-yl-benzenethiol 19 (228 mg, 0.644 mmol, 1 eq.) and DMF (5 mL). The solution was stirred at 60° C. for 15 min and then cooled to room temperature. 2-chloro-N-(4-chloro-3-trifluoromethylphenyl)-acetamide (250 mg, 0.92 mmol, 1.5 eq.), Cs$_2$CO$_3$ (699 mg, 2.15 mmol, 3.5 eq.), and a catalytic amount of KI were added to the reaction flask. The reaction mixture was stirred overnight at room temperature. The reaction mixture was diluted with ethyl acetate (100 mL) and washed with a succession of 10% aq. LiCl (3×50 mL) and sat'd aq. NaCl (50 mL). The organic phase was dried over anhydrous Na$_2$SO$_4$, filtered, and concentrated to give a solid which was purified first by column chromatography (0% to 1% CH$_3$OH in CH$_2$Cl$_2$) and then by preparative HPLC to give a white solid (20 mg, 7.5%). LC/MSD (HP Series 1100 MSD) MS (ES+) m/z 414.0 (M+H)$^{+1}$

Example 7

General Procedure for N-[4-chloro-3-(trifluoromethyl)phenyl]-2-[(4-aryl-phenyl-oxy]acetamides 23

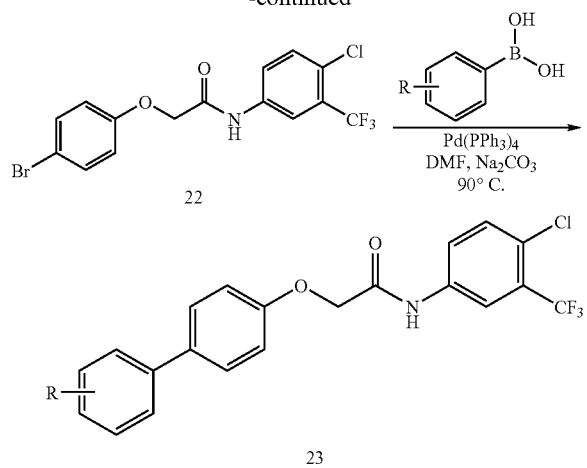

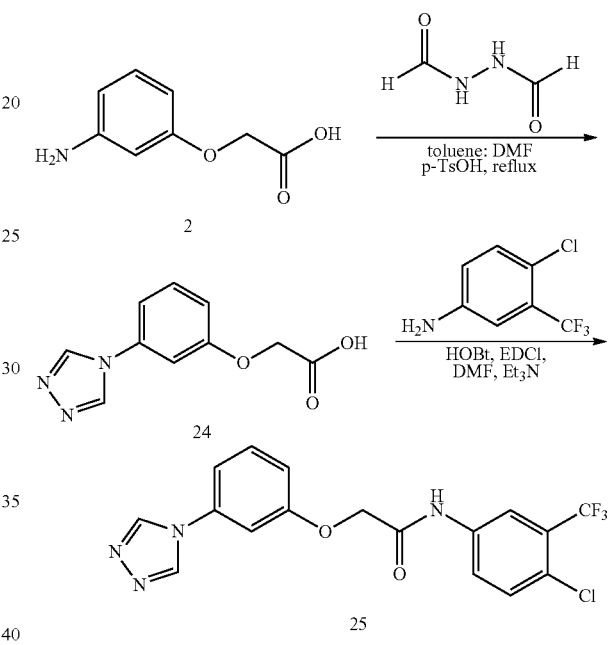

2-Chloro-N-(4-chloro-3-trifluoromethyl-phenyl)-acetamide 21: To a round bottom flask was added chloroacetyl chloride (2.0 mL, 25.0 mmol, 1.0 eq.) and $CH_2Cl_2$ (100 mL). The solution was cooled to 0° C. before a mixture of 5-amino-2-chloro-benzotrifluoride (4.88 g, 25.0 mmol, 1.0 eq.) and triethyl amine (3.56 mL, 27.5 mmol, 1.1 eq.) in $CH_2Cl_2$ (5.0 mL) was added dropwise. The reaction was then stirred at 0° C. for 1.5 h before quenching with $H_2O$ (50 mL). The organic layer was then separated, washed with brine, and dried with $Na_2SO_4$. Concentration via rotary evaporation gave acetamide 21 as a yellow solid (5.72 g, 84.7% yield). $^1$H-NMR, Varian 400 MHz (DMSO-$d_6$) δ 10.79 (br s, 1H), 8.20 (d, 1H), 7.87 (dd, 1H), 7.75 (d, 1H), 4.36 (s, 2H) ppm.

2-(4-bromo-phenoxy)-N-(4-chloro-3-trifluoromethyl-phenyl)acetamide 22: To a round bottom flask was added 4-bromophenol (1.7 g, 9.8 mmol, 1.0 eq.), acetamide 21 (2.79 g, 10.3 mmol, 1.05 eq.), potassium iodide (1.7 g, 10.3 mmol, 1.05 eq.), potassium carbonate (2.7 g, 19.6 mmol, 2.0 eq.), and acetonitrile (35.0 mL). The reaction mixture was then refluxed with vigorous stirring for 2 h. The hot reaction was then filtered to remove the insoluble potassium carbonate. The filtrate was concentrated to give 3.8 g of crude bromo-phenoxy-acetamide 22 as a light brown solid. The solid was then triturated with 10 mL of cold acetonitrile, filtered, and rinsed with 5 mL of cold acetonitrile to give pure bromo-phenoxy-acetamide 22 (1.85 g, 45% yield). Note: there was still an abundant amount of crude product in the mother liquor. LC/MSD (HP Series 1100 MSD) MS (ES+) m/z 409.9 $(M+H)^{+1}$ $^1$H-NMR, Varian 400 MHz (DMSO-$d_6$) δ 8.20 (d, 1H), 7.90 (dd, 1H), 7.68 (d, 1H), 7.48 (d, 2H), 6.99 (d, 2H), 4.75 (s, 2H) ppm.

Biphenyl-phenoxy-acetamides 23: To a sealed tube was added bromo-phenoxy-acetamide 22 (408 mg, 1.0 mmol, 1.0 eq.), an appropriate boronic acid (1.0 mmol, 1.0 eq.), DMF (5.0 mL), and 1M $Na_2CO_3$ (1.0 mL). The mixture was then degassed by bubbling in a stream of $N_2$ for approximately 1 min. before adding $Pd(PPh_3)_4$ (126 mg, 0.1 mmol, 0.1 eq.). The tube was then sealed and heated to 90° C. for 1.5-3 h or until the reaction was complete. Upon completion, the reaction was cooled to RT, and filtered. The filtrate was extracted with EtOAc and $H_2O$. The organic layer was then washed with 10% LiCl 3× to remove DMF, washed with brine, and dried with $Na_2SO_4$. Concentration for most cases gave a solid which could be purified via trituration with ether. Those compounds that could not be purified via trituration were then purified via column chromatography.

The above procedure was used to make N-[4-chloro-3-(trifluoromethyl)phenyl]-2-[(4-pyrimidin-5-ylphenyl)oxy] acetamide: LC/MSD (HP Series 1100 MSD) MS (ES+) m/z 408.1 $(M+H)^{+1}$ MS (ES+) m/z 406.0 $(M-H)^{-1}$ $^1$H-NMR, Varian 400 MHz (DMSO-$d_6$) δ 10.60 (br. s, 1H), 9.14 (s, 1H), 9.12 (s, 2H), 8.26 (d, 1H), 7.96 (dd, 1H), 7.81 (dd, 2H), 7.71 (d, 1H), 7.17 (dd, 2H), 4.84 (s, 2H) ppm.

Example 8

Synthesis of N-[4-chloro-3-(trifluoromethyl)phenyl]-2-{[4-(1H-1,2,4-triazol-4-yl)phenyl]oxyacetamide 25

(3-[1,2,4]Triazol-4-yl-phenoxy)-acetic acid 24: To a round bottom flask was added (3-amino-phenoxy)-acetic acid 2 (167 mg, 1.0 mmol, 1.0 eq.), toluene (5.0 mL), DMF (0.5 mL), p-toluene sulfonic acid monohydrate (209 mg, 1.1 mmol, 1.1 eq.), and sym-diformyl hydrazine (96.8 mg, 1.1 mmol, 1.1 eq.). The mixture was refluxed overnight. Upon cooling to RT, the reaction mixture separated out into two layers with product in the bottom brown oil layer and toluene in the clear top layer. The toluene layer was removed; water was added to the brown oil and then extracted with EtOAc 3×. The combined organic layers were then dried with $Na_2SO_4$, concentrated via rotary evaporation, and then triturated with ether to give (3-[1,2,4]Triazol-4-yl-phenoxy)-acetic acid 24 as an orange solid (65.0 mg, 30% yield). LC/MSD (HP Series 1100 MSD) MS (ES+) m/z 220.1 $(M+H)^{+1}$ $^1$H-NMR, Varian 400 MHz (DMSO-$d_6$) δ 9.10 (s, 2H), 7.48 (m, 1H), 7.39 (t, 1H), 7.31 (dd, 1H), 7.00 (dd, 1H), 4.80 (s, 2H) ppm.

N-[4-chloro-3-(trifluoromethyl)phenyl]-2-{[4-(1H-1,2,4-triazol-4-yl)phenyl]oxy}acetamide 25: To a round bottom flask was added triazole 24 (43.8 mg, 0.20 mmol, 1.0 eq.), DMF (2.0 mL), HOBt (29.7 mg, 0.22 mmol, 1.1 eq.), EDCI (42.0 mg, 0.22 mmol, 1.1 eq.), and triethylamine (0.076 mL, 0.60 mmol, 3.0 eq.). The reaction was stirred at RT for 30 min before adding 5-amino-2-chloro-benzotrifluoride (78.0 mg, 0.40 mmol, 2.0 eq.) and stirring overnight at RT. The reaction was quenched with water, extracted with EtOAc 3×, washed with 10% LiCl to remove DMF, dried with $Na_2SO_4$, and then concentrated via rotary evaporation. Trituration with ether gave triazole 25 in only 80% purity. Further purification by prep HPLC then gave pure triazole 25 as a white solid (21 mg, 23% yield). LC/MSD (BP Series 1100 MSD) MS (ES+) m/z 397.0 (M+H)$^{+1}$ $^1$H-NMR, Varian 400 MHz (DMSO-$d_6$) δ 10.56 (br. s, 1H), 9.17 (s, 2H), 8.25 (d, 1H), 7.95 (dd, 1H), 7.69 (d, 1H), 7.49 (t, 1H), 7.43 (m, 1H), 7.33 (dd, 1H), 7.10 (dd, 1H), 4.84 (s, 2H) ppm.

Example 9

Synthesis of N-[4-chloro-3-(trifluoromethyl)phenyl]-N'-{[3-(1H-tetrazol-1-yl)phenyl]methyl}urea 28

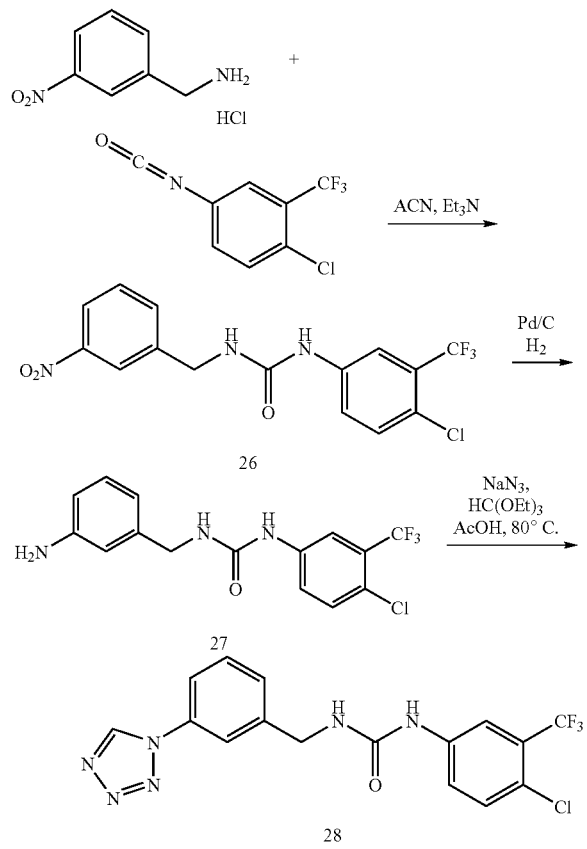

1-(4-Chloro-3-trifluoromethyl-phenyl)-3-(3-nitro-benzyl)-urea 26: To a round bottom flask was added 4-chloro-3-(trifluoromethyl)-phenyl isocyanate (443 mg, 2.0 mmol, 1.0 eq.) and acetonitrile (3.0 mL). The solution was cooled to 0° C. before a mixture of 3-nitrobenzylamine HCl (377 mg, 2.0 mmol, 1.0 eq.), DMP (1.0 mL), and triethyl amine (0.27 mL, 2.0 mmol, 1.0 eq.) was added dropwise. The reaction was then allowed to warm to RT slowly, and then stirred for an additional 2 h. The reaction was then concentrated to remove acetonitrile. EtOAc and water were added, and the mixture was extracted, washed with brine, dried with $Na_2SO_4$, and concentrated to give an oil. Upon sitting at RT, the oil crystallized to give urea 26 (728 mg, 97% yield). LC/MSD (HP Series 1100 MSD) MS (ES+) m/z 374.1 (M+H)$^{+1}$ $^1$H-NMR, Varian 400 MHz (DMSO-$d_6$) δ 9.23 (br. s, 1H), 8.14 (m, 1H), 8.09 (m, 1H), 8.04 (d, 1H), 7.74 (d, 1H), 7.62 (m, 2H), 7.52 (d, 1H), 7.04 (br t, 1H), 4.40 (s, 2H) ppm.

1-(3-amino-benzyl)-3-(4-chloro-3-trifluoromethyl-phenyl)-urea 27: To a round bottom flask was added urea 26 (700 mg, 1.87 mmol, 1.0 eq.) and methanol (15 mL). The flask was then flushed with $N_2$ before adding 10% Pd/C (35 mg, 5% by wt.). The reaction was placed under atmospheric $H_2$ and allowed to stir at RT for 2 h before filtering over celite and rinsing with methanol. Concentration via rotary evaporation followed by column chromatography with silica gel and 1:1 EtOAc:Hexanes afforded pure urea 27 as a white solid (415 mg, 65% yield). LC/MSD (BP Series 1100 MSD) MS (ES+) m/z 344.1 (M+H)$^{+1}$ $^1$H-NMR, Varian 400 M DMSO-$d_6$) δ 9.05 (br. s, 1H), 8.09 (d, 1H), 7.55 (m, 2H), 6.93 (t, 1H), 6.48 (s, 1H), 6.40 (d, 2H), 5.05 (s, 2H), 4.20 (s, 2H) ppm.

N-[4-chloro-3-(trifluoromethyl)phenyl]-N'-{[3-(1H-tetrazol-1-yl)phenyl]methyl}urea 28: To a round bottom flask was added urea 27 (100 mg, 0.29 mmol, 1.0 eq.), triethyl orthoformate (0.16 mL, 0.93 mmol, 6.4 eq.), sodium azide (25.0 mg, 0.36 mmol, 1.25 eq.), and acetic acid (0.26 ml, 4.64 mmol, 16.0 eq.). The reaction mixture was stirred at RT for 10 min. before heating to 75° C. for 1 h. The reaction was cooled to RT, and water (0.2 mL), 6N HCl (0.16 mL), and 25% aq. $NaNO_2$ (0.064 mL). The mixture was then extracted with EtOAc, washed with brine and dried with $Na_2SO_4$. Concentration via rotary evaporation followed by silica gel column chromatography with 60:40 EtOAc: Hexanes afforded urea 28 as a yellow solid (7.5 mg, 6% yield). LC/MSD (HP Series 1100 MSD) MS (ES+) m/z 397.0 (M+H)$^{+1}$ $^1$H-NMR, Varian 400 MHz (DMSO-$d_6$) δ 10.40 (s, 1H), 9.24 (s, 1H), 8.30 (d, 1H), 7.82 (s, 1H), 7.79 (d, 1H), 7.62-7.42 (m, 4H), 7.10 (t, 1H), 4.40 (s, 2H) ppm.

Example 10

Synthesis of N-[4-chloro-3-(trifluoromethyl)phenyl]-2-{3-(1H)-tetrazol-1-yl)phenyl]oxy}propanamide 32

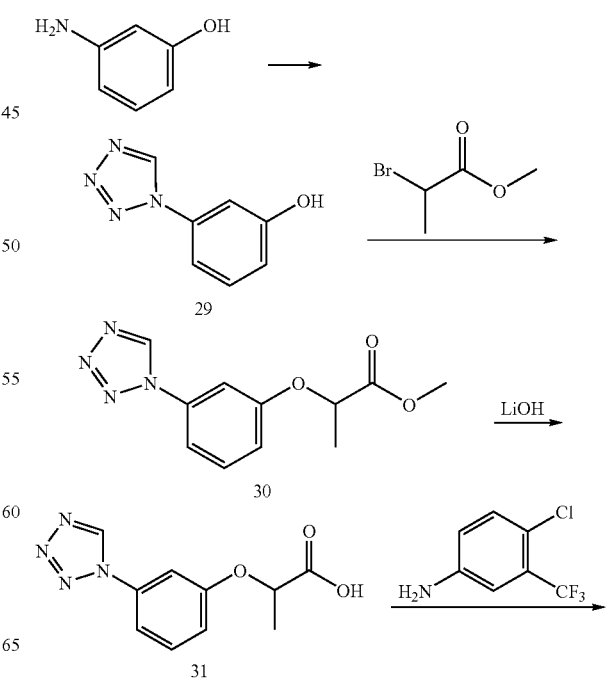

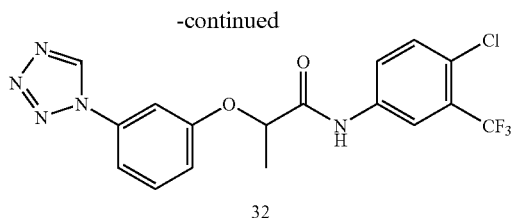

32

3-Tetrazol-1-yl-phenol 29: To a 200 ml round bottom flask equipped with a magnetic stir bar containing a solution of 3-aminophenol (5 g, 45.8 mmol, 1.0 eq) in triethyl orthoformate (24.4 ml, 146.5 mmol, 3.2 eq) was added sodium azide (3.73 g, 57.3 mmol, 1.25 eq) and acetic acid (41.95 ml, 732.8 mmol, 16.0 eq). The mixture was stirred for 10 min at room temperature and then heated at 80° C. for 1.5 h. After heating, the mixture was bronze and homogeneous. The mixture was cooled to room temperature. Water (30 mL) and 6 N HCl (17 mL) was added. A 25% aqueous solution of NaNO$_2$ (6 mL) was slowly added while the reaction mixture was cooled in an ice bath. A white solid, 3-tetrazol-1-yl-phenol 29 (5.3 g, 72% yield) was obtained upon filtration and washing with water. LC/MSD (HP Series 1100 MSD) MS (ES+) m/z 163.0 (M+H)$^{+1}$ $^1$H-NMR, Varian 400 MHz (MeOH-d$_4$) δ 9.71 (s, 1H), 7.41 (t, 1H), 7.28 (d, 2H), 6.96 (d, 1H) ppm.

2-(3-Tetrazol-1-yl-phenoxy)-propionic acid methyl ester 30: To a 25 ml round bottom flask equipped with a magnetic stir bar containing 3-tetrazol-1-yl-phenol 29 (0.5 g, 3.09 mmol, 1.0 eq), cesium carbonate (2.01 g, 6.18 mmol, 2.0 eq), and potassium iodide (25 mg, cat. amount) in anhydrous DMF (4 mL) was added methyl 2-bromopropionate (448 µL, 4.02 mmol, 1.3 eq). The reaction mixture was then allowed to stir overnight at room temperature. The reaction mixture was diluted with 10× the volume EtOAc and followed by washed 2× with water, 5× with 10% LiCl and 2× with brine. The organic layer was dried with Na$_2$SO$_4$, and concentrated to yield an oil (723 mg). Solid 2-(3-tetrazol-1-yl-phenoxy)-propionic acid methyl ester 30 was obtained after column chromatography (3:7 EtOAc/Hexane) (326 mg, 45% yield) LC/MSD (HP Series 1100 MSD) MS (ES+) m/z 249.0 (M+H)$^{+1}$ $^1$H-NMR, Varian 400 MHz (MeOH-d$_4$) δ 9.75 (s, 1H), 7.53-7.42 (m, 3H), 7.06 (d, 1H), 4.98 (q, 1H), 3.74 (s, 3H), 1.61 (d, 3H) ppm.

2-(3-Tetrazol-1-yl-phenoxy)-propionic acid 31: To a 25 mL round-bottom flask equipped with a magnetic stir bar was added 2-(3-tetrazol-1-yl-phenyl)-propionic acid methyl ester 30 (326 mg, 1.3 mmol, 1.0 eq.), 2N LiOH (2.6 mL, 2.6 mmol, 2.0 eq), and 1,4-dioxane (2.6 ml, 2.6 mmol, 2.0 eq). The reaction mixture was then stirred at room temperature for 3 hours. The reaction mixture was concentrated, diluted with water (5 mL), acidified with 1 N HCl (adjust pH=3.5), and then extracted with 3× EtOAc (25 mL each). The organic layer was dried with Na$_2$SO$_4$, concentrated, and dried under high vacuum to yield 2-(3-tetrazol-1-yl-phenoxy)-propionic acid 31 (230.3 mg, 98% yield). LC/MSD (HP Series 1100 MSD) MS (ES+) m/z 235.0 (M+H)$^{+1}$ $^1$H-NMR, Varian 400 MHz (MeOH-d$_4$) δ 9.76 (s, 1H), 7.52 (t, 1H), 7.45 (d, 2H), 7.08 (d, 1H), 4.93 (q, 1H), 1.62 (d, 3H) ppm.

N-[4-chloro-3-(trifluoromethyl)phenyl]-2-{3-(1H)-tetrazol-1-yl)phenyl]oxy}propanamide 32: To a 25 mL round-bottom flask equipped with a magnetic stir bar containing 4-chloro-3-trifluoromethyl-phenylamine (230.3 mg, 1.0 mmol, 1.0 eq.), EDCI (211 mg, 1.1 mmol, 1.1 eq.), HOBt (143 mg, 1.1 mmol, 1.1 eq) and DIEA (523 µL, 3.0 mmol, 3.0 eq) in anhydrous DMF (3 mL), was added 5-amino-2 chlorobenzotrifluoride (214.5 mg, 1.1 mmol, 1.1 eq). The reaction mixture was then allowed to stir at room temperature overnight. The reaction mixture was concentrated and diluted with 10× the volume EtOAc. This solution was then washed 2× with 10% LiOH and 2× with brine. The organic layer was dried with Na$_2$SO$_4$, concentrated. The solid was dissolved in MeOH and purified on prep HPLC. Lyophilization afforded 32 as a white solid (114.8 mg, 28% yield). LC/MSD (HP Series 1100 MSD) MS (ES+) m/z 472.7 (M+H)$^{+1}$ $^1$H-NMR, Varian 400 MHz (MeOH-d$_4$) δ 9.76 (s, 1H), 8.10 (d, 1H), 7.89 (q, 2H), 7.63-7.48 (m, 3H), 7.19 (s, 1H), 5.28 (s, 1H), 5.02 (s, 1H), 1.69 (d, 3H) ppm.

Example 11

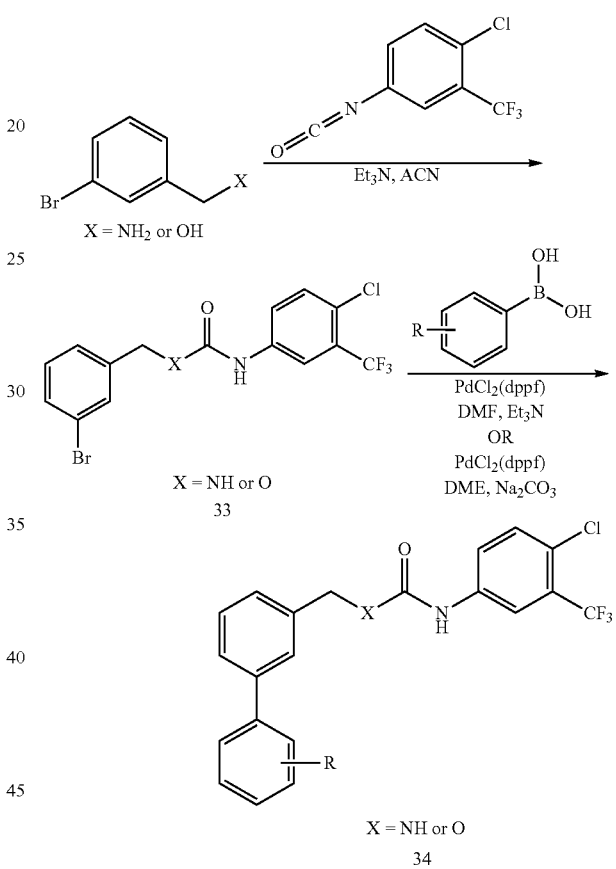

1-(3-Bromo-benzyl)-3-(4-Chloro-3-trifluoromethyl-phenyl)-urea 33. To a round bottom flask was added 4-Chloro-(3-trifluoromethyl)-phenyl isocyanate (2.0 g, 9.0 mmol, 1.0 eq.) and ACN (12 mL). The solution was cooled to 0° C. before a mixture of 3-bromobenzylamine HCl (2.0 g, 9.0 mmol, 1.0 eq.) and triethyl amine (1.16 mL, 9.0 mmol, 1.0 eq.) in DMF (10.0 mL) and Acetonitrile (6.0 mL) was added dropwise. The reaction was then warmed to RT and stirred for 3 h before concentrating via rotary evaporation. Addition of 25 mL of water resulted in the precipitation of urea 33, which was then filtered, rinsed with water, and dried under vacuum, yielding urea 33, as a white solid (3.6 g, 97.8% yield). LC/MSD (HP Series 1100 MSD) MS (ES+) m/z 407.0, 409.0 (Bromine isotope M+H)$^{+1}$ $^1$H-NMR, Varian 400 MHz (DMSO-d$_6$) δ 9.20 (s, 1H), 8.08 (d, 1H), 7.72-7.41 (m, 4H), 7.30 (m, 2H), 6.95 (t, 1H), 4.32 (d, 2H) ppm.

Biphenyl urea 34. To a sealed tube was added bromo urea 33 (204 mg, 0.5 mmol, 1.0 eq.), boronic acid (0.75 mmol, 1.5 eq.), DMF (5.0 mL) or DMF (5.0 mL), and 1M Na$_2$CO$_3$ (1.0 mL) or Et3N (0.14 mL, 1.0 mmol, 2.0 eq.). The mixture was then degassed by bubbling in a steam of N$_2$ for approximately 1 min. before adding PdCl$_2$ (dppf) (36.0 mg, 0.05 mmol, 0.1 eq.). The tube was then sealed and heated to 90° C. overnight or until the reaction was complete. The reaction was cooled to RT, filtered, and rinsed with EtOAc. The combined EtOAc layers were concentrated and then purified via column chromatography.

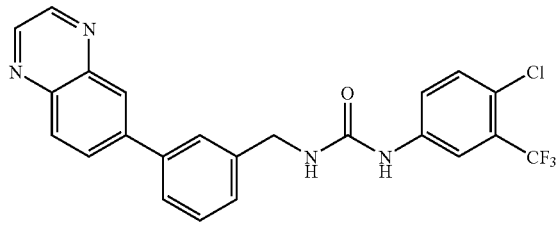

34a 1-(4-Chloro-3-trifluoromethyl-phenyl)-3-(3-quinoxalin-6-yl-benzyl)urea 34a: LC/MSD (HP Series 1100 MSD) MS (ES+) m/z 457.1 (M+H)$^{+1}$, 455.1 (M−H)$^{−1}$ $^1$H-NMR, Varian 400 MHz (DMSO-d$_6$) δ 9.18 (br. s, 1H), 8.99 (dd, 2H), 8.36 (s, 1H), 8.21 (s, 2H), 8.09 (d, 1H), 7.81 (m, 2H), 7.63-7.51 (m, 3H), 7.42 (d, 1H), 7.0 (t, 1H), 4.42 (d, 2H) ppm.

Example 12

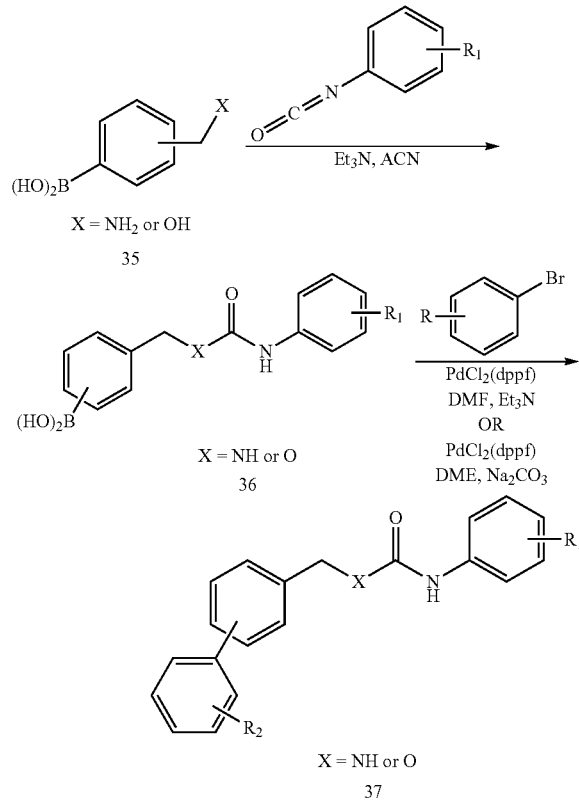

Boronic acid 36. To a round bottom flask was added the appropriately substituted isocyanate (12.0 mmol, 1.0 eq.) and ACN (24 mL). The solution was cooled to 0° C. before a mixture of benzyl boronic acid 35 (12.0 mmol, 1.0 eq.) and triethyl amine (1.6 mL, 12.0 mmol, 1.0 eq.) in DMF (10.0 mL) was added dropwise. The reaction was then warmed to RT and stirred for 1.5 h before concentrating via rotary evaporation. The oil was then taken up in EtOAc and water, and partitioned. The organic layer was washed twice with 10% LiCl, once with brine, dried with Na$_2$SO$_4$, and concentrated to give relatively pure boronic acid 36. Boronic acids that were not significantly pure after an aqueous work up were purified via column chromatorgraphy.

Urea 37. To a sealed tube was added boronic acid 36 (0.5 mmol, 1.0 eq.), the appropriate halide (0.5 mmol, 1.5 eq.), DMF (5.0 mL) or DMF (5.0 mL), and 1M Na$_2$CO$_3$ (1.0 mL) or Et3N (0.140 mL, 1.0 mmol, 2.0 eq.). The mixture was then degassed by bubbling in a steam of N$_2$ for approximately 1 min. before adding PdCl$_2$(dppf) (36.0 mg, 0.05 mmol, 0.1 eq.). The tube was then sealed and heated to 90° C. overnight or until the reaction was complete. The reaction was cooled to RT, filtered, and rinsed with EtOAc. The combined EtOAc layers were then washed with water, brine, and dried with Na$_2$SO$_4$ before column purification.

3-Amino-6-{3-[3-(4-chloro-3-trifluoromethyl-phenyl)-ureidomethyl]-phenyl}-pyrazine-2-carboxylic acid piperidin-3-ylaminde 37a LC/MSD (HP Series 1100 MSD) MS (ES+) m/z 548.1 (M+H)$^{+1}$ $^1$H-NMR, Varian 400 MHz (DMSO-d$_6$) δ 9.69 (s, 1H), 9.05 (br d, 1H), 8.95 (s, 2H), 8.70 (d, 1H), 8.11-8.00 (m, 3H), 7.52 (m, 3H), 7.42 (t, 1H), 7.30 (m, 2H), 4.40 (d, 2H), 4.15 (m, 1H), 3.25 (m, 3H), 2.80 (m, 1H), 1.80 (m, 4H) ppm.

Example 13

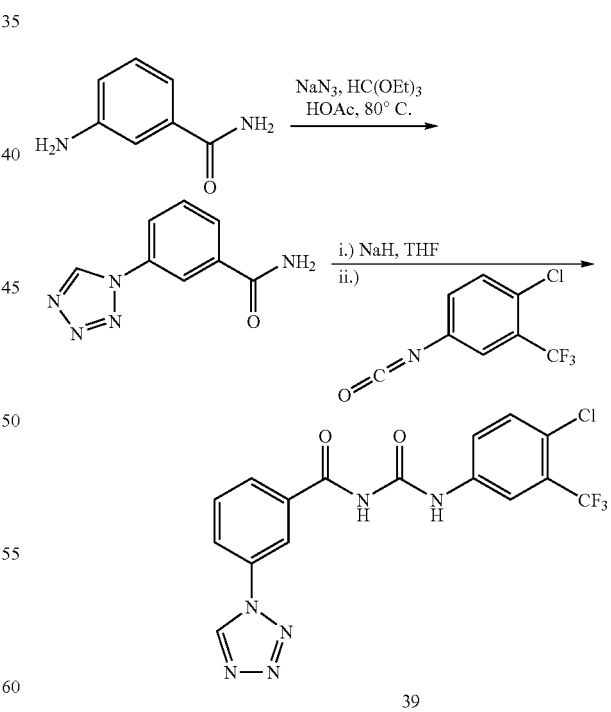

3-Tetrazol-1-yl-benzamide 38. To a round bottom flask was added 3-aminobenzamide (1.36 g, 10.0 mmol, 1.0 eq.), acetic acid (9.1 mL, 160 mmol, 16.0 eq.), triethyl orthoformate (5.4 mL, 32.0 mmol, 3.2 eq.), and sodium azide (0.812 g, 12.5 mmol, 1.25 eq.). The reaction mixture was then heated to 80° C. until all solids were dissolved. The reaction was stirred at 80° C. for an additional 2 h before cooling to RT. Water (6.0 mL,) was added, followed by 6N HCl (5.3 mL), and then 25% $NaNO_2$ (2.1 mL). The resulting precipitate was filtered and rinsed with water to give pure tetrazole 38 (1.5 g, 80% yield). LC/MSD (HP Series 1100 MSD) MS (ES+) m/z 189.9 $(M+H)^{+1}$, 187.9 $(M-H)^{+1}$ $^1$H-NMR, Varian 400 MHz (DMSO-$d_6$) δ 10.1 (s, 1H), 8.39 (t, 1H), 8.20 (br. s, 1H), 8.05 (m, 2H), 7.72 (t, 1H), 7.55 (s, 1H) ppm.

1-(4-chloro-3-trifluoromethyl-phenyl)-3-(3-tetrazol-1-yl-benzoyl)-urea 39. To a round bottom flask was added tetrazole 38 (189 mg, 1.0 mmol, 1.0 eq.), and THF (3.0 mL). The flask was cooled to 0° C. before sodium hydride (60% dispersion in mineral oil, 40 mg, 1.0 mmol, 1.0 eq.) was added. The reaction was then warmed to RT and stirred for an additional 15 min. before cooling back down to 0° C. and adding 4-chloro-3-trifluoro-methyl isocyanate (221 mg, 1.0 mmol, 1.0 eq.). The reaction was again warmed to RT and stirred for 15 min. before quenching with EtOAc (20.0 mL) and water (10 mL). The organic layer was washed with brine, dried with $Na_2SO_4$, and concentrated via rotary evaporation. The resulting solid was triturated with acetonitrile, filtered, rinsed with cold acetonitrile, and dried under vacuum to give pure urea 7 (230 mg, 56.1% yield). LC/MSD (HP Series 1100 MSD) MS (ES+) m/z 411.0 $(M+H)^{+1}$ $^1$H-NMR, Varian 400 MHz (DMSO-$d_6$) δ 11.40 (br. s, 1H), 11.0 (br. s, 1H), 10.19 (s, 1H), 8.60 (s, 1H), 8.20 (m, 3H), 7.90 (dd, 1H), 7.85 (t, 1H), 7.70 (d, 1H) ppm.

Example 14

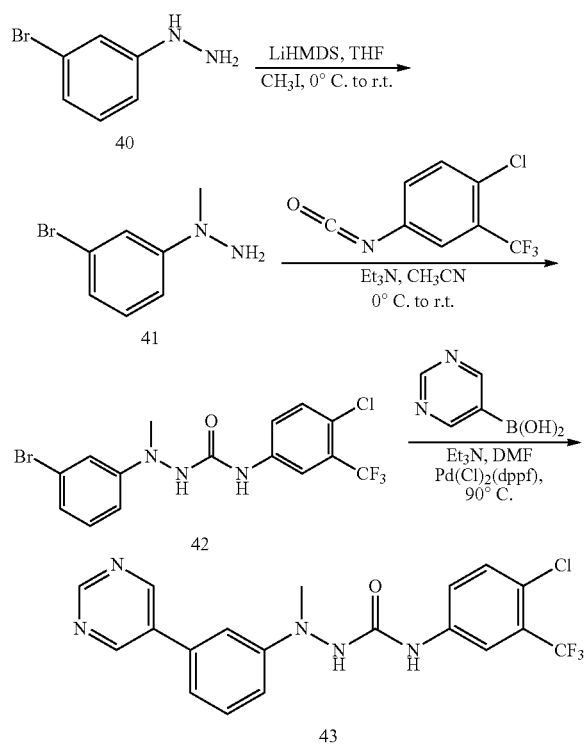

N-bromophenyl-N-methylhydrazine 41. To a 100 mL recovery flask was added 3-bromophenylhydrazine hydrochloride, 40 (2.00 g, 8.95 mmol, 1.0 eq.) and a stirbar. THF (50 mL) was added and the solution was cooled to 0° C. LiHMDS (1M solution in THF, 17.9 mL, 17.9 mmol, 2.0 eq.) was added dropwise over a period of 1 minute. The reaction was stirred for 30 min while warming to room temperature. The flask was recooled to 0° C. and $CH_3I$ (557 μL, 8.95 mmol, 1.0 eq.) was added. The reaction was stirred for 90 min and then was quenched with water (200 mL). The aqueous layer was extracted with $CH_2Cl_2$ (3×100 mL) and the combined organic layers were washed with brine (50 mL). The organic layer was dried over anhydrous $Na_2SO_4$, filtered, concentrated to give a yellow-orange oil, N-bromophenyl-N-methylhydrazine 41, whose LC/MS trace and TLC were sufficient for use in consequent reactions without further purification (759 mg, 42%). $^1$H-NMR, Varian 400 MHz, (DMSO-$d_6$) δ 7.14 (t, 1H), 7.04 (t, 1H), 6.86-6.83 (dd, 1H), 6.74-7.72 (m, 1H), 4.43 (s, 2H), 2.99 (s, 3H) ppm.

Bromophenylaminourea 42. To a 50 mL recovery flask was added 4-chloro-3-trifluoromethylphenyl isocyanate (759 mg, 3.80 mmol, 1.0 eq.) and $CH_3CN$ (8 mL). The solution was cooled to 0° C. In a separate flask was prepared a solution of N-bromophenyl-N-methylhydrazine 41 (759 mg, 3.80 mmol, 1.0 eq.) and $Et_3N$ (529 μL, 3.80 mmol, 1.0 eq.) in $CH_3CN$ (4 mL). DMF (2 mL) was added to the solution to aid in solubility of the hydrazine adduct. The solution was added to the reaction flask dropwise via syringe. After stirring for 1 h, LC/MS indicated the completion of the reaction. The reaction was concentrated and then diluted with EtOAc (100 mL). The organic phase was washed with water (50 mL) and brine (30 mL). The combined aqueous layers were extracted with EtOAc (30 mL). The combined organic layers were dried over anhydrous $Na_2SO_4$, filtered, and concentrated to give a yellowish oil which later crystallized (251 mg, 16%). The crude material was used without further purification.

Pyridylphenylaminourea 43. To a 15 mL pressure vessel was added 42 (250 mg, 0.594 mmol, 1.0 eq.), 5-pyrimidine boronic acid (74 mg, 0.594 mmol, 1.0 eq.), $PdCl_2(dppf)_2$ (43 mg, 0.0594 mmol, 0.1 eq.), DMF (5 mL), and $Et_3N$ (166 μL, 1.19 mmol, 2.0 eq.). The vessel was sealed and heated at 90° C. overnight upon which the reaction mixture turned from dark red to black. The reaction mixture was cooled and then diluted with EtOAc (100 mL) and the organic phase was washed with 10% aq LiCl (3×50 mL), and brine (50 mL). The combined aqueous phases were extracted with EtOAc (50 mL). The combined organic phases were dried over anhydrous $Na_2SO_4$, filtered and concentrated to give a black oil. The crude material was purified via flash chromatography (30% to 70% EtOAc/Hex) to give a white powder (32 mg, 10%). $^1$H-NMR, Varian 400 MHz, (DMSO-$d_6$) δ 9.38 (s, 1H), 9.18 (s, 1H), 9.10 (s, 1H), 8.78 (s, 1H), 8.17 (s, 1H), 7.93 (s, 1H), 7.56 (d, 1H), 7.40 (t, 1H), 7.24 (m, 2H), 7.00 (d, 1H), 3.17 (s, 3H) ppm.

Example 15

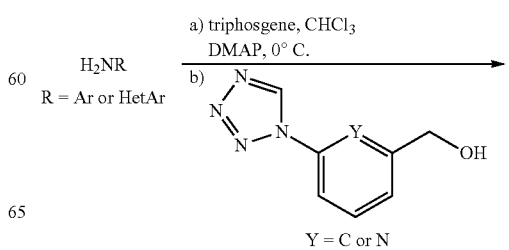

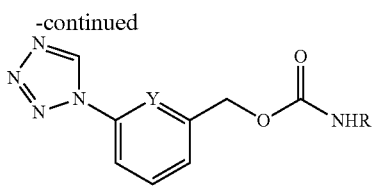

Carbamates. To a recovery flask was added triphosgene (0.6 eq.) and a stirbar. CHCl₃ was added and the solution was cooled to −10° C. In a separate flask, a solution of aryl- or heteroaryl amine (1.0 eq.) in CHCl₃ was prepared and added to the reaction flask via syringe. The reaction mixture was stirred for 5 min. A catalytic amount of DMAP was added. The appropriately substituted tetrazol-1-yl benzyl alcohol (1.0 eq.) was added and the reaction mixture became cloudy. After stirring for 30 min, LC/MS indicated the reaction was complete. The reaction was concentrated and purified via preparative HPLC to give a powder.

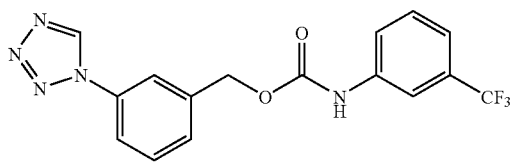

44

LC/MSD (HP Series 1100 MSD) MS (ES+) m/z 362.0 (M+H)⁺¹ ¹H-NMR, Varian 400 MHz (DMSO-d₆) δ 10.23 (s, 1H), 10.11 (s, 1H), 8.00 (s, 1H), 7.90-7.87 (m, 2H), 7.70-7.66 (m, 2H), 7.63-7.61 (m, 1H), 7.52 (t, 1H), 7.34 (d, 1H), 5.28 (s, 2H) ppm.

Example 16

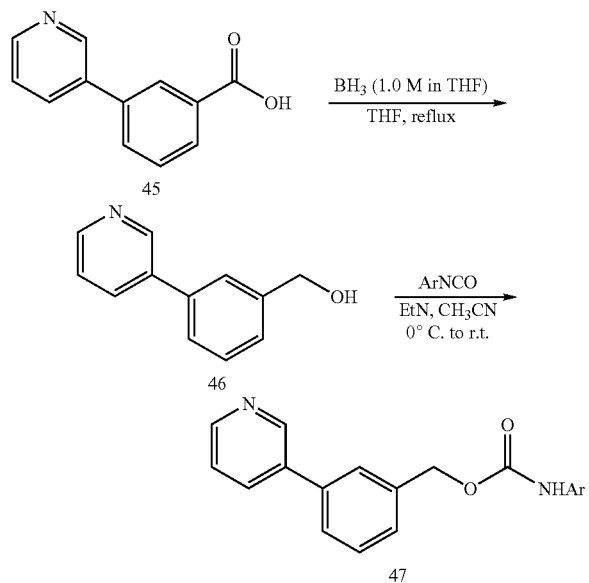

3-(3-pyridyl)-benzyl alcohol 46. To a 100 mL recovery flask was added 3-(3-pyridyl)-benzoic acid 45 (2.00 g, 10.0 mmol, 1.0 eq.) and THF (20 mL). The resulting suspension is stirred. BH₃ (1.0 M in THF, 15 mL, 15 mmol, 1.5 eq.) was added the resulting mixture was refluxed overnight. Incomplete reduction was observed by LC/MS. Additional BH₃ (10 mL) was added and the mixture was refluxed for an additional 6 h. LC/MS indicates complete reduction of the benzoic acid. The reaction mixture was concentrated and diluted with EtOAc. The organic layer was washed with a succession of water, HCl, brine. The combined aqueous layers were extracted with EtOAc. The organic phases were dried over anhydrous Na₂SO₄, filtered, and concentrated to give a clear oil. The crude material was purified via flash chromatography (40% to 60% EtOAc/Hex) to give a white solid (995 mg, 53%).

Carbamate 47. To a 25 mL recovery flask was added CH₃CN and aryl isocyanate (1.0 eq.) The solution was cooled to 0° C. upon which a solution of 3-(3-pyridyl)-benzyl alcohol 46 (1.0 eq.) and Et₃N (1.0 eq.) in CH₃CN was added via syringe. The reaction was stirred for 1.5 h while warming to room temperature. A light-colored precipitate formed during the reaction course. The reaction mixture was concentrated and taken up in a small amount of CH₃OH. The suspension is sonicated upon which a fine white powder developed. The solid was filtered to give pure product 47 as a white powder.

Example 17

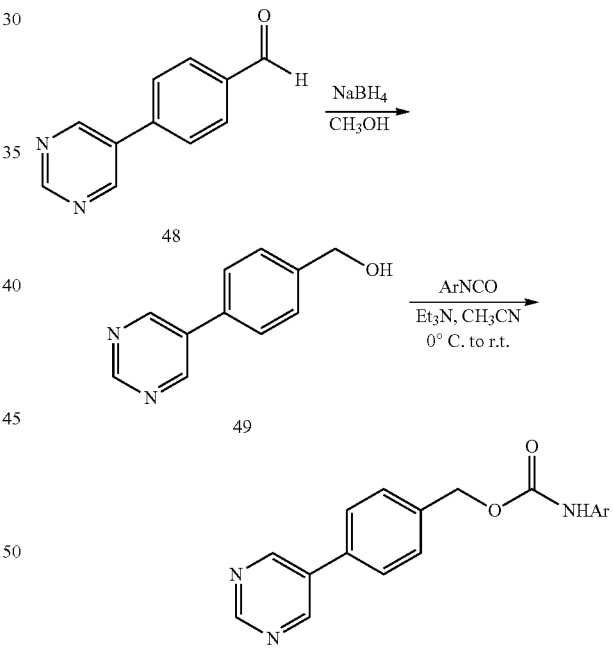

4-(5-pyrimidinyl)-benzyl alcohol 49. To a 100 mL recovery flask was added 4-(5-pyrimidinyl)-benzaldehyde 48 (1.01 g, 5.49 mmol, 1.0 eq.) and CH₃OH (30 mL). The resulting suspension was stirred upon which NaBH₄ (311 mg, 8.23 mmol, 1.5 eq.) was added. Upon addition of NaBH₄ the reaction became homogeneous. After stirring at room temperature for 2 h, the reaction was complete by LC/MS. The reaction mixture was concentrated and diluted with EtOAc upon which it was washed with a succession of water and brine. The aqueous phases were combined and extracted with EtOAc. The organic phases were dried over anhydrous Na$_2$SO$_4$, filtered, and concentrated to give a fine yellow powder that was used in subsequent reactions without further purification (523 mg, 51%).

Carbamate 50. To a 25 mL recovery flask was added CH$_3$CN and aryl isocyanate (1.0 eq.) The solution was cooled to 0° C. upon which a solution of 4-(5-pyrimidinyl)-benzyl alcohol 49 (1.0 eq.) and Et$_3$N (1.0 eq.) in CH$_3$CN was added via syringe. The reaction was stirred for 1.5 h while warming to room temperature. A light-colored precipitate formed during the reaction course. The reaction mixture was concentrated and taken up in a small amount of CH$_3$OH. The suspension is sonicated upon which a fine white powder developed. The solid was filtered to give pure product 50 as a white powder.

Example 18

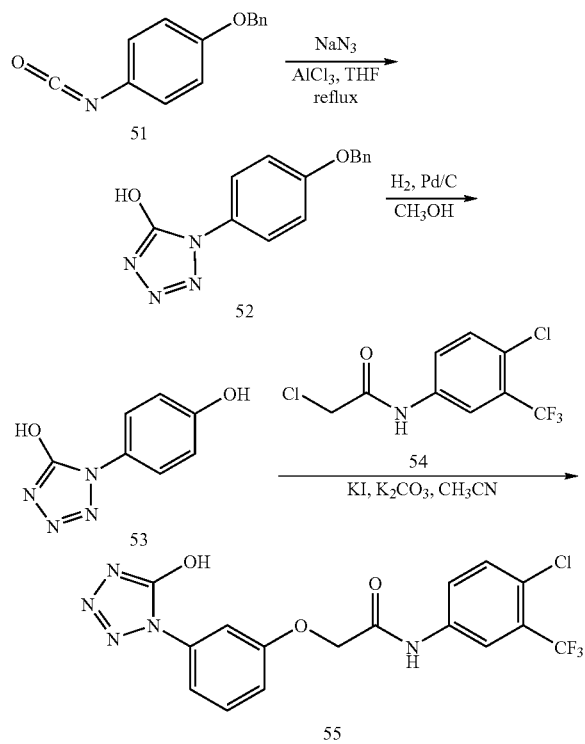

4-(2-hydroxytetrazol-1-yl)-1-benzyloxybenzene 52. To a 100 mL recovery flask was added THF (20 mL) and a stirbar. The flask was cooled to 0° C. whereupon AlCl$_3$ (751 mg, 5.63 mmol, 1.1 eq.) was added. The solution was stirred for 15 min whereupon NaN$_3$ (1.00 g, 15.4 mmol, 3.0 eq.) and 4-benzyloxy-phenylisocyanate 51 (1.15 g, 5.12 mmol, 1.0 eq.) was added. The reaction mixture was refluxed overnight. The reaction mixture was quenched with 1N HCl (50 mL) and diluted with EtOAc (100 mL). The organic phases were washed with brine and the combined aqueous phases were extracted with EtOAc (3×50 mL). The combined organic phases were dried over anhydrous Na$_2$SO$_4$, filtered, and concentrated to give an off-white solid that was used in subsequent reactions without further purification. (515 mg, 37%)

4-(2-hydroxytetrazol-1-yl)-phenol 53. To a 100 mL recovery flask was added 4-(2-hydroxytetrazol-1-yl)-1-benzyloxybenzene 52 (515 mg, 1.92 mmol, 1.0 eq.) and CH$_3$OH (20 mL). The solution was purged with N$_2$ upon which 10% Pd/C (50 mg) was added. The flask was sealed and fitted with a balloon filled with H$_2$. The reaction was stirred overnight at room temperature. The reaction was filtered through a pad of Celite and concentrated to give an off-white solid which was used in subsequent reactions without further purification (300 mg, 93%).

Amide 55. To a 25 mL recovery flask was added phenol 53 (150 mg, 0.842 μmmol, 1.0 eq.), chloroacetamide 54 (229 mg, 0.842 mmol, 1.0 eq.), K$_2$CO$_3$ (232 mg, 1.68 mmol, 2.0 eq.), and CH$_3$CN (10 mL). A catalytic amount of KI was added. The reaction was stirred overnight at room temperature upon which LC/MS analysis indicated the reaction was complete. The reaction mixture was filtered to remove excess K$_2$CO$_3$ and then concentrated. The crude material was purified via preparative HPLC to yield a white powder (15 mg, 4%). LC/MSD (HP Series 1100 MSD) MS (ES+) m/z 414.0 (M+H)$^{+1}$ $^1$H-NMR, Varian 400 MHz (DMSO-d$_6$) δ 10.91 (s, 1H), 9.93 (s, 1H), 8.15 (m, 1H), 7.80-7.77 (m, 1H), 7.70-7.68 (m, 1H), 7.58-7.56 (m, 2H), 6.93-6.91 (m, 2H), 4.99 (s, 2H) ppm.

Assays

Kinase assays were performed by measurement of incorporation of γ-$^{33}$P ATP into immobilized myelin basic protein (MBP). High binding white 384 well plates (Greiner) were coated with MBP (Sigma #M-1891) by incubation of 60 ul/well of 20 μg/ml MBP in Tris-buffered saline (TBS; 50 mM Tris pH 8.0, 138 mM NaCl, 2.7 mM KCl) for 24 hours at 4° C. Plates were washed 3× with 100 μl TBS. Kinase reactions were carried out in a total volume of 34 μl in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions were performed in DMSO and added to assay wells to a final DMSO concentration of 1%. Each data point was measured in duplicate, and at least two duplicate assays were performed for each individual compound determination. Enzyme was added to final concentrations of 10 nM or 20 nM, for example. A mixture of unlabeled ATP and γ-$^{33}$P ATP was added to start the reaction (2×10$^6$ cpm of γ-$^{33}$P ATP per well (3000 Ci/mmole) and either 10 μM or 30 μM unlabeled ATP, typically. The reactions were carried out for 1 hour at room temperature with shaking. Plates were washed 7× with TBS, followed by the addition of 50 μl/well scintillation fluid (Wallac). Plates were read using a Wallac Trilux counter. This is only one exemplary assay; various formats are possible, as known to one of ordinary skill in the art.

The above assay procedure can be used to determine the IC$_{50}$ for inhibition and/or the inhibition constant, K$_i$. The IC$_{50}$ is defined as the concentration of compound required to reduce the enzyme activity by 50% under the conditions of the assay. Exemplary compositions have IC$_{50}$'s of, for example, less than about 100 μM, less than about 10 μM, less than about 1 μM, and further for example having IC$_{50}$'s of less than about 100 nM, and still further, for example, less than about 10 nM. The K$_i$ for a compound may be determined from the IC$_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to equation (1) below; where V is the observed rate, V$_{max}$, is the rate of the free enzyme, I$_0$ is the inhibitor concentration, E$_0$ is the enzyme concentration, and K$_d$ is the dissociation constant of the enzyme-inhibitor complex.

$$V = V_{max}E_0\left[1 - \frac{(E_0 + I_0 + K_d) - \sqrt{(E_0 + I_0 + K_d)^2 - 4E_0 I_0}}{2E_0}\right]$$ Equation (1)

Kinase Specific Assays:

Kinase activity and compound inhibition are investigated using one or more of the three assay formats described below. The ATP concentrations for each assay are selected to be close to the Michaelis-Menten constant ($K_M$) for each individual kinase. Dose-response experiments are performed at 10 different inhibitor concentrations in a 384-well plate format. The data are fitted to four-parameter equation (2) below; where Y is the observed signal, X is the inhibitor concentration, Min is the background signal in the absence of enzyme (0% enzyme activity), Max is the signal in the absence of inhibitor (100% enzyme activity), $IC_{50}$ is the inhibitor concentration at 50% enzyme inhibition and H represents the empirical Hill's slope to measure the cooperativity. Typically H is close to unity.

$$Y = Min + (Max - Min)/(1 + (X/IC_{50})^H)$$ Equation (2)

c-Kit Assay c-Kit biochemical activity was assessed using AlphaScreen™ (Perkin Elmer) technology, described above. Test compounds, ATP, biotinylated poly(Glu, Tyr) and c-Kit kinase were combined in a volume of 20 μL in a 384-well white, medium binding microtiter plate (Greiner). Reaction mixtures were incubated for 1 hr at ambient temperature. Reactions were quenched by addition of 10 μL of 15-30 mg/mL AlphaScreen bead suspension containing 75 mM Hepes, pH 7.4, 300 mM NaCl, 120 mM EDTA, 0.3% BSA and 0.03% Tween-20. After 16 hr incubation at ambient temperature plates were read using an AlphaQuest reader (Perkin Elmer).

Structure Activity Relationships

Table 3 shows structure activity relationship data for selected compounds of the invention. Inhibition is indicated as $IC_{50}$ with the following key: A=$IC_{50}$ less than 50 nM, B=$IC_{50}$ greater than 50 nM, but less than 500 nM, C=$IC_{50}$ greater than 500 nM, but less than 5000 nM, and D=$IC_{50}$ equal to, or greater than 5,000 nM.

TABLE 3

| Entry | Name | c-Kit $IC_{50}$ |
|---|---|---|
| 1 | N-naphthalen-1-yl-2-{[3-(1H-tetrazol-1-yl)phenyl]oxy}acetamide | B |
| 2 | N-[4-(phenyloxy)phenyl]-2-{[3-(1H-tetrazol-1-yl)phenyl]oxy}acetamide | B |
| 3 | N-(3,4-dimethylphenyl)-2-{[3-(1H-tetrazol-1-yl)phenyl]oxyl}acetamide | A |
| 4 | N-(2,3-dimethylphenyl)-2-{[3-(1H-tetrazol-1-yl)phenyl]oxy}acetamide | C |
| 5 | N-(2,4-dimethylphenyl)-2-{[3-(1H-tetrazol-1-yl)phenyl]oxy}acetamide | C |
| 6 | N-(2,5-dimethylphenyl)-2-{[3-(1H-tetrazol-1-yl)phenyl]oxy}acetamide | D |
| 7 | N-(3,5-dimethylphenyl)-2-{[3-(1H-tetrazol-1-yl)phenyl]oxy}acetamide | B |
| 8 | N-(2,6-dimethylphenyl)-2-{[3-(1H-tetrazol-1-yl)phenyl]oxy}acetamide | D |
| 9 | 2-{[3-(1H-tetrazol-1-yl)phenyl]oxy}-N-(2,4,6-trimethylphenyl)acetamide | D |
| 10 | N-(2-ethylphenyl)-2-{[3-(1H-tetrazol-1-yl)phenyl]oxy}acetamide | D |
| 11 | N-(4-ethylphenyl)-2-{[3-(1H-tetrazol-1-yl)phenyl]oxy}acetamide | B |
| 12 | N-(2,6-diethylphenyl)-2-{[3-(1H-tetrazol-1-yl)phenyl]oxy}acetamide | D |
| 13 | N-[2-(methyloxy)phenyl]-2-{[3-(1H-tetrazol-1-yl)phenyl]oxy}acetamide | C |
| 14 | N-[2-(ethyloxy)phenyl]-2-{[3-(1H-tetrazol-1-yl)phenyl]oxy}acetamide | C |
| 15 | N-[3-(ethyloxy)phenyl]-2-{[3-(1H-tetrazol-1-yl)phenyl]oxy}acetamide | C |
| 16 | N-[2,4-bis(methyloxy)phenyl]-2-{[3-(1H-tetrazol-1-yl)phenyl]oxy}acetamide | B |
| 17 | N-[4-(dimethylamino)phenyl]-2-{[3-(1H-tetrazol-1-yl)phenyl]oxy}acetamide | C |
| 18 | N-(2,3-dichlorophenyl)-2-{[3-(1H-tetrazol-1-yl)phenyl]oxy}acetamide | D |
| 19 | N-(4-chloro-3-methylphenyl)-2-{[3-(1H-tetrazol-1-yl)phenyl]oxy}acetamide | B |
| 20 | N-(4-bromophenyl)-2-{[3-(1H-tetrazol-1-yl)phenyl]oxy}acetamide | B |
| 21 | N-(2-fluorophenyl)-2-{[3-(1H-tetrazol-1-yl)phenyl]oxy}acetamide | C |
| 22 | N-(4-fluorophenyl)-2-{[3-(1H-tetrazol-1-yl)phenyl]oxy}acetamide | C |
| 23 | 2-{[3-(1H-tetrazol-1-yl)phenyl]oxy}-N-[2-(trifluoromethyl)phenyl]acetamide | D |
| 24 | 2-{[3-(1H-tetrazol-1-yl)phenyl]oxy}-N-[3-(trifluoromethyl)phenyl]acetamide | A |
| 25 | methyl 4-[({[3-(1H-tetrazol-1-yl)phenyl]oxy}acetyl)amino]benzoate | C |

TABLE 3-continued

| Entry | Name | c-Kit IC$_{50}$ |
|---|---|---|
| 26 | ethyl 4-[({[3-(1H-tetrazol-1-yl)phenyl]oxy}acetyl)amino]benzoate | C |
| 27 | 3-[({[3-(1H-tetrazol-1-yl)phenyl]oxy}acetyl)amino]benzoic acid | C |
| 28 | N-[3-(methyloxy)phenyl]-2-{[3-(1H-tetrazol-1-yl)phenyl]oxy}acetamide | C |
| 29 | N-[4-(methyloxy)phenyl]-2-{[3-(1H-tetrazol-1-yl)phenyl]oxy}acetamide | C |
| 30 | N-[2-chloro-5-(trifluoromethyl)phenyl]-2-{[3-(1H-tetrazol-1-yl)phenyl]oxy}acetamide | C |
| 31 | N-[4-chloro-3-(trifluoromethyl)phenyl]-2-{[3-(4H-1,2,4-triazol-4-yl)phenyl]oxy}acetamide | A |
| 32 | N-(4-chlorophenyl)-2-{[3-(1H-tetrazol-1-yl)phenyl]oxy}acetamide | C |
| 33 | N-(4-aminophenyl)-2-{[3-(1H-tetrazol-1-yl)phenyl]oxy}acetamide | C |
| 34 | N-(4-acetylphenyl)-2-{[3-(1H-tetrazol-1-yl)phenyl]oxy}acetamide | C |
| 35 | N-[5-chloro-2-(methyloxy)phenyl]-2-{[3-(1H-tetrazol-1-yl)phenyl]oxy}acetamide | B |
| 36 | N-phenyl-2-{[3-(1H-tetrazol-1-yl)phenyl]oxy}acetamide | C |
| 37 | N-(2-methylphenyl)-2-{[3-(1H-tetrazol-1-yl)phenyl]oxy}acetamide | C |
| 38 | N-(2-chlorophenyl)-2-{[3-(1H-tetrazol-1-yl)phenyl]oxy}acetamide | D |
| 39 | N-[4-chloro-3-(trifluoromethyl)phenyl]-2-{[3-(1H-tetrazol-1-yl)phenyl]oxy}acetamide | A |
| 40 | ethyl 2-[({[3-(1H-tetrazol-1-yl)phenyl]oxy}acetyl)amino]-4,5,6,7-tetrahydro-1-benzothiophene-3-carboxylate | C |
| 41 | N-(3-chloro-2-methylphenyl)-2-{[3-(1H-tetrazol-1-yl)phenyl]oxy}acetamide | C |
| 42 | N-(3-fluorophenyl)-2-{[3-(1H-tetrazol-1-yl)phenyl]oxy}acetamide | C |
| 43 | N-[4-chloro-3-(trifluoromethyl)phenyl]-2-{[3-(2H-tetrazol-5-yl)phenyl]oxy}acetamide | D |
| 44 | N-(4-chloro-2-fluorophenyl)-2-{[3-(1H-tetrazol-1-yl)phenyl]oxy}acetamide | C |
| 45 | N-(4-bromo-3-methylphenyl)-2-{[3-(1H-tetrazol-1-yl)phenyl]oxy}acetamide | A |
| 46 | N-(4-morpholin-4-ylphenyl)-2-{[3-(1H-tetrazol-1-yl)phenyl]oxy}acetamide | D |
| 47 | N-[4-fluoro-3-(trifluoromethyl)phenyl]-2-{[3-(1H-tetrazol-1-yl)phenyl]oxy}acetamide | A |
| 48 | N-[4-bromo-3-(trifluoromethyl)phenyl]-2-{[3-(1H-tetrazol-1-yl)phenyl]oxy}acetamide | A |
| 49 | N-[4-chloro-3-(trifluoromethyl)phenyl]-2-{[4-(1H-tetrazol-1-yl)phenyl]oxy}acetamide | A |
| 50 | N-[4-chloro-3-(trifluoromethyl)phenyl]-2-{[3-(1H-tetrazol-1-yl)phenyl]oxy}propanamide | A |
| 51 | N-[4-chloro-3-(trifluoromethyl)phenyl]-2-{[3-(5-methyl-1H-tetrazol-1-yl)phenyl]oxy}acetamide | B |
| 52 | N-[4-chloro-3-(trifluoromethyl)phenyl]-2-{[2-methyl-5-(1H-tetrazol-1-yl)phenyl]oxy}acetamide | D |
| 53 | N-(4-chlorophenyl)-N-methyl-2-{[3-(1H-tetrazol-1-yl)phenyl]oxy}acetamide | D |
| 54 | N-[4-chloro-2-(trifluoromethyl)phenyl]-2-{[3-(1H-tetrazol-1-yl)phenyl]oxy}acetamide | D |
| 55 | N-[4-chloro-3-(trifluoromethyl)phenyl]-2-{[3-(2,5-dioxopyrrolidin-1-yl)phenyl]oxy}acetamide | D |
| 56 | (2E)-N-[4-chloro-3-(trifluoromethyl)phenyl]-3-[3-(1H-tetrazol-1-yl)phenyl]prop-2-enamide | C |
| 57 | N-[4-fluoro-3-(trifluoromethyl)phenyl]-2-{[4-(1H-tetrazol-1-yl)phenyl]oxy}acetamide | B |
| 58 | N-[4-chloro-3-(trifluoromethyl)phenyl]-2-{[3-(2-methyl-2H-tetrazol-5-yl)phenyl]oxy}acetamide | C |
| 59 | N-[4-chloro-3-(trifluoromethyl)phenyl]-2-{[2,4-dichloro-5-(1H-tetrazol-1-yl)phenyl]oxy}acetamide | C |
| 60 | N-[4-chloro-3-(trifluoromethyl)phenyl]-2-{[3-(1H-tetrazol-1-yl)phenyl]thio}acetamide | A |
| 61 | N-[4-chloro-3-(trifluoromethyl)phenyl]-N~2~-[3-(1H-tetrazol-1-yl)phenyl]glycinamide | A |
| 62 | N-[4-chloro-3-(trifluoromethyl)phenyl]-2-{[2-(1H-tetrazol-1-yl)phenyl]oxy}acetamide | C |
| 63 | methyl 1-{3-[2-{[4-chloro-3-(trifluoromethyl)phenyl]amino}-2-oxoethyl)oxy]phenyl}-1H-1,2,3-triazole-4-carboxylate | C |
| 64 | 1,1-dimethylethyl {4-[({[3-(1H-tetrazol-1-yl)phenyl]oxy}acetyl)amino]phenyl}carbamate | C |

TABLE 3-continued

| Entry | Name | c-Kit IC$_{50}$ |
|---|---|---|
| 65 | 1,1-dimethylethyl {4-[({[4-(1H-tetrazol-1-yl)phenyl]oxy}acetyl)amino]phenyl}carbamate | C |
| 66 | N-{4-[(1-ethylpiperidin-4-yl)amino]phenyl}-2-{[3-(1H-tetrazol-1-yl)phenyl]oxy}acetamide | C |
| 67 | N-{4-[(1-ethylpiperidin-3-yl)amino]phenyl}-2-{[3-(1H-tetrazol-1-yl)phenyl]oxy}acetamide | C |
| 68 | N-(4-aminophenyl)-2-{[4-(1H-tetrazol-1-yl)phenyl]oxy}acetamide | C |
| 69 | N-{4-[(1-ethylpiperidin-4-yl)amino]phenyl}-2-{[4-(1H-tetrazol-1-yl)phenyl]oxy}acetamide | C |
| 70 | N-{4-[(1-ethylpiperidin-3-yl)amino]phenyl}-2-{[4-(1H-tetrazol-1-yl)phenyl]oxy}acetamide | C |
| 71 | N-[4-chloro-3-(trifluoromethyl)phenyl]-2-[(3-pyridin-4-ylphenyl)oxy]acetamide | B |
| 72 | N-[4-chloro-3-(trifluoromethyl)phenyl]-N~2~-methyl-N~2~-[3-(1H-tetrazol-1-yl)phenyl]glycinamide | B |
| 73 | N-1,3-benzothiazol-2-yl-2-{[3-(1H-tetrazol-1-yl)phenyl]oxy}acetamide | A |
| 74 | N-quinolin-8-yl-2-{[3-(1H-tetrazol-1-yl)phenyl]oxy}acetamide | C |
| 75 | N-(2,3-dihydro-1,4-benzodioxin-6-yl)-2-{[3-(1H-tetrazol-1-yl)phenyl]oxy}acetamide | B |
| 76 | N-isoquinolin-5-yl-2-{[3-(1H-tetrazol-1-yl)phenyl]oxy}acetamide | C |
| 77 | N-{3-[(phenylmethyl)oxy]phenyl}-2-{[3-(1H-tetrazol-1-yl)phenyl]oxy}acetamide | C |
| 78 | N-[5-methyl-2-(methyloxy)phenyl]-2-{[3-(1H-tetrazol-1-yl)phenyl]oxy}acetamide | B |
| 79 | N-[2,5-bis(methyloxy)phenyl]-2-{[3-(1H-tetrazol-1-yl)phenyl]oxy}acetamide | C |
| 80 | N-(6-fluoro-1,3-benzothiazol-2-yl)-2-{[3-(1H-tetrazol-1-yl)phenyl]oxy}acetamide | C |
| 81 | methyl 3-[({[3-(1H-tetrazol-1-yl)phenyl]oxy}acetyl)amino]benzoate | C |
| 82 | 5-chloro-2-[({[3-(1H-tetrazol-1-yl)phenyl]oxy}acetyl)amino]benzamide | C |
| 83 | N-[5-chloro-2,4-bis(methyloxy)phenyl]-2-{[3-(1H-tetrazol-1-yl)phenyl]oxy}acetamide | A |
| 84 | N-[2-(phenyloxy)phenyl]-2-{[3-(1H-tetrazol-1-yl)phenyl]oxy}acetamide | B |
| 85 | N-[3-(aminosulfonyl)phenyl]-2-{[3-(1H-tetrazol-1-yl)phenyl]oxy}acetamide | C |
| 86 | N-[2-(methyloxy)-5-(trifluoromethyl)phenyl]-2-{[3-(1H-tetrazol-1-yl)phenyl]oxy}acetamide | B |
| 87 | N-(4-{[(4-methylphenyl)sulfonyl]amino}phenyl)-2-{[3-(1H-tetrazol-1-yl)phenyl]oxy}acetamide | C |
| 88 | N-(5-phenyl-1H-pyrazol-3-yl)-2-{[3-(1H-tetrazol-1-yl)phenyl]oxy}acetamide | C |
| 89 | N-1,3-benzothiazol-2-yl-2-{[4-(1H-tetrazol-1-yl)phenyl]oxy}acetamide | C |
| 90 | N-quinolin-8-yl-2-{[4-(1H-tetrazol-1-yl)phenyl]oxy}acetamide | C |
| 91 | 1,1-dimethylethyl 2-{3-[(2-{[4-chloro-3-(trifluoromethyl)phenyl]amino}-2-oxoethyl)oxy]phenyl}-1H-pyrrole-1-carboxylate | C |
| 92 | N-[4-chloro-3-(trifluoromethyl)phenyl]-2-{[3-(1H-pyrrol-2-yl)phenyl]oxy}acetamide | C |
| 93 | N-[4-chloro-3-(trifluoromethyl)phenyl]-2-[(3-pyrimidin-5-ylphenyl)oxy]acetamide | A |
| 94 | N-[4-chloro-3-(trifluoromethyl)phenyl]-2-{[3-(1H-1,2,3-triazol-1-yl)phenyl]oxy}acetamide | B |
| 95 | 4-chloro-N-(2-{[3-(1H-tetrazol-1-yl)phenyl]oxy}ethyl)-3-(trifluoromethyl)aniline | C |
| 96 | N-[4-chloro-3-(trifluoromethyl)phenyl]-N-(2-{[3-(1H-tetrazol-1-yl)phenyl]oxy}ethyl)formamide | C |
| 97 | N-[4-chloro-3-(trifluoromethyl)phenyl]-2-[(3-pyridin-3-ylphenyl)oxy]acetamide | B |
| 98 | N-[4-chloro-3-(trifluoromethyl)phenyl]-2-[(3-furan-3-ylphenyl)oxy]acetamide | C |
| 99 | (2E)-N-[4-fluoro-3-(trifluoromethyl)phenyl]-3-[3-(1H-tetrazol-1-yl)phenyl]prop-2-enamide | C |
| 100 | N-[4-fluoro-3-(trifluoromethyl)phenyl]-3-[3-(1H-tetrazol-1-yl)phenyl]propanamide | C |
| 101 | N-[4-chloro-3-(trifluoromethyl)phenyl]-2-{[6-(1H-tetrazol-1-yl)pyrimidin-4-yl]oxy}acetamide | C |
| 102 | N-[4-chloro-3-(trifluoromethyl)phenyl]-2-{[3-(3,5-dimethylisoxazol-4-yl)phenyl]oxy}acetamide | C |

TABLE 3-continued

| Entry | Name | c-Kit IC$_{50}$ |
|---|---|---|
| 103 | N-[4-chloro-3-(trifluoromethyl)phenyl]-2-[(3-quinolin-7-ylphenyl)oxy]acetamide | C |
| 104 | N-[4-chloro-3-(trifluoromethyl)phenyl]-2-[(3-furan-2-ylphenyl)oxy]acetamide | C |
| 105 | N-[4-chloro-3-(trifluoromethyl)phenyl]-2-[3-(1H-tetrazol-1-yl)phenyl]hydrazinecarboxamide | A |
| 106 | N-[4-chloro-3-(trifluoromethyl)phenyl]-2-[(3-dibenzo[b,d]furan-4-ylphenyl)oxy]acetamide | C |
| 107 | N-[4-chloro-3-(trifluoromethyl)phenyl]-2-[(4-pyrimidin-5-ylphenyl)oxy]acetamide | A |
| 108 | N-methyl-N-[4-(methyloxy)phenyl]-2-{[3-(1H-tetrazol-1-yl)phenyl]oxy}acetamide | C |
| 109 | N-[4-chloro-3-(trifluoromethyl)phenyl]-N'-{[3-(1H-tetrazol-1-yl)phenyl]methyl}urea | A |
| 110 | N-[4-chloro-3-(trifluoromethyl)phenyl]-N-methyl-2-{[3-(1H-tetrazol-1-yl)phenyl]oxy}acetamide | C |
| 111 | N-[4-fluoro-3-(trifluoromethyl)phenyl]-N~2~-[3-(1H-tetrazol-1-yl)phenyl]glycinamide | B |
| 112 | N-[4-fluoro-3-(trifluoromethyl)phenyl]-2-{[3-(pyridin-2-ylamino)phenyl]oxy}acetamide | C |
| 113 | N-[2-fluoro-5-(trifluoromethyl)phenyl]-2-[3-(1H-tetrazol-1-yl)phenyl]hydrazinecarboxamide | B |
| 114 | N-[4-chloro-3-(trifluoromethyl)phenyl]-2-[(4-pyridin-3-ylphenyl)oxy]acetamide | A |
| 115 | N-[4-chloro-3-(trifluoromethyl)phenyl]-N'-[(3-pyrimidin-5-ylphenyl)methyl]urea | A |
| 116 | N-[4-chloro-3-(trifluoromethyl)phenyl]-N'-[(4-pyrimidin-5-ylphenyl)methyl]urea | A |
| 117 | N-[4-chloro-3-(trifluoromethyl)phenyl]-N'-[(4-pyridin-3-ylphenyl)methyl]urea | B |
| 118 | [3-(1H-tetrazol-1-yl)phenyl]methyl [4-chloro-3-(trifluoromethyl)phenyl]carbamate | A |
| 119 | N-[4-fluoro-3-(trifluoromethyl)phenyl]-2-[(4-pyrimidin-5-ylphenyl)oxy]acetamide | A |
| 120 | N~2~-[4-chloro-3-(trifluoromethyl)phenyl]-N-[3-(1H-tetrazol-1-yl)phenyl]glycinamide | C |
| 121 | 2-{[4-chloro-3-(trifluoromethyl)phenyl]oxy}-N-[3-(1H-tetrazol-1-yl)phenyl]acetamide | C |
| 122 | N-[4-chloro-3-(trifluoromethyl)phenyl]-2-{[3-methyl-4-(1H-tetrazol-1-yl)phenyl]oxy}acetamide | C |
| 123 | N-[4-chloro-3-(trifluoromethyl)phenyl]-2-{[4-(1H-1,2,3-triazol-1-yl)phenyl]oxy}acetamide | B |
| 124 | N-[4-chloro-3-(trifluoromethyl)phenyl]-2-{[3-fluoro-4-(1H-tetrazol-1-yl)phenyl]oxy}acetamide | C |
| 125 | N-[4-chloro-3-(trifluoromethyl)phenyl]-2-{[2-fluoro-4-(1H-tetrazol-1-yl)phenyl]oxy}acetamide | A |
| 126 | N-({[4-chloro-3-(trifluoromethyl)phenyl]amino}carbonyl)-3-(1H-tetrazol-1-yl)benzenesulfonamide | C |
| 127 | N-({[4-chloro-3-(trifluoromethyl)phenyl]amino}carbonyl)-N-methyl-3-(1H-tetrazol-1-yl)benzenesulfonamide | C |
| 128 | N-[4-fluoro-3-(trifluoromethyl)phenyl]-2-[(4-pyridin-3-ylphenyl)oxy]acetamide | A |
| 129 | 2-({4-[2,4-bis(methyloxy)pyrimidin-5-yl]phenyl}oxy)-N-[4-fluoro-3-(trifluoromethyl)phenyl]acetamide | C |
| 130 | 2-({4-[2,4-bis(methyloxy)pyrimidin-5-yl]phenyl}oxy)-N-[4-chloro-3-(trifluoromethyl)phenyl]acetamide | C |
| 131 | N-[4-chloro-3-(trifluoromethyl)phenyl]-2-[(4-pyridin-4-ylphenyl)oxy]acetamide | C |
| 132 | N-[4-chloro-3-(trifluoromethyl)phenyl]-N~2~-[3-(methyloxy)-4-(1H-tetrazol-1-yl)phenyl]glycinamide | C |
| 133 | N-[4-chloro-3-(trifluoromethyl)phenyl]-N~2~-[4-(methyloxy)-3-(1H-tetrazol-1-yl)phenyl]glycinamide | C |
| 134 | N-[4-chloro-3-(trifluoromethyl)phenyl]-N~2~-[4-(1H-tetrazol-1-yl)phenyl]glycinamide | B |
| 135 | N-[4-chloro-3-(trifluoromethyl)phenyl]-2-(2,3,5,6-tetrafluoro-4-pyrimidin-5-ylphenyl)hydrazinecarboxamide | C |
| 136 | N-[4-chloro-3-(trifluoromethyl)phenyl]-N'-{[4-(1H-tetrazol-1-yl)phenyl]methyl}urea | B |
| 137 | N-[4-chloro-3-(trifluoromethyl)phenyl]-2-(4-pyrimidin-5-ylphenyl)hydrazinecarboxamide | A |
| 138 | N-[4-chloro-3-(trifluoromethyl)phenyl]-N'-[(3-pyridin-3-ylphenyl)methyl]urea | B |
| 139 | N-[4-chloro-3-(trifluoromethyl)phenyl]-2-methyl-2-{[3-(1H-tetrazol-1-yl)phenyl]oxy}propanamide | C |
| 140 | N-[4-chloro-3-(trifluoromethyl)phenyl]-2-{[4-(1H-tetrazol-1-yl)phenyl]oxy}propanamide | C |
| 141 | N-({4-[2,4-bis(methyloxy)pyrimidin-5-yl]phenyl}methyl)-N'-[4-chloro-3-(trifluoromethyl)phenyl]urea | C |

TABLE 3-continued

| Entry | Name | c-Kit IC$_{50}$ |
|---|---|---|
| 142 | N-[4-chloro-3-(trifluoromethyl)phenyl]-N'-({3-[2-(methyloxy)pyrimidin-5-yl]phenyl}methyl)urea | B |
| 143 | N-[4-chloro-3-(trifluoromethyl)phenyl]-N'-({3-[6-(methyloxy)pyridin-3-yl]phenyl}methyl)urea | B |
| 144 | N-[4-chloro-3-(trifluoromethyl)phenyl]-N'-({4-[2-(methyloxy)pyrimidin-5-yl]phenyl}methyl)urea | C |
| 145 | N-[4-chloro-3-(trifluoromethyl)phenyl]-N'-({4-[6-(methyloxy)pyridin-3-yl]phenyl}methyl)urea | C |
| 146 | 1,1-dimethylethyl 2-{4-[(2-{[4-chloro-3-(trifluoromethyl)phenyl]amino}-2-oxoethyl)oxy]phenyl}-1H-indole-1-carboxylate | C |
| 147 | N-({[4-chloro-3-(trifluoromethyl)phenyl]amino}carbonyl)-4-(1H-tetrazol-1-yl)benzenesulfonamide | C |
| 148 | N-[4-chloro-3-(trifluoromethyl)phenyl]-N~2~-[3-(2H-tetrazol-5-yl)phenyl]glycinamide | C |
| 149 | N-[4-chloro-3-(trifluoromethyl)phenyl]-2-{[2,6-difluoro-4-(1H-tetrazol-1-yl)phenyl]oxy}acetamide | C |
| 150 | (3-pyridin-3-ylphenyl)methyl [4-chloro-3-(trifluoromethyl)phenyl]carbamate | B |
| 151 | (3-pyrimidin-5-ylphenyl)methyl [4-chloro-3-(trifluoromethyl)phenyl]carbamate | A |
| 152 | (3-pyridin-4-ylphenyl)methyl [4-chloro-3-(trifluoromethyl)phenyl]carbamate | B |
| 153 | N-[4-chloro-3-(trifluoromethyl)phenyl]-2-[4-(1H-tetrazol-1-yl)phenyl]hydrazinecarboxamide | B |
| 154 | N-[4-chloro-3-(trifluoromethyl)phenyl]-2-(4-pyridin-3-ylphenyl)hydrazinecarboxamide | A |
| 155 | (4-pyridin-3-ylphenyl)methyl [4-chloro-3-(trifluoromethyl)phenyl]carbamate | C |
| 156 | (4-pyridin-4-ylphenyl)methyl [4-chloro-3-(trifluoromethyl)phenyl]carbamate | C |
| 157 | (4-pyrimidin-5-ylphenyl)methyl [4-chloro-3-(trifluoromethyl)phenyl]carbamate | C |
| 158 | N-[4-chloro-3-(trifluoromethyl)phenyl]-N'-[(4-pyridin-4-ylphenyl)methyl]urea | C |
| 159 | N-[4-chloro-3-(trifluoromethyl)phenyl]-2-(3-pyridin-3-ylphenyl)hydrazinecarboxamide | B |
| 160 | N-[4-chloro-3-(trifluoromethyl)phenyl]-2-(3-pyrimidin-5-ylphenyl)hydrazinecarboxamide | A |
| 161 | N-[5-chloro-2,4-bis(methyloxy)phenyl]-N'-[(4-pyrimidin-5-ylphenyl)methyl]urea | C |
| 162 | N-[5-chloro-2,4-bis(methyloxy)phenyl]-N'-[(4-pyridin-3-ylphenyl)methyl]urea | C |
| 163 | (4-pyrimidin-5-ylphenyl)methyl [5-chloro-2,4-bis(methyloxy)phenyl]carbamate | C |
| 164 | (4-pyridin-3-ylphenyl)methyl [5-chloro-2,4-bis(methyloxy)phenyl]carbamate | C |
| 165 | 1-(4-pyridin-3-ylphenyl)ethyl [4-chloro-3-(trifluoromethyl)phenyl]carbamate | C |
| 166 | 1-(4-pyrimidin-5-ylphenyl)ethyl [4-chloro-3-(trifluoromethyl)phenyl]carbamate | C |
| 167 | N-[5-chloro-2,4-bis(methyloxy)phenyl]-N'-[(3-pyridin-3-ylphenyl)methyl]urea | B |
| 168 | N-[5-chloro-2,4-bis(methyloxy)phenyl]-N'-[(3-pyrimidin-5-ylphenyl)methyl]urea | B |
| 169 | (3-pyridin-3-ylphenyl)methyl [5-chloro-2,4-bis(methyloxy)phenyl]carbamate | B |
| 170 | (3-pyrimidin-5-ylphenyl)methyl [5-chloro-2,4-bis(methyloxy)phenyl]carbamate | B |
| 171 | N-[4-chloro-3-(trifluoromethyl)phenyl]-2-methyl-2-(3-pyrimidin-5-ylphenyl)hydrazinecarboxamide | C |
| 172 | N-[4-fluoro-3-(trifluoromethyl)phenyl]-N'-[(4-pyridin-3-ylphenyl)methyl]urea | C |
| 173 | N-{[3-(6-aminopyridin-3-yl)phenyl]methyl}-N'-[4-chloro-3-(trifluoromethyl)phenyl]urea | C |
| 174 | N-{[4-(6-aminopyridin-3-yl)phenyl]methyl}-N'-[4-chloro-3-(trifluoromethyl)phenyl]urea | C |
| 175 | N-{[3-(2-aminopyrimidin-5-yl)phenyl]methyl}-N'-[4-chloro-3-(trifluoromethyl)phenyl]urea | B |
| 176 | N-{[4-(2-aminopyrimidin-5-yl)phenyl]methyl}-N'-[4-chloro-3-(trifluoromethyl)phenyl]urea | B |
| 177 | N-[4-chloro-3-(trifluoromethyl)phenyl]-N'-[1-(4-pyridin-3-ylphenyl)ethyl]urea | C |
| 178 | N-[4-chloro-3-(trifluoromethyl)phenyl]-N'-[1-(4-pyrimidin-5-ylphenyl)ethyl]urea | C |
| 179 | N-[4-chloro-3-(trifluoromethyl)phenyl]-2-{[4-(1H-indol-2-yl)phenyl]oxy}acetamide | C |

TABLE 3-continued

| Entry | Name | c-Kit IC$_{50}$ |
|---|---|---|
| 180 | N-[4-chloro-3-(trifluoromethyl)phenyl]-2-(isoquinolin-7-yloxy)acetamide | C |
| 181 | N-[4-chloro-3-(trifluoromethyl)phenyl]-2-(4-pyridin-4-ylphenyl)hydrazinecarboxamide | C |
| 182 | N-[4-chloro-3-(trifluoromethyl)phenyl]-2-(3-pyridin-4-ylphenyl)hydrazinecarboxamide | C |
| 183 | N-[4-chloro-3-(trifluoromethyl)phenyl]-N'-[(3-pyridin-4-ylphenyl)methyl]urea | B |
| 184 | N-[4-chloro-3-(trifluoromethyl)phenyl]-N'-[(3-quinoxalin-6-ylphenyl)methyl]urea | A |
| 185 | methyl 3-amino-6-(3-{[({[4-chloro-3-(trifluoromethyl)phenyl]amino}carbonyl)amino]methyl}phenyl)pyrazine-2-carboxylate | B |
| 186 | N-[4-chloro-3-(trifluoromethyl)phenyl]-N'-[(4-quinoxalin-6-ylphenyl)methyl]urea | C |
| 187 | N-{[3-(2-amino-5-methylpyridin-3-yl)phenyl]methyl}-N'-[4-chloro-3-(trifluoromethyl)phenyl]urea | B |
| 188 | methyl 3-amino-6-(4-{[({[4-chloro-3-(trifluoromethyl)phenyl]amino}carbonyl)amino]methyl}phenyl)pyrazine-2-carboxylate | C |
| 189 | [3-(1H-tetrazol-1-yl)phenyl]methyl [3-chloro-4-(methyloxy)phenyl]carbamate | A |
| 190 | N-[3-chloro-4-(methyloxy)phenyl]-N'-{[3-(1H-tetrazol-1-yl)phenyl]methyl}urea | B |
| 191 | N-[4-chloro-3-(trifluoromethyl)phenyl]-2-{[4-(5-hydroxy-1H-tetrazol-1-yl)phenyl]oxy}acetamide | C |
| 192 | N-{[3-(2-amino-5-chloropyridin-3-yl)phenyl]methyl}-N'-[4-chloro-3-(trifluoromethyl)phenyl]urea | B |
| 193 | N-{[4-(2-amino-5-chloropyridin-3-yl)phenyl]methyl}-N'-[4-chloro-3-(trifluoromethyl)phenyl]urea | C |
| 194 | N-{[3-(6-chloropyridin-3-yl)phenyl]methyl}-N'-[4-chloro-3-(trifluoromethyl)phenyl]urea | C |
| 195 | N-{[4-(6-chloropyridin-3-yl)phenyl]methyl}-N'-[4-chloro-3-(trifluoromethyl)phenyl]urea | C |
| 196 | N-[4-chloro-3-(trifluoromethyl)phenyl]-N'-{[4-(pyrimidin-2-yloxy)phenyl]methyl}urea | C |
| 197 | N-({[4-chloro-3-(trifluoromethyl)phenyl]amino}carbonyl)-3-(1H-tetrazol-1-yl)benzamide | C |
| 198 | 3-amino-6-(3-{[({[4-chloro-3-(trifluoromethyl)phenyl]amino}carbonyl)amino]methyl}phenyl)-N-[2-(dimethylamino)ethyl]pyrazine-2-carboxamide | C |
| 199 | N-[4-chloro-3-(trifluoromethyl)phenyl]-N'-{[3-(6-fluoropyridin-3-yl)phenyl]methyl}urea | C |
| 200 | N-[4-chloro-3-(trifluoromethyl)phenyl]-N'-({3-[2-(methyloxy)pyridin-3-yl]phenyl}methyl)urea | C |
| 201 | N-[4-chloro-3-(trifluoromethyl)phenyl]-N'-{[4-(6-fluoropyridin-3-yl)phenyl]methyl}urea | C |
| 202 | N-[4-chloro-3-(trifluoromethyl)phenyl]-N'-({4-[2-(methyloxy)pyridin-3-yl]phenyl}methyl)urea | C |
| 203 | N-[4-chloro-3-(trifluoromethyl)phenyl]-N'-{[4-(6-methylpyridin-3-yl)phenyl]methyl}urea | C |
| 204 | N-{[4-(2-amino-5-fluoropyridin-3-yl)phenyl]methyl}-N'-[4-chloro-3-(trifluoromethyl)phenyl]urea | C |
| 205 | N-[4-chloro-3-(trifluoromethyl)phenyl]-N'-{[3-(6-methylpyridin-3-yl)phenyl]methyl}urea | C |
| 206 | N-{[4-(2-aminopyridin-3-yl)phenyl]methyl}-N'-[4-chloro-3-(trifluoromethyl)phenyl]urea | C |
| 207 | N-{[3-(2-aminopyridin-3-yl)phenyl]methyl}-N'-[4-chloro-3-(trifluoromethyl)phenyl]urea | B |
| 208 | [3-(6-methylpyridin-3-yl)phenyl]methyl [4-chloro-3-(trifluoromethyl)phenyl]carbamate | C |
| 209 | [3-(2-amino-5-fluoropyridin-3-yl)phenyl]methyl [4-chloro-3-(trifluoromethyl)phenyl]carbamate | B |
| 210 | [3-(2-aminopyridin-3-yl)phenyl]methyl [4-chloro-3-(trifluoromethyl)phenyl]carbamate | B |
| 211 | (3-pyrazin-2-ylphenyl)methyl [4-chloro-3-(trifluoromethyl)phenyl]carbamate | C |
| 212 | N-[4-chloro-3-(trifluoromethyl)phenyl]-N'-({3-[6-(hydroxymethyl)pyridin-3-yl]phenyl}methyl)urea | C |
| 213 | N-{[3-(6-acetylpyridin-3-yl)phenyl]methyl}-N'-[4-chloro-3-(trifluoromethyl)phenyl]urea | C |
| 214 | N-[4-chloro-3-(trifluoromethyl)phenyl]-N'-{[3-(6-cyanopyridin-3-yl)phenyl]methyl}urea | C |
| 215 | 1,1-dimethylethyl (3S)-3-({[3-amino-6-(3-{[({[4-chloro-3-(trifluoromethyl)phenyl]amino}carbonyl)amino]methyl}phenyl)pyrazin-2-yl]carbonyl}amino)piperidine-1-carboxylate | C |

TABLE 3-continued

| Entry | Name | c-Kit IC$_{50}$ |
|---|---|---|
| 216 | 3-amino-6-(3-{[({[4-chloro-3-(trifluoromethyl)phenyl]amino}carbonyl)amino]methyl}phenyl)-N-[(3S)-piperidin-3-yl]pyrazine-2-carboxamide | A |
| 217 | 1,1-dimethylethyl (3S)-3-({[3-amino-6-(4-{[({[4-chloro-3-(trifluoromethyl)phenyl]amino}carbonyl)amino]methyl}phenyl)pyrazin-2-yl]carbonyl}amino)piperidine-1-carboxylate | C |
| 218 | 3-amino-6-(4-{[({[4-chloro-3-(trifluoromethyl)phenyl]amino}carbonyl)amino]methyl}phenyl)-N-[(3S)-piperidin-3-yl]pyrazine-2-carboxamide | A |
| 219 | [3-(7H-pyrrolo[2,3-d]pyrimidin-4-yl)phenyl]methyl [4-chloro-3-(trifluoromethyl)phenyl]carbamate | B |
| 220 | N-{[3-(2-amino-5-fluoropyridin-3-yl)phenyl]methyl}-N'-[4-chloro-3-(trifluoromethyl)phenyl]urea | B |
| 221 | [6-(1H-tetrazol-1-yl)pyridin-2-yl]methyl [4-chloro-3-(trifluoromethyl)phenyl]carbamate | A |
| 222 | [3-(1H-benzimidazol-2-yl)phenyl]methyl [4-chloro-3-(trifluoromethyl)phenyl]carbamate | C |
| 223 | [3-(6-amino-2-methylpyridin-3-yl)phenyl]methyl [4-chloro-3-(trifluoromethyl)phenyl]carbamate | C |
| 224 | N-[4-chloro-3-(trifluoromethyl)phenyl]-N'-({3-[5-(methylthio)pyridin-3-yl]phenyl}methyl)urea | C |
| 225 | [4-(6-methylpyridin-3-yl)phenyl]methyl [4-chloro-3-(trifluoromethyl)phenyl]carbamate | C |
| 226 | [4-(2-amino-5-fluoropyridin-3-yl)phenyl]methyl [4-chloro-3-(trifluoromethyl)phenyl]carbamate | C |
| 227 | [4-(2-aminopyridin-3-yl)phenyl]methyl [4-chloro-3-(trifluoromethyl)phenyl]carbamate | C |
| 228 | (4-pyrazin-2-ylphenyl)methyl [4-chloro-3-(trifluoromethyl)phenyl]carbamate | C |
| 229 | [4-(7H-pyrrolo[2,3-d]pyrimidin-4-yl)phenyl]methyl [4-chloro-3-(trifluoromethyl)phenyl]carbamate | C |
| 230 | [4-(6-amino-2-methylpyridin-3-yl)phenyl]methyl [4-chloro-3-(trifluoromethyl)phenyl]carbamate | C |
| 231 | [3-(1H-tetrazol-1-yl)phenyl]methyl 1,3-benzothiazol-2-ylcarbamate | C |
| 232 | [3-(1H-tetrazol-1-yl)phenyl]methyl (5-bromopyridin-2-yl)carbamate | C |
| 233 | (3-pyridin-3-ylphenyl)methyl (3,5-dimethylphenyl)carbamate | C |
| 234 | (3-pyridin-3-ylphenyl)methyl [5-chloro-2-(methyloxy)phenyl]carbamate | C |
| 235 | [4-(1H-tetrazol-1-yl)phenyl]methyl [4-chloro-3-(trifluoromethyl)phenyl]carbamate | C |
| 236 | (3-pyrimidin-5-ylphenyl)methyl [5-chloro-2-(methyloxy)phenyl]carbamate | C |
| 237 | (4-pyrimidin-5-ylphenyl)methyl (3,4-dimethylphenyl)carbamate | C |
| 238 | (3-pyridin-3-ylphenyl)methyl (3,4-dimethylphenyl)carbamate | B |
| 239 | 1,1-dimethylethyl 3-({[3-amino-6-(3-{[({[4-chloro-3-(trifluoromethyl)phenyl]amino}carbonyl)amino]methyl}phenyl)pyrazin-2-yl]carbonyl}amino)piperidine-1-carboxylate | C |
| 240 | 1,1-dimethylethyl 3-({[3-amino-6-(4-{[({[4-chloro-3-(trifluoromethyl)phenyl]amino}carbonyl)amino]methyl}phenyl)pyrazin-2-yl]carbonyl}amino)piperidine-1-carboxylate | C |
| 241 | 3-amino-6-(3-{[({[4-chloro-3-(trifluoromethyl)phenyl]amino}carbonyl)amino]methyl}phenyl)-N-piperidin-3-ylpyrazine-2-carboxamide | B |
| 242 | 3-amino-6-(4-{[({[4-chloro-3-(trifluoromethyl)phenyl]amino}carbonyl)amino]methyl}phenyl)-N-piperidin-3-ylpyrazine-2-carboxamide | B |
| 243 | 1,1-dimethylethyl 4-{[3-amino-6-(3-{[({[4-chloro-3-(trifluoromethyl)phenyl]amino}carbonyl)amino]methyl}phenyl)pyrazin-2-yl]carbonyl}piperazine-1-carboxylate | C |
| 244 | 1,1-dimethylethyl 4-{[3-amino-6-(4-{[({[4-chloro-3-(trifluoromethyl)phenyl]amino}carbonyl)amino]methyl}phenyl)pyrazin-2-yl]carbonyl}piperazine-1-carboxylate | C |
| 245 | N-({3-[5-amino-6-(piperazin-1-ylcarbonyl)pyrazin-2-yl]phenyl}methyl)-N'-[4-chloro-3-(trifluoromethyl)phenyl]urea | C |
| 246 | N-({4-[5-amino-6-(piperazin-1-ylcarbonyl)pyrazin-2-yl]phenyl}methyl)-N'-[4-chloro-3-(trifluoromethyl)phenyl]urea | C |
| 247 | N-[4-chloro-3-(trifluoromethyl)phenyl]-N'-{[3-(1H-pyrazol-4-yl)phenyl]methyl}urea | B |
| 248 | N-[4-chloro-3-(trifluoromethyl)phenyl]-N'-{[4-(1H-pyrazol-4-yl)phenyl]methyl}urea | C |
| 249 | [3-(2-piperazin-1-ylpyrimidin-5-yl)phenyl]methyl [4-chloro-3-(trifluoromethyl)phenyl]carbamate | C |

TABLE 3-continued

| Entry | Name | c-Kit IC$_{50}$ |
|---|---|---|
| 250 | [4-(2-piperazin-1-ylpyrimidin-5-yl)phenyl]methyl [4-chloro-3-(trifluoromethyl)phenyl]carbamate | C |
| 251 | N-{[3-(2-chloropyridin-3-yl)phenyl]methyl}-N'-[4-chloro-3-(trifluoromethyl)phenyl]urea | B |
| 252 | N-{[4-(2-chloropyridin-3-yl)phenyl]methyl}-N'-[4-chloro-3-(trifluoromethyl)phenyl]urea | C |
| 253 | N-[4-chloro-3-(trifluoromethyl)phenyl]-N'-{[3-(2-fluoropyridin-3-yl)phenyl]methyl}urea | C |
| 254 | N-[4-chloro-3-(trifluoromethyl)phenyl]-N'-{[4-(2-fluoropyridin-3-yl)phenyl]methyl}urea | C |
| 255 | [3-(1H-tetrazol-1-yl)phenyl]methyl [3-(trifluoromethyl)phenyl]carbamate | B |
| 256 | [3-(1H-tetrazol-1-yl)phenyl]methyl [6-(trifluoromethyl)pyridin-2-yl]carbamate | C |
| 257 | [3-(1H-tetrazol-1-yl)phenyl]methyl [4-(trifluoromethyl)pyridin-2-yl]carbamate | B |
| 258 | N-[4-chloro-3-(trifluoromethyl)phenyl]-N'-({3-[5-(methylthio)pyridin-2-yl]phenyl}methyl)urea | C |
| 259 | [3-(2,6-dimethylpyridin-3-yl)phenyl]methyl [4-chloro-3-(trifluoromethyl)phenyl]carbamate | C |
| 260 | {3-[5-(methyloxy)pyridin-3-yl]phenyl}methyl [4-chloro-3-(trifluoromethyl)phenyl]carbamate | B |
| 261 | 2,3'-bipyridin-6-ylmethyl [4-chloro-3-(trifluoromethyl)phenyl]carbamate | C |
| 262 | (6-pyrimidin-5-ylpyridin-2-yl)methyl [4-chloro-3-(trifluoromethyl)phenyl]carbamate | C |
| 263 | N-[4-chloro-3-(trifluoromethyl)phenyl]-N'-[(3-isoquinolin-4-ylphenyl)methyl]urea | C |
| 264 | N-[4-chloro-3-(trifluoromethyl)phenyl]-N'-[(4-isoquinolin-4-ylphenyl)methyl]urea | C |
| 265 | [6-(1H-tetrazol-1-yl)pyridin-2-yl]methyl [4-(trifluoromethyl)pyridin-2-yl]carbamate | B |
| 266 | [3-(1H-pyrazol-4-yl)phenyl]methyl [4-chloro-3-(trifluoromethyl)phenyl]carbamate | A |
| 267 | [4-(1H-pyrazol-4-yl)phenyl]methyl [4-chloro-3-(trifluoromethyl)phenyl]carbamate | C |

What is claimed is:

1. A compound for modulating c-Kit activity according to Formula I,

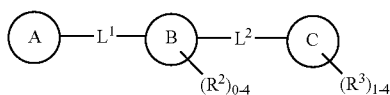

or a pharmaceutically acceptable salt, thereof, wherein, ring A is:

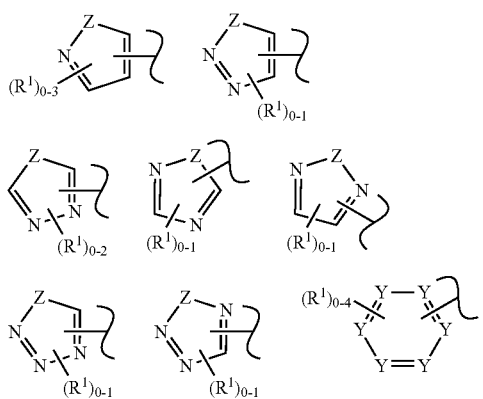

-continued

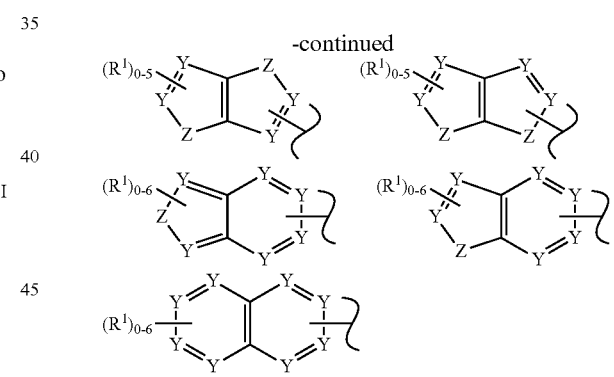

wherein each Y is independently either =C(H)— or =N—; and Z is selected from —O—, —S—, and —N(R$^7$)—, provided that the A ring contains at least one annular N, O, or S;

each R$^1$ is independently selected from —H, halogen, trihalomethyl, —CN, —NO$_2$, —OR$^4$, —S(O)$_{0-2}$R$^4$, —SO$_2$N(R$^4$)R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, —C(=O)R$^4$, optionally substituted alkoxy, optionally substituted C$_{1-6}$alkyl, optionally substituted aryl C$_{1-6}$alkyl, optionally substituted heterocyclyl, and optionally substituted heterocyclyl C$_{1-6}$alkyl;

two adjacent of R$^1$, together with the annular atoms to which they are attached, can form a five- to six-membered ring containing up to two heteroatoms and optionally substituted with up to three of R$^{10}$;

L$^1$ is a single bond;

ring B is phenyl;

each $R^2$ is independently selected from —H, halogen, trihalomethyl, —CN, —NO$_2$, —OR$^4$, —N(R$^4$)R$^4$, —S(O)$_{0-2}$R$^4$, —SO$_2$N(R$^4$)R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, —C(=O)R$^4$, optionally substituted alkoxy, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

two adjacent of $R^2$, together with the annular atoms to which they are attached, can form a five- to six-membered ring containing up to two heteroatoms and optionally substituted with up to three of $R^{15}$;

$L^2$ is selected from —N(H)N(H)C(=O)N(H)—, —CH$_2$N(H)C(=O)N(H)—, —CH$_2$OC(=O)N(H)—, and —XCH$_2$C(=O)N(H)—; wherein X is selected from —O—, —S(O)$_{0-2}$—, and —N(R$^7$)—; and any C—H of $L^2$ is optionally C—R$^{20}$;

ring C is phenyl;

each $R^3$ is independently selected from halogen, trihalomethyl, —CN, —NO$_2$, —OR$^4$, —S(O)$_{0-2}$R$^4$, —SO$_2$N(R$^4$)R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, —C(=O)R$^4$, optionally substituted alkoxy, optionally substituted C$_{1-6}$alkyl, optionally substituted aryl, optionally substituted aryl C$_{1-6}$alkyl, and optionally substituted heterocyclyl C$_{1-6}$alkyl; provided $R^3$ is not a cyclic sulfonamide attached to ring C via the nitrogen of said cyclic sulfonamide, wherein there exists at least one of $R^3$ that is trihalomethyl;

$R^4$ is selected from —H, optionally substituted C$_{1-6}$alkyl, optionally substituted aryl, optionally substituted aryl C$_{1-6}$alkyl, substituted heterocyclyl, and optionally substituted heterocyclyl C$_{1-6}$alkyl; or two of $R^4$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;

$R^5$ is selected from —H, —CN, —NO$_2$, —OR$^4$, —S(O)$_{0-2}$R$^4$, —CO$_2$R$^4$, optionally substituted C$_{1-6}$alkyl, optionally substituted C$_{1-6}$alkenyl, and optionally substituted C$_{1-6}$alkynyl;

$R^7$ is selected from —H, optionally substituted C$_{1-6}$alkyl, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —C(=O)R$^4$, optionally substituted alkoxy, optionally substituted aryl C$_{1-6}$alkyl, optionally substituted heterocyclyl, and optionally substituted heterocyclyl C$_{1-6}$alkyl; and each of $R^{10}$, each of $R^{15}$, each of $R^{20}$, and each of $R^{25}$ is independently selected from —H, halogen, trihalomethyl, —CN, —NO$_2$, —OR$^4$, —N(R$^4$)R$^4$, —S(O)$_{0-2}$R$^4$, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, —C(=O)R$^4$, optionally substituted alkoxy, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

provided:
the compound is not one of:
N-(2,3-dichlorophenyl)-2-{[3-(1H-tetrazol-1-yl)phenyl]oxy}acetamide,
N-(4-chloro-3-methylphenyl)-2-{[3-(1H-tetrazol-1-yl)phenyl]oxy}acetamide,
N-(4-bromophenyl)-2-{[3-(1H-tetrazol-1-yl)phenyl]oxy}acetamide
N-(2-fluorophenyl)-2-{[3-(1H-tetrazol-1-yl)phenyl]oxy}acetamide
N-(4-fluorophenyl)-2-{[3-(1H-tetrazol-1-yl)phenyl]oxy}acetamide
2-{[3-(1H-tetrazol-1-yl)phenyl]oxy}-N-[2-(trifluoromethyl)phenyl]acetamide
2-{[3-(1H-tetrazol-1-yl)phenyl]oxy}-N-[3-(trifluoromethyl)phenyl]acetamide
N-[2-chloro-5-(trifluoromethyl)phenyl]-2-{[3-(1H-tetrazol-1-yl)phenyl]oxy}acetamide
N-[4-chloro-3-(trifluoromethyl)phenyl]-2-{[3-(4H-1,2,4-triazol-4-yl)phenyl]oxy}acetamide or
N-(4-chlorophenyl)-2-{[3-(1H-tetrazol-1-yl)phenyl]oxy}acetamide.

2. The compound according to claim 1, wherein ring C is a phenyl comprising a trifluoromethyl radical meta- to $L^2$.

3. The compound according to claim 1, wherein each of $R^3$ is independently selected from halogen, trihalomethyl, —OR$^4$, —C(=O)R$^4$, and optionally substituted C$_{1-6}$alkyl.

4. A compound for modulating c-Kit activity according to the following Formula:

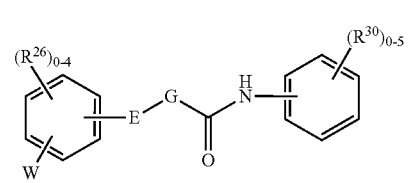

II or a pharmaceutically acceptable salt, thereof, wherein, W is selected from the following:

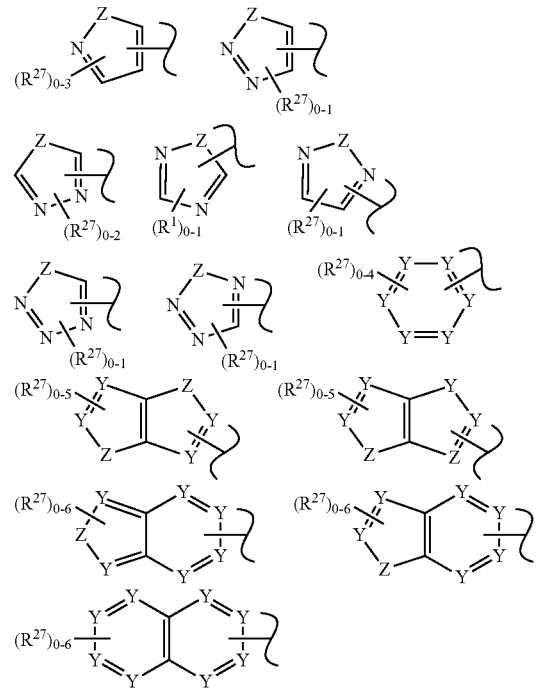

each of $R^{27}$ independently selected from halogen, trihalomethyl, —CN, —NO$_2$, —OR$^{55}$, —S(O)$_{0-2}$R$^{55}$, —C(=O)N(R$^{55}$)R$^{55}$, —C(=NR$^{50}$)N(R$^{55}$)R$^{55}$, —C(=NR$^{50}$)R$^{55}$, —N(R$^{55}$)SO$_2$R$^{55}$, —N(R$^{55}$)C(O)R$^{55}$, —NCO$_2$R$^{55}$, —C(=O)R$^{55}$, optionally substituted alkoxy, optionally substituted C$_{1-6}$alkyl, optionally substituted aryl C$_{1-6}$alkyl, optionally substituted heterocyclyl, and optionally substituted heterocyclyl C$_{1-6}$alkyl;

each Y is independently either =C(H)— or =N—;

Z is selected from —O—, —S(O)$_{0-2}$—, and —N(R$^7$)—, provided that the W ring contains at least one annular annular N, O, or S;

E and G are each independently selected from —O—, —S(O)$_{0-2}$—, —C(R$^{31}$)R$^{32}$—, and —N(R$^{33}$)—;

J$_1$ and J$_2$ are each independently =C(H)— or =N—;

R$^7$ is selected from —H, optionally substituted C$_{1-6}$alkyl, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —C(=O)R$^4$, optionally substituted alkoxy, optionally substituted aryl C$_{1-6}$alkyl, optionally substituted heterocyclyl, and optionally substituted heterocyclyl C$_{1-6}$alkyl;

R$^4$ is selected from —H, optionally substituted C$_{1-6}$alkyl, optionally substituted aryl, optionally substituted aryl C$_{1-6}$alkyl, substituted heterocyclyl, and optionally substituted heterocyclyl C$_{1-6}$alkyl; or two of R$^4$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;

R$^5$ is selected from —H, —CN, —NO$_2$, —OR$^4$, —S(O)$_{0-2}$R$^4$, —CO$_2$R$^4$, optionally substituted C$_{1-6}$alkyl, optionally substituted C$_{1-6}$alkenyl, and optionally substituted C$_{1-6}$alkynyl;

R$^{26}$ is independently selected from —H, halogen, trihalomethyl, —CN, —NO$_2$, —OR$^{40}$, —N(R$^{40}$)R$^{40}$, —S(O)$_{0-2}$R$^{40}$, —SO$_2$N(R$^{40}$)R$^{40}$, —CO$_2$R$^{40}$, —C(=O)N(R$^{40}$)R$^{40}$, —C(=NR$^{50}$)N(R$^{40}$)R$^{40}$, —C(=NR$^{50}$)R$^{40}$, —N(R$^{40}$)SO$_2$R$^{40}$, —N(R$^{40}$)C(O)R$^{40}$, —NCO$_2$R$^{40}$, —C(=O)R$^{40}$, optionally substituted alkoxy, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

R$^{30}$ is independently selected from halogen, trihalomethyl, —CN, —NO$_2$, —OR$^{40}$, —S(O)$_{0-2}$R$^{40}$, —SO$_2$N(R$^{40}$)R$^{40}$, —C(=O)N(R$^{40}$)R$^{40}$, —C(=NR$^{50}$)N(R$^{40}$)R$^{40}$, —C(NR$^{50}$)R$^{40}$, —N(R$^{40}$)SO$_2$R$^{40}$, —N(R$^{40}$)C(O)R$^{40}$, —NCO$_2$R$^{40}$, —C(=O)R$^{40}$, optionally substituted alkoxy, optionally substituted C$_{1-6}$alkyl, optionally substituted aryl, optionally substituted aryl C$_{1-6}$alkyl, and optionally substituted heterocyclyl C$_{1-6}$alkyl, wherein there exists at least one of R$^{30}$ that is trihalomethyl;

R$^{31}$ and R$^{32}$ are each independently selected from —H, halogen, trihalomethyl, —NO$_2$, —OR$^{40}$, —N(R$^{40}$)R$^{40}$, —S(O)$_{0-2}$R$^{40}$, —SO$_2$N(R$^{40}$)R$^{40}$, —CO$_2$R$^{40}$, —C(=O)N(R$^{40}$)R$^{40}$, —C(=NR$^{50}$)N(R$^{40}$)R$^{40}$, —C(=NR$^{50}$)R$^{40}$, —N(R$^{40}$)SO$_2$R$^{40}$, —N(R$^{40}$)C(O)R$^{40}$, —NCO$_2$R$^{40}$, —C(=O)R$^{40}$, optionally substituted alkoxy, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

R$^{33}$ is selected from —H, optionally substituted lower alkyl, —SO$_2$N(R$^{40}$)R$^{40}$, —CO$_2$R$^{40}$, —C(=O)N(R$^{40}$)R$^{40}$, —C(NR$^{50}$)N(R$^{40}$)R$^{40}$, —C(=NR$^{50}$)R$^{40}$, —C(=O)R$^{40}$, optionally substituted alkoxy, optionally substituted C$_{1-6}$alkyl, optionally substituted aryl, optionally substituted aryl C$_{1-6}$alkyl, and optionally substituted heterocyclyl C$_{1-6}$alkyl;

R$^{40}$ is selected from —H, optionally substituted alkoxy, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

two of R$^{40}$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;

R$^{50}$ is selected from —H, —NO$_2$, —OR$^{40}$, —S(O)$_{0-2}$R$^{40}$, —CO$_2$R$^{40}$, optionally substituted C$_{1-6}$alkyl, optionally substituted C$_{1-6}$alkenyl, and optionally substituted C$_{1-6}$alkynyl;

R$^{55}$ is selected from —H, optionally substituted C$_{1-6}$alkyl, substituted heterocyclyl, and optionally substituted heterocyclyl C$_{1-6}$alkyl; and two of R$^{55}$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P.

5. The compound according to claim 4, wherein R$^{30}$ is selected from halogen, trihalomethyl, —OR$^{40}$, —C(=O)R$^{40}$, optionally substituted alkoxy, optionally substituted C$_{1-6}$alkyl, optionally substituted aryl, optionally substituted aryl C$_{1-6}$alkyl, and optionally substituted heterocyclyl C$_{1-6}$alkyl, wherein there exists at least one of R$^{30}$ that is trifluoromethyl.

6. The compound according to claim 4, wherein E is selected from —O—, —S(O)$_{0-2}$—, and —NH—; and G is —CH$_2$—.

7. The compound according to claim 4, wherein E is either —CH$_2$— or —NH—; and G is selected from —O—, —S—, and —NH—.

8. A compound selected from the following Table:

TABLE 3

| Entry | Name | Structure |
|---|---|---|
| 1 | N-[5-chloro-2-(methyloxy)phenyl]-2-{[3-(1H-tetrazol-1-yl)phenyl]oxy}acetamide | 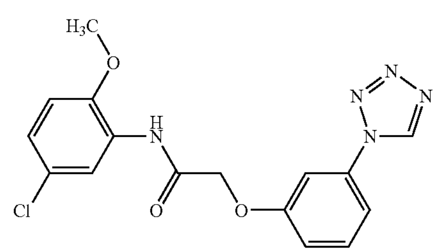 [SMILES: COc1ccc(Cl)cc1NC(=O)COc1cccc(-n2cnnn2)c1] |

TABLE 3-continued

| Entry | Name | Structure |
|---|---|---|
| 4 | N-(2-chlorophenyl)-2-{[3-(1H-tetrazol-1-yl)phenyl]oxy}acetamide | 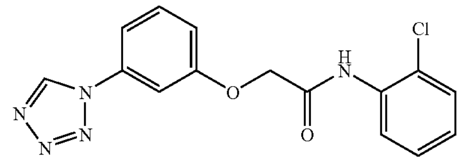 [SMILES: O=C(COc1cccc(-n2cnnn2)c1)Nc1ccccc1Cl] |
| 5 | N-[4-chloro-3-(trifluoromethyl)phenyl]-2-{[3-(1H-tetrazol-1-yl)phenyl]oxy}acetamide | 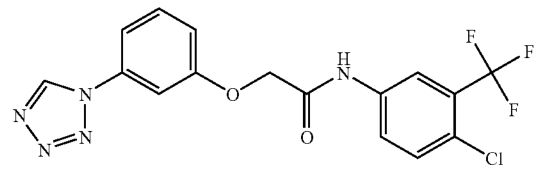 [SMILES: O=C(COc1cccc(-n2cnnn2)c1)Nc1ccc(Cl)c(C(F)(F)F)c1] |
| 7 | N-(3-chloro-2-methylphenyl)-2-{[3-(1H-tetrazol-1-yl)phenyl]oxy}acetamide | 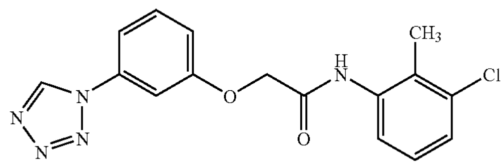 [SMILES: Cc1c(Cl)cccc1NC(=O)COc1cccc(-n2cnnn2)c1] |
| 8 | N-(3-fluorophenyl)-2-{[3-(1H-tetrazol-1-yl)phenyl]oxy}acetamide | 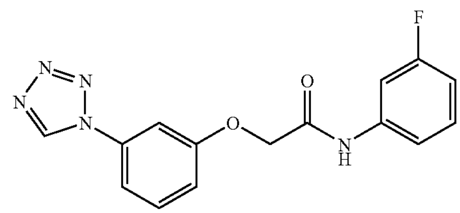 [SMILES: O=C(COc1cccc(-n2cnnn2)c1)Nc1cccc(F)c1] |
| 9 | N-[4-chloro-3-(trifluoromethyl)phenyl]-2-{[3-(2H-tetrazol-5-yl)phenyl]oxy}acetamide | 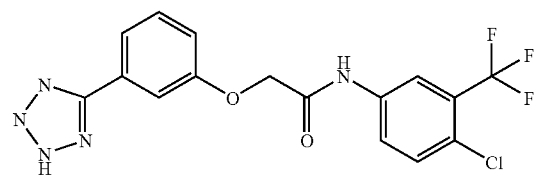 [SMILES: O=C(COc1cccc(C2=NNNN2)c1)Nc1ccc(Cl)c(C(F)(F)F)c1] |
| 10 | N-(4-chloro-2-fluorophenyl)-2-{[3-(1H-tetrazol-1-yl)phenyl]oxy}acetamide | 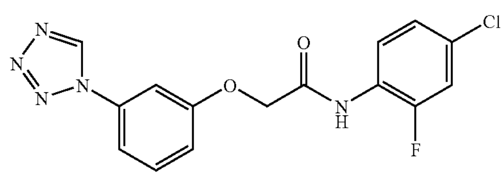 [SMILES: O=C(COc1cccc(-n2cnnn2)c1)Nc1ccc(Cl)cc1F] |
| 11 | N-(4-bromo-3-methylphenyl)-2-{[3-(1H-tetrazol-1-yl)phenyl]oxy}acetamide | 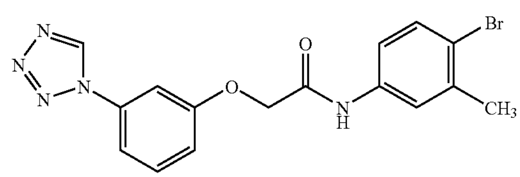 [SMILES: Cc1cc(NC(=O)COc2cccc(-n3cnnn3)c2)ccc1Br] |
| 13 | N-[4-fluoro-3-(trifluoromethyl)phenyl]-2-{[3-(1H-tetrazol-1-yl)phenyl]oxy}acetamide | 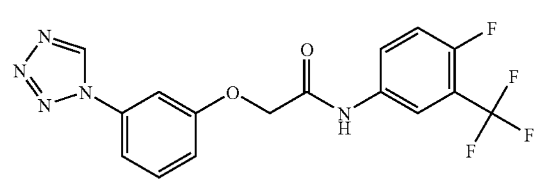 [SMILES: O=C(COc1cccc(-n2cnnn2)c1)Nc1ccc(F)c(C(F)(F)F)c1] |

TABLE 3-continued

| Entry | Name | Structure |
|---|---|---|
| 14 | N-[4-bromo-3-(trifluoromethyl)phenyl]-2-{[3-(1H-tetrazol-1-yl)phenyl]oxy}acetamide | 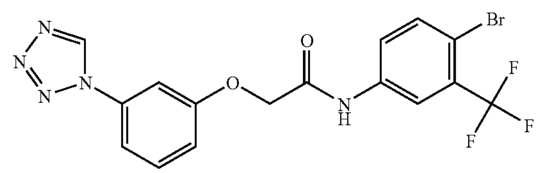 [SMILES: O=C(COc1cccc(-n2cnnn2)c1)Nc1ccc(Br)c(C(F)(F)F)c1] |
| 15 | N-[4-chloro-3-(trifluoromethyl)phenyl]-2-{[4-(1H-tetrazol-1-yl)phenyl]oxy}acetamide | 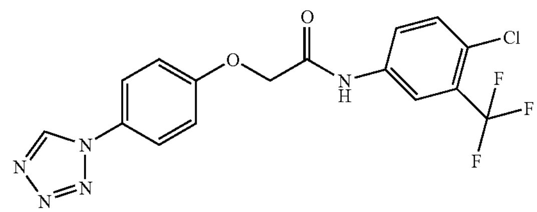 [SMILES: O=C(COc1ccc(-n2cnnn2)cc1)Nc1ccc(Cl)c(C(F)(F)F)c1] |
| 16 | N-[4-chloro-3-(trifluoromethyl)phenyl]-2-{[3-(1H-tetrazol-1-yl)phenyl]oxy}propanamide | 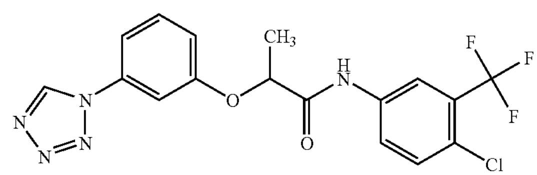 [SMILES: CC(Oc1cccc(-n2cnnn2)c1)C(=O)Nc1ccc(Cl)c(C(F)(F)F)c1] |
| 17 | N-[4-chloro-3-(trifluoromethyl)phenyl]-2-{[3-(5-methyl-1H-tetrazol-1-yl)phenyl]oxy}acetamide | 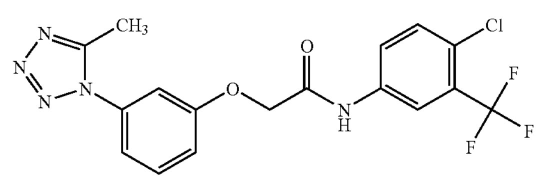 [SMILES: Cc1nnnn1-c1cccc(OCC(=O)Nc2ccc(Cl)c(C(F)(F)F)c2)c1] |
| 18 | N-[4-chloro-3-(trifluoromethyl)phenyl]-2-{[2-methyl-5-(1H-tetrazol-1-yl)phenyl]oxy}acetamide | 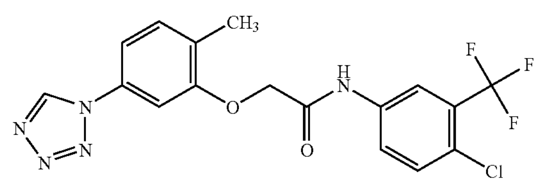 [SMILES: Cc1ccc(-n2cnnn2)cc1OCC(=O)Nc1ccc(Cl)c(C(F)(F)F)c1] |
| 19 | N-(4-chlorophenyl)-N-methyl-2-{[3-(1H-tetrazol-1-yl)phenyl]oxy}acetamide | 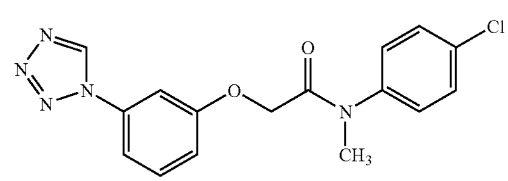 [SMILES: CN(C(=O)COc1cccc(-n2cnnn2)c1)c1ccc(Cl)cc1] |
| 20 | N-[4-chloro-2-(trifluoromethyl)phenyl]-2-{[3-(1H-tetrazol-1-yl)phenyl]oxy}acetamide | 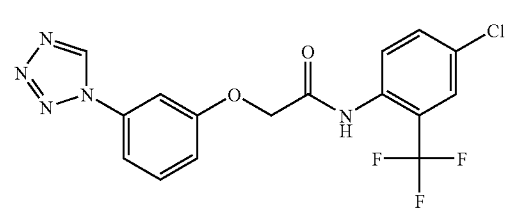 [SMILES: O=C(COc1cccc(-n2cnnn2)c1)Nc1ccc(Cl)cc1C(F)(F)F] |

TABLE 3-continued

| Entry | Name | Structure |
|---|---|---|
| 23 | N-[4-fluoro-3-(trifluoromethyl)phenyl]-2-{[4-(1H-tetrazol-1-yl)phenyl]oxy}acetamide | 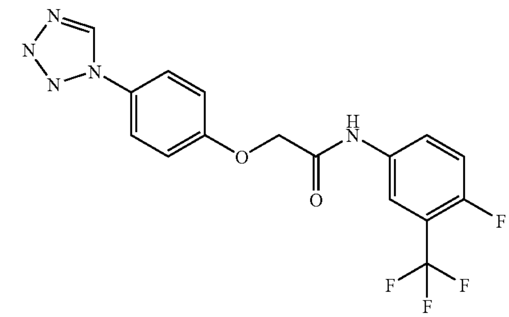 [SMILES: O=C(COc1ccc(N2C=NNN2)cc1)Nc1ccc(F)c(C(F)(F)F)c1] |
| 24 | N-[4-chloro-3-(trifluoromethyl)phenyl]-2-{[3-(2-methyl-2H-tetrazol-5-yl)phenyl]oxy}acetamide | 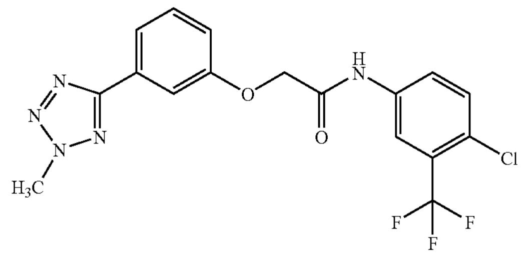 [SMILES: Cn1nnc(-c2cccc(OCC(=O)Nc3ccc(Cl)c(C(F)(F)F)c3)c2)n1] |
| 25 | N-[4-chloro-3-(trifluoromethyl)phenyl]-2-{[2,4-dichloro-5-(1H-tetrazol-1-yl)phenyl]oxy}acetamide | 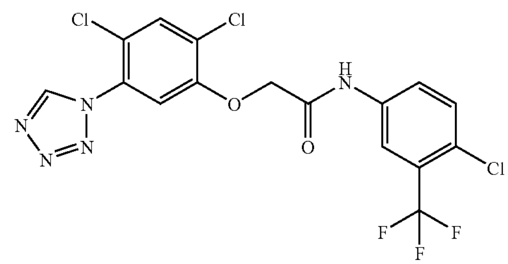 [SMILES: O=C(COc1cc(-n2cnnn2)c(Cl)cc1Cl)Nc1ccc(Cl)c(C(F)(F)F)c1] |
| 26 | N-[4-chloro-3-(trifluoromethyl)phenyl]-2-{[3-(1H-tetrazol-1-yl)phenyl]thio}acetamide | 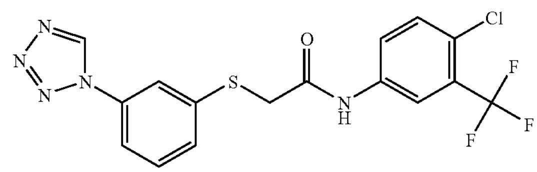 |
| 27 | N-[4-chloro-3-(trifluoromethyl)phenyl]-N~2~-[3-(1H-tetrazol-1-yl)phenyl]glycinamide | 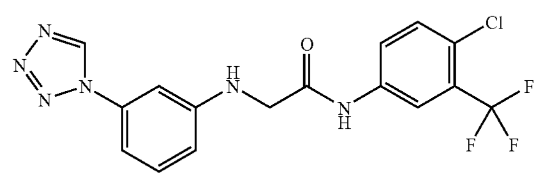 [SMILES: O=C(CNc1cccc(-n2cnnn2)c1)Nc1ccc(Cl)c(C(F)(F)F)c1] |
| 28 | N-[4-chloro-3-(trifluoromethyl)phenyl]-2-{[2-(1H-tetrazol-1-yl)phenyl]oxy}acetamide | 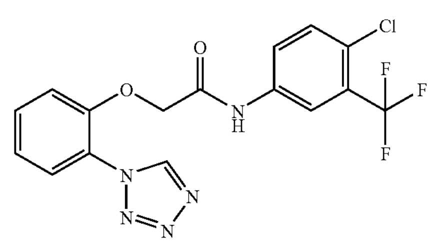 [SMILES: O=C(COc1ccccc1-n1cnnn1)Nc1ccc(Cl)c(C(F)(F)F)c1] |

TABLE 3-continued

| Entry | Name |
|---|---|
| 37 | N-[4-chloro-3-(trifluoromethyl)phenyl]-2-[(3-pyridin-4-ylphenyl)oxy]acetamide |
| 38 | N-[4-chloro-3-(trifluoromethyl)phenyl]-N~2~-methyl-N~2~-[3-(1H-tetrazol-1-yl)phenyl]glycinamide |
| 49 | N-[5-chloro-2,4-bis(methyloxy)phenyl]-2-{[3-(1H-tetrazol-1-yl)phenyl]oxy}acetamide |
| 52 | N-[2-(methyloxy)-5-(trifluoromethyl)phenyl]-2-{[3-(1H-tetrazol-1-yl)phenyl]oxy}acetamide |
| 57 | 1,1-dimethylethyl 2-{3-[(2-{[4-chloro-3-(trifluoromethyl)phenyl]amino}-2-oxoethyl)oxy]phenyl}-1H-pyrrole-1-carboxylate |
| 58 | N-[4-chloro-3-(trifluoromethyl)phenyl]-2-{[3-(1H-pyrrol-2-yl)phenyl]oxy}acetamide |
| 59 | N-[4-chloro-3-(trifluoromethyl)phenyl]-2-[(3-pyrimidin-5-ylphenyl)oxy]acetamide |

TABLE 3-continued

| Entry | Name | Structure |
|---|---|---|
| 60 | N-[4-chloro-3-(trifluoromethyl)phenyl]-2-{[3-(1H-1,2,3-triazol-1-yl)phenyl]oxy}acetamide | 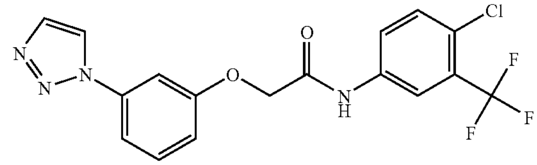 [SMILES: O=C(COc1cccc(-n2ccnn2)c1)Nc1ccc(Cl)c(C(F)(F)F)c1] |
| 63 | N-[4-chloro-3-(trifluoromethyl)phenyl]-2-[(3-pyridin-3-ylphenyl)oxy]acetamide | 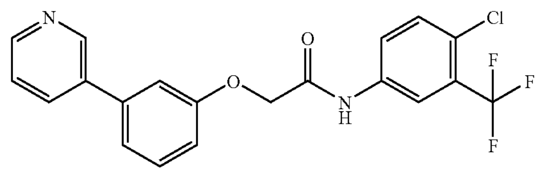 [SMILES: O=C(COc1cccc(-c2cccnc2)c1)Nc1ccc(Cl)c(C(F)(F)F)c1] |
| 68 | N-[4-chloro-3-(trifluoromethyl)phenyl]-2-{[3-(3,5-dimethylisoxazol-4-yl)phenyl]oxy}acetamide | 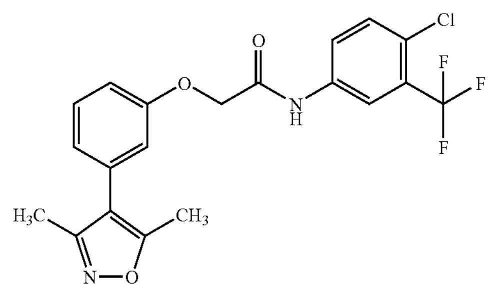 [SMILES: Cc1noc(C)c1-c1cccc(OCC(=O)Nc2ccc(Cl)c(C(F)(F)F)c2)c1] |
| 69 | N-[4-chloro-3-(trifluoromethyl)phenyl]-2-[(3-quinolin-7-ylphenyl)oxy]acetamide | 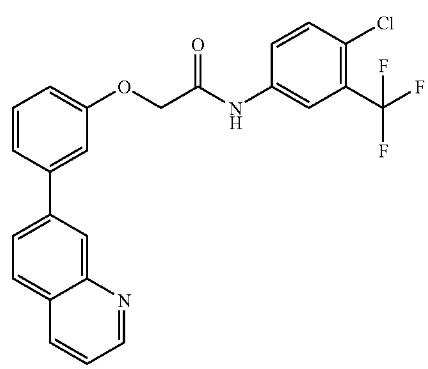 [SMILES: O=C(COc1cccc(-c2ccc3cccnc3c2)c1)Nc1ccc(Cl)c(C(F)(F)F)c1] |
| 71 | N-[4-chloro-3-(trifluoromethyl)phenyl]-2-[3-(1H-tetrazol-1-yl)phenyl]hydrazinecarboxamide | 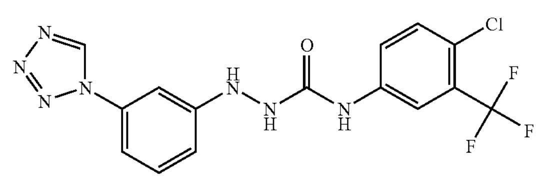 [SMILES: O=C(NNc1cccc(-n2cnnn2)c1)Nc1ccc(Cl)c(C(F)(F)F)c1] |
| 73 | N-[4-chloro-3-(trifluoromethyl)phenyl]-2-[(4-pyrimidin-5-ylphenyl)oxy]acetamide | 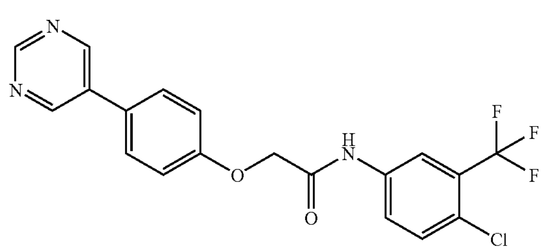 [SMILES: O=C(COc1ccc(-c2cncnc2)cc1)Nc1ccc(Cl)c(C(F)(F)F)c1] |

TABLE 3-continued

| Entry | Name | Structure |
|---|---|---|
| 75 | N-[4-chloro-3-(trifluoromethyl)phenyl]-N'-{[3-(1H-tetrazol-1-yl)phenyl]methyl}urea | 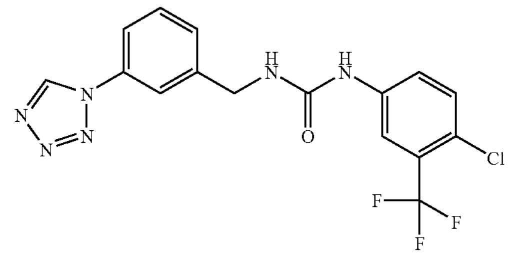 [SMILES: O=C(NCc1cccc(-n2cnnn2)c1)Nc1ccc(Cl)c(C(F)(F)F)c1] |
| 77 | N-[4-fluoro-3-(trifluoromethyl)phenyl]-N~2~-[3-(1H-tetrazol-1-yl)phenyl]glycinamide | 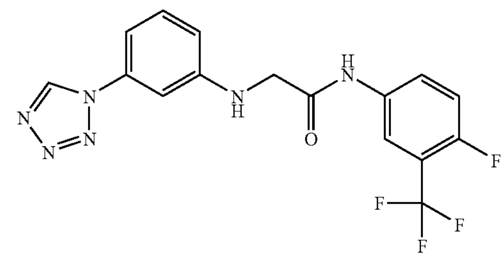 [SMILES: O=C(CNc1cccc(-n2cnnn2)c1)Nc1ccc(F)c(C(F)(F)F)c1] |
| 79 | N-[2-fluoro-5-(trifluoromethyl)phenyl]-2-[3-(1H-tetrazol-1-yl)phenyl]hydrazinecarboxamide | 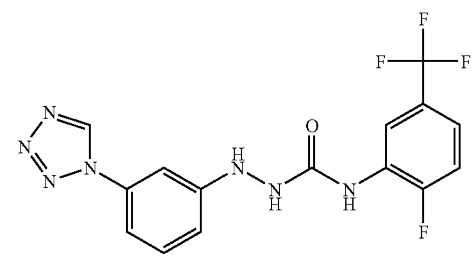 [SMILES: O=C(NNc1cccc(-n2cnnn2)c1)Nc1cc(C(F)(F)F)ccc1F] |
| 80 | N-[4-chloro-3-(trifluoromethyl)phenyl]-2-[(4-pyridin-3-ylphenyl)oxy]acetamide | 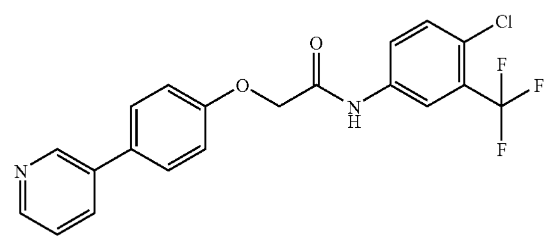 [SMILES: O=C(COc1ccc(-c2cccnc2)cc1)Nc1ccc(Cl)c(C(F)(F)F)c1] |
| 81 | N-[4-chloro-3-(trifluoromethyl)phenyl]-N'-[(3-pyrimidin-5-ylphenyl)methyl]urea | 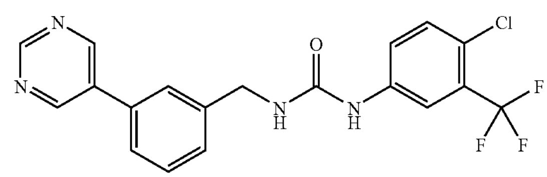 [SMILES: O=C(NCc1cccc(-c2cncnc2)c1)Nc1ccc(Cl)c(C(F)(F)F)c1] |
| 82 | N-[4-chloro-3-(trifluoromethyl)phenyl]-N'-[(4-pyrimidin-5-ylphenyl)methyl]urea | 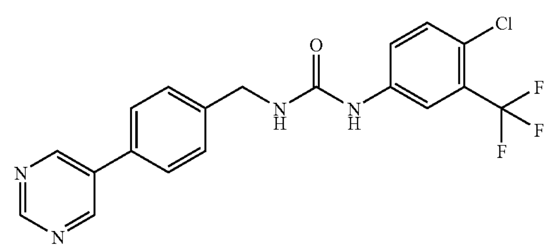 [SMILES: O=C(NCc1ccc(-c2cncnc2)cc1)Nc1ccc(Cl)c(C(F)(F)F)c1] |

TABLE 3-continued

| Entry | Name | Structure |
|---|---|---|
| 83 | N-[4-chloro-3-(trifluoromethyl)phenyl]-N'-[(4-pyridin-3-ylphenyl)methyl]urea | 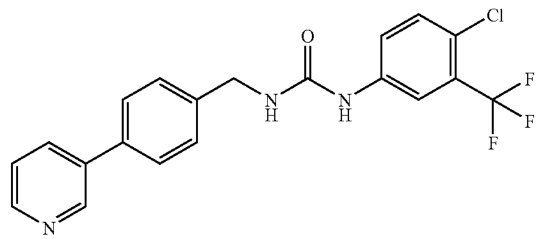 [SMILES: O=C(NCc1ccc(-c2cccnc2)cc1)Nc1ccc(Cl)c(C(F)(F)F)c1] |
| 84 | [3-(1H-tetrazol-1-yl)phenyl]methyl [4-chloro-3-(trifluoromethyl)phenyl]carbamate | 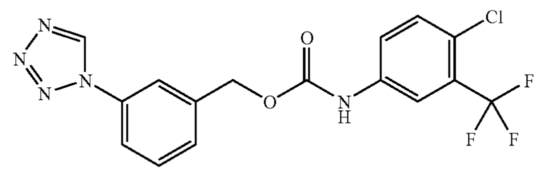 [SMILES: O=C(Nc1ccc(Cl)c(C(F)(F)F)c1)OCc1cccc(-n2cnnn2)c1] |
| 85 | N-[4-fluoro-3-(trifluoromethyl)phenyl]-2-[(4-pyrimidin-5-ylphenyl)oxy]acetamide | 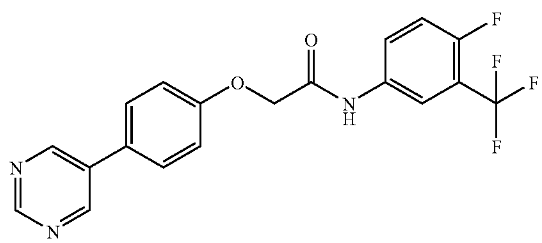 [SMILES: O=C(COc1ccc(-c2cncnc2)cc1)Nc1ccc(F)c(C(F)(F)F)c1] |
| 86 | N~2~-[4-chloro-3-(trifluoromethyl)phenyl]-N-[3-(1H-tetrazol-1-yl)phenyl]glycinamide | 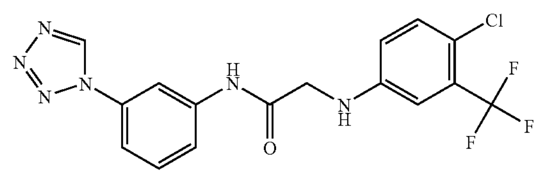 [SMILES: O=C(CNc1ccc(Cl)c(C(F)(F)F)c1)Nc1cccc(-n2cnnn2)c1] |
| 87 | 2-{[4-chloro-3-(trifluoromethyl)phenyl]oxy}-N-[3-(1H-tetrazol-1-yl)phenyl]acetamide | 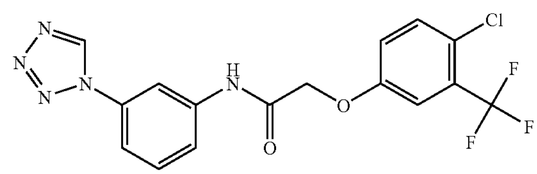 [SMILES: O=C(COc1ccc(Cl)c(C(F)(F)F)c1)Nc1cccc(-n2cnnn2)c1] |
| 88 | N-[4-chloro-3-(trifluoromethyl)phenyl]-2-{[3-methyl-4-(1H-tetrazol-1-yl)phenyl]oxy}acetamide | 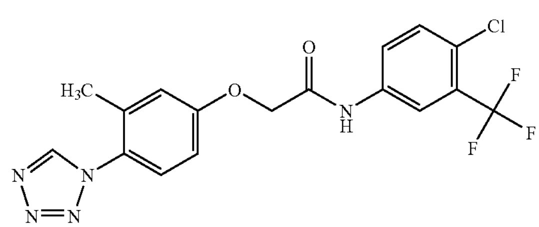 [SMILES: Cc1cc(OCC(=O)Nc2ccc(Cl)c(C(F)(F)F)c2)ccc1-n1cnnn1] |
| 89 | N-[4-chloro-3-(trifluoromethyl)phenyl]-2-{[4-(1H-1,2,3-triazol-1-yl)phenyl]oxy}acetamide | 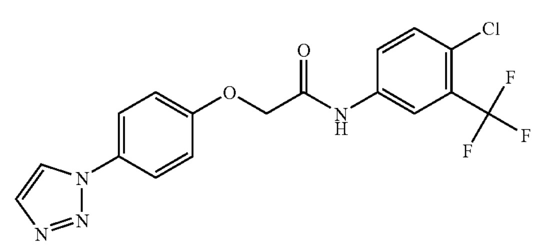 [SMILES: O=C(COc1ccc(-n2ccnn2)cc1)Nc1ccc(Cl)c(C(F)(F)F)c1] |

TABLE 3-continued

| Entry | Name | Structure |
|---|---|---|
| 90 | N-[4-chloro-3-(trifluoromethyl)phenyl]-2-{[3-fluoro-4-(1H-tetrazol-1-yl)phenyl]oxy}acetamide | 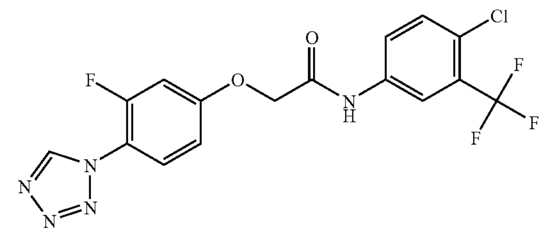 [SMILES: O=C(COc1ccc(-n2cnnn2)c(F)c1)Nc1ccc(Cl)c(C(F)(F)F)c1] |
| 91 | N-[4-chloro-3-(trifluoromethyl)phenyl]-2-{[2-fluoro-4-(1H-tetrazol-1-yl)phenyl]oxy}acetamide | 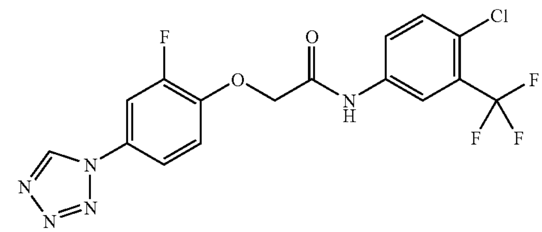 [SMILES: O=C(COc1ccc(-n2cnnn2)cc1F)Nc1ccc(Cl)c(C(F)(F)F)c1] |
| 94 | N-[4-fluoro-3-(trifluoromethyl)phenyl]-2-[(4-pyridin-3-ylphenyl)oxy]acetamide | 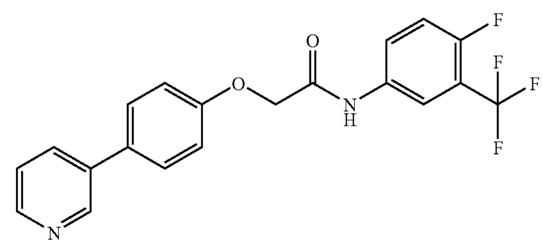 [SMILES: O=C(COc1ccc(-c2cccnc2)cc1)Nc1ccc(F)c(C(F)(F)F)c1] |
| 95 | 2-({4-[2,4-bis(methyloxy)pyrimidin-5-yl]phenyl}oxy)-N-[4-fluoro-3-(trifluoromethyl)phenyl]acetamide | 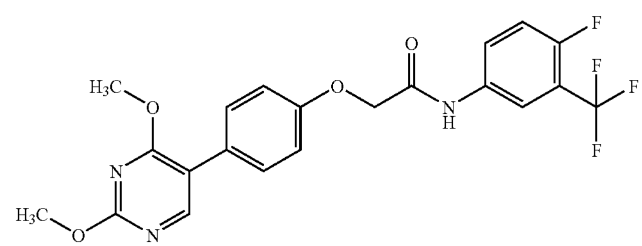 |
| 96 | 2-({4-[2,4-bis(methyloxy)pyrimidin-5-yl]phenyl}oxy)-N-[4-chloro-3-(trifluoromethyl)phenyl]acetamide | 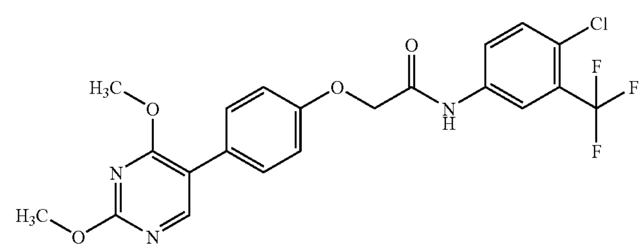 |
| 97 | N-[4-chloro-3-(trifluoromethyl)phenyl]-2-[(4-pyridin-4-ylphenyl)oxy]acetamide | 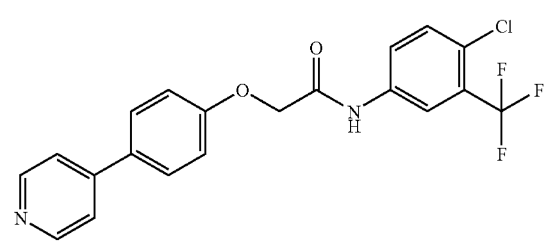 [SMILES: O=C(COc1ccc(-c2ccncc2)cc1)Nc1ccc(Cl)c(C(F)(F)F)c1] |

TABLE 3-continued

| Entry | Name | Structure |
|---|---|---|
| 98 | N-[4-chloro-3-(trifluoromethyl)phenyl]-N~2~-[3-(methyloxy)-4-(1H-tetrazol-1-yl)phenyl]glycinamide | 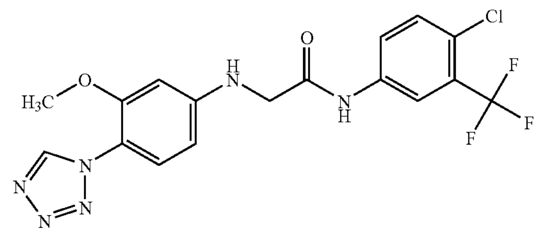 [SMILES: COc1cc(NCC(=O)Nc2ccc(Cl)c(C(F)(F)F)c2)ccc1-n1cnnn1] |
| 99 | N-[4-chloro-3-(trifluoromethyl)phenyl]-N~2~-[4-(methyloxy)-3-(1H-tetrazol-1-yl)phenyl]glycinamide | 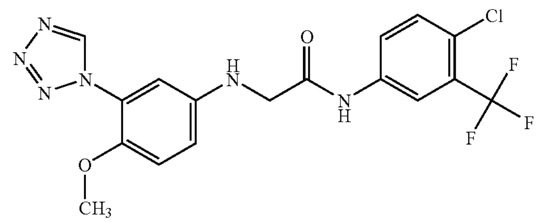 [SMILES: COc1ccc(NCC(=O)Nc2ccc(Cl)c(C(F)(F)F)c2)cc1-n1cnnn1] |
| 100 | N-[4-chloro-3-(trifluoromethyl)phenyl]-N~2~-[4-(1H-tetrazol-1-yl)phenyl]glycinamide | 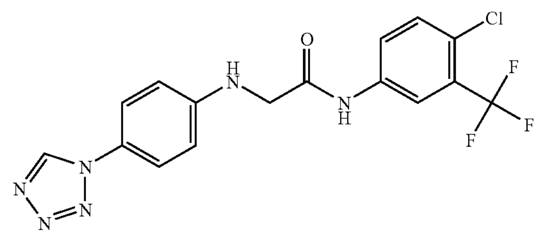 [SMILES: O=C(CNc1ccc(-n2cnnn2)cc1)Nc1ccc(Cl)c(C(F)(F)F)c1] |
| 101 | N-[4-chloro-3-(trifluoromethyl)phenyl]-2-(2,3,5,6-tetrafluoro-4-pyrimidin-5-ylphenyl)hydrazinecarboxamide | 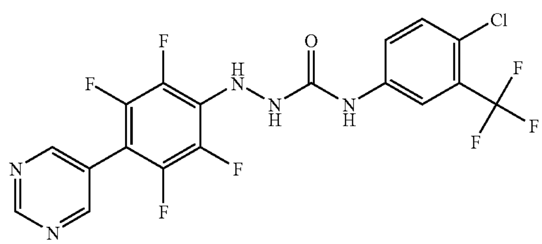 [SMILES: O=C(NNc1c(F)c(F)c(-c2cncnc2)c(F)c1F)Nc1ccc(Cl)c(C(F)(F)F)c1] |
| 102 | N-[4-chloro-3-(trifluoromethyl)phenyl]-N'-{[4-(1H-tetrazol-1-yl)phenyl]methyl}urea | 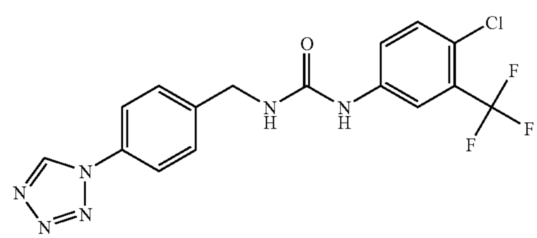 |
| 103 | N-[4-chloro-3-(trifluoromethyl)phenyl]-2-(4-pyrimidin-5-ylphenyl)hydrazinecarboxamide | 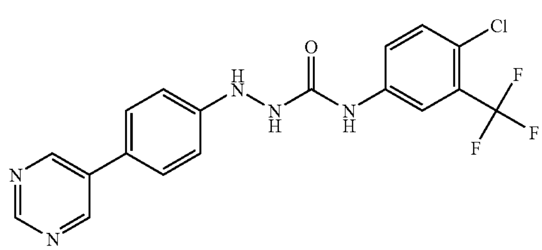 [SMILES: O=C(NNc1ccc(-c2cncnc2)cc1)Nc1ccc(Cl)c(C(F)(F)F)c1] |
| 104 | N-[4-chloro-3-(trifluoromethyl)phenyl]-N'-[(3-pyridin-3-ylphenyl)methyl]urea | 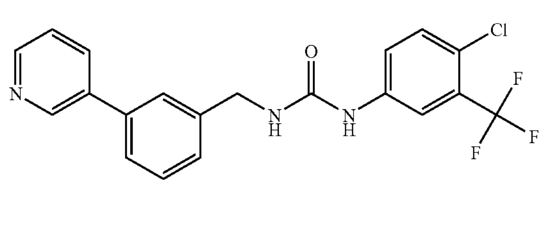 [SMILES: O=C(NCc1cccc(-c2cccnc2)c1)Nc1ccc(Cl)c(C(F)(F)F)c1] |

TABLE 3-continued

| Entry | Name | Structure |
|---|---|---|
| 105 | N-[4-chloro-3-(trifluoromethyl)phenyl]-2-methyl-2-{[3-(1H-tetrazol-1-yl)phenyl]oxy}propanamide | 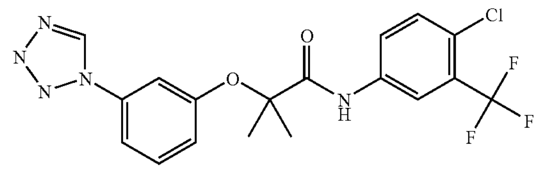 [SMILES: CC(C)(Oc1cccc(N2C=NNN2)c1)C(=O)Nc1ccc(Cl)c(C(F)(F)F)c1] |
| 106 | N-[4-chloro-3-(trifluoromethyl)phenyl]-2-{[4-(1H-tetrazol-1-yl)phenyl]oxy}propanamide | 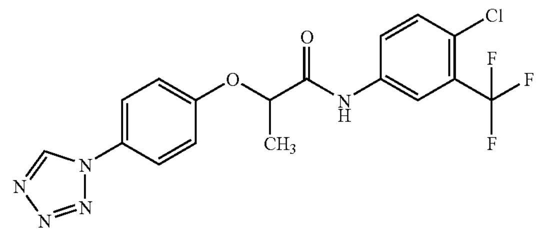 [SMILES: CC(Oc1ccc(-n2cnnn2)cc1)C(=O)Nc1ccc(Cl)c(C(F)(F)F)c1] |
| 107 | N-({4-[2,4-bis(methyloxy)pyrimidin-5-yl]phenyl}methyl)-N'-[4-chloro-3-(trifluoromethyl)phenyl]urea | 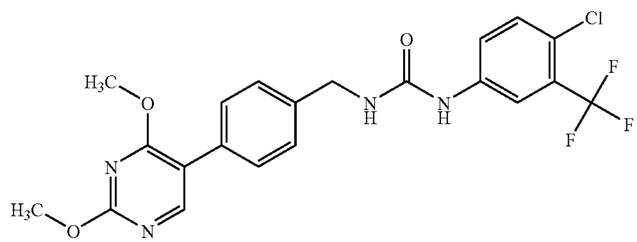 [SMILES: COc1ncc(-c2ccc(CNC(=O)Nc3ccc(Cl)c(C(F)(F)F)c3)cc2)c(OC)n1] |
| 108 | N-[4-chloro-3-(trifluoromethyl)phenyl]-N'-({3-[2-(methyloxy)pyrimidin-5-yl]phenyl}methyl)urea | 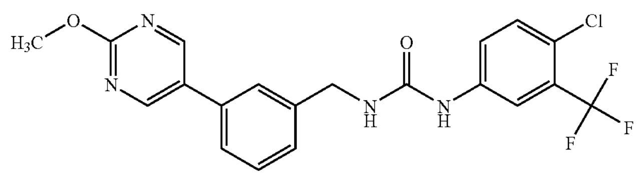 [SMILES: COc1ncc(-c2cccc(CNC(=O)Nc3ccc(Cl)c(C(F)(F)F)c3)c2)cn1] |
| 109 | N-[4-chloro-3-(trifluoromethyl)phenyl]-N'-({3-[6-(methyloxy)pyridin-3-yl]phenyl}methyl)urea | 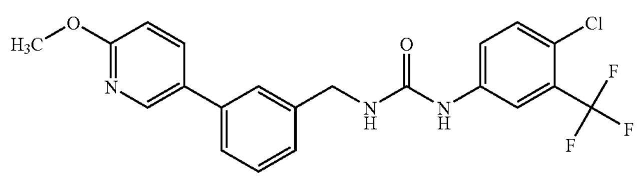 [SMILES: COc1ccc(-c2cccc(CNC(=O)Nc3ccc(Cl)c(C(F)(F)F)c3)c2)cn1] |
| 110 | N-[4-chloro-3-(trifluoromethyl)phenyl]-N'-({4-[2-(methyloxy)pyrimidin-5-yl]phenyl}methyl)urea | 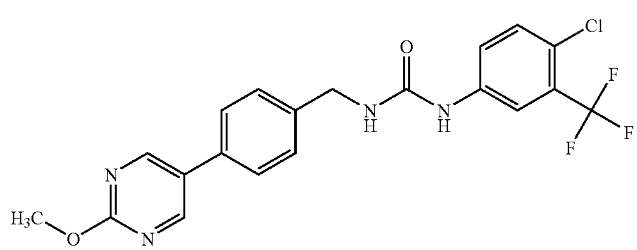 [SMILES: COc1ncc(-c2ccc(CNC(=O)Nc3ccc(Cl)c(C(F)(F)F)c3)cc2)cn1] |
| 111 | N-[4-chloro-3-(trifluoromethyl)phenyl]-N'-({4-[6-(methyloxy)pyridin-3-yl]phenyl}methyl)urea | 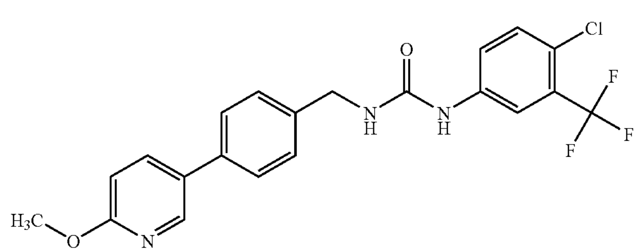 [SMILES: COc1ccc(-c2ccc(CNC(=O)Nc3ccc(Cl)c(C(F)(F)F)c3)cc2)cn1] |

TABLE 3-continued

| Entry | Name | Structure |
|---|---|---|
| 114 | N-[4-chloro-3-(trifluoromethyl)phenyl]-N~2~-[3-(2H-tetrazol-5-yl)phenyl]glycinamide | 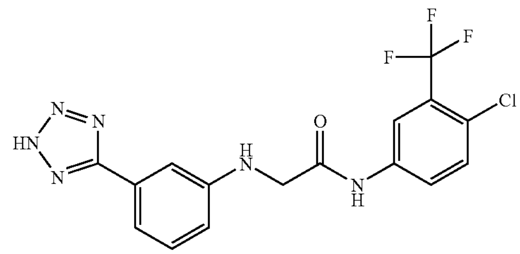 [SMILES: O=C(CNc1cccc(-c2nn[nH]n2)c1)Nc1ccc(Cl)c(C(F)(F)F)c1] |
| 115 | N-[4-chloro-3-(trifluoromethyl)phenyl]-2-{[2,6-difluoro-4-(1H-tetrazol-1-yl)phenyl]oxy}acetamide | 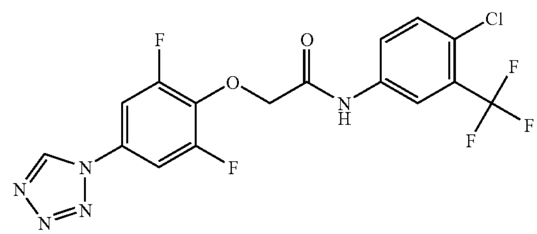 [SMILES: O=C(COc1c(F)cc(-n2cnnn2)cc1F)Nc1ccc(Cl)c(C(F)(F)F)c1] |
| 116 | (3-pyridin-3-ylphenyl)methyl [4-chloro-3-(trifluoromethyl)phenyl]carbamate | 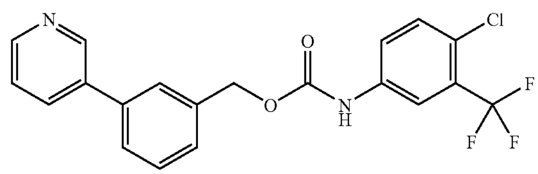 [SMILES: O=C(Nc1ccc(Cl)c(C(F)(F)F)c1)OCc1cccc(-c2cccnc2)c1] |
| 117 | (3-pyrimidin-5-ylphenyl)methyl [4-chloro-3-trifluoromethyl)phenyl]carbamate | 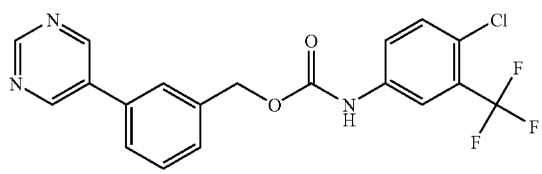 [SMILES: O=C(Nc1ccc(Cl)c(C(F)(F)F)c1)OCc1cccc(-c2cncnc2)c1] |
| 118 | (3-pyridin-4-ylphenyl)methyl [4-chloro-3-(trifluoromethyl)phenyl]carbamate | 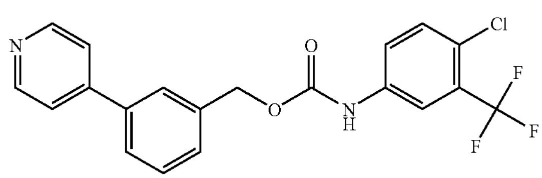 [SMILES: O=C(Nc1ccc(Cl)c(C(F)(F)F)c1)OCc1cccc(-c2ccncc2)c1] |
| 119 | N-[4-chloro-3-(trifluoromethyl)phenyl]-2-[4-(1H-tetrazol-1-yl)phenyl]hydrazinecarboxamide | 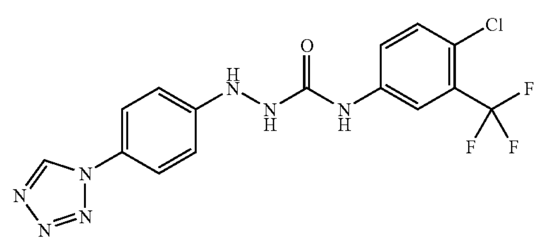 [SMILES: O=C(NNc1ccc(-n2cnnn2)cc1)Nc1ccc(Cl)c(C(F)(F)F)c1] |
| 120 | N-[4-chloro-3-(trifluoromethyl)phenyl]-2-(4-pyridin-3-ylphenyl)hydrazinecarboxamide | 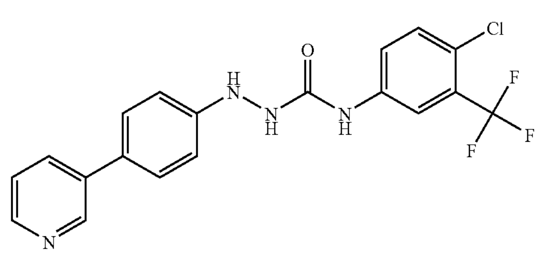 [SMILES: O=C(NNc1ccc(-c2cccnc2)cc1)Nc1ccc(Cl)c(C(F)(F)F)c1] |

TABLE 3-continued

| Entry | Name | Structure |
|---|---|---|
| 121 | (4-pyridin-3-ylphenyl)methyl [4-chloro-3-(trifluoromethyl)phenyl]carbamate | 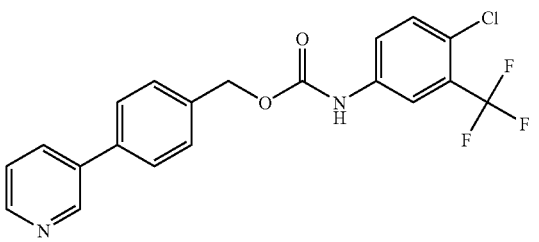 [SMILES: O=C(Nc1ccc(Cl)c(C(F)(F)F)c1)OCc1ccc(-c2cccnc2)cc1] |
| 122 | (4-pyridin-4-ylphenyl)methyl [4-chloro-3-(trifluoromethyl)phenyl]carbamate | 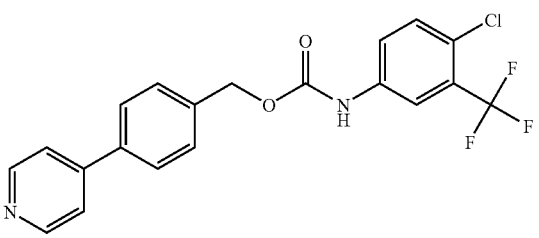 [SMILES: O=C(Nc1ccc(Cl)c(C(F)(F)F)c1)OCc1ccc(-c2ccncc2)cc1] |
| 123 | (4-pyrimidin-5-ylphenyl)methyl [4-chloro-3-(trifluoromethyl)phenyl]carbamate | 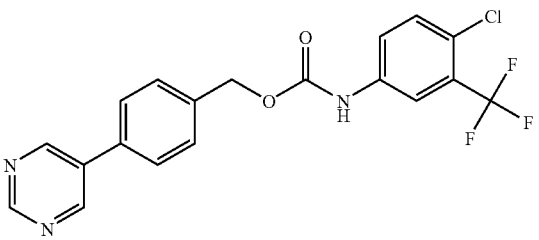 [SMILES: O=C(Nc1ccc(Cl)c(C(F)(F)F)c1)OCc1ccc(-c2cncnc2)cc1] |
| 124 | N-[4-chloro-3-(trifluoromethyl)phenyl]-N'-[(4-pyridin-4-ylphenyl)methyl]urea | 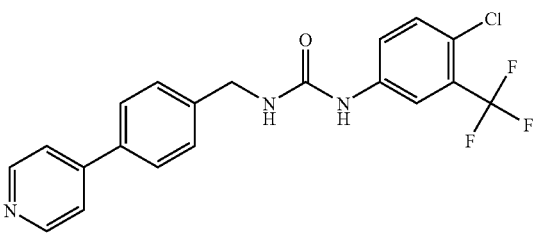 [SMILES: O=C(NCc1ccc(-c2ccncc2)cc1)Nc1ccc(Cl)c(C(F)(F)F)c1] |
| 125 | N-[4-chloro-3-(trifluoromethyl)phenyl]-2-(3-pyridin-3-ylphenyl)hydrazinecarboxamide | 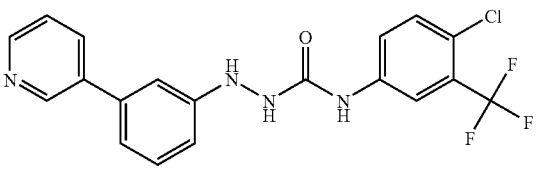 |
| 126 | N-[4-chloro-3-(trifluoromethyl)phenyl]-2-(3-pyrimidin-5-ylphenyl)hydrazinecarboxamide | 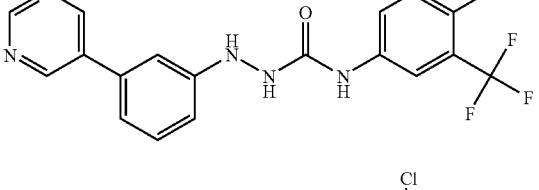 |
| 127 | N-[5-chloro-2,4-bis(methyloxy)phenyl]-N'-[(4-pyrimidin-5-ylphenyl)methyl]urea | 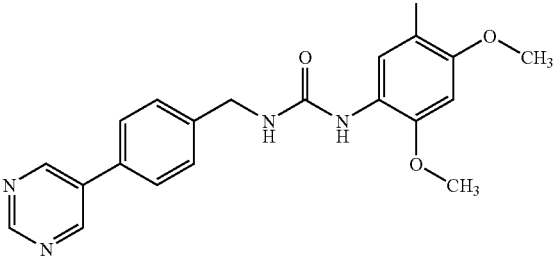 |

TABLE 3-continued

| Entry | Name | Structure |
|---|---|---|
| 128 | N-[5-chloro-2,4-bis(methyloxy)phenyl]-N'-[(4-pyridin-3-ylphenyl)methyl]urea | 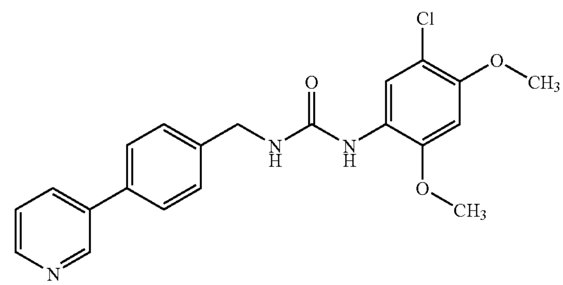 [SMILES: COc1cc(OC)c(NC(=O)NCc2ccc(-c3cccnc3)cc2)cc1Cl] |
| 129 | (4-pyrimidin-5-ylphenyl)methyl [5-chloro-2,4-bis(methyloxy)phenyl]carbamate | 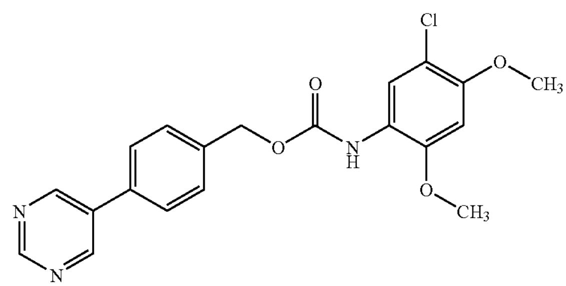 [SMILES: COc1cc(OC)c(NC(=O)OCc2ccc(-c3cncnc3)cc2)cc1Cl] |
| 130 | (4-pyridin-3-ylphenyl)methyl [5-chloro-2,4-bis(methyloxy)phenyl]carbamate | 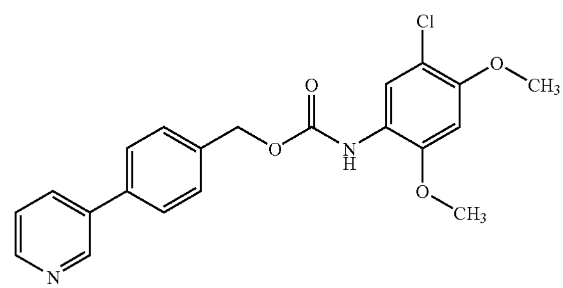 |
| 131 | 1-(4-pyridin-3-ylphenyl)ethyl [4-chloro-3-(trifluoromethyl)phenyl]carbamate | 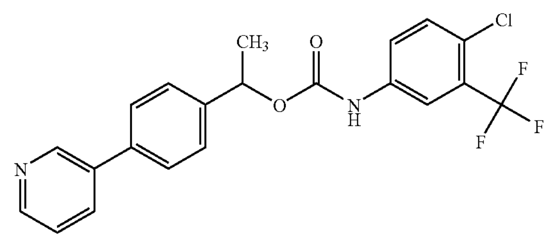 [SMILES: CC(OC(=O)Nc1ccc(Cl)c(C(F)(F)F)c1)c1ccc(-c2cccnc2)cc1] |
| 132 | 1-(4-pyrimidin-5-ylphenyl)ethyl [4-chloro-3-(trifluoromethyl)phenyl]carbamate | 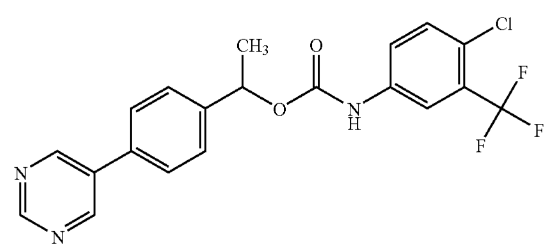 [SMILES: CC(OC(=O)Nc1ccc(Cl)c(C(F)(F)F)c1)c1ccc(-c2cncnc2)cc1] |
| 133 | N-[5-chloro-2,4-bis(methyloxy)phenyl]-N'-[(3-pyridin-3-ylphenyl)methyl]urea | 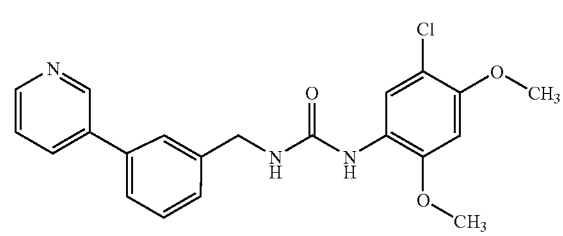 [SMILES: COc1cc(OC)c(NC(=O)NCc2cccc(-c3cccnc3)c2)cc1Cl] |

TABLE 3-continued

| Entry | Name | Structure |
|---|---|---|
| 134 | N-[5-chloro-2,4-bis(methyloxy)phenyl]-N'-[(3-pyrimidin-5-ylphenyl)methyl]urea | 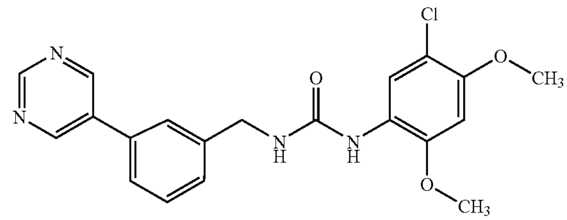 [SMILES: COc1cc(OC)c(NC(=O)NCc2cccc(-c3cncnc3)c2)cc1Cl] |
| 135 | (3-pyridin-3-ylphenyl)methyl [5-chloro-2,4-bis(methyloxy)phenyl]carbamate | 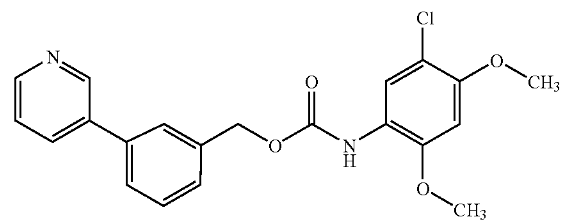 [SMILES: COc1cc(OC)c(NC(=O)OCc2cccc(-c3cccnc3)c2)cc1Cl] |
| 136 | (3-pyrimidin-5-ylphenyl)methyl [5-chloro-2,4-bis(methyloxy)phenyl]carbamate | 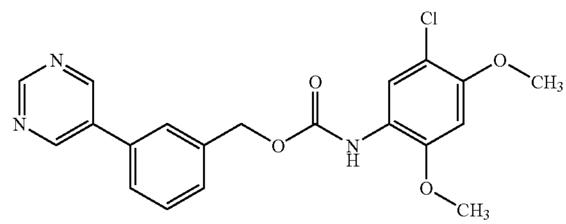 [SMILES: COc1cc(OC)c(NC(=O)OCc2cccc(-c3cncnc3)c2)cc1Cl] |
| 138 | N-[4-fluoro-3-(trifluoromethyl)phenyl]-N'-[(4-pyridin-3-ylphenyl)methyl]urea | 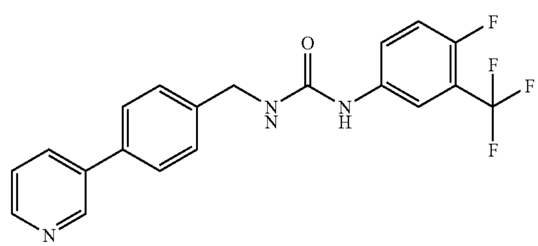 |
| 143 | N-[4-chloro-3-(trifluoromethyl)phenyl]-N'-[1-(4-pyridin-3-ylphenyl)ethyl]urea | 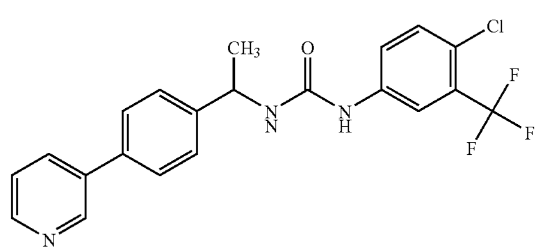 |
| 144 | N-[4-chloro-3-(trifluoromethyl)phenyl]-N'-[1-(4-pyrimidin-5-ylphenyl)ethyl]urea | 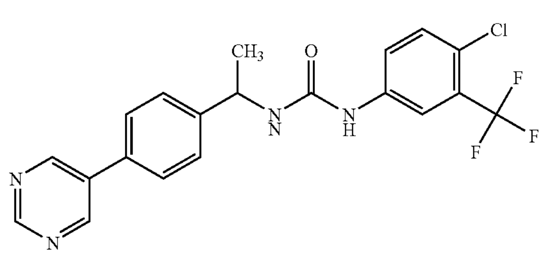 |

TABLE 3-continued

| Entry | Name | Structure |
|---|---|---|
| 145 | N-[4-chloro-3-(trifluoromethyl)phenyl]-2-{[4-(1H-indol-2-yl)phenyl]oxy}acetamide | 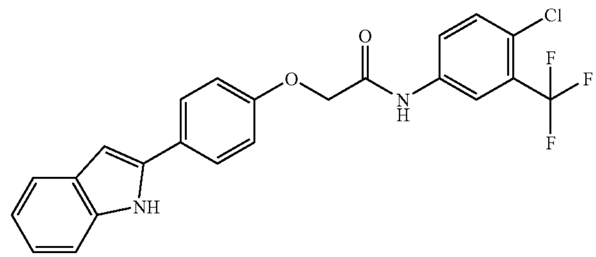 [SMILES: O=C(COc1ccc(-c2cc3ccccc3[nH]2)cc1)Nc1ccc(Cl)c(C(F)(F)F)c1] |
| 147 | N-[4-chloro-3-(trifluoromethyl)phenyl]-2-(4-pyridin-4-ylphenyl)hydrazinecarboxamide | 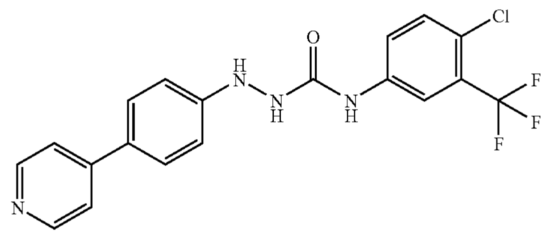 [SMILES: O=C(NNc1ccc(-c2ccncc2)cc1)Nc1ccc(Cl)c(C(F)(F)F)c1] |
| 148 | N-[4-chloro-3-(trifluoromethyl)phenyl]-2-(3-pyridin-4-ylphenyl)hydrazinecarboxamide | 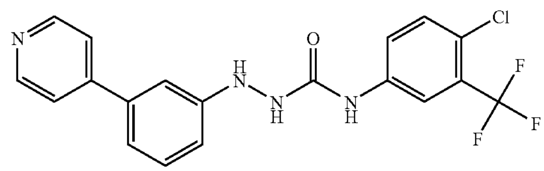 [SMILES: O=C(NNc1cccc(-c2ccncc2)c1)Nc1ccc(Cl)c(C(F)(F)F)c1] |
| 149 | N-[4-chloro-3-(trifluoromethyl)phenyl]-N'-[(3-pyridin-4-ylphenyl)methyl]urea | 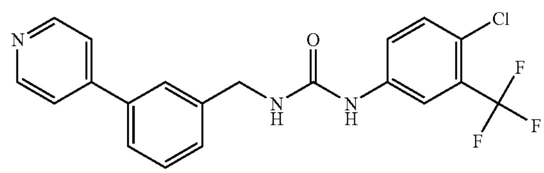 [SMILES: O=C(NCc1cccc(-c2ccncc2)c1)Nc1ccc(Cl)c(C(F)(F)F)c1] |
| 150 | N-[4-chloro-3-(trifluoromethyl)phenyl]-N'-[(3-quinoxalin-6-ylphenyl)methyl]urea | 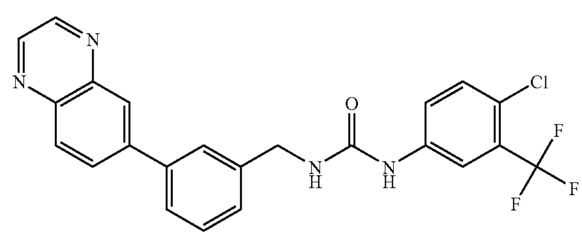 [SMILES: O=C(NCc1cccc(-c2ccc3nccnc3c2)c1)Nc1ccc(Cl)c(C(F)(F)F)c1] |
| 152 | N-[4-chloro-3-(trifluoromethyl)phenyl]-N'-[(4-quinoxalin-6-ylphenyl)methyl]urea | 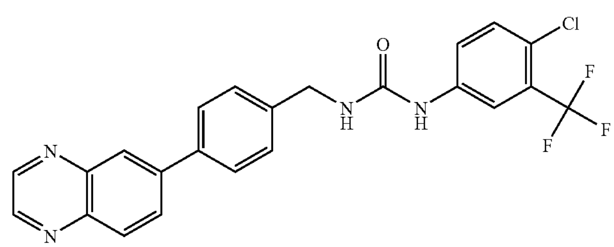 [SMILES: O=C(NCc1ccc(-c2ccc3nccnc3c2)cc1)Nc1ccc(Cl)c(C(F)(F)F)c1] |
| 155 | [3-(1H-tetrazol-1-yl)phenyl]methyl [3-chloro-4-(methyloxy)phenyl]carbamate | 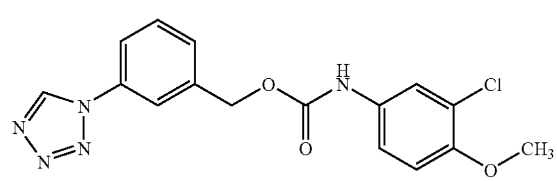 [SMILES: COc1ccc(NC(=O)OCc2cccc(-n3cnnn3)c2)cc1Cl] |

TABLE 3-continued

| Entry | Name | Structure |
|---|---|---|
| 156 | N-[3-chloro-4-(methyloxy)phenyl]-N'-{[3-(1H-tetrazol-1-yl)phenyl]methyl}urea | 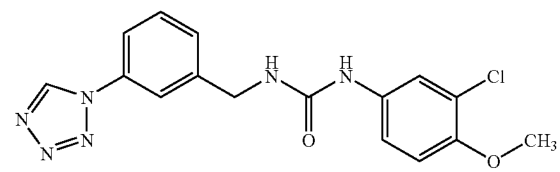 [SMILES: COc1ccc(NC(=O)NCc2cccc(-n3cnnn3)c2)cc1Cl] |
| 157 | N-[4-chloro-3-(trifluoromethyl)phenyl]-2-{[4-(5-hydroxy-1H-tetrazol-1-yl)phenyl]oxy}acetamide | 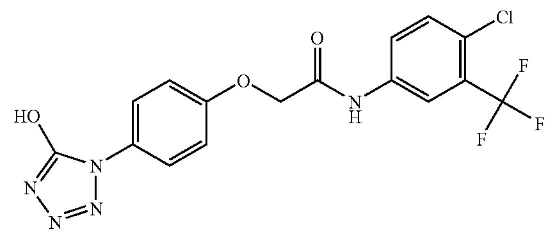 [SMILES: O=C(COc1ccc(-n2nnnc2O)cc1)Nc1ccc(Cl)c(C(F)(F)F)c1] |
| 160 | N-{[3-(6-chloropyridin-3-yl)phenyl]methyl}-N'-[4-chloro-3-(trifluoromethyl)phenyl]urea | 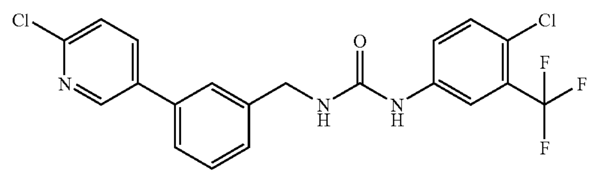 [SMILES: O=C(NCc1cccc(-c2ccc(Cl)nc2)c1)Nc1ccc(Cl)c(C(F)(F)F)c1] |
| 161 | N-{[4-(6-chloropyridin-3-yl)phenyl]methyl}-N'-[4-chloro-3-(trifluoromethyl)phenyl]urea | 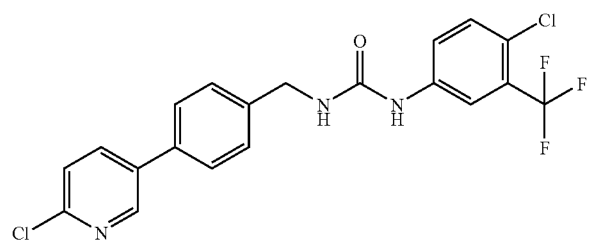 [SMILES: O=C(NCc1ccc(-c2ccc(Cl)nc2)cc1)Nc1ccc(Cl)c(C(F)(F)F)c1] |
| 165 | N-[4-chloro-3-(trifluoromethyl)phenyl]-N'-{[3-(6-fluoropyridin-3-yl)phenyl]methyl}urea | 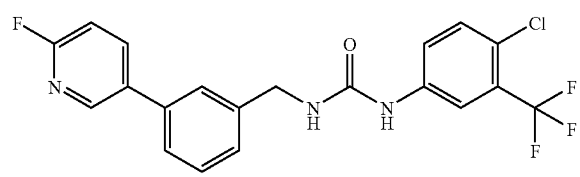 [SMILES: O=C(NCc1cccc(-c2ccc(F)nc2)c1)Nc1ccc(Cl)c(C(F)(F)F)c1] |
| 166 | N-[4-chloro-3-(trifluoromethyl)phenyl]-N'-({3-[2-(methyloxy)pyridin-3-yl]phenyl}methyl)urea | 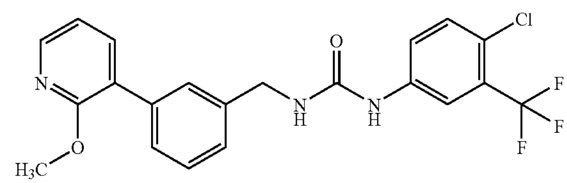 [SMILES: COc1ncccc1-c1cccc(CNC(=O)Nc2ccc(Cl)c(C(F)(F)F)c2)c1] |
| 167 | N-[4-chloro-3-(trifluoromethyl)phenyl]-N'-{[4-(6-fluoropyridin-3-yl)phenyl]methyl}urea | 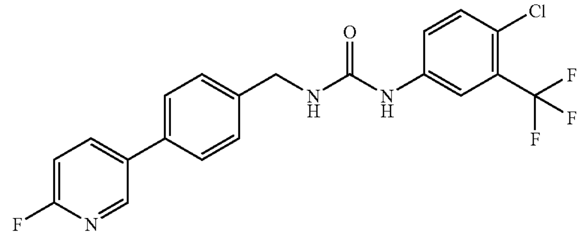 [SMILES: O=C(NCc1ccc(-c2ccc(F)nc2)cc1)Nc1ccc(Cl)c(C(F)(F)F)c1] |

TABLE 3-continued

| Entry | Name | Structure |
|---|---|---|
| 168 | N-[4-chloro-3-(trifluoromethyl)phenyl]-N'-({4-[2-(methyloxy)pyridin-3-yl]phenyl}methyl)urea | 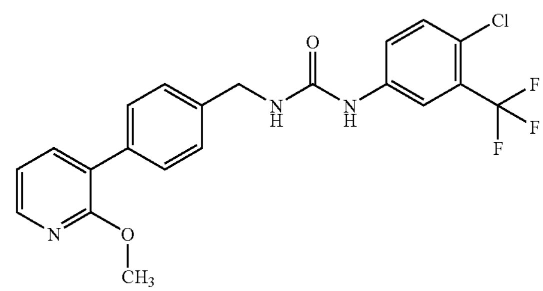 [SMILES: COc1ncccc1-c1ccc(CNC(=O)Nc2ccc(Cl)c(C(F)(F)F)c2)cc1] |
| 169 | N-[4-chloro-3-(trifluoromethyl)phenyl]-N'-{[4-(6-methylpyridin-3-yl)phenyl]methyl}urea | 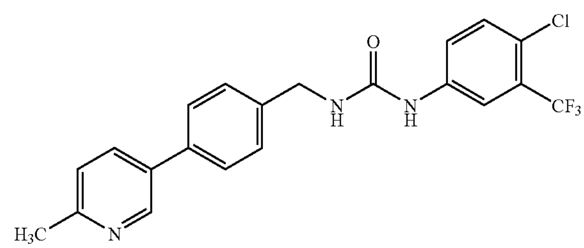 [SMILES: Cc1ccc(-c2ccc(CNC(=O)Nc3ccc(Cl)c(C(F)(F)F)c3)cc2)cn1] |
| 171 | N-[4-chloro-3-(trifluoromethyl)phenyl]-N'-{[3-(6-methylpyridin-3-yl)phenyl]methyl}urea | 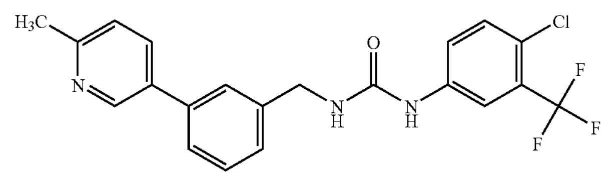 [SMILES: Cc1ccc(-c2cccc(CNC(=O)Nc3ccc(Cl)c(C(F)(F)F)c3)c2)cn1] |
| 174 | [3-(6-methylpyridin-3-yl)phenyl]methyl [4-chloro-3-(trifluoromethyl)phenyl]carbamate | 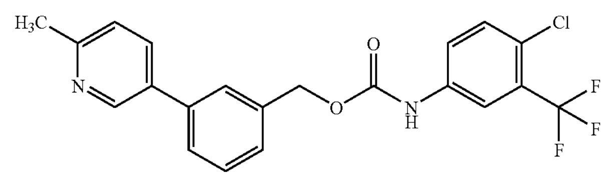 [SMILES: Cc1ccc(-c2cccc(COC(=O)Nc3ccc(Cl)c(C(F)(F)F)c3)c2)cn1] |
| 177 | (3-pyrazin-2-ylphenyl)methyl [4-chloro-3-(trifluoromethyl)phenyl]carbamate | 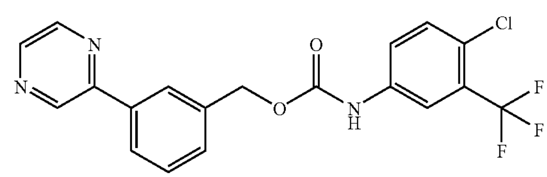 [SMILES: O=C(Nc1ccc(Cl)c(C(F)(F)F)c1)OCc1cccc(-c2cnccn2)c1] |
| 179 | N-{[3-(6-acetylpyridin-3-yl)phenyl]methyl}-N'-[4-chloro-3-(trifluoromethyl)phenyl]urea | 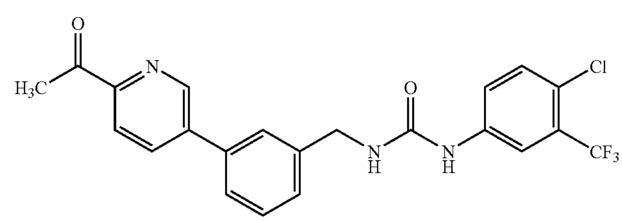 [SMILES: CC(=O)c1ccc(-c2cccc(CNC(=O)Nc3ccc(Cl)c(C(F)(F)F)c3)c2)cn1] |
| 180 | N-[4-chloro-3-(trifluoromethyl)phenyl]-N'-{[3-(6-cyanopyridin-3-yl)phenyl]methyl}urea | 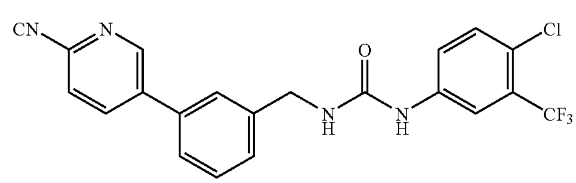 [SMILES: N#Cc1ccc(-c2cccc(CNC(=O)Nc3ccc(Cl)c(C(F)(F)F)c3)c2)cn1] |

TABLE 3-continued

| Entry | Name | Structure |
|---|---|---|
| 185 | [3-(7H-pyrrolo[2,3-d]pyrimidin-4-yl)phenyl]methyl [4-chloro-3-(trifluoromethyl)phenyl]carbamate | 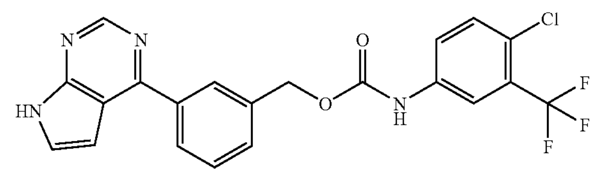 [SMILES: O=C(Nc1ccc(Cl)c(C(F)(F)F)c1)OCc1cccc(-c2ncnc3[nH]ccc23)c1] |
| 188 | [3-(1H-benzimidazol-2-yl)phenyl]methyl [4-chloro-3-(trifluoromethyl)phenyl]carbamate | 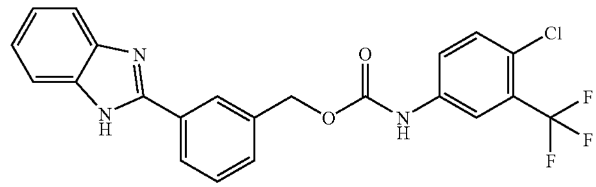 [SMILES: O=C(Nc1ccc(Cl)c(C(F)(F)F)c1)OCc1cccc(-c2nc3ccccc3[nH]2)c1] |
| 190 | N-[4-chloro-3-(trifluoromethyl)phenyl]-N'-({3-[5-(methylthio)pyridin-3-yl]phenyl}methyl)urea | 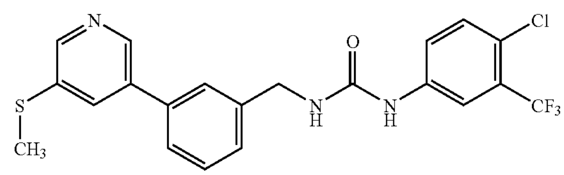 [SMILES: CSc1cncc(-c2cccc(CNC(=O)Nc3ccc(Cl)c(C(F)(F)F)c3)c2)c1] |
| 191 | [4-(6-methylpyridin-3-yl)phenyl]methyl [4-chloro-3-(trifluoromethyl)phenyl]carbamate | 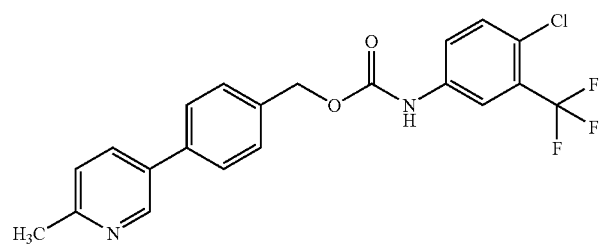 [SMILES: Cc1ccc(-c2ccc(COC(=O)Nc3ccc(Cl)c(C(F)(F)F)c3)cc2)cn1] |
| 194 | (4-pyrazin-2-ylphenyl)methyl [4-chloro-3-(trifluoromethyl)phenyl]carbamate | 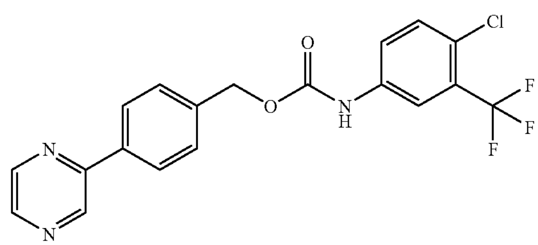 [SMILES: O=C(Nc1ccc(Cl)c(C(F)(F)F)c1)OCc1ccc(-c2cnccn2)cc1] |
| 195 | [4-(7H-pyrrolo[2,3-d]pyrimidin-4-yl)phenyl]methyl [4-chloro-3-(trifluoromethyl)phenyl]carbamate | 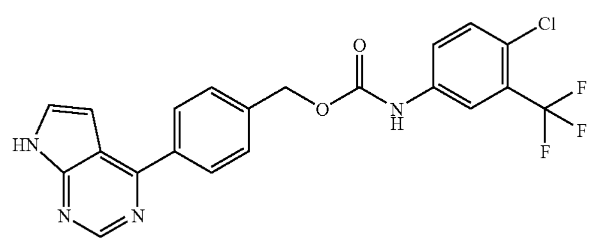 [SMILES: O=C(Nc1ccc(Cl)c(C(F)(F)F)c1)OCc1ccc(-c2ncnc3[nH]ccc23)cc1] |
| 200 | (3-pyridin-3-ylphenyl)methyl [5-chloro-2-(methyloxy)phenyl]carbamate | 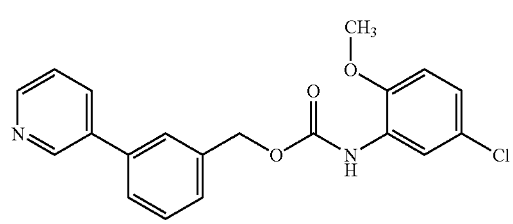 [SMILES: COc1ccc(Cl)cc1NC(=O)OCc1cccc(-c2cccnc2)c1] |

TABLE 3-continued

| Entry | Name | Structure |
|---|---|---|
| 201 | [4-(1H-tetrazol-1-yl)phenyl]methyl [4-chloro-3-(trifluoromethyl)phenyl]carbamate | 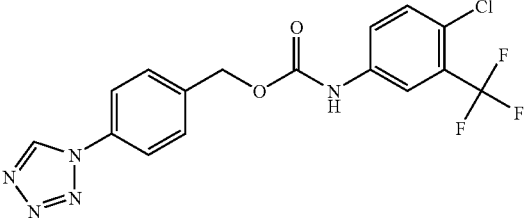 [SMILES: O=C(Nc1ccc(Cl)c(C(F)(F)F)c1)OCc1ccc(-n2cnnn2)cc1] |
| 202 | (3-pyrimidin-5-ylphenyl)methyl [5-chloro-2-(methyloxy)phenyl]carbamate | 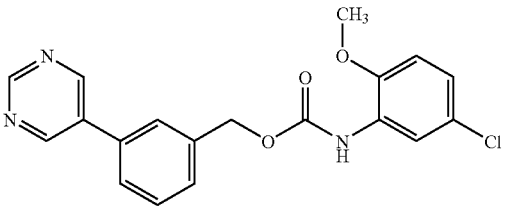 |
| 213 | N-[4-chloro-3-(trifluoromethyl)phenyl]-N'-{[3-(1H-pyrazol-4-yl)phenyl]methyl}urea | 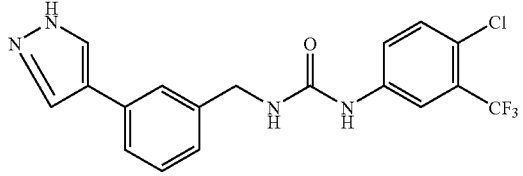 |
| 214 | N-[4-chloro-3-(trifluoromethyl)phenyl]-N'-{[4-(1H-pyrazol-4-yl)phenyl]methyl}urea | 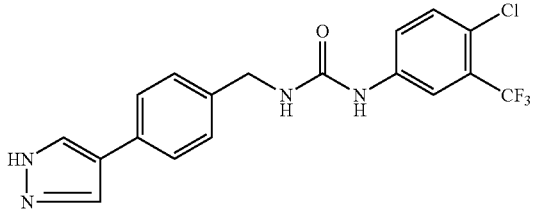 |
| 215 | [3-(2-piperazin-1-ylpyrimidin-5-yl)phenyl]methyl [4-chloro-3-(trifluoromethyl)phenyl]carbamate | 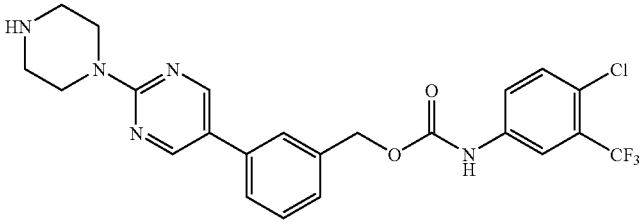 [SMILES: O=C(Nc1ccc(Cl)c(C(F)(F)F)c1)OCc1cccc(-c2cnc(N3CCNCC3)nc2)c1] |
| 216 | [4-(2-piperazin-1-ylpyrimidin-5-yl)phenyl]methyl [4-chloro-3-(trifluoromethyl)phenyl]carbamate | 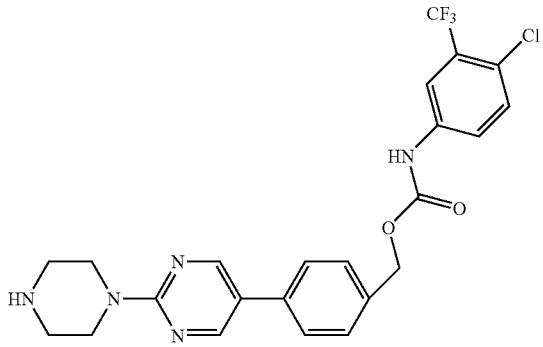 [SMILES: O=C(Nc1ccc(Cl)c(C(F)(F)F)c1)OCc1ccc(-c2cnc(N3CCNCC3)nc2)cc1] |

TABLE 3-continued

| Entry | Name | Structure |
|---|---|---|
| 217 | N-{[3-(2-chloropyridin-3-yl)phenyl]methyl}-N'-[4-chloro-3-(trifluoromethyl)phenyl]urea | 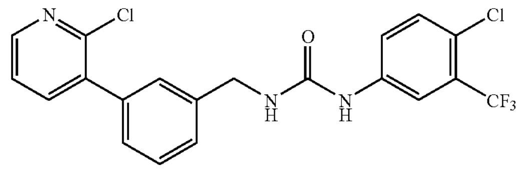 |
| 218 | N-{[4-(2-chloropyridin-3-yl)phenyl]methyl}-N'-[4-chloro-3-(trifluoromethyl)phenyl]urea | 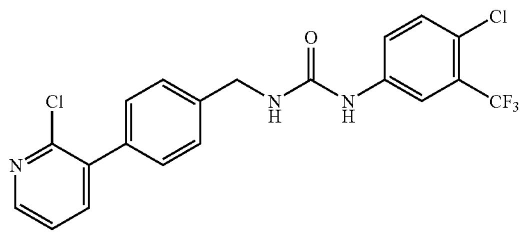 |
| 219 | N-[4-chloro-3-(trifluoromethyl)phenyl]-N'-{[3-(2-fluoropyridin-3-yl)phenyl]methyl}urea | 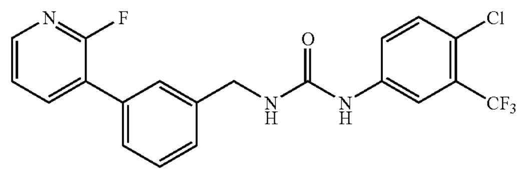 [SMILES: O=C(NCc1cccc(-c2cccnc2F)c1)Nc1ccc(Cl)c(C(F)(F)F)c1] |
| 220 | N-[4-chloro-3-(trifluoromethyl)phenyl]-N'-{[4-(2-fluoropyridin-3-yl)phenyl]methyl}urea | 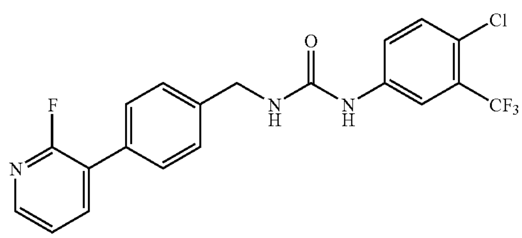 [SMILES: O=C(NCc1ccc(-c2cccnc2F)cc1)Nc1ccc(Cl)c(C(F)(F)F)c1] |
| 221 | [3-(1H-tetrazol-1-yl)phenyl]methyl [3-(trifluoromethyl)phenyl]carbamate | 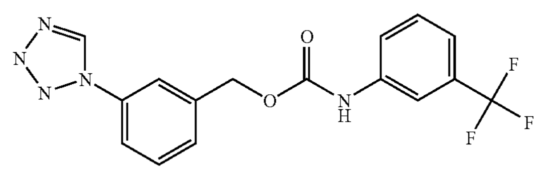 [SMILES: O=C(Nc1cccc(C(F)(F)F)c1)OCc1cccc(N2C=NNN2)c1] |
| 224 | N-[4-chloro-3-(trifluoromethyl)phenyl]-N'-({3-[5-(methylthio)pyridin-2-yl]phenyl}methyl)urea | 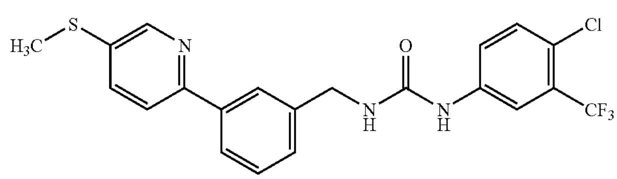 [SMILES: CSc1ccc(-c2cccc(CNC(=O)Nc3ccc(Cl)c(C(F)(F)F)c3)c2)nc1] |
| 225 | [3-(2,6-dimethylpyridin-3-yl)phenyl]methyl [4-chloro-3-(trifluoromethyl)phenyl]carbamate | 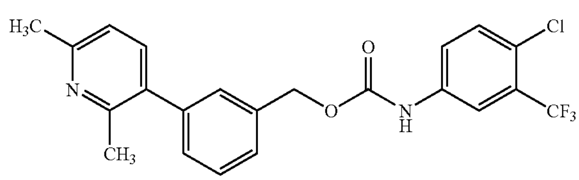 [SMILES: Cc1ccc(-c2cccc(COC(=O)Nc3ccc(Cl)c(C(F)(F)F)c3)c2)c(C)n1] |
| 226 | {3-[5-(methyloxy)pyridin-3-yl]phenyl}methyl [4-chloro-3-(trifluoromethyl)phenyl]carbamate | 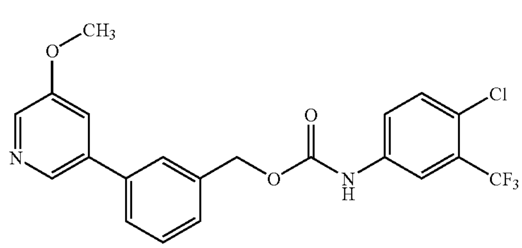 [SMILES: COc1cncc(-c2cccc(COC(=O)Nc3ccc(Cl)c(C(F)(F)F)c3)c2)c1] |

TABLE 3-continued

| Entry | Name | Structure |
|---|---|---|
| 229 | N-[4-chloro-3-(trifluoromethyl)phenyl]-N'-[(3-isoquinolin-4-ylphenyl)methyl]urea | 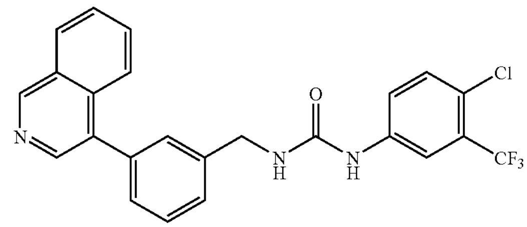 [SMILES: O=C(NCc1cccc(-c2cncc3ccccc23)c1)Nc1ccc(Cl)c(C(F)(F)F)c1] |
| 230 | N-[4-chloro-3-(trifluoromethyl)phenyl]-N'-[(4-isoquinolin-4-ylphenyl)methyl]urea | 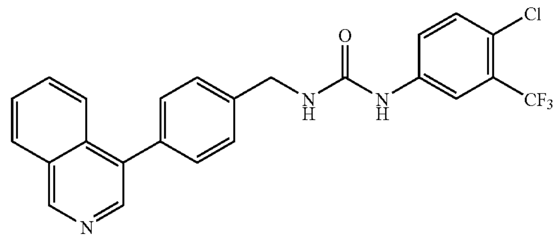 [SMILES: O=C(NCc1ccc(-c2cncc3ccccc23)cc1)Nc1ccc(Cl)c(C(F)(F)F)c1] |
| 232 | [3-(1H-pyrazol-4-yl)phenyl]methyl [4-chloro-3-(trifluoromethyl)phenyl]carbamate | 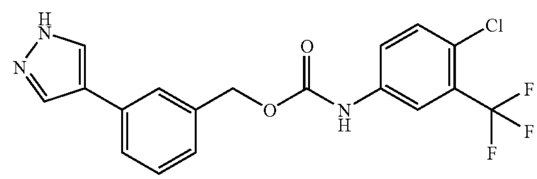 [SMILES: O=C(Nc1ccc(Cl)c(C(F)(F)F)c1)OCc1cccc(-c2cn[nH]c2)c1] |
| 233 | [4-(1H-pyrazol-4-yl)phenyl]methyl [4-chloro-3-(trifluoromethyl)phenyl]carbamate | 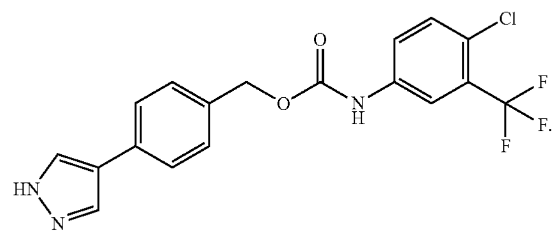 [SMILES: O=C(Nc1ccc(Cl)c(C(F)(F)F)c1)OCc1ccc(-c2cn[nH]c2)cc1] |

9. A pharmaceutical composition comprising the compound according to claim 1 and a pharmaceutically acceptable carrier.

10. A method for modulating the in-vivo activity of a kinase, the method comprising administering to a subject an effective amount of the compound according to claim 1.

11. The method according to claim 10, wherein the kinase is c-Kit.

12. The method according to claim 11, wherein modulating the in vivo activity of c-Kit comprises inhibition of c-Kit.

13. A method of treating rheumatoid arthritis, graft-host diseases, multiple sclerosis, psoriasis; artheroscrosis, myocardioinfarction, ischemia, stroke, restenosis; interbowel diseases, osteoarthritus, macular degeneration, or diabetic retinopathy, the method comprising administering, to a mammal in need thereof, a therapeutically effective amount of the compound or the pharmaceutical composition as described in claim 1.

14. A method of screening for modulators of c-Kit, the method comprising combining the compound according to claim 1 and at least one candidate agent and determining the effect of the candidate agent on c-Kit activity.

15. A method of inhibiting proliferative activity in a cell, the method comprising administering an effective amount of a composition comprising the compound according to claim 1 to a cell or a plurality of cells.

* * * * *